US007981425B2

(12) United States Patent
Min et al.

(10) Patent No.: US 7,981,425 B2
(45) Date of Patent: Jul. 19, 2011

(54) THROMBOPOIETIC COMPOUNDS

(75) Inventors: Hosung Min, Westlake Village, CA (US); Kenneth W. Walker, Newbury Park, CA (US); Colin V. Gegg, Jr., Newbury Park, CA (US); Francesco Galimi, Westlake Village, CA (US); Jeonghoon Sun, Thousand Oaks, CA (US); Mei-Mei Tsai, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 11/820,463

(22) Filed: Jun. 18, 2007

(65) Prior Publication Data
US 2008/0070840 A1 Mar. 20, 2008

Related U.S. Application Data

(60) Provisional application No. 60/844,301, filed on Sep. 13, 2006, provisional application No. 60/814,990, filed on Jun. 19, 2006.

(51) Int. Cl.
*A61K 38/16* (2006.01)
*A61K 39/00* (2006.01)
*C07K 16/46* (2006.01)
*C07K 14/435* (2006.01)

(52) U.S. Cl. .................. 424/185.1; 424/192.1; 530/350
(58) Field of Classification Search .................. None
See application file for complete search history.

(56) References Cited

U.S. PATENT DOCUMENTS

| | | | |
|---|---|---|---|
| 3,691,016 A | 9/1972 | Patel | |
| 3,941,763 A | 3/1976 | Sarantakis | |
| 3,969,287 A | 7/1976 | Jaworek et al. | |
| 4,179,337 A | 12/1979 | Davis et al. | |
| 4,195,128 A | 3/1980 | Hildebrand et al. | |
| 4,229,537 A | 10/1980 | Hodgins et al. | |
| 4,247,642 A | 1/1981 | Hirohara et al. | |
| 4,289,872 A | 9/1981 | Denkewalter et al. | |
| 4,301,144 A | 11/1981 | Iwashita et al. | |
| 4,330,440 A | 5/1982 | Ayers et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 4,925,673 A | 5/1990 | Steiner et al. | |
| 5,013,556 A | 5/1991 | Woodle et al. | |
| 5,223,409 A | 6/1993 | Ladner et al. | |
| 5,229,490 A | 7/1993 | Tam | |
| 5,284,656 A | 2/1994 | Platz et al. | |
| 5,338,665 A | 8/1994 | Schatz et al. | |
| 5,432,018 A | 7/1995 | Dower et al. | |
| 5,480,981 A | 1/1996 | Goodwin et al. | |
| 5,498,530 A | 3/1996 | Schatz et al. | |
| 5,733,731 A | 3/1998 | Schatz et al. | |
| 5,739,277 A | 4/1998 | Presta et al. | |
| 5,792,451 A | 8/1998 | Sarubbi et al. | |
| 5,869,451 A | 2/1999 | Dover et al. | |
| 5,922,545 A | 7/1999 | Mattheakis et al. | |
| 6,660,843 B1 | 12/2003 | Feige et al. | |
| 6,835,809 B1 | 12/2004 | Liu et al. | |
| 6,919,426 B2 | 7/2005 | Boone et al. | |
| 7,442,778 B2 * | 10/2008 | Gegg et al. ............. | 530/391.7 |
| 2003/0176352 A1 | 9/2003 | Min et al. | |
| 2003/0195156 A1 | 10/2003 | Min et al. | |
| 2003/0229023 A1 | 12/2003 | Oliner et al. | |
| 2003/0236193 A1 | 12/2003 | Oliner et al. | |
| 2004/0087778 A1 * | 5/2004 | Feige et al. ............. | 530/391.1 |
| 2006/0140934 A1 | 6/2006 | Gegg et al. | |
| 2009/0012272 A1 * | 1/2009 | Gegg et al. ............. | 530/391.7 |
| 2009/0022744 A1 * | 1/2009 | Gegg et al. ............. | 424/178.1 |
| 2009/0041768 A1 * | 2/2009 | Gegg et al. ............. | 424/133.1 |
| 2009/0234104 A1 * | 9/2009 | Gegg et al. ............. | 530/387.3 |
| 2009/0281286 A1 * | 11/2009 | Gregg et al. ............. | 530/391.7 |
| 2009/0286964 A1 * | 11/2009 | Gegg et al. ............. | 530/391.9 |

FOREIGN PATENT DOCUMENTS

| | | |
|---|---|---|
| CL | 991 1996 | 6/1997 |
| CL | 2697 1997 | 8/1998 |
| CL | 2201 2004 | 4/2006 |
| CL | 284 2007 | 12/2007 |
| EP | 0 315 456 | 5/1989 |
| WO | WO 90/04606 | 5/1990 |
| WO | WO 93/21259 | 10/1993 |
| WO | WO 95/18858 | 7/1995 |
| WO | WO 95/21919 | 8/1995 |
| WO | WO 95/21920 | 8/1995 |
| WO | WO 95/26746 | 10/1995 |
| WO | WO 96/11953 | 4/1996 |
| WO | WO 96/32478 | 10/1996 |
| WO | WO 96/40189 | 12/1996 |
| WO | WO 96/40987 | 12/1996 |
| WO | WO 97/34631 | 9/1997 |
| WO | WO 98/15833 | 4/1998 |
| WO | WO 00/24770 | 5/2000 |
| WO | WO 03/057134 | 7/2003 |
| WO | WO 2004/026329 | 4/2004 |
| WO | WO 2005/023834 A2 | 3/2005 |
| WO | WO 2006/010057 | 1/2006 |
| WO | WO 2007/022070 A2 | 2/2007 |

OTHER PUBLICATIONS

Stryer et al, in Biochemistry, Third edition, W H Freeman Company, New York, pp. 31-33, 1998.* Abuchowski et al., "Soluble Polymer-Enzyme Adducts", Enzymes as Drugs, Hocenberg and Roberts, eds., Wiley-Interscience, New York, NY, 367-383 (1981).
Adjei et al., "Bioavailability of Leuprolide Following Intratracheal Administration of Beagle Dogs", Internatl. J. Pharmaceutics, 61:135-144 (1990).
Adjei et al., "Pulmonary Delivery of Peptide Drugs: Effect of Particle Size on Bioavailability of Leuprolide Acetate in Healthy Male Volunteers", Pharma. Res., 7(6):565-569 (1990).
Alberts et al., "Synthesis of a Novel Hematopoietic Peptide, SK&F 107647", Thirteenth Am. Pep. Symp., 367-369 (1993).
Alexander et al., "Deficiencies in Progenitor Cells of Multiple Hematopoietic Lineages and Defective Megakaryocytopoiesis in Mice Lacking the Thrombopoietin Receptor c-Mpl", Blood 87(6):2162-2170 (1996).

(Continued)

*Primary Examiner* — Phuong Huynh

(57) ABSTRACT

The invention relates to the field of compounds, especially peptides or polypeptides, that have thrombopoietic activity. The peptides and polypeptides of the invention may be used to increase platelets or platelet precursors (e.g., megakaryocytes) in a mammal.

1 Claim, 5 Drawing Sheets

OTHER PUBLICATIONS

Bartley et al., "Identification and Cloning of a Megakaryocyte Growth and Development Factor That Is a Ligand for the Cytokine Receptor Mpl", Cell 77:1117-1124 (1994).

Basser et al., "Thrombopoietic Effects of Pegylated Recombinant Human Megakaryocyte Growth and Development Factor (Peg-rHuMGDF) in Patients with Advanced Cancer", The Lancet 348:1279-1281 (1996).

Bhatnagar et al., Structure-Activity Relationships of Novel Hemtoregulatory Peptides, J. Med. Chem., 39:3814-3819 (1996).

Braquet et al., "Effect of Endothelin-1 on Blood Pressure and Bronchopulmonary System of the Guinea Pig", J. Cardiovasc. Pharmacol., 13 (suppl. 5): 143-146 (1989).

Capon et al.,"Designing CD4 Immunoadhesins for AIDS Therapy," Nature, 337:525-531 (1989).

Chang et al., "Cloning and Characterization of the Human Megakaryocyte Growth and Development Factor (MGDF) Gene", Journal of Biological Chemistry 270:511-514 (1995).

Choi et al., "Platelets Generated in Vitro From Proplatelet-Displaying Human Megakaryocytes Are Functional", Blood 85:402-413 (1995).

Clackson et al., "A Hot Spot of Binding Energy in a Hormone-Receptor Interface," Science, 267: 383-386 (1995).

Cortese et al., "Selection of Biologically Active Peptides by Phage Display of Random Peptide Libraries," Curr. Opin. Biotech., 7:616-621 (1996).

Creighton, T.E., Proteins: Structure and Molecule Principles, W.H. Freeman & Co., New York, 79-86 (1983).

Cwirla et al., "Peptide Agonist of the Thrombopoietin Receptor as Potent as the Natural Cytokine," Science, 276:1696-1699 (1997).

Davis et al., "Preparation and Characterization of Antibodies with Specificity for the Amino-Terminal Tetrapeptide Sequence of the Platelet-Derived Connective Tissue," Biochem. Intl., 10(3):395-404 (1985).

de Sauvage et al., "Stimulation of Megakaryocytopoiesis and thrombopoiesis by the c-Mpl ligand", Nature 369:533-538 (1994).

Debili et al., "The Mpl Receptor Is Expressed in the Megakaryocytic Lineage From Late Progenitors to Platelets", Blood 85:391-401 (1995).

Debs et al., "Lung-Specific Delivery of Cytokines Induces Sustained Pulmonary and Systemic Immunomodulation in Rats" J. Immunol. 140:3482-3488 (1988).

Dedman et al., "Selection of Targeted Biological Modifiers from a Bacteriophage Library of Random Peptides," J. Biol. Chem., 268(31): 23025-23030 (1993).

Delgado et al., "Coupling of PEG to Protein by Activation With Tresyl Chloride, Applications in Immunoaffinity Cell Partitioning," Fisher et al., eds., Separations Using Aqueous Phase Systems, Applications in Cell Biology and Biotechnology, Plenum Press, N.Y. N.Y., 211-213 (1989).

Devlin et al., "Random Peptide Libraries: A Source of Specific Protein Binding Molecules," Science, 249:404-406 (1990).

Ellison et al., "The Nucleotide Sequence of a Human Immunoglobulin $C_{\gamma 1}$ gene," Nucleic Acids Res., 10(13): 4071-4079 (1982).

Erickson et al., "Solid-Phase Peptide Synthesis," The Proteins, 3rd Ed., 2:255-517 (1976).

Finn et al., "The Synthesis of Peptides by Solution Methods with Emphasis on Peptide Hormones," The Proteins, 3rd Ed., 2:105-253 (1976).

Fisher et al., "Treatment of Septic Shock with the Tumor Necrosis Factor Receptor:Fc Fusion Protein", N. Engl. J. Med. 334(26):1697-1702 (1996).

Francis et al., "PEG-Modified Proteins," Stability of protein pharmaceuticals: Part B in vivo pathways of degradation and strategies for protein stabilization, Eds. Ahern., T. Manning, M.C., Plenum, N.Y., pp. 235-263 (1991).

Francis, Gillian E., "Protein Modification and Fusion Proteins", Focus on Growth Factors, 3:4-11 (1992).

Gurney et al., "Genomic Structure, Chromosomal Localization, and Conserved Alternative Splice Forms of Thrombopoietin", Blood 85(4):981-988 (1995).

Harvill et al., "An IgG3-IL2 Fusion Protein Activates Complement, Binds FcγRI, Generates LAK Activity and Shows Enhanced Binding to the High Affinity IL-2R", Immunotechnology, 1:95-105 (1995).

Hokom et al., "Pegylated Megakaryocyte Growth and Development Factor Abrogates the Lethal Thrombocytopenia Associated With Carboplatin and Irradiation in Mice", Blood 86(12):4486-4492 (1995).

Hubbard et al., "Anti-Neutrophil-Elastase Defenses of the Lower Respiratory Tract in α1-Antitrypsin Deficiency Directly Augmented with an Aerosol of α1-Antitrypsin", Annals Int. Med. 111(3)::206-212 (1989).

Kato et al., "Purification and Characterization of Thrombopoietin", Journal of Biochemistry 118:229-236 (1995).

Kay et al., "From Peptides to Drugs Via Phage Display," Drug Disc. Today, 3(8):370-378 (1998).

Kreeger, Karen Y., "Immunological Applications Top List of Peptide-Synthesis Services," The Scientist, 10(13): 18-20 (1996).

Kuter et al., "The Purification of Megapoietin: A Physiological Regulator of Megakaryocyte Growth and Platelet Production", Proc. Natl. Acad. Sci. USA 91:11104-11108 (1994).

Lok et al., "Cloning and Expression of Murine Thrombopoietin cDNA and Stimulation of Platelet Production in vivo", Letters to Nature 369: 565-568 (1994).

Lowman, H.B., "Bacteriophage Display and Discovery of Peptide Leads for Drug Development," Ann. Rev. Biophys. Biomol. Struct., 26: 401-424 (1997).

Marshall, K., "Solid Oral Dosage Forms", Modern Pharmaceutics, ed. G. S. Banker and C. T. Rhodes, Chapter 10, 359-427 (1979).

Merrifield, R.B., "Solid Phase Peptide Synthesis. I. The Synthesis of a Tetrapeptide," J. Am. Chem, Soc., 85: 2149-2154 (1963).

Merrifield, R.B., "Solid-Phase Peptide Synthesis," Chem Polypeptides, Katsoyannis and Panayotis eds., pp. 335-361 (1973).

Methia et al., "Oligodeoxynucleotides Antisense to the Protooncogene c-*mpl* Specifically Inhibit in Vitro Megakaryocytopoiesis", Blood 82(5):1395-1401 (1993).

Newmark et al., "Preparation and Properties of Adducts of Streptokinase and Streptokinase-Plasmin Complex with Polyethylene Glycol and Pluronic Polyol F38", J. Appl. Biochem., 4:185-189 (1982).

Oeswein et al., "Aerosolization of Protein Pharmaceuticals", Proc. Symp. Resp. Drug Delivery II, Keystone, Colorado, pp. 14, 16-48(Mar. 1990).

Rasko et al., "Mpl Ligand (MGDF) Alone and in Combination with Stem Cell Factor (SCF) Promotes Proliferation and Survival of Human Megakaryocyte, Erythroid and Granulocyte/Macrophage Progenitors", Stem Cells 15:33-42 (1997).

Ravin et al., "Preformulation," Remington's Pharmaceutical Sciences, 18th Ed., Mack Publishing Co., Easton, PA 18042, 75:1435-1450 (1990).

Roberts et al., "RNA-Peptide Fusions for the in vitro Selection of Peptides and Proteins," Proc. Natl. Acad. Sci. USA, 94:12297-12302 (1997).

Sarmay et al., "Mapping and Comparison of the Interaction Sites on the Fc Region of IgG Responsible for Triggering Antibody Dependent Cellular Cytotoxicity (ADCC) Through Different Types of Human Fcγ Receptor," Molecular Immunology, 29(5):633-639 (1992).

Scott et al., "Searching for Peptide Ligands with an Epitope Library," Science, 249:386-390 (1990).

Smith et al., "Pulmonary Deposition and Clearance of Aerosolized Alpha-1-Proteinase Inhibitor Administered to Dogs and to Sheep", J. Clin. Invest., 84:1145-1154 (1989).

Smith et al., "Isolation of Glucagon Antagonists by Random Molecular Mutagenesis and Screening," Mol. Pharmacol. 43: 741-748 (1993).

Takasaki et al., "Structure-based Design and Characterization of Exocyclic Peptidomimetics that Inhibit TNFα Binding to its Receptor," Nature Biotech., 15:1266-1270 (1997).

Ulich et al., "Megakaryocyte Growth and Development Factor Ameliorates Carboplatin-Induced Thrombocytopenia in Mice", Blood 86(3):971-976 (1995).

Van Zee et al., "Protection Against Lethal *Escherichia coli* Bacteremia in Baboons (*Papio Anubis*) by Pretreatment with a 55-kDa TNF Receptor (CD120a)-Ig Fusion Protein, Ro 45-2081", The Journal of Immunology, 156: 2221-2230 (1996).

Vigon et al., "Molecular Cloning and Characterization of MPL, the Human Homolog of the v-mpl Oncogene: Identification of a Member of the Hematopoietic Growth Factor Receptor Superfamily", Proc. Natl. Acad. Sci. USA 89:5640-5644 (1992).

Wells et al., "Rapid Evolution of Peptide and Protein Binding Properties in vitro", Curr. Opin. Biotechnol., 3:355-362 (1992).

Wilson et al., "Phage Display: Applications, Innovations, and Issues in Phage and Host Biology", Can. J. Microbiol., 44:313-329 (1998).

Zeigler et al., "In Vitro Megakaryocytopoietic and Thrombopoietic Activity of c-mpl Ligand (TPO) on Purified Murine Hematopoietic Stem Cells", Blood 84(12):4045-4052 (1994).

Zheng et al., "Administration of Noncytolytic IL-10/Fc in Murine Models of Lipopolysaccharide-Induced Septic Shock and Allogeneic Islet Transplantation", Journal of Immunology, 154:5590-5600 (1995).

* cited by examiner

```
        ATGGACAAAACTCACACATGTCCACCTTGTCCAGCTCCGGAACTCCTGGGGGGACCGTCA
     1  ------------+-----------+-----------+-----------+-----------+-----------+  60
        TACCTGTTTTGAGTGTGTACAGGTGGAACAGGTCGAGGCCTTGAGGACCCCCCTGGCAGT a       M  D  K  T  H  T  C  P  P  C  P  A  P  E  L  L  G  G  P  S    -

GTCTTCCTCTTCCCCCCAAAACCCAAGGACACCCTCATGATCTCCCGGACCCCTGAGGTC
    61  ------------+-----------+-----------+-----------+-----------+-----------+  120
        CAGAAGGAGAAGGGGGGTTTTGGGTTCCTGTGGGAGTACTAGAGGGCCTGGGGACTCCAG a       V  F  L  F  P  P  K  P  K  D  T  L  M  I  S  R  T  P  E  V    -

ACATGCGTGGTGGTGGACGTGAGCCACGAAGACCCTGAGGTCAAGTTCAACTGGTACGTG
   121  ------------+-----------+-----------+-----------+-----------+-----------+  180
        TGTACGCACCACCACCTGCACTCGGTGCTTCTGGGACTCCAGTTCAAGTTGACCATGCAC a       T  C  V  V  V  D  V  S  H  E  D  P  E  V  K  F  N  W  Y  V    -

GACGGCGTGGAGGTGCATAATGCCAAGACAAAGCCGCGGGAGGAGCAGTACAACAGCACG
   181  ------------+-----------+-----------+-----------+-----------+-----------+  240
        CTGCCGCACCTCCACGTATTACGGTTCTGTTTCGGCGCCCTCCTCGTCATGTTGTCGTGC a       D  G  V  E  V  H  N  A  K  T  K  P  R  E  E  Q  Y  N  S  T    -

TACCGTGTGGTCAGCGTCCTCACCGTCCTGCACCAGGACTGGCTGAATGGCAAGGAGTAC
   241  ------------+-----------+-----------+-----------+-----------+-----------+  300
        ATGGCACACCAGTCGCAGGAGTGGCAGGACGTGGTCCTGACCGACTTACCGTTCCTCATG a       Y  R  V  V  S  V  L  T  V  L  H  Q  D  W  L  N  G  K  E  Y    -

AAGTGCAAGGTCTCCAACAAAGCCCTCCCAGCCCCCATCGAGAAAACCATCTCCAAAGCC
   301  ------------+-----------+-----------+-----------+-----------+-----------+  360
        TTCACGTTCCAGAGGTTGTTTCGGGAGGGTCGGGGGTAGCTCTTTTGGTAGAGGTTTCGG a       K  C  K  V  S  N  K  A  L  P  A  P  I  E  K  T  I  S  K  A    -

AAAGGGCAGCCCCGAGAACCACAGGTGTACACCCTGCCCCCATCCCGGGATGAGCTGACC
   361  ------------+-----------+-----------+-----------+-----------+-----------+  420
        TTTCCCGTCGGGGCTCTTGGTGTCCACATGTGGGACGGGGGTAGGGCCCTACTCGACTGG a       K  G  Q  P  R  E  P  Q  V  Y  T  L  P  P  S  R  D  E  L  T    -

AAGAACCAGGTCAGCCTGACCTGCCTGGTCAAAGGCTTCTATCCCAGCGACATCGCCGTG
   421  ------------+-----------+-----------+-----------+-----------+-----------+  480
        TTCTTGGTCCAGTCGGACTGGACGGACCAGTTTCCGAAGATAGGGTCGCTGTAGCGGCAC a       K  N  Q  V  S  L  T  C  L  V  K  G  F  Y  P  S  D  I  A  V    -

GAGTGGGAGAGCAATGGGCAGCCGGAGAACAACTACAAGACCACGCCTCCCGTGCTGGAC
   481  ------------+-----------+-----------+-----------+-----------+-----------+  540
        CTCACCCTCTCGTTACCCGTCGGCCTCTTGTTGATGTTCTGGTGCGGAGGGCACGACCTG
```

TCCGACGGCTCCTTCTTCCTCTACAGCAAGCTCACCGTGGACAAGAGCAGGTGGCAGCAG
541    ---------+---------+---------+---------+---------+---------+  600
       AGGCTGCCGAGGAAGAAGGAGATGTCGTTCGAGTGGCACCTGTTCTCGTCCACCGTCGTC a      S   D   G   S   F   F   L   Y   S   K   L   T   V   D   K   S   R   W   Q   Q    -

GGGAACGTCTTCTCATGCTCCGTGATGCATGAGGCTCTGCACAACCACTACACGCAGAAG
601    ---------+---------+---------+---------+---------+---------+  660
       CCCTTGCAGAAGAGTACGAGGCACTACGTACTCCGAGACGTGTTGGTGATGTGCGTCTTC a      G   N   V   F   S   C   S   V   M   H   E   A   L   H   N   H   Y   T   Q   K    -

AGCCTCTCCCTGTCTCCGGGTAAA
661    ---------+---------+----  684
       TCGGAGAGGGACAGAGGCCCATTT a      S   L   S   L   S   P   G   K
```

Figure 1B

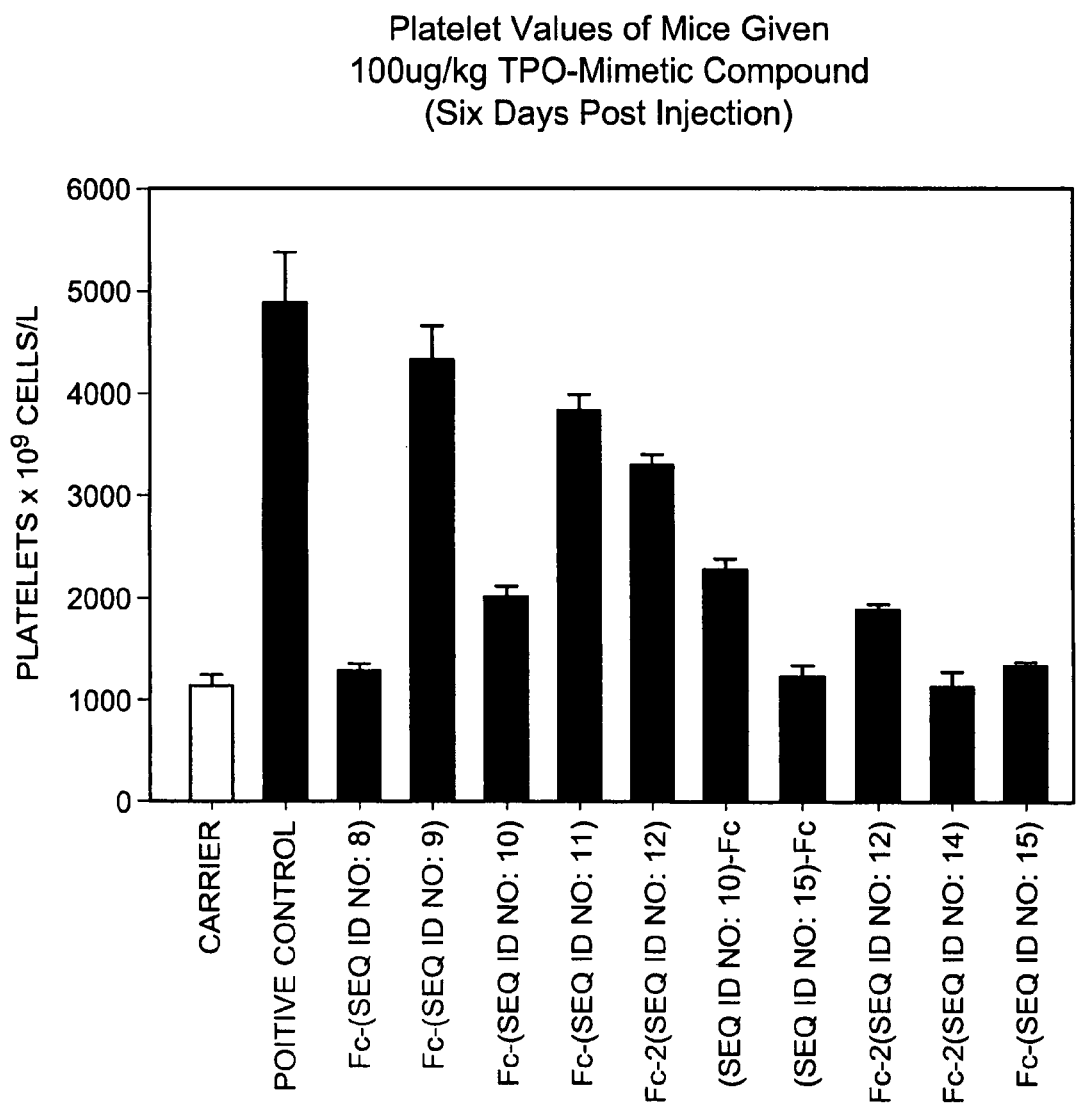

… # THROMBOPOIETIC COMPOUNDS

The present application claims benefit under 35 U.S.C §119 of U.S. Patent Application No. 60/814,990, which was filed Jun. 19, 2006, and U.S. Patent Application No. 60/844,301, which was filed Sep. 13, 2006, each of which is incorporated herein by reference in its entirety.

FIELD OF THE INVENTION

Generally, the invention relates to the field of compounds, especially peptides and polypeptides that have thrombopoietic activity. The compounds of the invention may be used to increase of production platelets or platelet precursors (e.g., megakaryocytes) in a mammal

BACKGROUND OF THE INVENTION

The cloning of endogenous thrombopoietin (TPO) (Lok et al., Nature 369:568-571 (1994); Bartley et al., Cell 77:1117-1124 (1994); Kuter et al., Proc. Natl. Acad. Sci. USA 91:11104-11108 (1994); de Sauvage et al., Nature 369:533-538 (1994); Kato et al., Journal of Biochemistry 119:229-236 (1995); Chang et al., Journal of Biological Chemistry 270:511-514 (1995)) has rapidly increased our understanding of megakaryopoiesis (megakaryocyte production) and thrombopoiesis (platelet production).

Endogenous human TPO, a 60 to 70 kDa glycosylated protein primarily produced in the liver and kidney, consists of 332 amino acids (Bartley et al., Cell 77:1117-1124 (1994); Chang et al., Journal of Biological Chemistry 270:511-514 (1995)). The protein is highly conserved between different species, and has 23% homology with human erythropoietin (Gurney et al., Blood 85:981-988 (1995)) in the amino terminus (amino acids 1 to 172) (Bartley et al., Cell 77:1117-1124 (1994)). Endogenous TPO has been shown to possess all of the characteristics of the key biological regulator of thrombopoiesis. Its in vitro actions include specific induction of megakaryocyte colonies from both purified murine hematopoietic stem cells (Zeigler et al., Blood 84:4045-4052 (1994)) and human $CD34^+$ cells (Lok et al., Nature 369:568-571 (1994); Rasko et al., Stem Cells 15:33-42 (1997)), the generation of megakaryocytes with increased ploidy (Broudy et al., Blood 85:402-413 (1995)), and the induction of terminal megakaryocyte maturation and platelet production (Zeigler et al., Blood 84:4045-4052 (1994); Choi et al., Blood 85:402-413 (1995)). Conversely, synthetic antisense oligodeoxynucleotides to the TPO receptor (c-Mp1) significantly inhibit the colony-forming ability of megakaryocyte progenitors (Methia et al., Blood 82:1395-1401 (1993)). Moreover, c-Mp1 knock-out mice are severely thrombocytopenic and deficient in megakaryocytes (Alexander et al., Blood 87:2162-2170 (1996)).

Recombinant human MGDF (rHuMGDF, Amgen Inc., Thousand Oaks, Calif.) is another thrombopoietic polypeptide related to TPO. It is produced using *E. coli* transformed with a plasmid containing cDNA encoding a truncated protein encompassing the amino-terminal receptor-binding domain of human TPO (Ulich et al., Blood 86:971-976 (1995)). The polypeptide is extracted, refolded, and purified, and a poly[ethylene glycol] (PEG) moiety is covalently attached to the amino terminus. The resulting molecule is referred to herein as PEG-rHuMGDF or MGDF for short.

Various studies using animal models (Ulich, T. R. et al., Blood 86:971-976 (1995); Hokom, M. M. et al., Blood 86:4486-4492 (1995)) have clearly demonstrated the therapeutic efficacies of TPO and MGDF in bone marrow transplantation and in the treatment of thrombocytopenia, a condition that often results from chemotherapy or radiation therapy. Preliminary data in humans have confirmed the utility of MGDF in elevating platelet counts in various settings. (Basser et al., Lancet 348:1279-81 (1996); Kato et al., Journal of Biochemistry 119:229-236 (1995); Ulich et al., Blood 86:971-976 (1995)). MGDF might be used to enhance the platelet donation process, since administration of MGDF increases circulating platelet counts to about three-fold the original value in healthy platelet donors.

TPO and MGDF exert their action through binding to the c-Mp1 receptor which is expressed primarily on the surface of certain hematopoietic cells, such as megakaryocytes, platelets, $CD34^+$ cells and primitive progenitor cells (Debili, N. et al., Blood 85:391-401 (1995); de Sauvage, F. J. et al, Nature 369:533-538 (1994); Bartley, T. D., et al., Cell 77:1117-1124 (1994); Lok, S. et al., Nature 369: 565-8 (1994)). Like most receptors for interleukins and protein hormones, c-Mp1 belongs to the class I cytokine receptor superfamily (Vigon, I. et al., Proc. Natl. Acad. Sci. USA 89:5640-5644 (1992)). Activation of this class of receptors involves ligand-binding induced receptor homodimerization which in turn triggers the cascade of signal transducing events.

In general, the interaction of a protein ligand with its receptor often takes place at a relatively large interface. However, as demonstrated in the case of human growth hormone bound to its receptor, only a few key residues at the interface actually contribute to most of the binding energy (Clackson, T. et al., Science 267:383-386 (1995)). This and the fact that the bulk of the remaining protein ligand serves only to display the binding epitopes in the right topology makes it possible to find active ligands of much smaller size.

In an effort toward this, the phage peptide library display system has emerged as a powerful technique in identifying small peptide mimetics of large protein ligands (Scott, J. K. et al., Science 249:386 (1990); Devlin, J. J. et al., Science 249: 404 (1990)).

Further, in an effort to seek small structures as lead compounds in the development of therapeutic agents with more desirable properties, a different type of dimer of TMP and related structures were designed in which the C-terminus of one TMP peptide was linked to the N-terminus of a second TMP peptide, either directly or via a linker and the effects of this dimerization strategy on the bioactivity of the resulting dimeric molecules were then investigated (U.S. Pat. No. 6,835,809, Liu et al.; incorporated herein by reference in its entirety). In some cases, these so-called tandem dimers (C-N link) were designed to have linkers between the two monomers, the linkers being preferably composed of natural amino acids, therefore rendering their synthesis accessible to recombinant technologies (U.S. Pat. No. 6,835,809, supra). In addition, the tandem dimers may be further attached to one or more moieties that are derived from immunoglobulin proteins, referred to generally as the Fc region of such immunoglobulins. The resulting compounds are referred to as Fc fusions of TMP tandem dimers (U.S. Pat. No. 6,835,809, supra).

Antibodies comprise two functionally independent parts, a variable domain known as "Fab", which binds antigen, and a constant domain, known as "Fc" which provides the link to effector functions such as complement fixation or phagocytosis. The Fc portion of an immunoglobulin has a long plasma half-life, whereas the Fab is short-lived. (Capon, et al., Nature 337:525-531 (1989)).

Therapeutic protein products have been constructed using the Fc domain to attempt to provide longer half-life or to incorporate functions such as Fc receptor binding, protein A binding, complement fixation, and placental transfer which all reside in the Fc region of immunoglobulins (Capon, et al., Nature 337:525-531 (1989)). For example, the Fc region of an IgG1 antibody has been fused to CD30-L, a molecule which binds CD30 receptors expressed on Hodgkin's Disease tumor cells, anaplastic lymphoma cells, T-cell leukemia cells and other malignant cell types. See, U.S. Pat. No. 5,480,981. IL-10, an anti-inflammatory and antirejection agent has been fused to murine Fcγ2a in order to increase the cytokine's short circulating half-life (Zheng, X. et al., Journal of Immunology, 154: 5590-5600 (1995)). Studies have also evaluated the use of tumor necrosis factor receptor linked with the Fc protein of human IgG1 to treat patients with septic shock (Fisher, C. et al., N. Engl. J. Med., 334: 1697-1702 (1996); Van Zee, K. et al., The Journal of Immunology, 156: 2221-2230 (1996)). Fc has also been fused with CD4 receptor to produce a therapeutic protein for treatment of AIDS. See, Capon et al., Nature, 337:525-531 (1989). In addition, interleukin 2 has been fused to the Fc portion of IgG1 or IgG3 to overcome the short half life of interleukin 2 and its systemic toxicity. See, Harvill et al., Immunotechnology, 1: 95-105 (1995).

The development of therapeutic agents can also be achieved by the use of peptide library screening. The interaction of a protein ligand with its receptor often takes place at a relatively large interface. However, as demonstrated for human growth hormone and its receptor, only a few key residues at the interface contribute to most of the binding energy. Clackson et al., Science 267: 383-6 (1995). The bulk of the protein ligand merely displays the binding epitopes in the right topology or serves functions unrelated to binding. Thus, molecules of only "peptide" length (2 to 40 amino acids and even 2 to 80 amino acids) can bind to the receptor protein of a given large protein ligand. Such peptides may mimic the bioactivity of the large protein ligand ("peptide agonists") or, through competitive binding, inhibit the bioactivity of the large protein ligand ("peptide antagonists").

Phage display peptide libraries have emerged as a powerful method in identifying such peptide agonists and antagonists. See, for example, Scott et al., Science 249: 386 (1990); Devlin et al., Science 249: 404 (1990); U.S. Pat. No. 5,223,409, issued Jun. 29, 1993; U.S. Pat. No. 5,733,731, issued Mar. 31, 1998; U.S. Pat. No. 5,498,530, issued Mar. 12, 1996; U.S. Pat. No. 5,432,018, issued Jul. 11, 1995; U.S. Pat. No. 5,338,665, issued Aug. 16, 1994; U.S. Pat. No. 5,922,545, issued Jul. 13, 1999; WO 96/40987, published Dec. 19, 1996; and WO 98/15833, published Apr. 16, 1998 (each of which is incorporated herein by reference). In such libraries, random peptide sequences are displayed by fusion with coat proteins of filamentous phage. Typically, the displayed peptides are affinity-eluted against an antibody-immobilized extracellular domain of a receptor. The retained phages may be enriched by successive rounds of affinity purification and repropagation. The best binding peptides may be sequenced to identify key residues within one or more structurally related families of peptides. See, e.g., Cwirla et al., Science 276: 1696-9 (1997), in which two distinct families were identified. The peptide sequences may also suggest which residues may be safely replaced by alanine scanning or by mutagenesis at the DNA level. Mutagenesis libraries may be created and screened to further optimize the sequence of the best binders. Lowman, Ann. Rev. Biophys. Biomol. Struct. 26: 401-24 (1997).

Other methods compete with phage display in peptide research. A peptide library can be fused to the carboxyl terminus of the lac repressor and expressed in E. coli. Another E. coli-based method allows display on the cell's outer membrane by fusion with a peptidoglycan-associated lipoprotein (PAL). Hereinafter, these and related methods are collectively referred to as "E. coli display." Another biological approach to screening soluble peptide mixtures uses yeast for expression and secretion. See Smith et al., Mol. Pharmacol. 43: 741-8 (1993). Hereinafter, the method of Smith et al. and related methods are referred to as "yeast-based screening." In another method, translation of random RNA is halted prior to ribosome release, resulting in a library of polypeptides with their associated RNA still attached. Hereinafter, this and related methods are collectively referred to as "ribosome display." Other methods employ chemical linkage of peptides to RNA; see, for example, Roberts & Szostak, Proc. Natl. Acad. Sci. USA, 94: 12297-12303 (1997). Hereinafter, this and related methods are collectively referred to as "RNA-peptide screening." Chemically derived peptide libraries have been developed in which peptides are immobilized on stable, non-biological materials, such as polyethylene rods or solvent-permeable resins. Another chemically derived peptide library uses photolithography to scan peptides immobilized on glass slides. Hereinafter, these and related methods are collectively referred to as "chemical-peptide screening." Chemical-peptide screening may be advantageous in that it allows use of D-amino acids and other unnatural analogues, as well as non-peptide elements. Both biological and chemical methods are reviewed in Wells & Lowman, Curr. Opin. Biotechnol. 3: 355-362 (1992).

In the case of known bioactive peptides, rational design of peptide ligands with favorable therapeutic properties can be completed. In such an approach, one makes stepwise changes to a peptide sequence and determines the effect of the substitution upon bioactivity or a predictive biophysical property of the peptide (e.g., solution structure). Hereinafter, these techniques are collectively referred to as "rational design." In one such technique, one makes a series of peptides in which one replaces a single residue at a time with alanine. This technique is commonly referred to as an "alanine walk" or an "alanine scan." When two residues (contiguous or spaced apart) are replaced, it is referred to as a "double alanine walk." The resultant amino acid substitutions can be used alone or in combination to result in a new peptide entity with favorable therapeutic properties.

Structural analysis of protein-protein interaction may also be used to suggest peptides that mimic the binding activity of large protein ligands. In such an analysis, the crystal structure may suggest the identity and relative orientation of critical residues of the large protein ligand, from which a peptide may be designed. See, e.g., Takasaki et al., Nature Biotech. 15: 1266-1270 (1997). Hereinafter, these and related methods are referred to as "protein structural analysis." These analytical methods may also be used to investigate the interaction between a receptor protein and peptides selected by phage display, which may suggest further modification of the peptides to increase binding affinity.

Conceptually, one may discover peptide mimetics of any protein using phage display and the other methods mentioned above. These methods have been used for epitope mapping, for identification of critical amino acids in protein-protein interactions, and as leads for the discovery of new therapeutic agents. E.g., Cortese et al., Curr. Opin. Biotech. 7: 616-621 (1996). Peptide libraries are now being used most often in immunological studies, such as epitope mapping. Kreeger, The Scientist 10(13): 19-20 (1996).

Of particular interest here is use of peptide libraries and other techniques in the discovery of pharmacologically active peptides. Some of these peptides have been modified (e.g., to form C-terminally cross-linked dimers). Typically, peptide libraries were screened for binding to a receptor for a pharmacologically active protein (e.g., EPO receptor). In at least one instance (CTLA4), the peptide library was screened for binding to a monoclonal antibody.

Peptides identified by peptide library screening were for a long time regarded simply as "leads" in development of therapeutic agents rather than as therapeutic agents themselves. Like other proteins and peptides, they would be rapidly removed in vivo either by renal filtration, cellular clearance mechanisms in the reticuloendothelial system, or proteolytic degradation. Francis, *Focus on Growth Factors* 3: 4-11 (1992). As a result, the art used the identified peptides to validate drug targets or as scaffolds for design of organic compounds that might not have been as easily or as quickly identified through chemical library screening. Lowman, *Ann. Rev. Biophys. Biomol. Struct.* 26: 401-424 (1997); Kay et al., *Drug Disc. Today* 3: 370-378 (1998).

A more recent development is fusion of randomly generated peptides with the Fc domain. See U.S. Pat. No. 6,660,843, issued Dec. 9, 2003 to Feige et al. (incorporated herein by reference in its entirety). Such molecules have come to be known as "peptibodies." They include one or more peptides linked to the N-terminus, C-terminus, amino acid sidechains, or to more than one of these sites. Peptibody technology enables design of therapeutic agents that incorporate peptides that target one or more ligands or receptors, tumor-homing peptides, membrane-transporting peptides, and the like. Peptibody technology has proven useful in design of a number of such molecules, including linear and disulfide-constrained peptides, "tandem peptide multimers" (i.e., more than one peptide on a single chain of an Fc domain). See, for example, U.S. Pat. No. 6,660,843; U.S. Pat. App. No. 2003/0195156, published Oct. 16, 2003 (corresponding to WO 02/092620, published Nov. 21, 2002); U.S. Pat. App. No. 2003/0176352, published Sep. 18, 2003 (corresponding to WO 03/031589, published Apr. 17, 2003); U.S. Ser. No. 09/422,838, filed Oct. 22, 1999 (corresponding to WO 00/24770, published May 4, 2000); U.S. Pat. App. No. 2003/0229023, published Dec. 11, 2003; WO 03/057134, published Jul. 17, 2003; U.S. Pat. App. No. 2003/0236193, published Dec. 25, 2003 (corresponding to PCT/US04/010989, filed Apr. 8, 2004); U.S. Ser. No. 10/666,480, filed Sep. 18, 2003 (corresponding to WO 04/026329, published Apr. 1, 2004), each of which is hereby incorporated by reference in its entirety.

The art would benefit from further technology enabling such rational design of polypeptide therapeutic agents, because there remains a need in the art for additional compounds that have a biological activity of stimulating the production of platelets (thrombopoietic activity) and/or platelet precursor cells, especially megakaryocytes (megakaryopoietic activity).

SUMMARY OF THE INVENTION

Provided herein is a group of compounds that are capable of binding to and triggering a transmembrane signal through, i.e., activating, the c-Mp1 receptor, which is the same receptor that mediates the activity of endogenous thrombopoietin (TPO). Thus, the compounds have thrombopoietic activity, i.e., the ability to stimulate, in vivo and in vitro, the production of platelets, and/or megakaryocytopoietic activity, i.e., the ability to stimulate, in vivo and in vitro, the production of platelet precursors.

The compounds comprise polypeptides or peptides modified to include at least one antibody Fc region and, optionally, one or more water soluble polymers.

In one aspect, a substantially homogenous compound is provided comprising a structure set out in Formula I, $$[(X^1)_a—(F^1)_z—(X^2)_b]\text{-}(L^1)_c\text{-}WSP_d \qquad \text{Formula I}$$

and multimers thereof, wherein:

F$^1$ is a vehicle;
X$^1$ is independently selected from:
P$^1$-(L$^2$)$_e$-
P$^2$-(L$^3$)$_f$—P$^1$-(L$^2$)$_e$-
P$^3$-(L$^4$)$_g$—P$^2$-(L$^3$)$_f$—P$^1$-(L$^2$)$_e$- and
P$^4$-(L$^5$)$_h$—P$^3$-(L$^4$)$_g$—P$^2$-(L$^3$)$_f$—P$^1$-(L$^2$)$_e$-
X$^2$ is independently selected from:
-(L$^2$)$_e$—P$^1$,
-(L$^2$)$_e$—P$^1$-(L$^3$)$_f$—P$^2$,
-(L$^2$)$_e$—P$^1$-(L$^3$)$_f$—P$^2$-(L$^4$)$_g$—P$^3$, and
-(L$^2$)$_e$—P$^1$-(L$^3$)$_f$—P$^2$-(L$^4$)$_g$—P$^3$-(L$^5$)$_h$—P$^4$
wherein P$^1$, P$^2$, P$^3$, and P$^4$ are each independently sequences of pharmacologically active peptides;
L$^1$, L$^2$, L$^3$, L$^4$, and L$^5$ are each independently linkers;
a, b, c, d, e, f, g, and h are each independently 0 or 1;
z is 0, 1, 2, or more; and
WSP is a water soluble polymer, the attachment of which is effected at any reactive moiety in F$^1$;

said compound having a property of improved bioefficacy when administered in a multidose regimen. In one aspect, the compound is a multimer, and in another aspect, the compound is a dimer.

In one embodiment, the invention provides a compound of Formula I comprising a structure set out in Formula II $$[X^1—(F^1)_z]\text{-}(L^1)_c\text{-}WSP_d \qquad \text{Formula II}$$

wherein F$^1$ is an Fc domain and is attached at the C-terminus of X$^1$, and zero, one, or more WSP is attached to the Fc domain, optionally through linker L$^1$. Compounds having this structure are provided as a multimer in one aspect and a dimer in another aspect.

In another embodiment, the invention provides a compound of Formula I comprising a structure set out in Formula III $$[(F^1)_z—X^2]\text{-}(L^1)_c\text{-}WSP_d \qquad \text{Formula III}$$

wherein F$^1$ is an Fc domain and is attached at the N-terminus of X$^2$, and zero, one, or more WSP is attached to the Fc domain, optionally through linker L$^1$. Multimers and dimers of a compound having this structure are also provided.

The invention also provides a compound of Formula I comprising a structure set out in Formula IV $$[(F^1)_z\text{-}(L^1)_e—P^1]\text{-}(L^1)_c\text{-}WSP_d \qquad \text{Formula IV}$$

wherein F$^1$ is an Fc domain and is attached at the N-terminus of -(L$^1$)$_c$—P$^1$ and, zero, one, or more WSP is attached to the Fc domain, optionally through linker L$^1$. Multimers and dimers of a compound having this structure are also provided.

The invention further contemplates a compound of Formula I comprising a structure set out in Formula V $$[(F^1)_z\text{-}(L^1)_e—P^1\text{-}(L^2)_f—P^2]\text{-}(L^1)_c\text{-}WSP_d \qquad \text{Formula V}$$

wherein F$^1$ is an Fc domain and is attached at the N-terminus of -L$^1$—P$^1$-L$^2$—P$^2$ and, zero, one, or more WSP is attached to the Fc domain, optionally through linker L$^1$. Multimers and dimers of a compound having this structure are also provided.

In one aspect, a compound is provided as described above wherein P$^1$ and/or P$^2$ are independently selected from a TPO mimetic set out in any of Tables 1-6 and 8 (see Examples herein). In one aspect, P$^1$ and/or P$^2$ have the same amino acid sequence.

In another aspect, a compound is provided as described above wherein L$_1$ is a linker group which is optional and, if present, is independently selected from the linker groups consisting of $Y_n$, wherein Y is a naturally-occurring amino acid or a stereoisomer thereof and n is 1 through 20;

$(Gly)_n$, wherein n is 1 through 20, and when n is greater than 1, up to half of the Gly residues may be substituted by another amino acid selected from the remaining 19 natural amino acids or a stereoisomer thereof;

$(Gly)_3Lys(Gly)_4$ (SEQ ID NO: 4);

$(Gly)_3AsnGlySer(Gly)_2$ (SEQ ID NO: 5);

$(Gly)_3Cys(Gly)_4$ (SEQ ID NO: 6);

GlyProAsnGly (SEQ ID NO: 7);

a Cys residue; and $(CH_2)_n$, wherein n is 1 through 20.

In one aspect, L is selected from the group consisting of $Y_n$, wherein Y is selected a naturally-occurring amino acid or a stereoisomer thereof and n is 1 through 20. In another aspect, L comprises $(Gly)_n$, wherein n is 1 through 20, and when n is greater than 1, up to half of the Gly residues may be substituted by another amino acid selected from the remaining 19 natural amino acids or a stereoisomer thereof. In yet another aspect, L is selected from the group consisting of

```
(Gly)3Lys(Gly)4;          (SEQ ID NO: 4)

(Gly)3AsnGlySer(Gly)2;    (SEQ ID NO: 5)

(Gly)3Cys(Gly)4;          (SEQ ID NO: 6)
and

GlyProAsnGly.             (SEQ ID NO: 7)
```

In a further aspect of the invention, L comprises a Cys residue. In another aspect, the invention includes a compound wherein L comprises $(CH_2)_n$, wherein n is 1 through 20.

In another aspect, a compound of the invention is provided as described herein wherein $F^1$ is an Fc domain. In another aspect, a compound is provided wherein WSP is PEG. In yet another aspect, a compound as described above is provided wherein $F^1$ is an Fc domain and WSP is PEG.

In one aspect, the PEG component of a compound described herein has a molecular weight of between about 2 kDa and 100 kDa. In another aspect, the PEG component of a compound described herein has a molecular weight of between about 6 kDa and 25 kDa.

The invention further provides a composition comprising a compound described herein wherein the composition comprises at least 50% PEGylated compound. In another aspect, the composition comprises at least 75% PEGylated compound, at least 85% PEGylated compound, at least 90% PEGylated compound, at least 95% PEGylated compound, and at least 99% PEGylated compound.

The invention also provides a method of treating a hematopoietic disorder comprising administering a compound or composition described herein in a regimen effective to treat said disorder.

In one embodiment, P comprises the following general structure:

$U^1$—$Y^1$(Cys, Leu, Met, Pro, Gln, Val, or $X_1$)—$Y^2$(Phe, Lys, Leu, Asn, Gln, Arg, Ser, Thr, Val, or $X_2$)—$Y^3$(Cys, Phe, Ile, Leu, Met, Arg, Ser, Val, Trp, or $X_3$)—$Y^4$—$Y^5$(Ala, Asp, Glu, Gly, Lys, Met, Gln, Arg, Ser, Thr, Val, Tyr, or $X_5$)—$Y^6$(Cys, Phe, Gly, Leu, Met, Ser, Val, Trp, Tyr, or $X_6$)—$Y^7$(Cys, Gly, Ile, Lys, Leu, Met, Asn, Arg, Val, or $X_7$)—$U^2$, wherein at least one of $Y^1$—$Y^3$ and $Y^5$—$Y^7$ corresponds to a respective $X_1$—$X_3$ and $X_5$—$X_7$;

wherein $U^1$ or $U^2$ is any amino acid or peptide, wherein when $Y^1$ is not an amino acid selected from the group consisting of Cys, Leu, Met, Pro, Gln, and Val, then $X_1$ is selected from the group consisting of Ala, Asp, Glu, Phe, Gly, His, Ile, Lys, Asn, Arg, Ser, Thr, Trp, and Tyr;

wherein when $Y^2$ is not an amino acid selected from the group consisting of Phe, Lys, Leu, Asn, Gln, Arg, Ser, Thr, and Val, then $X_2$ is selected from the group consisting of Ala, Cys, Asp, Glu, Gly, His, Ile, Met, Pro, Trp, and Tyr;

wherein when $Y^3$ is not an amino acid selected from the group consisting of Cys, Phe, Ile, Leu, Met, Arg, Ser, Val, and Trp, then $X_3$ is selected from the group consisting of Ala, Asp, Glu, Gly, His, Lys, Asn, Pro, Gln, Thr, and Tyr;

wherein $Y^4$ is any amino acid;

wherein when $Y^5$ is not an amino acid selected from the group consisting of Ala, Asp, Glu, Gly, Lys, Met, Gln, Arg, Ser, Thr, Val, and Tyr, then $X_5$ is selected from the group consisting of Cys, Phe, His, Ile, Leu, Asn, Pro, and Trp;

wherein when $Y^6$ is not an amino acid selected from the group consisting of Cys, Phe, Gly, Leu, Met, Ser, Val, Trp, and Tyr, then $X_6$ is selected from the group consisting of Ala, Asp, Glu, His, Ile, Lys, Asn, Pro, Gln, Arg, and Thr; and wherein $Y^7$ is not an amino acid selected from the group consisting of Cys, Gly, Ile, Lys, Leu, Met, Asn, Arg, and Val, then $X_7$ is selected from the group consisting of Ala, Asp, Glu, Phe, His, Pro, Gln, Ser, Thr, Trp, and Tyr;

and physiologically acceptable salts thereof.

In another aspect, the invention contemplates compounds, wherein at least two of $Y^1$—$Y^7$ corresponds to two of $X_1$—$X_7$, respectively; at least three of $Y^1$—$Y^7$ corresponds to three of $X_1$—$X_7$, respectively; at least four of $Y^1$—$Y^7$ corresponds to four of $X_1$—$X_7$, respectively; at least five of $Y^1$—$Y^7$ corresponds to five of $X_1$—$X_7$, respectively; at least six of $Y^1$—$Y^7$ corresponds to six of $X_1$—$X_7$, respectively; and only one of $Y^1$—$Y^7$ corresponds to one of $X_1$—$X_7$, respectively.

In one embodiment, the invention includes a compound of a structure set out in Formula I wherein at least a or b is 1.

In another embodiment, the invention includes a compound of a structure set out in Formula I wherein b, c, d, e, f, g, and h are 0.

In a further embodiment, the invention includes a compound that binds to an mp1 receptor consisting essentially of a structure set out in Formula I.

In another embodiment, the invention includes a compound of a structure set out in Formula I wherein $F^1$ is an Fc domain modified so that it comprises at least one $X^3$ in a loop region;

$X^3$ is independently selected from

-$(L^6)_i$—$P^5$-$(L^7)_j$,

-$(L^6)_i$—$P^5$-$(L^7)_j$—$P^6$-$(L^8)_k$,

-$(L^6)_i$—$P^5$-$(L^7)_j$—$P^6$-$(L^8)_k$—$P^7$-$(L^9)_l$, and

-$(L^6)_i$—$P^5$-$(L^7)_j$—$P^6$-$(L^8)_k$—$P^7$-$(L^9)_l$—$P^8$-$(L^{10})_m$;

$P^5$, $P^6$, $P^7$, and $P^8$ are each independently sequences of pharmacologically active peptides;

$L^6$, $L^7$, $L^8$, $L^9$, and $L^{10}$ are each independently linkers;

i, j, k, l, and m are each independently 0 or 1; and z is 1, 2, or more.

The invention includes a compound of the aforementioned structure wherein a and b are each 0.

In one embodiment, the invention includes a compound wherein the Fc domain comprises an IgG Fc domain. In one aspect, this IgG Fc domain is an IgG1 Fc domain.

In another embodiment, the Fc domain comprises a sequence selected from any of SEQ ID NOS: 3 and 344-352. In a further aspect, the IgG1 Fc domain comprises SEQ ID NO: 3 and $X^3$ is inserted into or replaces all or part of a sequence selected from SEQ ID NOS: 428, 429, 431, 432, 434, 435, 437, 439, 441, and 443. In yet another aspect, $X^3$ is inserted into or replaces all or part of a sequence selected from SEQ ID NOS: 430, 433, 436, 438, 440, 442, and 444. In a more particular aspect, $X^3$ is inserted at $Leu_{139}/Thr_{140}$.

In yet another embodiment, the IgG1 Fc domain comprises SEQ ID NO: 347 and $X^3$ is inserted into or replaces all or part of a sequence selected from SEQ ID NOS: 428, 429, 431, 432, 434, 435, 437, 439, 441, and 443. In one aspect, $X^3$ is inserted at $H_{53}/E_{54}$, $Y_{81}/N_{82}$, $N_{110}/K_{111}$, $L_{143}/T_{144}$, $Q_{171}/P_{172}$, $E_{173}/N_{174}$, $S_{186}/D_{187}$, $G_{188}/S_{189}$, or $G_{205}/N_{206}$.

In a further embodiment, the IgG1 Fc domain comprises SEQ ID NO: 348 and $X^3$ is inserted into or replaces all or part of a sequence selected from SEQ ID NOS: 428, 429, 431, 432, 434, 435, 439, 441, 443, and 451. In one aspect, $X^3$ is inserted at $H_{53}/E_{54}$, $Y_{81}/N_{82}$, $N_{110}/K_{111}$, $L_{143}/T_{144}$, $Q_{171}/P_{172}$, $E_{173}/N_{174}$, $S_{186}/D_{187}$, $G_{188}/S_{189}$, or $G_{205}/N_{206}$.

The invention also includes a compound wherein the Fc domain comprises an IgG3 Fc domain. In one aspect, the IgG3 Fc domain comprises SEQ ID NO: 349 and $X^3$ is inserted into or replaces all or part of a sequence selected from SEQ ID NOS: 426, 428, 429, 431, 434, 446, 448, 451, 452, and 453. In another aspect, $X^3$ is inserted at $H_{100}/E_{101}$, $F_{128}/N_{129}$, $N_{157}/K_{158}$, $M_{190}/T_{191}$, $Q_{218}/P_{219}$, $E_{220}/N_{221}$, $S_{232}/D_{233}$, $G_{234}/S_{235}$, or $G_{252}/N_{253}$.

In yet another embodiment, the invention includes a compound wherein the Fc domain comprises an IgG2 Fc domain. In one aspect, the Fc domain comprises SEQ ID NO: 350 and $X^3$ is inserted into or replaces all or part of a sequence selected from SEQ ID NOS: 428, 429, 431, 439, 443, 446, 447, 449, 451, and 453. In another aspect, $X^3$ is inserted at $H_{49}/E_{50}$, $F_{77}/N_{78}$, $N_{106}/K_{107}$, $M_{139}/T_{140}$, $Q_{167}/P_{168}$, $E_{169}/N_{170}$, $S_{181}/D_{182}$, $G_{183}/S_{184}$, or $G_{201}/N_{202}$.

In another embodiment, the invention includes a compound wherein the Fc domain comprises an IgG4 Fc domain. In one aspect, the Fc domain comprises SEQ ID NO: 351 and $X^3$ is inserted into or replaces all or part of a sequence selected from SEQ ID NOS: 427, 428, 431, 434, 439, 441, 445, 446, 450, and 451. In another aspect, $X^3$ is inserted at $Q_{50}/E_{51}$, $F_{78}/N_{79}$, $N_{107}/K_{108}$, $M_{140}/T_{141}$, $Q_{168}/P_{169}$, $E_{170}/N_{171}$, $S_{182}/D_{183}$, $G_{184}/S_{185}$, or $G_{202}/N_{203}$.

In a further embodiment, the invention includes a compound wherein the Fc domain comprises SEQ ID NO: 352 and $X^3$ is inserted into or replaces all or part of a sequence selected from SEQ ID NOS: 428, 429, 435, 431, 434, 439, 443, 446, 451, and 453. In one aspect, $X^3$ is inserted at $H_{112}/E_{113}$, $F_{140}/N_{141}$, $N_{169}/K_{170}$, $M_{204}/T_{205}$, $Q_{232}/P_{233}$, $E_{234}/N_{235}$, $S_{246}/D_{247}$, $G_{248}/S_{249}$, or $G_{268}/N_{269}$.

In yet another embodiment, the invention includes compounds wherein at least two, or at least three, or at least four, or at least five, or at least six of $Y^1$—$Y^7$ corresponds to two of $X_1$—$X_7$, respectively. However, the invention also includes compounds wherein only one of $Y^1$—$Y^7$ corresponds to one of $X_1$—$X_7$, respectively.

Exemplary compounds of the general structure are shown below. Single letter amino acid abbreviations are used for these peptides.

```
QGCSSGGPTQREWLQCRRMQHS        (SEQ ID NO: 8)
QGCSSGGPTLREWQQCRRMQHS        (SEQ ID NO: 9)
QGCSWGGPTLKIWLQCVRAKHS        (SEQ ID NO: 10)
QGCSWGGPTLKNWLQCVRAKHS        (SEQ ID NO: 11)
QGCSWGGPTLKLWLQCVRAKHS        (SEQ ID NO: 12)
QGCSWGGPTLKHWLQCVRAKHS        (SEQ ID NO: 13)
QGGCRSGPTNREWLACREVQHS        (SEQ ID NO: 14)
QGTCEQGPTLRQWPLCRQGRHS        (SEQ ID NO: 15)
QGTCEQGPTLRLWLLCRQGRHS        (SEQ ID NO: 16)
QGTCEQGPTLRIWLLCRQGRHS        (SEQ ID NO: 17)
```

Further exemplary compounds comprising one or more Fc regions linked to a peptide are provided below. Single letter amino acid abbreviations for the peptide are used.

```
Fc-QGCSSGGPTQREWLQCRRMQHS     (SEQ. ID NO: 18)
Fc-QGCSSGGPTLREWQQCRRMQHS     (SEQ. ID NO: 19)
Fc-QGCSWGGPTLKIWLQCVRAKHS     (SEQ ID NO: 20)
Fc-QGCSWGGPTLKNWLQCVRAKHS,    (SEQ ID NO: 21)
Fc-QGCSWGGPTLKLWLQCVRAKHS,    (SEQ ID NO: 22)
QGCSWGGPTLKIWLQCVRAKHS-Fc     (SEQ ID NO: 23)
Fc2-QGGCRSGPTNREWLACREVQHS    (SEQ ID NO: 24)
Fc2-QGCSWGGPTLKLWLQCVRAKHS    (SEQ ID NO: 25)
QGTCEQGPTLRQWPLCRQGRHS-Fc     (SEQ ID NO: 26)
Fc-QGTCEQGPTLRQWPLCRQGRHS     (SEQ ID NO: 27)
```

Further exemplary compounds ($Y^1$—$Y^7$) are provided below. Single letter amino acid abbreviations for the peptide are used. $Y^4$ may comprise any of the 20 naturally-occurring amino acids or non-naturally occurring amino acids well known in the art.

```
ETLY4QWL          (SEQ ID NO: 28)
HTLY4QWL          (SEQ ID NO: 29)
KTLY4QWL          (SEQ ID NO: 30)
GTGY4QWL          (SEQ ID NO: 31)
PTLY4IWL          (SEQ ID NO: 32)
PTLY4LWL          (SEQ ID NO: 33)
PTLY4EWF          (SEQ ID NO: 34)
PTLY4HWL          (SEQ ID NO: 35)
PILY4EWL          (SEQ ID NO: 36)
KTLY4EWL          (SEQ ID NO: 37)
PTLY4LWL          (SEQ ID NO: 38)
PMLY4EWL          (SEQ ID NO: 39)
PTLY4NWL          (SEQ ID NO: 40)
PPLY4EWL          (SEQ ID NO: 41)
PTQY4EWQ          (SEQ ID NO: 42)
PTLY4EWS          (SEQ ID NO: 43)
PTYY4EWL          (SEQ ID NO: 44)
PTAY4QWL          (SEQ ID NO: 45)
PCLY4QWL          (SEQ ID NO: 46)
```

```
            -continued
PTLY⁴FWL              (SEQ ID NO: 47)
PTGY⁴QWL              (SEQ ID NO: 48)
PTLY⁴HWL              (SEQ ID NO: 49)
PILY⁴IWL              (SEQ ID NO: 50)
PTLY⁴LWL              (SEQ ID NO: 51)
PMLY⁴QWL              (SEQ ID NO: 52)
PTLY⁴NWL              (SEQ ID NO: 53)
PTPY⁴QWL              (SEQ ID NO: 54)
PTLY⁴QWQ              (SEQ ID NO: 55)
PTLY⁴QWS              (SEQ ID NO: 56)
PTTY⁴QWT              (SEQ ID NO: 57)
PTLY⁴WWL              (SEQ ID NO: 58)
PTYY⁴QWL              (SEQ ID NO: 59)
PTLY⁴EWF              (SEQ ID NO: 60)
GTLY⁴EWL              (SEQ ID NO: 61)
PTLY⁴HWL              (SEQ ID NO: 62)
PILY⁴EWL              (SEQ ID NO: 63)
PTLY⁴LWL              (SEQ ID NO: 64)
PTQY⁴EWL              (SEQ ID NO: 65)
PTLY⁴EWS              (SEQ ID NO: 66)
PTLY⁴FWF              (SEQ ID NO: 67)
GTLY⁴QWL              (SEQ ID NO: 68)
PTLY⁴IWL              (SEQ ID NO: 69)
PTLY⁴LWL              (SEQ ID NO: 70)
PTLY⁴NWL              (SEQ ID NO: 71)
PTLY⁴QWP              (SEQ ID NO: 72)
PTLY⁴WWL              (SEQ ID NO: 73)
PTYY⁴QWL              (SEQ ID NO: 74)
```

Further exemplary compounds are provided below. Single letter amino acid abbreviations for the peptide are used.

```
KDTEVTAPRLWMVASVDE    (SEQ ID NO: 75)
REMEGPTMRQWLAYRAVL    (SEQ ID NO: 76)
CQNAGPTLRCWLAGRAYM    (SEQ ID NO: 77)
CEREGPTLRCWLATREGS    (SEQ ID NO: 78)
WRIEGPTLRHWLAARAWD    (SEQ ID NO: 79)
ANMEGPTLRHWLAMRARV    (SEQ ID NO: 80)
LDMEGPTLRHWLAARANG    (SEQ ID NO: 81)
WRMEGPTLRHWLAARAWG    (SEQ ID NO: 82)
WAMEGPTLRHWLAARAVL    (SEQ ID NO: 83)
KSMEGPSLRQWLAARAQL    (SEQ ID NO: 84)
```

```
            -continued
TKIEGPTLRHWLAARAEL    (SEQ ID NO: 85)
PRIEGPTLRLWLVTRALS    (SEQ ID NO: 86)
IYMEGPTLRHWLANRAAK    (SEQ ID NO: 87)
WPIEGATLRQWLKIRAGY    (SEQ ID NO: 88)
RNMEGPTLRNWLAARAQH    (SEQ ID NO: 89)
NGIEGPTLRLWLSERAKK    (SEQ ID NO: 90)
MWMEGPTLRHWLEARARY    (SEQ ID NO: 91)
YGIDGPTLRHWLAARARY    (SEQ ID NO: 92)
RIIDGQTLRHWLAAGADP    (SEQ ID NO: 93)
NGRDGPTVRHRLAGRAQK    (SEQ ID NO: 94)
THIEGPTLRIWLASRAKA    (SEQ ID NO: 95)
KGMEGPTLRHWLAARAHL    (SEQ ID NO: 96)
QRIEGPTLRHWLAARASH    (SEQ ID NO: 97)
KDTEVTAPRLWMVASVDE    (SEQ ID NO: 98)
```

Further exemplary compounds are provided below. Single letter amino acid abbreviations for the peptide are used.

```
ENMEGPTLRHWLAARAHE    (SEQ ID NO: 99)
SWMEGPTLRHWLMNRATY    (SEQ ID NO: 100)
SMMEGPTLRHWLAARAKD    (SEQ ID NO: 101)
QGIEGPTLRLWLAARTHP    (SEQ ID NO: 102)
YMMEGPTLRHWLATRAGR    (SEQ ID NO: 103)
GNMEGPTLRHWLAANERD    (SEQ ID NO: 104)
NRMEGPTLRHWLAERAGS    (SEQ ID NO: 105)
NMMEGPTLRHWLAARVAA    (SEQ ID NO: 106)
SPIEGPTLRQQLCARAVK    (SEQ ID NO: 107)
VQMEGTTLRQWLAERALD    (SEQ ID NO: 108)
KRKDGHRPRQWLAPLACK    (SEQ ID NO: 109)
EMMEGPTLRHWLAARAEK    (SEQ ID NO: 110)
NMIEGPTLRHWLAERASQ    (SEQ ID NO: 111)
KLMEGPTLRHWLAYRAGL    (SEQ ID NO: 112)
YMMEGPTLRHWLAARALV    (SEQ ID NO: 113)
GNMEGPTLRHWLAARALL    (SEQ ID NO: 114)
WMMEGPTLRHWLAARARY    (SEQ ID NO: 115)
TDRGGYTLRQWLAARAVL    (SEQ ID NO: 116)
SAIEGPTLRHWLAWRAML    (SEQ ID NO: 117)
RAIEGPTLRHCLAAGAGL    (SEQ ID NO: 118)
VKRKGPTLRHWLAAWAFP    (SEQ ID NO: 119)
TCMEGPTLRHWLAARAEG    (SEQ ID NO: 120)
WFMEGPTLRHWLAARAYR    (SEQ ID NO: 121)
ADIEGPTLRHWLAARALV    (SEQ ID NO: 122)
```

```
WVMEGPTLRHWLAARASL    (SEQ ID NO: 123)
PPGDGPTLRHWLAARARM    (SEQ ID NO: 124)
DFMEGPTLRQRVDARAHY    (SEQ ID NO: 125)
RWIEGPTQRQWLAARAYF    (SEQ ID NO: 126)
IRMEGPTLRHWLASRAEI    (SEQ ID NO: 127)
YYLEGPTLRHWLAARAYL    (SEQ ID NO: 128)
GVIEGPTLRHWLAARAAQ    (SEQ ID NO: 129)
GAMEGPTLRCWLAASDEK    (SEQ ID NO: 130)
SVIDGPTLRQRLAARARY    (SEQ ID NO: 131)
GGIERPTLRHCLAARPTS    (SEQ ID NO: 132)
TKMEGPTLRHWLAWRAAY    (SEQ ID NO: 133)
LKMEGPTLRNWLAWRAFQ    (SEQ ID NO: 134)
GLVEGPTLRFWLAARAAE    (SEQ ID NO: 135)
GLTDGPNLRHCLAARAPI    (SEQ ID NO: 136)
DRNKGPTLRHWLAARAHA    (SEQ ID NO: 137)
ASMVGPKLRHGLAAVAKK    (SEQ ID NO: 138)
DAIEGPTLRLWLEARRKQ    (SEQ ID NO: 139)
NIIKRATDREWLDARTAL    (SEQ ID NO: 140)
GDNEGPSPRVCLAARAVL    (SEQ ID NO: 141)
EFMEGPTLRHWLASRARV    (SEQ ID NO: 142)
WGMEGPTLRHWLAARGKR    (SEQ ID NO: 143)
RWMEGPTLRHWLAERAML    (SEQ ID NO: 144)
LMVEGPTLRHWLAARWRM    (SEQ ID NO: 145)
NYIEGPTLRHWLAARAKL    (SEQ ID NO: 146)
TWMEGPTLRLWLMARALY    (SEQ ID NO: 147)
QYMEGPTLRHWLAARAAL    (SEQ ID NO: 148)
AWMEGPTLRHWLAARAAY    (SEQ ID NO: 149)
KQFEGPPMRRSLAGVNTP    (SEQ ID NO: 150)
ALMEGPTLRQRLAARAAQ    (SEQ ID NO: 151)
ARMKGTTLRQWVAARAFV    (SEQ ID NO: 152)
DKIEIPTVQLRRAAYACQ    (SEQ ID NO: 153)
YRMEGPTLRHWLAARAGV    (SEQ ID NO: 154)
ALMEGPTLRHWLAARALM    (SEQ ID NO: 155)
IWAGGPTLRHWLAARAAL    (SEQ ID NO: 156)
GWVDGPTLRHWLAARARM    (SEQ ID NO: 157)
ARMEGPTLRHWLAARAKM    (SEQ ID NO: 158)
ESMEGASQRHCMAARAGG    (SEQ ID NO: 159)
MPVDGPVLRTWHAAQAIE    (SEQ ID NO: 160)
LEHNRPLTNPIPKPRTPIRP  (SEQ ID NO: 161)
TTMEDPTLRHWLATGAPT    (SEQ ID NO: 162)
HPIEGPTLRLWLAARARA    (SEQ ID NO: 163)
FPMEGTTLRHWLAARVQM    (SEQ ID NO: 164)
RGMNGPTLRHWLEESAKD    (SEQ ID NO: 165)
DQMEGSMVHQWLARHVWG    (SEQ ID NO: 166)
RNMEGPTLRHWLAARATY    (SEQ ID NO: 167)
DGMEGPTLRLWMAARAGE    (SEQ ID NO: 168)
ASMYGPTVSQRLAARTRG    (SEQ ID NO: 169)
PMMEGPTLRHWLAARALR    (SEQ ID NO: 170)
WPMEGPTLRHWLAARAAR    (SEQ ID NO: 171)
VQMEGPTLRHWLAGRAPN    (SEQ ID NO: 172)
HGIEGPTHRQWLAARADI    (SEQ ID NO: 173)
GMMEGPTLRHWLAARAML    (SEQ ID NO: 174)
HDMEGPTLRHWLALRATG    (SEQ ID NO: 175)
DNMERTRRHSLAAHFML    (SEQ ID NO: 176)
RNMEGPTLRHWLAARADR    (SEQ ID NO: 177)
WKFEGFTLRQWLTARAFG    (SEQ ID NO: 178)
RGMEGPTLRQRLVERAQM    (SEQ ID NO: 179)
DVMEGTTLRQWLACRALM    (SEQ ID NO: 180)
RKMERATLRQWLTARANM    (SEQ ID NO: 181)
GTKEGPTLRQWPAARANE    (SEQ ID NO: 182)
CAIEGPTLRHWLAARAAT    (SEQ ID NO: 183)
LTMEGPTLRHWLRARAYA    (SEQ ID NO: 184)
MTMEGPTLRQWFAARADT    (SEQ ID NO: 185)
SPMEGPTLRHSAAGRPWG    (SEQ ID NO: 186)
VHMEDPTLRHGNAARAAE    (SEQ ID NO: 187)
YPMEGPTLRHWLAARARH    (SEQ ID NO: 188)
GKTQGPKQLKWQVGSSLP    (SEQ ID NO: 189)
GEMEGPTLLHWRAARAMQ    (SEQ ID NO: 190)
INMEGPTLRLWLAARAAA    (SEQ ID NO: 191)
FRIEGPTLRNWLAARAAK    (SEQ ID NO: 192)
GRMEGPTLRHWLAARAHP    (SEQ ID NO: 193)
VLIQGHTVRNCMVARVDA    (SEQ ID NO: 194)
DWIEGPTLRHWLAARALY    (SEQ ID NO: 195)
SWTEGPTLRHWLAARARN    (SEQ ID NO: 196)
RELEGPTLRLWLVERARM    (SEQ ID NO: 197)
VSMEGPTLRNWLAARARM    (SEQ ID NO: 198)
TTMEGPTLRHWLATRAVD    (SEQ ID NO: 199)
AKLEGPTLRLWLAERAGR    (SEQ ID NO: 200)
ARMEGPTLRHWLAARARY    (SEQ ID NO: 201)
NIMDGPALRHWLPARAIQ    (SEQ ID NO: 202)
NMIGGPTLGHRLADPAIQ    (SEQ ID NO: 203)
```

| | |
|---|---|
| VWMEGATLRQWLAARALI | (SEQ ID NO: 204) |
| RVMEGPTLLQRLAARARS | (SEQ ID NO: 205) |
| QPMDEPARRQWLSARAGL | (SEQ ID NO: 206) |
| AWTEGPTLRHWLAARGRS | (SEQ ID NO: 207) |
| ATMEGPTLRHWLAARAAL | (SEQ ID NO: 208) |
| GRMEGPTLRHWLAARALF | (SEQ ID NO: 209) |
| ENMQGRTLRHWLAARDYF | (SEQ ID NO: 210) |
| KGVEGPTLRLWLAARALM | (SEQ ID NO: 211) |
| VEMEGPTLRHWLAARASV | (SEQ ID NO: 212) |
| AFIEGPTLKNWLAARAIM | (SEQ ID NO: 213) |
| TVMEGPTLRHWLAARSRS | (SEQ ID NO: 214) |
| AHMEGPTLRHWLATRAKM | (SEQ ID NO: 215) |
| KDIEGPTLRHWLAARANY | (SEQ ID NO: 216) |
| RIHDGRKLRQWLTVRDTM | (SEQ ID NO: 217) |
| KPIEGPTLKLWLAERMAA | (SEQ ID NO: 218) |
| AKDVGTRLRQWLAAGARA | (SEQ ID NO: 219) |
| QSQEGPTLRLWLAERAKW | (SEQ ID NO: 220) |
| MYTEGATLRQWLAARARI | (SEQ ID NO: 221) |
| PKMEGPTRRTRLADRSTS | (SEQ ID NO: 222) |
| NVMEGPTLRHWLAYRARM | (SEQ ID NO: 223) |
| TWMEGPTLRHWLAARALG | (SEQ ID NO: 224) |
| LTMEGPTLRHWLAARATR | (SEQ ID NO: 225) |
| YTMEGPTLRHWLAARALH | (SEQ ID NO: 226) |
| NEMEGATLRQWLAARAKW | (SEQ ID NO: 227) |
| FSKEGATLRQWLAARALD | (SEQ ID NO: 228) |
| SNGVCRTLRQWLAARAEE | (SEQ ID NO: 229) |
| KGMEGPTLRNWLAERAML | (SEQ ID NO: 230) |
| QDMVGPTLRHWLAARARL | (SEQ ID NO: 231) |
| YSHEGPTLRHWLAARALL | (SEQ ID NO: 232) |
| GVIEGPTLRHWLAARMKV | (SEQ ID NO: 233) |
| MHMEGPTLRHWLATRALI | (SEQ ID NO: 234) |
| CRSEGPTLRCWLAARAGY | (SEQ ID NO: 235) |
| MCIEGPTLRQWQVCRVGL | (SEQ ID NO: 236) |
| CRVEGPSQRQCLAARACW | (SEQ ID NO: 237) |
| CTMEGPTLRHWLAARACI | (SEQ ID NO: 238) |
| CQVDGPTVRHCRAARAGL | (SEQ ID NO: 239) |
| CDMAGATLRQWLACRSGT | (SEQ ID NO: 240) |
| ICTEGCTLRLWLAERSRV | (SEQ ID NO: 241) |
| CGMEGPALRQWLACRAVD | (SEQ ID NO: 242) |

In yet another embodiment, further exemplary compounds are provided below. Single letter amino acid abbreviations for the peptide are used.

| | |
|---|---|
| QGCSSGGPTLREWQQCVRMQHS | (SEQ ID NO: 243) |
| QGCSSGGPTLREWQQCRRAQHS | (SEQ ID NO: 244) |
| QGCSSGGPTLREWQQCVRAQHS | (SEQ ID NO: 245) |
| IEGQSWEFENDRVPAHSLERVLLLRRVPTEPSGPSICAQIEGPTFKQWQECINGHS; | (SEQ ID NO: 246) |
| IEGPTFKQWQKCRNMHS; | (SEQ ID NO: 247) |
| IEGPTFKQWQKLRRVHS; | (SEQ ID NO: 248) |
| IEGEPVSDGKRRPVHSLERVDAVHAKVGPSICAQIEGPTFKQWQKCKRAHS; | (SEQ ID NO: 249) |
| IEGRWPPPQFPVTQQHSLERVGRPPPSVELPRPTFVCAQIEGPTFKQWQRCLREHS; | (SEQ ID NO: 250) |
| IEGPTFKQWQRWRLLHS; | (SEQ ID NO: 251) |
| IEGPTFKQWQAWRKKHS; | (SEQ ID NO: 252) |
| IEGPTFKQWQRWRKMHS; | (SEQ ID NO: 253) |
| IEGRWPPPQFPVTEHHSLERVGRRPPNAQMPQSIFICGQNEGPTFQYCQRCLREHS; | (SEQ ID NO: 254) |
| IEGWWWQFYFHAKEDHS; | (SEQ ID NO: 255) |
| PSICAQIEGPTFKQWQTCMRAHS; | (SEQ ID NO: 256) |
| IEGYVGGPYEQTNSLERVPPTLAWKYGPRTPSICAQIEGPTFKQWQQCLSDHS; | (SEQ ID NO: 257) |
| IEGPTFKQWQGRSKRHS; | (SEQ ID NO: 258) |
| IEGWPWQLYVHPEGEHS; | (SEQ ID NO: 259) |
| IEGWWWQLYFHAKDDHS; | (SEQ ID NO: 260) |
| IEGPTFKQWQKLRRSHS; | (SEQ ID NO: 261) |
| IEGWWWQFYFHPKEDHS; | (SEQ ID NO: 262) |
| IEGPTFKQWQKSRTKHS; | (SEQ ID NO: 263) |
| IEGWTWQFYVHPKGDHS; | (SEQ ID NO: 264) |
| IEGPTFKQWQAARMHHS; | (SEQ ID NO: 265) |
| IEGPTFKQWQACLHSHS; | (SEQ ID NO: 266) |

IEGWSWQFYAHPQGDHS; (SEQ ID NO: 267)

IEGPSFTPWFHERRSHS; (SEQ ID NO: 268)

IEGPTFKQWQWLRRHHS; (SEQ ID NO: 269)

IEGWWWQFYVHAKGDHS; (SEQ ID NO: 270)

IEGPTFKQWQVWRNRHS; (SEQ ID NO: 271)

IEGQSWLRRLHWKEEHS; (SEQ ID NO: 272)

IEGWPWQFYALSRESGTSPSSAARTSSYLRSCAQIEGPTFKQWQICKDQHS; (SEQ ID NO: 273)

IEGPTFKQWQKWRKTHS; (SEQ ID NO: 274)

IEGPTFKQWQYWRAKHS; (SEQ ID NO: 275)

IEGPTFKQWQVRQKTHS; (SEQ ID NO: 276)

IEGWSWQFYFHAKGDHS; (SEQ ID NO: 277)

IEGRTWQLYFHAKEEHS; (SEQ ID NO: 278)

IEGWSWQFYAHPQGDHS; (SEQ ID NO: 279)

IEGWPRQLYAHAKEDHS; (SEQ ID NO: 280)

IEGWWWQFYAHPQGDHS; (SEQ ID NO: 281)

IEGWSWQFYAHPQGDHS; (SEQ ID NO: 282)

IEGWSWQFYAHPQGDHS; (SEQ ID NO: 283)

IEGHGSQKPTAARALESTSSLTTRTRTTSICAQQDMVGPTIRQWLAARACI; (SEQ ID NO: 284)

IEGPTFEQWQHWRRGHS; (SEQ ID NO: 285)

IEGWIWRQWLAARA; (SEQ ID NO: 286)

IEGWIWRPWLAARA; (SEQ ID NO: 287)

IEGYWWYASWAARA; (SEQ ID NO: 288)

IEGWPWQFYAHPQGDHS; (SEQ ID NO: 289)

IEGWVWCQWLAARA; (SEQ ID NO: 290)

IEGPTLHEWLRWLRQHS; (SEQ ID NO: 291)

IEGWVWRPWLAARA; (SEQ ID NO: 292)

IEGWVWCPWLAARA; (SEQ ID NO: 293)

IEGEALVFWWRVGGHS; (SEQ ID NO: 294)

IEGWVWCPWLAARA; (SEQ ID NO: 295)

IEGWVWWPWLAARA; (SEQ ID NO: 296)

IEGWTWQFYALPRGDHS; (SEQ ID NO: 297)

IEGWPWQFYALSRESGTSPSSAARTSSYLRSCAQIEGPTFKQWQICKDQHS; (SEQ ID NO: 298)

IEGPTLRQRLAARA; (SEQ ID NO: 299)

IEGWSWQFYAHPKGDHS; (SEQ ID NO: 300)

IEGWVWRQWLAARA; (SEQ ID NO: 301)

IEGRHYQKWPARRLGHS; (SEQ ID NO: 302)

IEGFVGTVDWRQGRPHS; (SEQ ID NO: 303)

IEGQEPTRLRLqMDRHS; (SEQ ID NO: 304)

IAQVRMLGRFTLLVLSRARAASTQLSFQHSICAQIEGGAQTQWDAARA; (SEQ ID NO: 305)

IEGEIWAGPGAARA; (SEQ ID NO: 306)

IEGEALVFWWAARA; (SEQ ID NO: 307)

IEGSYRERQQAARA; (SEQ ID NO: 308)

IEGWVWRPWLAARA; (SEQ ID NO: 309)

IEGWNPWRGAASRV; (SEQ ID NO: 310)

IEGWTRRQWLAARA; (SEQ ID NO: 311)

IEGWVWRPWLAARA; (SEQ ID NO: 312)

IEGPTFKQWQAMRRHS; (SEQ ID NO: 313)

IEGMVKLGVIRLLVL; (SEQ ID NO: 314)

IEGPTFKQWQAWRRWHS; (SEQ ID NO: 315)

IEVWQSHWYQAARALESTSSRLLPMRPPPSICAQIEGPTLPQRMAARA; (SEQ ID NO: 316)

IEGWTWQFYAHPQGDHS; (SEQ ID NO: 317)

-continued

IEGPTFKQWQALRKRHS; (SEQ ID NO: 318)

IEGPTFKQWQKLRLGHS; (SEQ ID NO: 319)

IEGPTFKQWQLMGFPHS; (SEQ ID NO: 320)

IEGWIWRQWLMQTLWHS; (SEQ ID NO: 321)

IEGPTFKQWQAMRKNHS; (SEQ ID NO: 322)

IEGPTFKQWQKWRLSHS; (SEQ ID NO: 323)

IEGWQEGRQSAARA; (SEQ ID NO: 324)

IEGPTFKQWQRWLKYHS; (SEQ ID NO: 325)

IEGNYWFWQQVGQENTLSREWIQTLGQKYWYRPPSICAQIEGWSRHQHYSAMSGHS; (SEQ ID NO: 326)

IEGPTFKQWQLWRLQHS; (SEQ ID NO: 327)

IEGPTFKQWQMLRRHHS; (SEQ ID NO: 328)

IEGPTFKQWQRLRKNHS; (SEQ ID NO: 329)

IEGLLSQLWQAARA; (SEQ ID NO: 330)

IEGPSLPEWLHVWRHHS; (SEQ ID NO: 331)

IEGPTLHEWLAERRKHS; (SEQ ID NO: 332)

IEGPTLHEWLALLRSHS; (SEQ ID NO: 333)

IEGPTLHEWLAQRREHS; (SEQ ID NO: 334)

IEGPTLHEWLLYRRAHS; (SEQ ID NO: 335)

IEGPTLHEWLRQRRQHS; (SEQ ID NO: 336)

CSSGGPTLREWQQCSRAQ; (SEQ ID NO: 454)

CSSGGPTLREWQQCQRAQ; and (SEQ ID NO: 455)

CSSGGPTLREWQQCGRAQ. (SEQ ID NO: 456)

In another embodiment, any of the exemplary compounds comprising a TPO-mimetic peptide may be fused to either an Fc region or inserted into an Fc-Loop, a modified Fc molecule. Fc-Loops are described herein and in U.S. Patent Application Publication No. US2006/0140934 incorporated herein by reference in its entirety. The invention includes such molecules comprising an Fc domain modified to comprise a peptide as an internal sequence (preferably in a loop region) of the Fc domain. The Fc internal peptide molecules may include more than one peptide sequence in tandem in a particular internal region, and they may include further peptides in other internal regions. While the putative loop regions are exemplified, insertions in any other non-terminal domains of the Fc are also considered part of this invention.

In a further embodiment, the invention contemplates a compound comprising a peptide inserted into an Fc amino acid sequence. In one aspect, the peptide is inserted into a loop region of the Fc amino acid sequence. In a further aspect, the Fc amino acid sequence is SEQ ID NO: 3. In still another aspect, the peptide is inserted into the loop region of the Fc amino acid sequence of SEQ ID NO: 3 between amino acids 139 (Leu) and 140 (Thr). Such peptide may be inserted into the loop region of the Fc using one or more linkers. In one aspect, the linker comprises four glycine residues at the N-terminus of the peptide. In another aspect, the linker comprises two glycine residues at the N-terminus of the peptide and two glycine residues at the C-terminus of the peptide. Other linkers, as discussed in U.S. Patent Application Publication No. US2006/0140934, are also contemplated for use modifying Fc molecules in the invention. Exemplary TPO-mimetic fusion proteins comprise a peptide comprising the amino acid sequence of SEQ ID NO: 9 or SEQ ID NO: 243.

Exemplary compounds of the invention include a compound which is selected from the group consisting of SEQ ID NOS: 353-422.

Derivatives of any of the above compounds are also provided in the invention. The compounds provided may be derivatized as set forth in one or more of the following:

one or more of the peptidyl [—C(O)NR—] linkages (bonds) have been replaced by a non-peptidyl linkage such as a —CH$_2$-carbamate linkage [—CH$_2$—OC(O)NR—]; a phosphonate linkage; a —CH$_2$-sulfonamide [—CH$_2$—S(O)$_2$NR—] linkage; a urea [—NHC(O)NH—] linkage; a —CH$_2$-secondary amine linkage; or an alkylated peptidyl linkage [—C(O)NR$^6$— where R$^6$ is lower alkyl];

the N-terminus is a —NRR$^1$ group; to a —NRC(O)R group; to a —NRC(O)OR group; to a —NRS(O)$_2$R group; to a —NHC(O)NHR group where R and R$^1$ are hydrogen and lower alkyl with the proviso that R and R$^1$ are not both hydrogen; to a succinimide group; to a benzyloxycarbonyl-NH— (CBZ—NH—) group; or to a benzyloxycarbonyl-NH— group having from 1 to 3 substituents on the phenyl ring selected from the group consisting of lower alkyl, lower alkoxy, chloro, and bromo;

the C terminus is —C(O)R$^2$ where R$^2$ is selected from the group consisting of lower alkoxy and —NR$^3$R$^4$ where R$^3$ and R$^4$ are independently selected from the group consisting of hydrogen and lower alkyl. By "lower" is meant a group having from 1 to 6 carbon atoms.

In another aspect, compounds are provided wherein all of the amino acids have a D configuration, or at least one of the amino acids has a D configuration. In a further aspect, the compounds may be cyclic. In yet a further aspect, P is constrained through a disulfide bond between cysteine residues such that P is cyclic. In another aspect, P comprises four glycine residues at its N-terminus. The invention also includes a compound wherein P comprises two glycine residues at the N-terminus of P and two glycine residues at the C-terminus of P.

The compounds in one aspect are peptides, and they may be prepared by standard synthetic methods, by phage library, or by any other methods of preparing peptides. The compounds that encompass non-peptide portions may be synthesized by standard organic chemistry reactions, in addition to standard peptide chemistry reactions when applicable.

The compounds provided may be used for therapeutic or prophylactic purposes by incorporating them with appropriate pharmaceutical carrier materials and administering an effective amount to a subject, such as a human (or other mammal).

Also provided are methods of increasing megakaryocytes or platelets in a patient in need thereof, which comprise administering to said patient an effective amount of the compounds of the invention. In one aspect, the amount is from 1 μg/kg to 100 mg/kg.

The invention further provides pharmaceutical compositions comprising any of the compounds of the invention in admixture with a pharmaceutically acceptable carrier thereof.

In another embodiment, the invention provides polynucleotides that encode the compounds of the invention, vectors that comprise the polynucleotides, and host cells that comprise such vectors.

In a further embodiment, the invention provides methods of producing the compounds of the invention which comprise growing such host cells in a suitable nutrient medium and isolating said compound from said cell or nutrient medium.

Other related aspects are also provided in the instant invention.

BRIEF DESCRIPTION OF THE FIGURES

Numerous other aspects and advantages of the present invention will be apparent upon consideration of the following detailed description thereof, reference being made to the drawings wherein:

FIG. 1 shows exemplary Fc polynucleotide and protein sequences (SEQ ID NO: 1 is the coding strand reading 5'63'; SEQ ID NO: 2 is the complementary strand reading 3'65'; and SEQ ID NO: 3 is the encoded amino acids sequence) of human IgG1 that may be used in the Fc fusion compounds of this invention.

FIG. 2 shows exemplary platelet values of mice given positive control or a TPO-mimetic compound of the invention (100 μg/kg).

DETAILED DESCRIPTION OF THE EMBODIMENTS

Definitions

Figure 3:
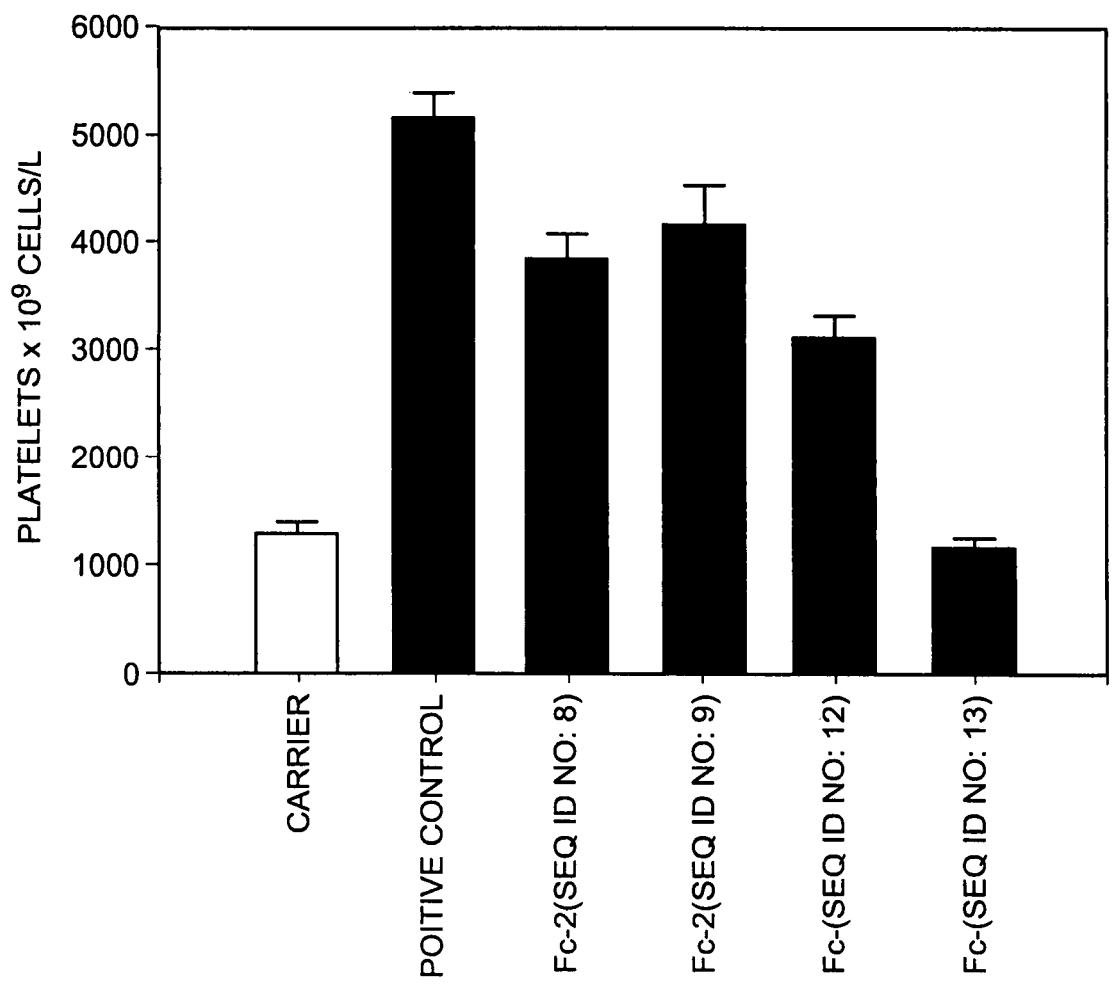
FIG. 3 shows exemplary platelet values of mice given positive control or a TPO-mimetic compound of the invention (100 μg/kg) six days post-injection.

The term "comprising" means that a compound may include additional amino acids on either or both of the N- or C-termini of the given sequence. Of course, these additional amino acids should not significantly interfere with the activity of the compound.

The term "vehicle" refers to a molecule that prevents degradation and/or increases half-life, reduces toxicity, reduces immunogenicity, or increases biological activity of a therapeutic protein. Exemplary vehicles include an Fc domain as well as a linear polymer; a branched-chain polymer (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published 28 Oct. 1993); a lipid; a cholesterol group; a carbohydrate or oligosaccharide; or any natural or synthetic protein, polypeptide or peptide that binds to a salvage receptor. Vehicles are further described hereinafter.

The term "native Fc" refers to molecule or sequence comprising the sequence of a non-antigen-binding fragment resulting from digestion of whole antibody, whether in monomeric or multimeric form. The original immunoglobulin source of the native Fc is in one aspect of human origin and may be any of the immunoglobulins. A native Fc is a monomeric polypeptide that may be linked into dimeric or multimeric forms by covalent association (i.e., disulfide bonds), non-covalent association or a combination of both. The number of intermolecular disulfide bonds between monomeric subunits of native Fc molecules ranges from one to four depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG. Ellison et al. (1982), Nucleic Acids Res. 10: 4071-9. The term "native Fc" as used herein is generic to the monomeric, dimeric, and multimeric forms.

The term "Fc variant" refers to a molecule or sequence that is modified from a native Fc, but preferably still comprises a binding site for the salvage receptor, FcRn. International applications WO 97/34631 (published 25 Sep. 1997) and WO 96/32478 describe exemplary Fc variants, as well as interaction with the salvage receptor, and are hereby incorporated by reference. In one aspect, the term "Fc variant" comprises a molecule or sequence that is humanized from a non-human native Fc. In another aspect, a native Fc comprises sites that may be removed because they provide structural features or biological activity that are not required for the fusion molecules of the present invention. Thus, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, (7) binding to the FcRn salvage receptor in cases where a shorter half-life is desired, or (8) antibody-dependent cellular cytotoxicity (ADCC). Fc variants are described in further detail hereinafter.

The term "Fc domain" encompasses native Fc and Fc variant molecules and sequences as defined above. As with Fc variants and native Fcs, the term "Fc domain" includes molecules in monomeric or multimeric form, whether digested from whole antibody or produced by other means. In one embodiment, for example, the Fc domain or the Fc region can comprise:

```
                                            (SEQ ID NO: 3)
MDKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCLV

KGFYPSDIAVEWESNGQPENNYKTTPPVLDSDGSFFLYSKLTVDKSRWQQ

GNVFSCSVMHEALHNHYTQKSLSLSPGK.
```

In another embodiment, other exemplary amino acid sequences (SEQ ID NOS: 344 to 352) of human Fc regions from IgA, IgM and IgG subtypes are also used in the invention.

The term "multimer" as applied to Fc domains or molecules comprising Fc domains refers to molecules having two or more polypeptide chains associated covalently, noncovalently, or by both covalent and non-covalent interactions. IgG molecules typically form dimers; IgM, pentamers; IgD, dimers; and IgA, monomers, dimers, trimers, or tetramers.

Multimers may be formed by exploiting the sequence and resulting activity of the native Ig source of the Fc or by derivatizing (as defined below) such a native Fc.

The term "dimer" as applied to Fc domains or molecules comprising Fc domains refers to molecules having two polypeptide chains associated covalently or non-covalently.

The terms "derivatizing," "derivative" or "derivatized" comprise processes and resulting compounds in which, for example and without limitation, (1) the compound has a cyclic portion; for example, cross-linking between cysteinyl residues within the compound; (2) the compound is cross-linked or has a cross-linking site; for example, the compound has a cysteinyl residue and thus forms cross-linked dimers in culture or in vivo; (3) one or more peptidyl linkage is replaced by a non-peptidyl linkage; (4) the N-terminus is replaced by —$NRR_1$, $NRC(O)R_1$, —$NRC(O)OR_1$, —$NRS(O)_2R^1$, —NHC(O)NHR, a succinimide group, or substituted or unsubstituted benzyloxycarbonyl-NH—, wherein R and $R_1$ and the ring substituents are as defined hereinafter; (5) the C-terminus is replaced by —$C(O)R_2$ or —$NR_3R_4$ wherein $R_2$, $R_3$ and $R_4$ are as defined hereinafter; and (6) compounds in which individual amino acid moieties are modified through treatment with agents capable of reacting with selected side chains or terminal residues. Derivatives are further described hereinafter.

The term "peptide" refers to molecules of approximately 2 to 80 amino acids, molecules of 2 to 40 amino acids, molecules of 3 to 20 amino acids, and those of 6 to 15 amino acids. For example, peptides having a size selected from no greater than 75, no greater than 70, no greater than 65, no greater than 60, no greater than 55, no greater than 50, no greater than 45, no greater than 40, no greater than 35, no greater than 30, no greater than 25, no greater than 20 amino acids and/or no greater than 15 amino acids, are contemplated herein. Exemplary peptides may be randomly generated by any of the methods cited described herein, carried in a peptide library (e.g., a phage display library), derived by digestion of proteins, or chemically synthesized and the like. Peptides include D and L form, either purified or in a mixture of the two forms. Exemplary peptides are the "biologically active" moieties of the compounds provided herein, i.e., provide the compound with Mp1-binding capacity.

The term "randomized" as used to refer to peptide sequences refers to fully random sequences (e.g., selected by phage display methods) and sequences in which one or more residues of a naturally occurring molecule is replaced by an amino acid residue not appearing in that position in the naturally occurring molecule. Exemplary methods for identifying peptide sequences include phage display, *E. coli* display, ribosome display, yeast-based screening, RNA-peptide screening, chemical screening, rational design, protein structural analysis, and the like.

The term "pharmacologically active" means that a substance so described is determined to have activity that affects a medical parameter (e.g., blood pressure, blood cell count, cholesterol level) or disease state (e.g., cancer, autoimmune disorders). Thus, pharmacologically active peptides comprise agonistic or mimetic and antagonistic peptides as defined below.

The terms "-mimetic peptide" and "-agonist peptide" refer to a peptide having biological activity comparable to a protein (e.g., TPO) that interacts with a protein of interest. These terms further include peptides that indirectly mimic the activity of a protein of interest, such as by potentiating the effects of the natural ligand of the protein of interest. Those of ordinary skill in the art appreciate that each of these references enables one to select different peptides than actually disclosed therein by following the disclosed procedures with different peptide libraries. Such peptides may mimic the bioactivity of the large protein ligand or, through competitive binding, inhibit the bioactivity of the large protein ligand, and are commonly referred to as "peptide mimetics" or "mimetic peptides."

The term "TPO-mimetic peptide" or "TMP" comprises peptides that can be identified or derived as described in International application WO 00/24770, published May 4, 2000, and U.S. Pat. No. 6,835,809, hereby incorporated by reference in their entirety, and any other reference identified as having TPO-mimetic subject matter. Those of ordinary skill in the art appreciate that each of these references enables one to select different peptides than actually disclosed therein by following the disclosed procedures with different peptide libraries.

The term "physiologically acceptable salts" comprises any salts that are known or later discovered to be pharmaceutically acceptable. Some specific examples are: acetate; trifluoroacetate; hydrohalides, such as hydrochloride and hydrobromide; sulfate; citrate; tartrate; glycolate; and oxalate.

The term "WSP" refers to a water soluble polymer which prevents a peptide, protein or other compound to which it is attached from precipitating in an aqueous environment, such as, by way of example, a physiological environment.

The term "PEG" refers to polyethylene glycol, and as used herein is meant to include various forms described in detail infra.

"Substantially homogenous" as used herein with reference to a preparation of the invention means that the preparation includes a single species of a therapeutic compound detectable in the preparation of total therapeutic molecules in the preparation, unless otherwise stated at a specific percentage of total therapeutic molecules. In general, a substantially homogenous preparation is homogenous enough to display the advantages of a homogenous preparation, e.g., ease in clinical application in predictability of lot to lot pharmacokinetics.

"Bioefficacy" refers to the capacity to produce a desired biological effect. Bioefficacy of different compounds, or different dosages of the same compound, or different administrations of the same compound are generally normalized to the amount of compound(s) to permit appropriate comparison.

Structure of Compounds

Provided herein is a group of compounds that are capable of binding to and triggering a transmembrane signal through, i.e., activating, the c-Mp1 receptor, which is the same receptor that mediates the activity of endogenous thrombopoietin (TPO). Thus, the compounds have thrombopoietic activity, i.e., the ability to stimulate, in vivo and in vitro, the production of platelets, and/or megakaryocytopoietic activity, i.e., the ability to stimulate, in vivo and in vitro, the production of platelet precursors.

The compounds comprise polypeptides or peptides modified to include at least one vehicle (i.e., Fc region) attached to the peptide at either the N- or C-terminus and, optionally, one or more WSP covalently attached to the vehicle-peptide molecule at any reactive moiety in the vehicle-peptide molecule.

In one aspect, a substantially homogenous compound is provided comprising a structure set out in Formula I,

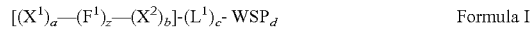    Formula I and multimers thereof, wherein:
$F^1$ is a vehicle;
$X^1$ is independently selected from:
$P^1$-$(L^2)_e$—

P²-(L³)_f—P¹-(L²)_e—
P³-(L⁴)_g—P²-(L³)_f—P¹-(L²)_e- and
P⁴-(L⁵)_h—P³-(L⁴)_g—P²-(L³)_f—P¹-(L²)_e—
X² is independently selected from:
-(L²)_e—P¹,
-(L²)_e—P¹-(L³)_f—P²,
-(L²)_e—P¹-(L³)_f—P²-(L⁴)_g—P³, and
-(L²)_e—P¹-(L³)_f—P²-(L⁴)_g—P³-(L⁵)_h—P⁴
wherein P¹, P², P³, and P⁴ are each independently sequences of pharmacologically active peptides;
L¹, L², L³, L⁴, and L⁵ are each independently linkers;
a, b, c, d, e, f, g, and h are each independently 0 or 1;
z is 0, 1, 2, or more; and
WSP is a water soluble polymer, the attachment of which is effected at any reactive moiety in F¹;
said compound having a property of improved bioefficacy when administered in a multidose regimen. In one aspect, the compound a multimer, and in another aspect, the compound is a dimer.

The invention also provides a compound of Formula I comprising a structure set out in Formula II

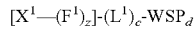  Formula II wherein F¹ is an Fc domain and is attached at the C-terminus of X¹, and zero, one, or more WSP is attached to the Fc domain, optionally through linker L¹. Compounds having this structure are provided as a multimer in one aspect and a dimer in another aspect.

The invention also provides a compound of Formula I comprising a structure set out in Formula III

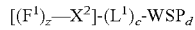  Formula III wherein F¹ is an Fc domain and is attached at the N-terminus of X², and zero, one, or more WSP is attached to the Fc domain, optionally through linker L¹. Multimers and dimers of a compound having this structure are also provided.

The invention also provides a compound of Formula I comprising a structure set out in Formula IV

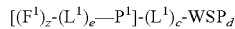  Formula IV wherein F¹ is an Fc domain and is attached at the N-terminus of -(L¹)_c—P¹ and, zero, one, or more WSP is attached to the Fc domain, optionally through linker L¹. Multimers and dimers of a compound having this structure are also provided.

The invention further provides a compound of Formula I comprising a structure set out in Formula V

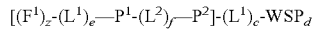  Formula V wherein F¹ is an Fc domain and is attached at the N-terminus of -L¹—P¹-L²—P² and, zero, one, or more WSP is attached to the Fc domain, optionally through linker L¹. Multimers and dimers of a compound having this structure are also provided.

Provided herein are compounds, as described above, wherein P¹ and/or P² are independently selected from a TPO-mimetic set out in any of Tables 1-6 and 8 herein. In one aspect, P¹ and/or P² have the same amino acid sequence.

The term "P" is used in the formula to mean a moiety made up of, i.e., comprising, at least 7 subunits (Y¹—Y⁷) wherein Y¹—Y⁷ comprises the core structure. U¹ and U² comprise any amino acid or peptide on either side of the Y¹—Y⁷ core structure. The Y¹—Y⁷ subunits are preferably amino acids independently selected from among the 20 naturally-occurring amino acids, however, the invention embraces compounds where Y¹—Y⁷ are independently selected from the group of atypical, non-naturally occurring amino acids well known in the art. In certain embodiments, specific amino acids are identified for each position. For example, Y¹ is Cys, Leu, Met, Pro, Gln, Val, or X₁; Y² is Phe, Lys, Leu, Asn, Gln, Arg, Ser, Thr, Val, or X₂; Y³ is Cys, Phe, Ile, Leu, Met, Arg, Ser, Val, Trp, or X₃; Y⁴ is any amino acid; Y⁵ is Ala, Asp, Glu, Gly, Lys, Met, Gln, Arg, Ser, Thr, Val, Tyr, or X₅; Y⁶ is Cys, Phe, Gly, Leu, Met, Ser, Val, Trp, Tyr, or X₆; and Y⁷ is Cys, Gly, Ile, Lys, Leu, Met, Asn, Arg, Val, or X₇. X₁—X₇ subunits are preferably amino acids independently selected from among the 20 naturally-occurring amino acids, however, the invention embraces compounds where X₁—X₇ are independently selected from the group of atypical, non-naturally occurring amino acids known in the art. Wherein it is stated that Y¹—Y⁷ corresponds to a respective X₁—X₇, it is understood that Y¹ corresponds to X₁, Y² corresponds to X₂, Y³ corresponds to X₃, Y⁵ corresponds to X₅, Y⁶ corresponds to X₆; Y⁷ corresponds to X₇; and Y⁴ does not have a corresponding X₄ per se because X₄ may be any amino acid or non-naturally occurring amino acid known in the art.

In one embodiment, P comprises the following general structure:

U¹—Y¹(Cys, Leu, Met, Pro, Gln, Val, or X₁)—Y²(Phe, Lys, Leu, Asn, Gln, Arg, Ser, Thr, Val, or X₂)—Y³(Cys, Phe, Ile, Leu, Met, Arg, Ser, Val, Trp, or X₃)—Y⁴—Y⁵(Ala, Asp, Glu, Gly, Lys, Met, Gln, Arg, Ser, Thr, Val, Tyr, or X₅)—Y⁶ (Cys, Phe, Gly, Leu, Met, Ser, Val, Trp, Tyr, or X₆)—Y⁷(Cys, Gly, Ile, Lys, Leu, Met, Asn, Arg, Val, or X₇)—U², wherein at least one of Y¹—Y³ and Y⁵—Y⁷ corresponds to a respective X₁—X₃ and X₅—X₇;

wherein U¹ or U² is any amino acid or peptide, wherein when Y¹ is not an amino acid selected from the group consisting of Cys, Leu, Met, Pro, Gln, and Val, then X₁ is selected from the group consisting of Ala, Asp, Glu, Phe, Gly, His, Ile, Lys, Asn, Arg, Ser, Thr, Trp, and Tyr;

wherein when Y² is not an amino acid selected from the group consisting of Phe, Lys, Leu, Asn, Gln, Arg, Ser, Thr, and Val, then X₂ is selected from the group consisting of Ala, Cys, Asp, Glu, Gly, His, Ile, Met, Pro, Trp, and Tyr;

wherein when Y³ is not an amino acid selected from the group consisting of Cys, Phe, Ile, Leu, Met, Arg, Ser, Val, and Trp, then X₃ is selected from the group consisting of Ala, Asp, Glu, Gly, His, Lys, Asn, Pro, Gln, Thr, and Tyr;

wherein when Y⁴ is any amino acid;

wherein when Y⁵ is not an amino acid selected from the group consisting of Ala, Asp, Glu, Gly, Lys, Met, Gln, Arg, Ser, Thr, Val, and Tyr, then X₅ is selected from the group consisting of Cys, Phe, His, Ile, Leu, Asn, Pro, and Trp;

wherein when Y⁶ is not an amino acid selected from the group consisting of Cys, Phe, Gly, Leu, Met, Ser, Val, Trp, and Tyr, then X₆ is selected from the group consisting of Ala, Asp, Glu, His, Ile, Lys, Asn, Pro, Gln, Arg, and Thr; and wherein when Y⁷ is not an amino acid selected from the group consisting of Cys, Gly, Ile, Lys, Leu, Met, Asn, Arg, and Val, then X₇ is selected from the group consisting of Ala, Asp, Glu, Phe, His, Pro, Gln, Ser, Thr, Trp, and Tyr;

and physiologically acceptable salts thereof.

In another aspect, the invention contemplates compounds, wherein at least two of Y¹—Y⁷ corresponds to two of X₁—X₇, respectively; at least three of Y¹—Y⁷ corresponds to three of X₁—X₇, respectively; at least four of Y¹—Y⁷ corresponds to four of X₁—X₇, respectively; at least five of Y¹—Y⁷ corresponds to five of X₁—X₇, respectively; at least six of Y¹—Y⁷ corresponds to six of X₁—X₇, respectively; and only one of Y¹—Y⁷ corresponds to one of X₁—X₇, respectively.

In one embodiment, the invention includes a compound of a structure set out in Formula I wherein at least a or b is 1.

In another embodiment, the invention includes a compound of a structure set out in Formula I wherein b, c, d, e, f, g, and h are 0.

In a further embodiment, the invention includes a compound that binds to an mp1 receptor consisting essentially of a structure set out in Formula I.

In another embodiment, the invention includes a compound of a structure set out in Formula I wherein $F^1$ is an Fc domain modified so that it comprises at least one $X^3$ in a loop region;

$X^3$ is independently selected from
-$(L^6)_i$—$P^5$-$(L^7)_j$,
-$(L^6)_i$—$P^5$-$(L^7)_j$—$P^6$-$(L^8)_k$,
-$(L^6)_i$—$P^5$-$(L^7)_j$—$P^6$-$(L^8)_k$—$P^7$-$(L^9)_l$, and
-$(L^6)_i$—$P^5$-$(L^7)_j$—$P^6$-$(L^8)_k$—$P^7$-$(L^9)_l$—$P^8$-$(L^{10})_m$;

$P^5$, $P^6$, $P^7$, and $P^8$ are each independently sequences of pharmacologically active peptides;

$L^6$, $L^7$, $L^8$, $L^9$, and $L^{10}$ are each independently linkers;

i, j, k, l, and m are each independently 0 or 1; and z is 1, 2, or more.

The invention includes a compound of the aforementioned structure wherein a and b are each 0.

Both three-letter and single letter abbreviations for amino acids are used herein; in each case, the abbreviations are the standard ones used for the 20 naturally-occurring amino acids or well-known variations thereof. These amino acids may have either L or D stereochemistry (except for Gly, which is neither L nor D), and $P^1$ may comprise a combination of stereochemistries. However, the L stereochemistry is preferred for all of the amino acids in the $P^1$ chain. The invention also provides reverse $P^1$ molecules wherein the amino terminal to carboxy terminal sequence of the amino acids is reversed. For example, the reverse of a molecule having the normal sequence $Y^1$—$Y^7$ would be $Y^7$—$Y^1$. The invention also provides retro-reverse $P^1$ molecules wherein, like a reverse $P^1$, the amino terminal to carboxy terminal sequence of amino acids is reversed and residues that are normally "L" enantiomers in $P^1$ are altered to the "D" stereoisomer form.

In addition to the core structure set forth above, $Y^1$—$Y^7$ ($X_1$—$X_7$), other structures that are specifically contemplated are those in which one or more additional Y groups are attached to the core structure. Thus, one or more Y groups make up the structures $U^1$ and $U^2$. Thus, $U^1$ and or $U^2$ may be attached to the core structure.

Exemplary compounds of the general structure are shown below. Single letter amino acid abbreviations are used for these peptides.

```
QGCSSGGPTQREWLQCRRMQHS      (SEQ ID NO: 8)
QGCSSGGPTLREWQQCRRMQHS      (SEQ ID NO: 9)
QGCSWGGPTLKIWLQCVRAKHS      (SEQ ID NO: 10)
QGCSWGGPTLKNWLQCVRAKHS      (SEQ ID NO: 11)
QGCSWGGPTLKLWLQCVRAKHS      (SEQ ID NO: 12)
QGCSWGGPTLKHWLQCVRAKHS      (SEQ ID NO: 13)
QGGCRSGPTNREWLACREVQHS      (SEQ ID NO: 14)
QGTCEQGPTLRQWPLCRQGRHS      (SEQ ID NO: 15)
QGTCEQGPTLRLWLLCRQGRHS      (SEQ ID NO: 16)
QGTCEQGPTLRIWLLCRQGRHS      (SEQ ID NO: 17)
```

Further exemplary compounds comprising one or more Fc regions linked to a peptide are provided below. Single letter amino acid abbreviations for the peptide are used.

```
Fc-QGCSSGGPTQREWLQCRRMQHS    (SEQ. ID NO: 18)
Fc-QGCSSGGPTLREWQQCRRMQHS    (SEQ. ID NO: 19)
Fc-QGCSWGGPTLKIWLQCVRAKHS    (SEQ ID NO: 20)
Fc-QGCSWGGPTLKNWLQCVRAKHS    (SEQ ID NO: 21)
Fc-QGCSWGGPTLKLWLQCVRAKHS    (SEQ ID NO: 22)
QGCSWGGPTLKIWLQCVRAKHS-Fc    (SEQ ID NO: 23)
Fc2-QGGCRSGPTNREWLACREVQHS   (SEQ ID NO: 24)
Fc2-QGCSWGGPTLKLWLQCVRAKHS   (SEQ ID NO: 25)
QGTCEQGPTLRQWPLCRQGRHS-Fc    (SEQ ID NO: 26)
Fc-QGTCEQGPTLRQWPLCRQGRHS    (SEQ ID NO: 27)
ETLY4QWL                     (SEQ ID NO: 28)
HTLY4QWL                     (SEQ ID NO: 29)
KTLY4QWL                     (SEQ ID NO: 30)
GTGY4QWL                     (SEQ ID NO: 31)
PTLY4IWL                     (SEQ ID NO: 32)
PTLY4LWL                     (SEQ ID NO: 33)
PTLY4EWF                     (SEQ ID NO: 34)
PTLY4HWL                     (SEQ ID NO: 35)
PILY4EWL                     (SEQ ID NO: 36)
KTLY4EWL                     (SEQ ID NO: 37)
PTLY4LWL                     (SEQ ID NO: 38)
PMLY4EWL                     (SEQ ID NO: 39)
PTLY4NWL                     (SEQ ID NO: 40)
PPLY4EWL                     (SEQ ID NO: 41)
PTQY4EWQ                     (SEQ ID NO: 42)
PTLY4EWS                     (SEQ ID NO: 43)
PTYY4EWL                     (SEQ ID NO: 44)
PTAY4QWL                     (SEQ ID NO: 45)
PCLY4QWL                     (SEQ ID NO: 46)
PTLY4FWL                     (SEQ ID NO: 47)
PTGY4QWL                     (SEQ ID NO: 48)
PTLY4HWL                     (SEQ ID NO: 49)
PILY4IWL                     (SEQ ID NO: 50)
PTLY4LWL                     (SEQ ID NO: 51)
PMLY4QWL                     (SEQ ID NO: 52)
PTLY4NWL                     (SEQ ID NO: 53)
PTPY4QWL                     (SEQ ID NO: 54)
PTLY4QWQ                     (SEQ ID NO: 55)
```

| | |
|---|---|
| PTLY⁴QWS | (SEQ ID NO: 56) |
| PTTY⁴QWT | (SEQ ID NO: 57) |
| PTLY⁴WWL | (SEQ ID NO: 58) |
| PTYY⁴QWL | (SEQ ID NO: 59) |
| PTLY⁴EWF | (SEQ ID NO: 60) |
| GTLY⁴EWL | (SEQ ID NO: 61) |
| PTLY⁴HWL | (SEQ ID NO: 62) |
| PILY⁴EWL | (SEQ ID NO: 63) |
| PTLY⁴LWL | (SEQ ID NO: 64) |
| PTQY⁴EWL | (SEQ ID NO: 65) |
| PTLY⁴EWS | (SEQ ID NO: 66) |
| PTLY⁴FWF | (SEQ ID NO: 67) |
| GTLY⁴QWL | (SEQ ID NO: 68) |
| PTLY⁴IWL | (SEQ ID NO: 69) |
| PTLY⁴LWL | (SEQ ID NO: 70) |
| PTLY⁴NWL | (SEQ ID NO: 71) |
| PTLY⁴QWP | (SEQ ID NO: 72) |
| PTLY⁴WWL | (SEQ ID NO: 73) |
| PTYY⁴QWL | (SEQ ID NO: 74) |

Further exemplary compounds are provided below. Single letter amino acid abbreviations for the peptide are used.

| | |
|---|---|
| KDTEVTAPRLWMVASVDE | (SEQ ID NO: 75) |
| REMEGPTMRQWLAYRAVL | (SEQ ID NO: 76) |
| CQNAGPTLRCWLAGRAYM | (SEQ ID NO: 77) |
| CEREGPTLRCWLATREGS | (SEQ ID NO: 78) |
| WRIEGPTLRHWLAARAWD | (SEQ ID NO: 79) |
| ANMEGPTLRHWLAMRARV | (SEQ ID NO: 80) |
| LDMEGPTLRHWLAARANG | (SEQ ID NO: 81) |
| WRMEGPTLRHWLAARAWG | (SEQ ID NO: 82) |
| WAMEGPTLRHWLAARAVL | (SEQ ID NO: 83) |
| KSMEGPSLRQWLAARAQL | (SEQ ID NO: 84) |
| TKIEGPTLRHWLAARAEL | (SEQ ID NO: 85) |
| PRIEGPTLRLWLVTRALS | (SEQ ID NO: 86) |
| IYMEGPTLRHWLANRAAK | (SEQ ID NO: 87) |
| WPIEGATLRQWLKIRAGY | (SEQ ID NO: 88) |
| RNMEGPTLRNWLAARAQH | (SEQ ID NO: 89) |
| NGIEGPTLRLWLSERAKK | (SEQ ID NO: 90) |
| MWMEGPTLRHWLEARARY | (SEQ ID NO: 91) |
| YGIDGPTLRHWLAARARY | (SEQ ID NO: 92) |
| RIIDGQTLRHWLAAGADP | (SEQ ID NO: 93) |
| NGRDGPTVRHRLAGRAQK | (SEQ ID NO: 94) |
| THIEGPTLRIWLASRAKA | (SEQ ID NO: 95) |
| KGMEGPTLRHWLAARAHL | (SEQ ID NO: 96) |
| QRIEGPTLRHWLAARASH | (SEQ ID NO: 97) |
| KDTEVTAPRLWMVASVDE | (SEQ ID NO: 98) |
| ENMEGPTLRHWLAARAHE | (SEQ ID NO: 99) |
| SWMEGPTLRHWLMNRATY | (SEQ ID NO: 100) |
| SMMEGPTLRHWLAARAKD | (SEQ ID NO: 101) |
| QGIEGPTLRLWLAARTHP | (SEQ ID NO: 102) |
| YMMEGPTLRHWLATRAGR | (SEQ ID NO: 103) |
| GNMEGPTLRHWLAANERD | (SEQ ID NO: 104) |
| NRMEGPTLRHWLAERAGS | (SEQ ID NO: 105) |
| NMMEGPTLRHWLAARVAA | (SEQ ID NO: 106) |
| SPIEGPTLRQQLCARAVK | (SEQ ID NO: 107) |
| VQMEGTTLRQWLAERALD | (SEQ ID NO: 108) |
| KRKDGHRPRQWLAPLACK | (SEQ ID NO: 109) |
| EMMEGPTLRHWLAARAEK | (SEQ ID NO: 110) |
| NMIEGPTLRHWLAERASQ | (SEQ ID NO: 111) |
| KLMEGPTLRHWLAYRAGL | (SEQ ID NO: 112) |
| YMMEGPTLRHWLAARALV | (SEQ ID NO: 113) |

| Sequence | SEQ ID NO |
|---|---|
| GNMEGPTLRHWLAARALL | 114 |
| WMMEGPTLRHWLAARARY | 115 |
| TDRGGYTLRQWLAARAVL | 116 |
| SAIEGPTLRHWLAWRAML | 117 |
| RAIEGPTLRHCLAAGAGL | 118 |
| VKRKGPTLRHWLAAWAFP | 119 |
| TCMEGPTLRHWLAARAEG | 120 |
| WFMEGPTLRHWLAARAYR | 121 |
| ADIEGPTLRHWLAARALV | 122 |
| WVMEGPTLRHWLAARASL | 123 |
| PPGDGPTLRHWLAARARM | 124 |
| DFMEGPTLRQRVDARAHY | 125 |
| RWIEGPTQRQWLAARAYF | 126 |
| IRMECPTLRHWLASRAEI | 127 |
| YYLEGPTLRHWLAARAYL | 128 |
| GVIEGPTLRHWLAARAAQ | 129 |
| GAMEGPTLRCWLAASDEK | 130 |
| SVIDGPTLRQRLAARARY | 131 |
| GGIERPTLRHCLAARPTS | 132 |
| TKMEGPTLRHWLAWRAAY | 133 |
| LKMEGPTLRNWLAWRAFQ | 134 |
| GLVEGPTLRFWLAARAAE | 135 |
| GLTDCPNLRHCLAARAPI | 136 |
| DRNKGPTLRHWLAARAHA | 137 |
| ASMVGPKLRHGLAAVAKK | 138 |
| DAIEGPTLRLWLEARRKQ | 139 |
| NIIKRATDREWLDARTAL | 140 |
| GDNEGPSPRVCLAARAVL | 141 |
| EFMEGPTLRHWLASRARV | 142 |
| WGMEGPTLRHWLAARGKR | 143 |
| RWMEGPTLRHWLAERAML | 144 |
| LMVEGPTLRHWLAARWRM | 145 |
| NYIEGPTLRHWLAARAKL | 146 |
| TWMEGPTLRLWLMARALY | 147 |
| QYMEGPTLRHWLAARAAL | 148 |
| AWMEGPTLRHWLAARAAY | 149 |
| KQFEGPPMRRSLAGVNTP | 150 |
| ALMEGPTLRQRLAARAAQ | 151 |
| ARMKGTTLRQWVAARAFV | 152 |
| DKIEIPTVQLRRAAYACQ | 153 |
| YRMEGPTLRHWLAARAGV | 154 |
| ALMEGPTLRHWLAARALM | 155 |
| IWAGGPTLRHWLAARAAL | 156 |
| GWVDGPTLRHWLAARARM | 157 |
| ARMEGPTLRHWLAARAKM | 158 |
| ESMEGASQRHCMAARAGG | 159 |
| MPVDGPVLRTWHAAQAIE | 160 |
| LEHNRPLTNPIPKPRTPIRP | 161 |
| TTMEDPTLRHWLATGAPT | 162 |
| HPIEGPTLRLWLAARARA | 163 |
| FPMEGTTLRHWLAARVQM | 164 |
| RGMNGPTLRHWLEESAKD | 165 |
| DQMEGSMVHQWLARHVWG | 166 |
| RNMEGPTLRHWLAARATY | 167 |

DGMEGPTLRLWMAARAGE (SEQ ID NO: 168)

ASMYGPTVSQRLAARTRG (SEQ ID NO: 169)

PMMEGPTLRHWLAARALR (SEQ ID NO: 170)

WPMEGPTLRHWLAARAAR (SEQ ID NO: 171)

VQMEGPTLRHWLAGRAPN (SEQ ID NO: 172)

HGIEGPTHRQWLAARADI (SEQ ID NO: 173)

GMMEGPTLRHWLAARAML (SEQ ID NO: 174)

HDMEGPTLRHWLALRATG (SEQ ID NO: 175)

DNMERTRRRHSLAAHFML (SEQ ID NO: 176)

RNMEGPTLRHWLAARADR (SEQ ID NO: 177)

WKFEGFTLRQWLTARAFG (SEQ ID NO: 178)

RGMEGPTLRQRLVERAQM (SEQ ID NO: 179)

DVMEGTTLRQWLACRALM (SEQ ID NO: 180)

RKMERATLRQWLTARANM (SEQ ID NO: 181)

GTKEGPTLRQWPAARANE (SEQ ID NO: 182)

CAIEGPTLRHWLAARAAT (SEQ ID NO: 183)

LTMEGPTLRHWLRARAYA (SEQ ID NO: 184)

MTMEGPTLRQWFAARADT (SEQ ID NO: 185)

SPMEGPTLRHSAAGRPWG (SEQ ID NO: 186)

VHMEDPTLRHGNAARAAE (SEQ ID NO: 187)

YPMEGPTLRHWLAARARH (SEQ ID NO: 188)

GKTQGPKQLKWQVGSSLP (SEQ ID NO: 189)

GEMEGPTLLHWRAARAMQ (SEQ ID NO: 190)

INMEGPTLRLWLAARAAA (SEQ ID NO: 191)

FRIEGPTLRNWLAARAAK (SEQ ID NO: 192)

GRMEGPTLRHWLAARAHP (SEQ ID NO: 193)

VLIQGHTVRNCMVARVDA (SEQ ID NO: 194)

DWIEGPTLRHWLAARALY (SEQ ID NO: 195)

SWTEGPTLRHWLAARARN (SEQ ID NO: 196)

RELEGPTLRLWLVERARM (SEQ ID NO: 197)

VSMEGPTLRNWLAARARM (SEQ ID NO: 198)

TTMEGPTLRHWLATRAVD (SEQ ID NO: 199)

AKLEGPTLRLWLAERAGR (SEQ ID NO: 200)

ARMEGPTLRHWLAARARY (SEQ ID NO: 201)

NIMDCPALRHWLPARAIQ (SEQ ID NO: 202)

NMIGGPTLGHRLADPAIQ (SEQ ID NO: 203)

VWMEGATLRQWLAARALI (SEQ ID NO: 204)

RVMEGPTLLQRLAARARS (SEQ ID NO: 205)

QPMDEPARRQWLSARAGL (SEQ ID NO: 206)

AWTEGPTLRHWLAARGRS (SEQ ID NO: 207)

ATMEGPTLRHWLAARAAL (SEQ ID NO: 208)

GRMEGPTLRHWLAARALF (SEQ ID NO: 209)

ENMQGRTLRHWLAARDYF (SEQ ID NO: 210)

KGVEGPTLRLWLAARALM (SEQ ID NO: 211)

VEMEGPTLRHWLAARASV (SEQ ID NO: 212)

AFIEGPTLKNWLAARAIM (SEQ ID NO: 213)

TVMEGPTLRHWLAARSRS (SEQ ID NO: 214)

AHMEGPTLRHWLATRAKM (SEQ ID NO: 215)

KDIEGPTLRHWLAARANY (SEQ ID NO: 216)

RIHDGRKLRQWLTVRDTM (SEQ ID NO: 217)

KPIEGPTLKLWLAERMAA (SEQ ID NO: 218)

AKDVGTRLRQWLAAGARA (SEQ ID NO: 219)

QSQEGPTLRLWLAERAKW (SEQ ID NO: 220)

MYTEGATLRQWLAARARI (SEQ ID NO: 221)

-continued

PKMEGPTRRTRLADRSTS (SEQ ID NO: 222)

NVMEGPTLRHWLAYRARM (SEQ ID NO: 223)

TWMEGPTLRHWLAARALG (SEQ ID NO: 224)

LTMEGPTLRHWLAARATR (SEQ ID NO: 225)

YTMEGPTLRHWLAARALH (SEQ ID NO: 226)

NEMEGATLRQWLAARAKW (SEQ ID NO: 227)

FSKEGATLRQWLAARALD (SEQ ID NO: 228)

SNGVCRTLRQWLAARAEE (SEQ ID NO: 229)

KGMEGPTLRNWLAERAML (SEQ ID NO: 230)

QDMVGPTLRHWLAARARL (SEQ ID NO: 231)

YSHEGPTLRHWLAARALL (SEQ ID NO: 232)

GVIEGPTLRHWLAARMKV (SEQ ID NO: 233)

MHMEGPTLRHWLATRALI (SEQ ID NO: 234)

CRSEGPTLRCWLAARAGY (SEQ ID NO: 235)

MCIEGPTLRQWQVCRVGL (SEQ ID NO: 236)

CRVEGPSQRQCLAARACW (SEQ ID NO: 237)

CTMEGPTLRHWLAARACI (SEQ ID NO: 238)

CQVDGPTVRHCRAARAGL (SEQ ID NO: 239)

CDMAGATLRQWLACRSGT (SEQ ID NO: 240)

ICTEGCTLRLWLAERSRV (SEQ ID NO: 241)

CGMEGPALRQWLACRAVD (SEQ ID NO: 242)

QGCSSGGPTLREWQQCVRMQHS (SEQ ID NO: 243)

QGCSSGGPTLREWQQCRRAQHS (SEQ ID NO: 244)

QGCSSGGPTLREWQQCVRAQHS (SEQ ID NO: 245)

IEGQSWEFENDRVPAHSLERVLLLRRVPTEPSGPSICAQIEGPTFKQWQECINGHS; (SEQ ID NO: 246)

IEGPTFKQWQKCRNMHS; (SEQ ID NO: 247)

IEGPTFKQWQKLRRVHS; (SEQ ID NO: 248)

IEGEPVSDGKRRPRVHSLERVDAVHAKVGPSICAQIEGPTFKQWQKCKRAHS; (SEQ ID NO: 249)

IEGRWPPPQFPVTQQHSLERVGRPPPSVELPRPTFVCAQIEGPTFKQWQRCLREHS; (SEQ ID NO: 250)

IEGPTFKQWQRWRLLHS; (SEQ ID NO: 251)

IEGPTFKQWQAWRKKHS; (SEQ ID NO: 252)

IEGPTFKQWQRWRKMHS; (SEQ ID NO: 253)

IEGRWPPPQFPVTEHHSLERVGRRPPNAQMPQSIFICGQNEGPTFQYCQRCLREHS; (SEQ ID NO: 254)

IEGWWWQFYFHAKEDHS; (SEQ ID NO: 255)

PSICAQIEGPTFKQWQTCMRAHS; (SEQ ID NO: 256)

IEGYVGGPYEQTNSLERVPPTLAWKYGPRTPSICAQIEGPTFKQWQQCLSDHS; (SEQ ID NO: 257)

IEGPTFKQWQGRSKRHS; (SEQ ID NO: 258)

IEGWPWQLYVHPEGEHS; (SEQ ID NO: 259)

IEGWWWQLYFHAKDDHS; (SEQ ID NO: 260)

IEGPTFKQWQKLRRSHS; (SEQ ID NO: 261)

IEGWWWQFYFHPKEDHS; (SEQ ID NO: 262)

IEGPTFKQWQKSRTKHS; (SEQ ID NO: 263)

IEGWTWQFYVHPKGDHS; (SEQ ID NO: 264)

IEGPTFKQWQAARMHHS; (SEQ ID NO: 265)

IEGPTFKQWQACLHSHS; (SEQ ID NO: 266)

IEGWSWQFYAHPQGDHS; (SEQ ID NO: 267)

IEGPSFTPWFHERRSHS; (SEQ ID NO: 268)

IEGPTFKQWQWLRRHHS; (SEQ ID NO: 269)

IEGWWWQFYVHAKGDHS; (SEQ ID NO: 270)

IEGPTFKQWQVWRNRHS; (SEQ ID NO: 271)

IEGQSWLRRLHWKEEHS; (SEQ ID NO: 272)

IEGWPWQFYALSRESGTSPSSAARTSSYLRSCAQIEGPTFKQWQICKDQHS; (SEQ ID NO: 273)

IEGPTFKQWQKWRKTHS; (SEQ ID NO: 274)

IEGPTFKQWQYWRAKHS; (SEQ ID NO: 275)

IEGPTFKQWQVRQKTHS; (SEQ ID NO: 276)

IEGWSWQFYFHAKGDHS; (SEQ ID NO: 277)

IEGRTWQLYFHAKEEHS; (SEQ ID NO: 278)

IEGWSWQFYAHPQGDHS; (SEQ ID NO: 279)

IEGWPRQLYAHAKEDHS; (SEQ ID NO: 280)

IEGWWWQFYAHPQGDHS; (SEQ ID NO: 281)

IEGWSWQFYAHPQGDHS; (SEQ ID NO: 282)

IEGWSWQFYAHPQGDHS; (SEQ ID NO: 283)

IEGHGSQKPTAARALESTSSLTTRTRTTSICAQQDMVGPTIRQWLAARACI; (SEQ ID NO: 284)

IEGPTFEQWQHWRRGHS; (SEQ ID NO: 285)

IEGWIWRQWLAARA; (SEQ ID NO: 286)

IEGWIWRPWLAARA; (SEQ ID NO: 287)

IEGYWWYASWAARA; (SEQ ID NO: 288)

IEGWPWQFYAHPQGDHS; (SEQ ID NO: 289)

IEGWVWCQWLAARA; (SEQ ID NO: 290)

IEGPTLHEWLRWLRQHS; (SEQ ID NO: 291)

IEGWVWRPWLAARA; (SEQ ID NO: 292)

IEGWVWCPWLAARA; (SEQ ID NO: 293)

IEGEALVFWWRVRGGHS; (SEQ ID NO: 294)

IEGWVWCPWLAARA; (SEQ ID NO: 295)

IEGWVWWPWLAARA; (SEQ ID NO: 296)

IEGWTWQFYALPRGDHS; (SEQ ID NO: 297)

IEGWPWQFYALSRESGTSPSSAARTSSYLRSCAQIEGPTFKQWQICKDQHS; (SEQ ID NO: 298)

IEGPTLRQRLAARA; (SEQ ID NO: 299)

IEGWSWQFYAHPKGDHS; (SEQ ID NO: 300)

IEGWVWRQWLAARA; (SEQ ID NO: 301)

IEGRHYQKWPARRLGHS; (SEQ ID NO: 302)

IEGFVGTVDWRQGRPHS; (SEQ ID NO: 303)

IEGQEPTRLRLqMDRHS; (SEQ ID NO: 304)

IAQVRMLGRFTLLVLSRARAASTQLSFQHSICAQIEGGAQTQWDAARA; (SEQ ID NO: 305)

IEGEIWAGPGAARA; (SEQ ID NO: 306)

IEGEALVFWWAARA; (SEQ ID NO: 307)

IEGSYRERQQAARA; (SEQ ID NO: 308)

IEGWVWRPWLAARA; (SEQ ID NO: 309)

IEGWNPWRGAASRV; (SEQ ID NO: 310)

IEGWTRRQWLAARA; (SEQ ID NO: 311)

IEGWVWRPWLAARA; (SEQ ID NO: 312)

IEGPTFKQWQAMRRHS; (SEQ ID NO: 313)

IEGMVKLGVLRLLVL; (SEQ ID NO: 314)

IEGPTFKQWQAWRRWHS; (SEQ ID NO: 315)

IEVWQSHWYQAARALESTSSRLLPMRPPPSICAQIEGPTLPQRMAARA; (SEQ ID NO: 316)

IEGWTWQFYAHPQGDHS; (SEQ ID NO: 317)

IEGPTFKQWQALRKRHS; (SEQ ID NO: 318)

IEGPTFKQWQKLRLGHS; (SEQ ID NO: 319)

IEGPTFKQWQLMGFPHS; (SEQ ID NO: 320)

IEGWIWRQWLMQTLWHS; (SEQ ID NO: 321)

IEGPTFKQWQAMRKNHS; (SEQ ID NO: 322)

IEGPTFKQWQKWRLSHS; (SEQ ID NO: 323)

IEGWQEGRQSAARA; (SEQ ID NO: 324)

IEGPTFKQWQRWLKYHS; (SEQ ID NO: 325)

-continued

IEGNYWFWQQVGQENTLSREWIQTLGQKYWYRPPSICAQIEGWSRHQHYSAMSGHS; (SEQ ID NO: 326)

IEGPTFKQWQLWRLQHS; (SEQ ID NO: 327)

IEGPTFKQWQMLRRHHS; (SEQ ID NO: 328)

IEGPTFKQWQRLRKNHS; (SEQ ID NO: 329)

IEGLLSQLWQAARA; (SEQ ID NO: 330)

IEGPSLPEWLHVWRHHS; (SEQ ID NO: 331)

IEGPTLHEWLAERRKHS; (SEQ ID NO: 332)

IEGPTLHEWLALLRSHS; (SEQ ID NO: 333)

IEGPTLHEWLAQRREHS; (SEQ ID NO: 334)

IEGPTLHEWLLYRRAHS; (SEQ ID NO: 335)

IEGPTLHEWLRQRRQHS; (SEQ ID NO: 336)

CSSGGPTLREWQQCSRAQ; (SEQ ID NO: 454)

CSSGGPTLREWQQCQRAQ; and (SEQ ID NO: 455)

CSSGGPTLREWQQCGRAQ. (SEQ ID NO: 456)

Some exemplary compounds of this invention, as set out above, are also shown in Tables 1-6, 8, and 12, and are set out in the Examples herein. Single letter amino acid abbreviations are used, and the linker is shown separated by dashes for clarity. Additional exemplary compounds of the invention are set out in Table 10 herein.

Linkers

Any "linker" group ($L^1$, $L^2$, $L^3$, $L^4$, and $L^5$) is optional. When present, its chemical structure is not critical, since it serves primarily as a spacer. Thus, the terms "linker" and "spacer" may be used interchangeably herein. In one aspect, the linker is made up of amino acids linked together by peptide bonds. Thus, in some embodiments, the linker is made up of from 1 to 20 amino acids linked by peptide bonds, wherein the amino acids are selected from the 20 naturally occurring amino acids. Some of these amino acids may be glycosylated, as is well understood by those in the art. In another embodiment, the 1 to 20 amino acids are selected from glycine, alanine, proline, asparagine, glutamine, and lysine. In a further aspect, a linker is made up of a majority of amino acids that are sterically unhindered, such as glycine and alanine. Thus, linkers are polyglycines (particularly $(Gly)_4$, $(Gly)_5$), poly(Gly-Ala), and polyalanines. Other specific examples of linkers are:

$(Gly)_3Lys(Gly)_4$; (SEQ ID NO: 4)

$(Gly)_3AsnGlySer(Gly)_2$ (SEQ ID NO: 5)

(this structure provides a site for glycosylation, when it is produced recombinantly in a mammalian cell system that is capable of glycosylating such sites);

$(Gly)_3Cys(Gly)_4$; and (SEQ ID NO: 6)

GlyProAsnGly. (SEQ ID NO: 7)

To explain the above nomenclature, for example, $(Gly)_3$ Lys$(Gly)_4$ means Gly-Gly-Gly-Lys-Gly-Gly-Gly-Gly. Combinations of Gly and Ala are also contemplated. The linkers shown here are exemplary; linkers within the scope of this invention may be much longer and may include other residues.

In another embodiment, glycine linkers (or spacers) are used in inserting the TPO-mimetic compounds of the invention into Fc-Loops. These linkers (or spacers) may be symmetric or asymmetric. When linkers (or spacers) are used to connect tandem or multiple peptide sequences, the linkers may be the same or different. Moreover, to the extent where peptides are inserted into other sequences, the linkers at the N- and C-termini may be the same or different.

Non-peptide linkers are also possible. For example, alkyl linkers such as —NH—$(CH_2)$s-C(O)—, wherein s=2-20 could be used. These alkyl linkers may further be substituted by any non-sterically hindering group such as lower alkyl (e.g., C1-C6) lower acyl, halogen (e.g., Cl, Br), CN, $NH_2$, phenyl, etc. An exemplary non-peptide linker is a PEG linker, which has a molecular weight of 100 to 5000 kD, or 100 to 500 kD. The peptide linkers may be altered to form derivatives as described herein below.

Derivatives

It is also contemplated that "derivatives" of a TMP (peptide and/or vehicle portion of the TMP) may be substituted for a TMP described above. Such derivatives may improve the solubility, absorption, biological half life, and the like of the compounds. The moieties may alternatively eliminate or attenuate any undesirable side-effect of the compounds and the like.

Such derivative TMPs include compounds in which:

1. The compound or some portion thereof is cyclic. For example, the peptide portion may be modified to contain two or more Cys residues (e.g., in the linker), which could cyclize by disulfide bond formation.

2. The compound is cross-linked or is rendered capable of cross-linking between molecules. For example, the peptide portion may be modified to contain one Cys residue and thereby be able to form an intermolecular disulfide bond with a like molecule. The compound may also be cross-linked through its C-terminus.

3. One or more peptidyl [—C(O)NR—] linkages (bonds) is replaced by a non-peptidyl linkage. Exemplary non-peptidyl linkages are —CH2-carbamate [—CH2-OC(O)NR—], phosphonate, —CH2-sulfonamide [—CH2-S(O)2NR—], urea [—NHC(O)NH—], —CH2-secondary amine, and alkylated peptide [—C(O)NR6- wherein R6 is lower alkyl].

4. The N-terminus is derivatized. Typically, the N-terminus may be acylated or modified to a substituted amine. Exemplary N-terminal derivative groups include —NRR1 (other than —NH2), —NRC(O)R1, —NRC(O)OR1, —NRS(O)2R1, —NHC(O)NHR1, succinimide, or benzyloxycarbonyl-NH—(CBZ—NH—), wherein R and R1 are each independently hydrogen or lower alkyl with the proviso that R and R1 are not both hydrogen and wherein the phenyl ring may be substituted with 1 to 3 substituents selected from the group consisting of C1-C4 alkyl, C1-C4 alkoxy, chloro, and bromo; to a succinimide group; to a benzyloxycarbonyl-NH— (CBZ—NH—) group; and peptides wherein the free C terminus is derivatized to —C(O)R2 where R2 is selected from the group consisting of lower alkoxy and —NR3R4 where R3 and R4 are independently selected from the group consisting of hydrogen and lower alkyl. By "lower" is meant a group having from 1 to 6 carbon atoms.

5. The free C-terminus is derivatized. Typically, the C-terminus is esterified or amidated. For example, one may use methods described in the art to add (NH—CH2-CH2-NH2)2 to compounds of this invention at the C-terminus. Likewise, one may use methods described in the art to add —NH2 to compounds of this invention at the C-terminus. Exemplary C-terminal derivative groups include, for example, —C(O)R2 wherein R2 is lower alkoxy or —NR3R4 wherein R3 and R4 are independently hydrogen or C1-C8 alkyl (preferably C1-C4 alkyl).

6. A disulfide bond is replaced with another, preferably more stable, cross-linking moiety (e.g., an alkylene). See, e.g., Bhatnagar et al. (1996), J. Med. Chem. 39: 3814-9; Alberts et al. (1993) Thirteenth Am. Pep. Symp., 357-9.

7. One or more individual amino acid residues is modified. Various derivatizing agents are known to react specifically with selected side chains or terminal residues, as described in detail below.

Additionally, modifications of individual amino acids may be introduced into the TMP sequence by reacting targeted amino acid residues of the peptide with an organic derivatizing agent that is capable of reacting with selected side chains or terminal residues. The following are exemplary.

Lysinyl and amino terminal residues may be reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine guanidino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizole and tetranitromethane may be used to form O-acetyl tyrosyl species and 3-nitro derivatives, respectively.

Carboxyl side groups (aspartyl or glutamyl) may be selectively modified by reaction with carbodiimides (R'—N=C=N—R') such as 1-cyclohexyl-3-(2-morpholinyl-(4-ethyl)carbodiimide or 1-ethyl-3-(4-azonia-4,4-dimethylpentyl)carbodiimide. Furthermore, aspartyl and glutamyl residues may be converted to asparaginyl and glutaminyl residues by reaction with ammonium ions.

Glutaminyl and asparaginyl residues are frequently deamidated to the corresponding glutamyl and aspartyl residues. Alternatively, these residues may be deamidated under mildly acidic conditions. Either form of these residues falls within the scope of this invention.

Cysteinyl residues can be replaced by amino acid residues or other moieties either to eliminate disulfide bonding or, conversely, to stabilize cross-linking. See, e.g., Bhatnagar et al. (1996), J. Med. Chem. 39: 3814-9.

Derivatization with bifunctional agents is useful for cross-linking the peptides or their functional derivatives to a water-insoluble support matrix or to other macromolecular carriers. Commonly used cross-linking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 may be employed for protein immobilization.

Other possible modifications include hydroxylation of proline and lysine, phosphorylation of hydroxyl groups of seryl or threonyl residues, oxidation of the sulfur atom in Cys, methylation of the alpha-amino groups of lysine, arginine, and histidine side chains (Creighton, T. E., Proteins: Structure and Molecule Properties, W. H. Freeman & Co., San Francisco, pp. 79-86 (1983)), acetylation of the N-terminal amine, and, in some instances, amidation of the C-terminal carboxyl groups.

Such derivatized moieties preferably improve one or more characteristics including thrombopoietic activity, solubility, absorption, biological half life, and the like of the inventive compounds. Alternatively, derivatized moieties result in compounds that have the same, or essentially the same, characteristics and/or properties of the compound that is not derivatized. The moieties may alternatively eliminate or attenuate any undesirable side effect of the compounds and the like.

As ascertained by peptide mapping and N-terminal sequencing, a preparation is provided which is at least 50% dipolymer/peptide conjugate and at most 50% unreacted peptide and/or monopolymer/peptide conjugate. In other embodiments, preparations are provided which are at least 75% dipolymer/peptide conjugate and at most 25% unreacted peptide and/or monopolymer/peptide conjugate; at least 85% dipolymer/peptide conjugate and at most 15% unreacted peptide and/or monopolymer/peptide conjugate; at least 90% dipolymer/peptide conjugate and at most 10% unreacted peptide and/or monopolymer/peptide conjugate; at least 95% dipolymer/peptide conjugate and at most 5% unreacted peptide and/or monopolymer/peptide conjugate; and at least 99% dipolymerpeptide conjugate and at most 1% unreacted peptide and/or monopolymer/peptide conjugate.

Carbohydrate (oligosaccharide) groups may conveniently be attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn—-Ser/Thr, where X can be any amino acid except proline. X is preferably one of the 19 naturally occurring amino acids other than proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, may confer acidic properties to the glycosylated compound. Such site(s) may be incorporated in the linker of the compounds of this invention and are preferably glycosylated by a cell during recombinant production of the polypeptide compounds (e.g., in mammalian cells such as CHO, BHK, COS). However, such sites may further be glycosylated by synthetic or semi-synthetic procedures known in the art.

Compounds of the present invention may be changed at the DNA level, as well. The DNA sequence of any portion of the compound may be changed to codons more compatible with the chosen host cell. For *E. coli*, which is the host cell in one aspect, optimized codons are known in the art. Codons may be substituted to eliminate restriction sites or to include silent restriction sites, which may aid in processing of the DNA in the selected host cell. The vehicle, linker and peptide DNA sequences may be modified to include any of the foregoing sequence changes.

Isotope- and toxin-conjugated derivatives. Another set of useful derivatives are the above-described molecules conjugated to toxins, tracers, or radioisotopes. Such conjugation is especially useful for molecules comprising peptide sequences that bind to tumor cells or pathogens. Such molecules may be used as therapeutic agents or as an aid to surgery (e.g., radioimmunoguided surgery or RIGS) or as diagnostic agents (e.g., radioimmunodiagnostics or RID).

As therapeutic agents, these conjugated derivatives possess a number of advantages. They facilitate use of toxins and radioisotopes that would be toxic if administered without the specific binding provided by the peptide sequence. They also can reduce the side-effects that attend the use of radiation and chemotherapy by facilitating lower effective doses of the conjugation partner.

Useful conjugation partners include:
radioisotopes, such as $^{90}$Yttrium, $^{131}$Iodine, $^{225}$Actinium, and $^{213}$Bismuth;
ricin A toxin, microbially derived toxins such as *Pseudomonas* endotoxin (e.g., PE38, PE40), and the like;
partner molecules in capture systems (see below);
biotin, streptavidin (useful as either partner molecules in capture systems or as tracers, especially for diagnostic use); and
cytotoxic agents (e.g., doxorubicin).

One useful adaptation of these conjugated derivatives is use in a capture system. In such a system, the molecule of the present invention would comprise a benign capture molecule. This capture molecule would be able to specifically bind to a separate effector molecule comprising, for example, a toxin or radioisotope. Both the vehicle-conjugated molecule and the effector molecule would be administered to the patient. In such a system, the effector molecule would have a short half-life except when bound to the vehicle-conjugated capture molecule, thus minimizing any toxic side-effects. The vehicle-conjugated molecule would have a relatively long half-life but would be benign and non-toxic. The specific binding portions of both molecules can be part of a known specific binding pair (e.g., biotin, streptavidin) or can result from peptide generation methods such as those described herein.

Such conjugated derivatives may be prepared by methods known in the art. In the case of protein effector molecules (e.g., *Pseudomonas* endotoxin), such molecules can be expressed as fusion proteins from correlative DNA constructs. Radioisotope conjugated derivatives may be prepared, for example, as described for the BEXA antibody (Coulter). Derivatives comprising cytotoxic agents or microbial toxins may be prepared, for example, as described for the BR96 antibody (Bristol-Myers Squibb). Molecules employed in capture systems may be prepared, for example, as described by the patents, patent applications, and publications from NeoRx. Molecules employed for RIGS and RID may be prepared, for example, by the patents, patent applications, and publications from NeoProbe.

The compounds of the invention may also be covalently or noncovalently associated with a carrier molecule, such as a linear polymer (e.g., polyethylene glycol, polylysine, dextran, etc.), a branched-chain polymer (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published 28 Oct. 1993); a lipid; a cholesterol group (such as a steroid); or a carbohydrate or oligosaccharide. Other possible carriers include one or more water soluble polymer attachments such as polyoxyethylene glycol, or polypropylene glycol as described U.S. Pat. Nos. 4,640,835, 4,496,689, 4,301,144, 4,670,417, 4,791,192 and 4,179,337. Still other useful polymers known in the art include monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide copolymer, polyoxyethylated polyols (e.g., glycerol) and polyvinyl alcohol, as well as mixtures of these polymers.

In one aspect, the carrier is polyethylene glycol (PEG). The PEG group may be of any convenient molecular weight and may be straight chain or branched. The average molecular weight of the PEG will range from about 2 kDa to about 100 kDa, or from about 5 kDa to about 50 kDa, or from about 5 kDa to about 10 kDa.

The PEG groups will generally be attached to the compounds of the invention via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the target compound (e.g., an aldehyde, amino, ester, thiol, α-haloacetyl, maleimido or hydrazino group).

Vehicles

This invention requires the presence of at least one vehicle ($F^1$, $F^2$) attached to a peptide through the N-terminus, C-terminus or a side chain of one of the amino acid residues. An Fc domain is a vehicle provided herein. Thus, an Fc domain may be fused to the N or C termini of the peptides or at both the N and C termini. Multiple vehicles may also be used; e.g., Fc's at each terminus or an Fc at a terminus and a PEG group at the other terminus or a side chain.

In various embodiments, the Fc component is either a native Fc or an Fc variant. By way of example and without limitation, the Fc component is preferably the Fc region of the human immunoglobulin IgG1 heavy chain or a biologically active fragment, derivative, or dimer thereof, see Ellison, J. W. et al., Nucleic Acids Res. 10:4071-4079 (1982). Native Fc domains are made up of monomeric polypeptides that may be linked into dimeric or multimeric forms by covalent (i.e., disulfide bonds) and/or non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), Nucleic Acids Res. 10: 4071-9).

In one aspect, the Fc sequence shown in SEQ ID NO: 3 is an Fc sequence for the compounds provided herein. Also provided are compounds in which the Fc is a dimeric form of the sequence of SEQ ID NO: 3 and each Fc chain is attached to a TMP tandem dimer. Additional Fc sequences are known in the art and are contemplated for use in the invention. For example, Fc IgG1 (GenBank Accession No. P01857), Fc IgG2 (GenBank Accession No. P01859), Fc IgG3 (GenBank Accession No. P01860), Fc IgG4 (GenBank Accession No. P01861), Fc IgA1 (GenBank Accession No. P01876), Fc IgA2 (GenBank Accession No. P01877), Fc IgD (GenBank Accession No. P01880), Fc IgM (GenBank Accession No. P01871), and Fc IgE (GenBank Accession No. P01854) are some additional Fc sequences contemplated for use herein.

Variants, analogs or derivatives of the Fc portion may be constructed by, for example, making various substitutions of residues or sequences. In one aspect, an Fc variant is incorporated which comprises a molecule or sequence that is humanized from a non-human native Fc. Alternately, an Fc variant comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC), each of which is described in detail in U.S. Patent Application No. 20040087778, the disclosure of which is incorporated by reference in its entirety.

Variant (or analog) polypeptides include insertion variants, wherein one or more amino acid residues supplement an Fc amino acid sequence. Insertions may be located at either or both termini of the protein, or may be positioned within internal regions of the Fc amino acid sequence. Insertion variants, with additional residues at either or both termini, can include for example, fusion proteins and proteins including amino acid tags or labels. For example, the Fc molecule may optionally contain an N-terminal Met, especially when the molecule is expressed recombinantly in a bacterial cell such as E. coli.

In Fc deletion variants, one or more amino acid residues in an Fc polypeptide are removed. Deletions can be effected at one or both termini of the Fc polypeptide, or with removal of one or more residues within the Fc amino acid sequence. Deletion variants, therefore, include all fragments of an Fc polypeptide sequence.

In Fc substitution variants, one or more amino acid residues of an Fc polypeptide are removed and replaced with alternative residues. In one aspect, the substitutions are conservative in nature and conservative substitutions of this type are well known in the art. Alternatively, the invention embraces substitutions that are also non-conservative.

For example, cysteine residues can be deleted or replaced with other amino acids to prevent formation of some or all disulfide crosslinks of the Fc sequences. Each cysteine residue can be removed and/or substituted with other amino acids, such as Ala or Ser. As another example, modifications may also be made to introduce amino acid substitutions to (1) ablate the Fc receptor binding site; (2) ablate the complement (C1q) binding site; and/or to (3) ablate the antibody dependent cell-mediated cytotoxicity (ADCC) site. Such sites are known in the art, and any known substitutions are within the scope of Fc as used herein. For example, see Molecular Immunology, Vol. 29, No. 5, 633-639 (1992) with regard to ADCC sites in IgG1.

Likewise, one or more tyrosine residues can be replaced by phenylalanine residues. In addition, other variant amino acid insertions, deletions and/or substitutions are also contemplated and are within the scope of the present invention. Conservative amino acid substitutions will generally be preferred. Furthermore, alterations may be in the form of altered amino acids, such as peptidomimetics or D-amino acids.

As noted above, both native Fcs and Fc variants are suitable Fc domains for use within the scope of this invention. A native Fc may be extensively modified to form an Fc variant provided binding to the salvage receptor is maintained; see, for example WO 97/34631 and WO 96/32478. In such Fc variants, one may remove one or more sites of a native Fc that provide structural features or functional activity not required by the fusion molecules of this invention. One may remove these sites by, for example, substituting or deleting residues, inserting residues into the site, or truncating portions containing the site. The inserted or substituted residues may also be altered amino acids, such as peptidomimetics or D-amino acids. Fc variants may be desirable for a number of reasons, several of which are described below. Exemplary Fc variants include molecules and sequences in which:

Sites involved in disulfide bond formation are removed. Such removal may avoid reaction with other cysteine-containing proteins present in the host cell used to produce the molecules of the invention. For this purpose, the cysteine-containing segment at the N-terminus may be truncated or cysteine residues may be deleted or substituted with other amino acids (e.g., alanyl, seryl). In particular, one may truncate the N-terminal 20-amino acid segment of SEQ ID NO: 3 or delete or substitute the cysteine residues at positions 7 and 10 of SEQ ID NO: 3. Even when cysteine residues are removed, the single chain Fc domains can still form a dimeric Fc domain that is held together non-covalently.

A native Fc is modified to make it more compatible with a selected host cell. For example, one may remove the PA sequence near the N-terminus of a typical native Fc, which may be recognized by a digestive enzyme in E. coli such as proline iminopeptidase. One may also add an N-terminal methionine residue, especially when the molecule is expressed recombinantly in a bacterial cell such as E. coli. The Fc domain of SEQ ID NO: 3 is one such Fc variant.

A portion of the N-terminus of a native Fc is removed to prevent N-terminal heterogeneity when expressed in a selected host cell. For this purpose, one may delete any of the first 20 amino acid residues at the N-terminus, particularly those at positions 1, 2, 3, 4 and 5.

One or more glycosylation sites are removed. Residues that are typically glycosylated (e.g., asparagine) may confer cytolytic response. Such residues may be deleted or substituted with unglycosylated residues (e.g., alanine).

Sites involved in interaction with complement, such as the C1q binding site, are removed. For example, one may delete or substitute the EKK sequence of human IgG1. Complement recruitment may not be advantageous for the molecules of this invention and so may be avoided with such an Fc variant.

Sites are removed that affect binding to Fc receptors other than a salvage receptor. A native Fc may have sites for interaction with certain white blood cells that are not required for the fusion molecules of the present invention and so may be removed.

The ADCC site is removed. ADCC sites are known in the art; see, for example, Molec. Immunol. 29 (5): 633-9 (1992) with regard to ADCC sites in IgG1. These sites, as well, are not required for the fusion molecules of the present invention and so may be removed.

When the native Fc is derived from a non-human antibody, the native Fc may be humanized. Typically, to humanize a native Fc, one will substitute selected residues in the non-human native Fc with residues that are normally found in human native Fc. Techniques for antibody humanization are well known in the art.

Preferred Fc variants include the following. In SEQ ID NO: 3, the leucine at position 15 may be substituted with a glutamate; the glutamate at position 99, with alanine; and the lysines at positions 101 and 103, with alanines. In addition, one or more tyrosine residues can be replaced by phenylalanine residues.

It should be noted that Fc monomers will spontaneously dimerize when the appropriate cysteine residues are present, unless particular conditions are present that prevent dimerization through disulfide bond formation. Even if the cysteine residues that normally form disulfide bonds in the Fc dimer are removed or replaced by other residues, the monomeric chains will generally form a dimer through non-covalent interactions. The term "Fc" herein is used to mean any of these forms: the native monomer, the native dimer (disulfide bond linked), modified dimers (disulfide and/or non-covalently linked), and modified monomers (i.e., derivatives).

Fc sequences may also be derivatized, i.e., bearing modifications other than insertion, deletion, or substitution of amino acid residues. In one aspect, the modifications are covalent in nature, and include for example, chemical bonding with polymers, lipids, other organic, and inorganic moieties. However, non-covalent modifications are also contemplated. Derivatives of the invention may be prepared to increase circulating half-life, or may be designed to improve targeting capacity for the polypeptide to desired cells, tissues, or organs.

It is also possible to use the salvage receptor binding domain of the intact Fc molecule as the Fc part of a compound of the invention, such as described in WO 96/32478, entitled "Altered Polypeptides with Increased Half-Life." Additional members of the class of molecules designated as Fc herein are those that are described in WO 97/34631, entitled "Immunoglobulin-Like Domains with Increased Half-Lives." Both of the published PCT applications cited in this paragraph are hereby incorporated by reference.

As discussed herein, the Fc fusions may be at the N or C terminus of a TMP of the invention, or at both the N and C termini of the TMP. It has been previously been shown that peptides in which an Fc moiety is ligated to the N terminus of the TMP group is more bioactive than the other possibilities. When the Fc is fused at the N-terminus of the TMP or linker, such fusion will generally occur at the C-terminus of the Fc chain, and vice versa.

An alternative vehicle would be a protein, polypeptide, peptide, antibody, antibody fragment, or small molecule (e.g., a peptidomimetic compound) capable of binding to a salvage receptor. For example, one could use as a vehicle a polypeptide as described in U.S. Pat. No. 5,739,277, issued Apr. 14, 1998 to Presta et al. Peptides could also be selected by phage display for binding to the FcRn salvage receptor. Such salvage receptor-binding compounds are also included within the meaning of "vehicle" and are within the scope of this invention. Such vehicles should be selected for increased half-life (e.g., by avoiding sequences recognized by proteases) and decreased immunogenicity (e.g., by favoring non-immunogenic sequences, as discovered in antibody humanization).

As noted above, polymer vehicles may also be used for $F^1$ and $F^2$. Various means for attaching chemical moieties useful as vehicles are currently available, see, e.g., Patent Cooperation Treaty ("PCT") International Publication No. WO 96/11953, entitled "N-Terminally Chemically Modified Protein Compositions and Methods," herein incorporated by reference in its entirety. This PCT publication discloses, among other things, the selective attachment of water soluble polymers to the N-terminus of proteins.

Water-soluble Polymers

This invention contemplates compounds comprising a water-soluble polymer (WSP). Suitable, clinically acceptable, WSP include without limitation, PEG, polyethylene glycol propionaldehyde, copolymers of ethylene glycol/propylene glycol, monomethoxy-polyethylene glycol, carboxymethylcellulose, polyacetals, polyvinyl alcohol (PVA), polyvinyl pyrrolidone, poly-1,3-dioxolane, poly-1,3,6-trioxane, ethylene/maleic anhydride copolymer, poly (.beta.-amino acids) (either homopolymers or random copolymers), poly(n-vinyl pyrrolidone)polyethylene glycol, propropylene glycol homopolymers (PPG) and other polyakylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll or dextran and mixtures thereof. In fact, any of the forms of PEG that have been used to derivatize other proteins, such as and without limitation mono-(C1-C10) alkoxy- or aryloxy-polyethylene glycol, are provided. Polyethylene glycol propionaldehyde may have advantages in manufacturing due to its stability in water.

The PEG group may be of any convenient molecular weight and may be linear or branched. The average molecular weight of PEG contemplated for use in the invention ranges from about 2 kDa to about 100 kDa, from about 5 kDa to about 50 kDa, from about 5 kDa to about 10 kDa. In another aspect, the PEG moiety has a molecular weight from about 6 kDa to about 25 kDa. PEG groups generally are attached to peptides or proteins via acylation or reductive alkylation through a reactive group on the PEG moiety (e.g., an aldehyde, amino, thiol, or ester group) to a reactive group on the target peptide or protein (e.g., an aldehyde, amino, or ester group). Using methods described herein, a mixture of polymer/peptide conjugate molecules can be prepared, and the advantage provided herein is the ability to select the proportion of polymer/peptide conjugate to include in the mixture. Thus, if desired, a mixture of peptides with various numbers of polymer moieties attached (i.e., zero, one or two) can be prepared with a predetermined proportion of polymer/protein conjugate.

A useful strategy for the PEGylation of synthetic peptides consists of combining, through forming a conjugate linkage in solution, a peptide and a WSP (PEG) moiety, each bearing a special functionality that is mutually reactive toward the other. The peptides can be easily prepared with conventional solid phase synthesis. The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Polysaccharide polymers are another type of WSP which may be used for protein modification. Dextrans are polysaccharide polymers comprised of individual subunits of glucose predominantly linked by α1-6 linkages. The dextran itself is available in many molecular weight ranges, and is readily available in molecular weights from about 1 kD to about 70 kD. Dextran is a suitable water soluble polymer for use in the present invention as a vehicle by itself or in combination with another vehicle (e.g., Fc). See, for example, WO 96/11953 and WO 96/05309. The use of dextran conjugated to therapeutic or diagnostic immunoglobulins has been reported; see, for example, European Patent Publication No. 0 315 456, which is hereby incorporated by reference. Dextran of about 1 kD to about 20 kD is preferred when dextran is used as a vehicle in accordance with the present invention.

The WSP moiety of the molecule may be branched or unbranched. For therapeutic use of the end-product preparation, the polymer is pharmaceutically acceptable. In general, a desired polymer is selected based on such considerations as whether the polymer conjugate will be used therapeutically, and if so, the desired dosage, circulation time, resistance to proteolysis, and other considerations. In various aspects, the average molecular weight of each WSP is between about 2 kDa and about 100 kDa, between about 5 kDa and about 50 kDa, between about 12 kDa and about 40 kDa and between about 20 kDa and about 35 kDa. In yet another aspect the molecular weight of each polymer is between about 6 kDa and about 25 kDa. The term "about" as used herein and throughout, indicates that in preparations of a water soluble polymer, some molecules will weigh more, some less, than the stated molecular weight. Generally, the higher the molecular weight or the more branches, the higher the polymer/protein ratio. Other sizes may be used, depending on the desired therapeutic profile including for example, the duration of sustained release; the effects, if any, on biological activity; the ease in handling; the degree or lack of antigenicity and other known effects of a water soluble polymer on a therapeutic protein.

The WSP should be attached to a peptide or protein with consideration given to effects on functional or antigenic domains of the peptide or protein. In general, chemical derivatization may be performed under any suitable condition used to react a protein with an activated polymer molecule. Activating groups which can be used to link the water soluble polymer to one or more proteins include without limitation sulfone, maleimide, sulfhydryl, thiol, triflate, tresylate, azidirine, oxirane and 5-pyridyl. If attached to the peptide by reductive alkylation, the polymer selected should have a single reactive aldehyde so that the degree of polymerization is controlled.

Production of Compounds/Methods of Making

The compounds described herein largely may be made in transformed host cells using recombinant DNA techniques. To do so, a recombinant DNA molecule coding for the peptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidate method. Also, a combination of these techniques could be used.

The invention also includes a vector capable of expressing the peptides in an appropriate host. The vector comprises the DNA molecule that codes for the peptides operatively linked to appropriate expression control sequences. Methods of effecting this operative linking, either before or after the DNA molecule is inserted into the vector, are well known. Expression control sequences include promoters, activators, enhancers, operators, ribosomal binding sites, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be used in the practice of this invention. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial hosts include bacteria (such as *E. coli* sp.), yeast (such as *Saccharomyces* sp.) and other fungi, insects, plants, mammalian (including human) cells in culture, or other hosts known in the art.

Next, the transformed host is cultured and purified. Host cells may be cultured under conventional fermentation conditions so that the desired compounds are expressed. Such fermentation conditions are well known in the art. Finally, the peptides are purified from culture by methods well known in the art.

The compounds may also be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. Solid phase synthesis is a preferred technique of making individual peptides since it is the most cost-effective method of making small peptides.

The compounds in one aspect are peptides, and they may be prepared by standard synthetic methods or any other methods of preparing peptides. The compounds that encompass non-peptide portions may be synthesized by standard organic chemistry reactions, in addition to standard peptide chemistry reactions when applicable.

Phage display, in particular, is useful in generating peptides for use in the present invention. It has been stated that affinity selection from libraries of random peptides can be used to identify peptide ligands for any site of any gene product. Dedman et al. (1993), J. Biol. Chem. 268: 23025-30. Phage display is particularly well suited for identifying peptides that bind to such proteins of interest as cell surface receptors or any proteins having linear epitopes. Wilson et al. (1998), Can. J. Microbiol. 44: 313-29; Kay et al. (1998), Drug Disc. Today 3: 370-8. Such proteins are extensively reviewed in Herz et al. (1997), J. Receptor & Signal Transduction Res. 17(5): 671-776, which is hereby incorporated by reference. Such proteins of interest are contemplated for use in this invention.

Peptide compounds are contemplated wherein all of the amino acids have a D configuration, or at least one of the amino acids has a D configuration. It is also contemplated that the peptide compounds may be cyclic.

Compounds that contain derivatized peptides or which contain non-peptide groups may be synthesized by well-known organic chemistry techniques.

A TMP of a preparation of the invention can be prepared using recombinant DNA techniques. Alternatively, a polynucleotide encoding a TMP is prepared using chemical synthesis techniques known in the art, such as the phosphoramidate method. In yet another alternative, a combination of these techniques is used.

Vectors

For recombinant protein expression, the invention provides a vector encoding a TMP polypeptide which can be expressed in an appropriate host. Such a vector comprises a polynucleotide that encodes a TMP in monomeric or multimer (generally in a tandem structure) arrangement, with or without an Fc domain modification, operatively linked to appropriate expression control sequences. Methods of effecting operative linking, either before or after the DNA molecule is inserted into the vector, are well known in the art. Expression control sequences include promoters, activators, enhancers, operators, ribosomal binding sites, start signals, stop signals, cap signals, polyadenylation signals, and/or other signals involved with the control of transcription or translation. The worker of skill in the art will appreciate that various combinations of these control sequences can be utilized, depending on, for example, the choice of host cell in which the TMP is to be expressed. The resulting vector is transformed into an appropriate host using methods well known in the art.

Host Cells

Any of a large number of available and well-known host cells is used to express a TMP polypeptide. Selection of a host is dependent upon a number of factors including, for example and without limitation, compatibility with the chosen expression vector, toxicity of the expressed TMP encoded by a transformed polynucleotide, rate of transformation, ease of recovery of the expressed TMP, expression characteristics, degree and type of glycosylation, if desired, bio-safety and costs. A balance of these factors must be struck with the understanding that not all host cells may be equally effective for the expression of a particular TMP. Depending upon the host cell employed, the TMP expression product may be glycosylated with mammalian or other eukaryotic carbohydrates, or it may be non-glycosylated. The TMP expression product may also include an initial methionine amino acid residue (at amino acid residue position –1) if expressed in, for example, a bacterial host cell. Within these general guidelines, useful host cells include bacteria, yeast and other fungi, insects, plants, mammalian (including human) cells in culture, or other host cells known in the art. Host cells are cultured under conventional fermentation conditions well known in the art to permit expression of the desired compounds and the TMP expression product is purified using techniques also known in the art.

Depending on the host cell utilized to express a TMP, carbohydrate (oligosaccharide) groups may conveniently be attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn—-Ser/Thr, where X can be any amino acid except proline. X is preferably one of the 19 naturally occurring amino acids not counting proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, may confer acidic properties to the glycosylated compound. Such site(s) may be incorporated in the linker of the compounds of this invention and are preferably glycosylated by a cell during recombinant production of the polypeptide compounds (e.g., in mammalian cells such as CHO, BHK, COS). However, such sites may further be glycosylated by synthetic or semi-synthetic procedures known in the art.

WSP Modification of a Compound

A process for preparing conjugation derivatives is also contemplated. Tumor cells, for example, exhibit epitopes not found on their normal counterparts. Such epitopes include, for example, different post-translational modifications resulting from their rapid proliferation. Thus, one aspect of this invention is a process comprising: a) selecting at least one randomized peptide that specifically binds to a target epitope; and b) preparing a pharmacologic agent comprising (i) at least one vehicle (Fc domain preferred), (ii) at least one amino acid sequence of the selected peptide or peptides, and (iii) an effector molecule.

In one aspect, the target epitope is a tumor-specific epitope or an epitope specific to a pathogenic organism. The effector molecule may be any of the above-noted conjugation partners and is preferably a radioisotope.

For obtaining a compound, with or without an Fc modification and/or linker(s), modified to include a covalently attached to WSP, any method described herein or otherwise known in the art is employed. By way of example and without limitation, a reductive alkylation chemical modification procedure method may be utilized. An alternative method for WSP modification is described in Francis et al., In: Stability of protein pharmaceuticals: in vivo pathways of degradation and strategies for protein stabilization (Eds. Ahern., T. and Manning, M. C.) Plenum, N.Y., 1991, is used. In still another aspect, the method described in Delgado et al., "Coupling of PEG to Protein By Activation With Tresyl Chloride, Applications In Immunoaffinity Cell Preparation", In: Fisher et al., eds., Separations Using Aqueous Phase Systems, Applications In Cell Biology and Biotechnology, Plenum Press, N.Y.N.Y., 1989 pp. 211-213, which involves the use of tresyl chloride, which results in no linkage group between the WSP moiety and the TMP polypeptide moiety. This alternative method, however, may be difficult to use to produce therapeutic products as the use of tresyl chloride may produce toxic by-products. In other aspects, attachment of a WSP is effected through use of N-hydroxy succinimidyl esters of carboxymethyl methoxy polyethylene glycol, as well known in the art.

Depending on the method of WSP attachment chosen, the proportion of WSP molecules attached to the target peptide or protein molecule will vary, as will their concentrations in the reaction mixture. In general, the optimum ratio (in terms of efficiency of reaction in that there is no excess unreacted protein or polymer) is determined by the molecular weight of the WSP selected. In addition, when using methods that involve non-specific attachment and later purification of a desired species, the ratio may depend on the number of reactive groups (typically amino groups) available.

Reductive Alkylation

In one aspect, covalent attachment of a WSP to a TMP, with or without Fc modification and with or without a linker, is carried out by reductive alkylation chemical modification procedures as provided herein to selectively modify the N-terminal α-amino group, and testing the resultant product for the desired biological characteristic, such as the biological activity assays provided herein.

Reductive alkylation for attachment of a WSP to a protein or peptide exploits differential reactivity of different types of primary amino groups (e.g., lysine versus the N-terminal) available for derivatization in a particular protein. Under the appropriate reaction conditions, substantially selective derivatization of the protein at the N-terminus with a carbonyl group containing polymer is achieved.

Using reductive alkylation, the reducing agent should be stable in aqueous solution and preferably be able to reduce only the Schiff base formed in the initial process of reductive alkylation. Reducing agents are selected from, and without limitation, sodium borohydride, sodium cyanoborohydride, dimethylamine borate, timethylamine borate and pyridine borate.

The reaction pH affects the ratio of polymer to protein to be used. In general, if the reaction pH is lower than the pKa of a target reactive group, a larger excess of polymer to protein will be desired. If the pH is higher than the target pKa, the polymer:protein ratio need not be as large (i.e., more reactive groups are available, so fewer polymer molecules are needed).

Accordingly, the reaction is performed in one aspect at a pH which allows one to take advantage of the pKa differences between the ε-amino groups of the lysine residues and that of the α-amino group of the N-terminal residue of the protein. By such selective derivatization, attachment of a water soluble polymer to a protein is controlled; the conjugation with the polymer takes place predominantly at the N-terminus of the protein and no significant modification of other reactive groups, such as the lysine side chain amino groups, occurs.

In one aspect, therefore, methods are provided for covalent attachment of a WSP to a target TMP and which provide a substantially homogenous preparation of WSP/protein conjugate molecules, in the absence of further extensive purification as is required using other chemical modification chemistries. More specifically, if polyethylene glycol is used, methods described allow for production of an N-terminally PEGylated protein lacking possibly antigenic linkage groups, i.e., the polyethylene glycol moiety is directly coupled to the protein moiety without potentially toxic by-products.

Purification of a WSP-modified Compound

The method of obtaining a substantially homogeneous WSP-TMP preparation is, in one aspect, by purification of a predominantly single species of modified TMP from a mixture of TMP species. By way of example, a substantially homogeneous TMP species is first separated by ion exchange chromatography to obtain material having a charge characteristic of a single species (even though other species having the same apparent charge may be present), and then the desired species is separated using size exclusion chromatography. Other methods are reported and contemplated by the invention, includes for example, PCT WO 90/04606, published May 3, 1990, which describes a process for fractionating a mixture of PEG-protein adducts comprising partitioning the PEG/protein adducts in a PEG-containing aqueous biphasic system.

Thus, one aspect of the present invention is a method for preparing a WSP-TMP conjugate comprised of (a) reacting a TMP having more than one amino group with a water soluble polymer moiety under reducing alkylation conditions, at a pH suitable to selectively activate the α-amino group at the amino terminus of the protein moiety so that said water soluble polymer selectively attaches to said α-amino group; and (b) obtaining the reaction product. Optionally, and particularly for a therapeutic product, the reaction products are separated from unreacted moieties.

Bioassays

For assessing biological activity for a preparation of the invention, standard assays are contemplated, such as, for example and without limitation, those described in WO95/26746 entitled "Compositions and Methods for Stimulating Megakaryocyte Growth and Differentiation" and in U.S. Pat. No. 6,835,809, incorporated herein in its entirety.

In one such assay, normal mice of similar age are administered a preparation of the invention either with a bolus treatment or continuous delivery. Compounds administered include any preparation, whether in pharmaceutical composition for or not, with appropriate control(s).

Mice are bled at specified time points, generally with a minimum number of bleeds per week. At a set end time point, blood parameters, for example, white blood cells, red blood cells, hematocrit, hemoglobin, platelets, neutrophils are measured.

Pharmaceutical Compositions

The present invention also provides methods of using pharmaceutical compositions of the inventive compounds. Such pharmaceutical compositions may be for administration for injection, or for oral, pulmonary, nasal, transdermal or other forms of administration. In general, the invention encompasses pharmaceutical compositions comprising effective amounts of a compound of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hyaluronic acid may also be used, and this may have the effect of promoting sustained duration in the circulation. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder, such as lyophilized form. Implantable sustained release formulations are also contemplated, as are transdermal formulations.

Oral Dosage Forms

Contemplated for use herein are oral solid dosage forms, which are described generally in Chapter 89 of Remington's Pharmaceutical Sciences (1990), 18th Ed., Mack Publishing Co. Easton Pa. 18042, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given in Chapter 10 of Marshall, K., Modern Pharmaceutics (1979), edited by G. S. Banker and C. T. Rhodes, herein incorporated by reference. In general, the formulation will include the inventive compound, and inert ingredients which allow for protection against the stomach environment, and release of the biologically active material in the intestine.

If necessary, the compounds may be chemically modified so that oral delivery is efficacious. Generally, the chemical modification contemplated is the attachment of at least one moiety to the compound molecule itself, where said moiety permits (a) inhibition of proteolysis; and (b) uptake into the blood stream from the stomach or intestine. Also desired is the increase in overall stability of the compound and increase in circulation time in the body. Moieties useful as covalently attached vehicles in this invention may also be used for this purpose. Examples of such moieties include: PEG, copolymers of ethylene glycol and propylene glycol, carboxymethyl cellulose, dextran, polyvinyl alcohol, polyvinyl pyrrolidone and polyproline. See, for example, Abuchowski and Davis, Soluble Polymer-Enzyme Adducts, Enzymes as Drugs (1981), Hocenberg and Roberts, eds., Wiley-Interscience, New York, N.Y., pp 367-83; Newmark, et al. (1982), J. Appl. Biochem. 4:185-9. Other polymers that could be used are poly-1,3-dioxolane and poly-1,3,6-tioxocane. In one aspect, PEG moieties are provided for pharmaceutical usage, as indicated above.

For oral delivery dosage forms, it is also possible to use a salt of a modified aliphatic amino acid, such as sodium N-(8-[2-hydroxybenzoyl]amino)caprylate (SNAC), as a carrier to enhance absorption of the therapeutic compounds of this invention. The clinical efficacy of a heparin formulation using SNAC has been demonstrated in a Phase II trial conducted by Emisphere Technologies. See U.S. Pat. No. 5,792,451, "Oral drug delivery composition and methods".

The compounds of this invention can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the compound of the invention with an inert material. These diluents could include carbohydrates, especially mannitol, α-lactose, anhydrous lactose, cellulose, sucrose, modified dextrans and starch. Certain inorganic salts may also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the compound of this invention into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethonium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives may also be included in the formulation to enhance uptake of the compound. Additives potentially having this property are for instance the fatty acids oleic acid, linoleic acid and linolenic acid.

Controlled release formulation may be desirable. The compound of this invention could be incorporated into an inert matrix which permits release by either diffusion or leaching mechanisms e.g., gums. Slowly degenerating matrices may also be incorporated into the formulation, e.g., alginates, polysaccharides. Another form of a controlled release of the compounds of this invention is by a method based on the Oros therapeutic system (Alza Corp.), i.e., the drug is enclosed in a semipermeable membrane which allows water to enter and push drug out through a single small opening due to osmotic effects. Some enteric coatings also have a delayed release effect.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Pulmonary Delivery Forms

Also contemplated herein is pulmonary delivery of the present protein (or derivatives thereof). The protein (or derivative) is delivered to the lungs of a mammal while inhaling and traverses across the lung epithelial lining to the blood stream. (Other reports of this include Adjei et al., Pharma. Res. (1990) 7: 565-9; Adjei et al. (1990), Internatl. J. Pharmaceutics 63: 135-44 (leuprolide acetate); Braquet et al. (1989), J. Cardiovasc. Pharmacol. 13 (suppl. 5): s. 143-146 (endothelin-1); Hubbard et al. (1989), Annals Int. Med. 3: 206-12 (α1-antitrypsin); Smith et al. (1989), J. Clin. Invest. 84: 1145-6 (α1-proteinase); Oswein et al. (March 1990), "Aerosolization of Proteins", Proc. Symp. Resp. Drug Delivery II, Keystone, Colo. (recombinant human growth hormone); Debs et al. (1988), J. Immunol. 140: 3482-8 (interferon-γ and tumor necrosis factor α) and Platz et al., U.S. Pat. No. 5,284,656 (granulocyte colony stimulating factor).

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the inventive compound. Typically, each formulation is specific to the type of device employed and may involve the use of an appropriate propellant material, in addition to diluents, adjuvants and/or carriers useful in therapy.

The inventive compound should most advantageously be prepared in particulate form with an average particle size of less than 10 μm (or microns), most preferably 0.5 to 5 μm, for most effective delivery to the distal lung.

Pharmaceutically acceptable carriers include carbohydrates such as trehalose, mannitol, xylitol, sucrose, lactose, and sorbitol. Other ingredients for use in formulations may include DPPC, DOPE, DSPC and DOPC. Natural or synthetic surfactants may be used. PEG may be used (even apart from its use in derivatizing the protein or analog). Dextrans, such as cyclodextran, may be used. Bile salts and other related enhancers may be used. Cellulose and cellulose derivatives may be used. Amino acids may be used, such as use in a buffer formulation.

Also, the use of liposomes, microcapsules or microspheres, inclusion complexes, or other types of carriers is contemplated.

Formulations suitable for use with a nebulizer, either jet or ultrasonic, will typically comprise the inventive compound dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the inventive compound suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the inventive compound and may also include a bulking agent, such as lactose, sorbitol, sucrose, mannitol, trehalose, or xylitol in amounts which facilitate dispersal of the powder from the device, e.g., 50 to 90% by weight of the formulation.

Nasal Delivery Forms

Nasal delivery of the inventive compound is also contemplated. Nasal delivery allows the passage of the protein to the blood stream directly after administering the therapeutic product to the nose, without the necessity for deposition of the product in the lung. Formulations for nasal delivery include those with dextran or cyclodextran. Delivery via transport across other mucous membranes is also contemplated.

Buccal Delivery Forms

Buccal delivery of the inventive compound is also contemplated. Buccal delivery formulations are known in the art for use with peptides.

Dosages

The dosage regimen involved in a method for treating the above-described conditions will be determined by the attending physician, considering various factors which modify the action of drugs, e.g. the age, condition, body weight, sex and diet of the patient, the severity of any infection, time of administration and other clinical factors. Generally, the daily regimen should be in the range of 0.1-1000 micrograms of the inventive compound per kilogram of body weight, preferably 0.1-150 micrograms per kilogram.

Provided herein are pharmaceutical compositions comprising preparations of the invention. Such pharmaceutical compositions may be for administration for injection, or for oral, nasal, transdermal or other forms of administration, including, e.g., by intravenous, intradermal, intramuscular, intramammary, intraperitoneal, intrathecal, intraocular, retrobulbar, intrapulmonary (e.g., aerosolized drugs) or subcutaneous injection (including depot administration for long term release); by sublingual, anal, vaginal, or by surgical implantation, e.g., embedded under the splenic capsule, brain, or in the cornea. The treatment may consist of a single dose or a plurality of doses over a period of time. In general, comprehended by the invention are pharmaceutical compositions comprising effective amounts of a compound of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hyaluronic acid may also be used, and this may have the effect of promoting sustained duration in the circulation. The pharmaceutical compositions optionally may include still other pharmaceutically acceptable liquid, semisolid, or solid diluents that serve as pharmaceutical vehicles, excipients, or media, including but are not limited to, polyoxyethylene sorbitan monolaurate, magnesium stearate, methyl- and propylhydroxybenzoate, starches, sucrose, dextrose, gum acacia, calcium phosphate, mineral oil, cocoa butter, and oil of *theobroma*. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder, such as lyophilized form. Implantable sustained release formulations are also contemplated, as are transdermal formulations.

The therapeutic methods, compositions and compounds of the present invention may also be employed, alone or in combination with other cytokines, soluble c-Mp1 receptor, hematopoietic factors, interleukins, growth factors or antibodies in the treatment of disease states characterized by other symptoms as well as platelet deficiencies. It is anticipated that the preparations of the invention will prove useful in treating some forms of thrombocytopenia in combination with general stimulators of hematopoiesis, such as IL-3 or GM-CSF. Other megakaryocytic stimulatory factors, i.e., meg-CSF, stem cell factor (SCF), leukemia inhibitory factor (LIF), oncostatin M (OSM), or other molecules with megakaryocyte stimulating activity may also be employed with Mp1 ligand.

Additional exemplary cytokines or hematopoietic factors for such co-administration include IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IL-7, IL-8, IL-9, IL-10, IL-12, IL-13, IL-14, IL-15, IL-16, IL-17, IL-18, thrombopoietin (TPO), angiopoietins, for example Ang-1, Ang-2, Ang-4, Ang-Y, the human angiopoietin-like polypeptide, vascular endothelial growth factor (VEGF), angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor, cytokine-induced neutrophil chemotactic factor 1, cytokine-induced neutrophil, chemotactic factor 2α, cytokine-induced neutrophil chemotactic factor 2β, β endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor α1, glial cell line-derived neutrophic factor receptor α2, growth related protein, growth related protein α, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor receptor, TNF, including TNF0, TNF1, TNF2, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, vascular endothelial growth factor, and chimeric proteins and biologically or immunologically active fragments thereof.

It may further be useful to administer, either simultaneously or sequentially, an effective amount of a soluble mammalian c-Mp1, which appears to have an effect of causing megakaryocytes to fragment into platelets once the megakaryocytes have reached mature form. Thus, administration of a preparation of the invention (to enhance the number of mature megakaryocytes) followed by administration of the soluble c-Mp1 (to inactivate the ligand and allow the mature megakaryocytes to produce platelets) is expected to be a particularly effective means of stimulating platelet production. The dosage recited above would be adjusted to compensate for such additional components in the therapeutic composition. Progress of the treated patient can be monitored by conventional methods.

Therapeutic Uses

For the compounds herein, one can utilize such standard assays as those described in WO95/26746 entitled "Compositions and Methods for Stimulating Megakaryocyte Growth and Differentiation". In vivo assays also appear in the Examples hereinafter.

The conditions to be treated are generally those that involve an existing megakaryocyte/platelet deficiency or an expected megakaryocyte/platelet deficiency (e.g., because of planned surgery or platelet donation). Such conditions will usually be the result of a deficiency (temporary or permanent) of active thrombopoietin in vivo. The generic term for platelet deficiency is thrombocytopenia, and the methods and compositions of the present invention are generally available for treating thrombocytopenia in patients in need thereof.

Thrombocytopenia (platelet deficiencies) may be present for various reasons, including chemotherapy and other therapy with a variety of drugs, radiation therapy, surgery, accidental blood loss, and other specific disease conditions. Exemplary specific disease conditions that involve thrombocytopenia and may be treated in accordance with this invention are: aplastic anemia; idiopathic or immune thrombocytopenia (ITP), including idiopathic thrombocytopenic purpura associated with breast cancer; HIV associated ITP and HIV-related thrombotic thrombocytopenic purpura; metastatic tumors which result in thrombocytopenia; systemic lupus erythematosus; including neonatal lupus syndrome splenomegaly; Fanconi's syndrome; vitamin B12 deficiency; folic acid deficiency; May-Hegglin anomaly; Wiskott-Aldrich syndrome; chronic liver disease; myelodysplastic syndrome associated with thrombocytopenia; paroxysmal nocturnal hemoglobinuria; acute profound thrombocytopenia following C7E3 Fab (Abciximab) therapy; alloimmune thrombocytopenia, including maternal alloimmune thrombocytopenia; thrombocytopenia associated with antiphospholipid antibodies and thrombosis; autoimmune thrombocytopenia; drug-induced immune thrombocytopenia, including carboplatin-induced thrombocytopenia, heparin-induced thrombocytopenia; fetal thrombocytopenia; gestational thrombocytopenia; Hughes' syndrome; lupoid thrombocytopenia; accidental and/or massive blood loss; myeloproliferative disorders; thrombocytopenia in patients with malignancies; thrombotic thrombocytopenia purpura, including thrombotic microangiopathy manifesting as thrombotic thrombocytopenic purpura/hemolytic uremic syndrome in cancer patients; autoimmune hemolytic anemia; occult jejunal diverticulum perforation; pure red cell aplasia; autoimmune thrombocytopenia; nephropathia epidemica; rifampicin-associated acute renal failure; Paris-Trousseau thrombocytopenia; neonatal alloimmune thrombocytopenia; paroxysmal nocturnal hemoglobinuria; hematologic changes in stomach cancer; hemolytic uremic syndromes in childhood; hematologic manifestations related to viral infection including hepatitis A virus and CMV-associated thrombocytopenia. Other hepatic diseases or conditions that involve thrombocytopenia and may be treated in accordance with this invention, in addition to viral hepatitis A (HAV) include, but are not limited to, alcoholic hepatitis, autoimmune hepatitis, drug-induced hepatitis, epidemic hepatitis, infectious hepatitis, long-incubation hepatitis, noninfectious hepatitis, serum hepatitis, short-incubation hepatitis, toxic hepatitis, transfusion hepatitis, viral hepatitis B (HBV), viral hepatitis C(HCV), viral hepatitis D (HDV), delta hepatitis, viral hepatitis E (HEV), viral hepatitis F (HFV), viral hepatitis G (HGV), liver disease, inflammation of the liver, hepatic failure, and other hepatic disease. Also, certain treatments for AIDS result in thrombocytopenia (e.g., AZT). Certain wound healing disorders might also benefit from an increase in platelet numbers.

With regard to anticipated platelet deficiencies, e.g., due to future surgery, a compound of the present invention could be administered several days to several hours prior to the need for platelets. With regard to acute situations, e.g., accidental and massive blood loss, a compound of this invention could be administered along with blood or purified platelets.

The compounds of this invention may also be useful in stimulating certain cell types other than megakaryocytes if such cells are found to express Mp1 receptor. Conditions associated with such cells that express the Mp1 receptor, which are responsive to stimulation by the Mp1 ligand, are also within the scope of this invention.

In addition, the compounds of this invention may be used in any situation in which production of platelets or platelet precursor cells is desired, or in which stimulation of the c-Mp1 receptor is desired. Thus, for example, the compounds of this invention may be used to treat any condition in a mammal wherein there is a need of platelets, megakaryocytes, and the like. Such conditions are described in detail in the following exemplary sources: WO95/26746; WO95/21919; WO95/18858; WO95/21920 and are incorporated herein.

The compounds of this invention may also be useful in maintaining the viability or storage life of platelets and/or megakaryocytes and related cells. Accordingly, it could be useful to include an effective amount of one or more such compounds in a composition containing such cells.

The therapeutic methods, compositions and compounds of the present invention may also be employed, alone or in combination with other cytokines, soluble Mp1 receptor, hematopoietic factors, interleukins, growth factors or antibodies in the treatment of disease states characterized by other symptoms as well as platelet deficiencies. It is anticipated that the inventive compound will prove useful in treating some forms of thrombocytopenia in combination with general stimulators of hematopoiesis, such as IL-3 or GM-CSF. Other megakaryocytic stimulatory factors, i.e., meg-CSF, stem cell factor (SCF), leukemia inhibitory factor (LIF), oncostatin M (OSM), or other molecules with megakaryocyte stimulating activity may also be employed with Mp1 ligand. Additional exemplary cytokines or hematopoietic factors for such co-administration include IL-1 alpha, IL-1 beta, IL-2, IL-3, IL-4, IL-5, IL-6, IL-11, colony stimulating factor-1 (CSF-1), SCF, GM-CSF, granulocyte colony stimulating factor (G-CSF), EPO, interferon-alpha (IFN-alpha), consensus interferon, IFN-beta, or IFN-gamma. It may further be useful to administer, either simultaneously or sequentially, an effective amount of a soluble mammalian Mp1 receptor, which appears to have an effect of causing megakaryocytes to fragment into platelets once the megakaryocytes have reached mature form. Thus, administration of an inventive compound (to enhance the number of mature megakaryocytes) followed by administration of the soluble Mp1 receptor (to inactivate the ligand and allow the mature megakaryocytes to produce platelets) is expected to be a particularly effective means of stimulating platelet production. The dosage recited above would be adjusted to compensate for such additional components in the therapeutic composition. Progress of the treated patient can be monitored by conventional methods.

In cases where the inventive compounds are added to compositions of platelets and/or megakaryocytes and related cells, the amount to be included will generally be ascertained experimentally by techniques and assays known in the art. An exemplary range of amounts is 0.1 µg-1 mg inventive compound per $10^6$ cells.

In addition to therapeutic uses, the compounds of the present invention are useful in diagnosing diseases characterized by dysfunction of their associated protein of interest. In one embodiment, a method of detecting in a biological sample a protein of interest (e.g., a receptor) that is capable of being activated comprising the steps of: (a) contacting the sample with a compound of this invention; and (b) detecting activation of the protein of interest by the compound. The biological samples include tissue specimens, intact cells, or extracts thereof. The compounds of this invention may be used as part of a diagnostic kit to detect the presence of their associated proteins of interest in a biological sample. Such kits employ the compounds of the invention having an attached label to allow for detection. The compounds are useful for identifying normal or abnormal proteins of interest.

It is understood that the application of the teachings of the present invention to a specific problem or situation will be within the capabilities of one having ordinary skill in the art in light of the teachings contained herein. Examples of the products of the present invention and representative processes for their isolation, use, and manufacture appear below.

EXAMPLES

The following sets forth exemplary methods for making some of the compounds of the first group disclosed herein.

Materials and Methods

All amino acid derivatives (all of L-configurations) and resins used in peptide synthesis may be purchased from Novabiochem. Peptide synthesis reagents (DCC, HOBt, etc.) may be purchased in the solution forms from Applied Biosystems, Inc. The two PEG derivatives are from Shearwater Polymers, Inc. All solvents (dichloromethane, N-methylpyrrolidinone, methanol, acetonitrile) are from EM Sciences. Analytical HPLC is run on a Beckman system with a Vydac column (0.46 cm×25 cm, C18 reversed phase, 5 mm), at a flow rate of 1 ml/min and with dual UV detection at 220 and 280 nm. Linear gradients are used for all HPLC operations with two mobile phases: Buffer A—$H_2O$ (0.1% TFA) and Buffer B—acetonitrile (0.1% TFA). The TPO mimetics referred to herein are provided in Tables 1-6, 8, 10, and 12, and some of them are further illustrated in FIGS. 2 through 4.

Peptide Synthesis

Peptides are prepared using a variety of methods known in the art, including the well established stepwise solid phase synthesis method. Solid-phase synthesis with Fmoc chemistry is carried out using an ABI Peptide Synthesizer. Typically, peptide synthesis begins with a preloaded Wang resin on a 0.1 mmol scale. Fmoc deprotection is carried out with the standard piperidine protocol. The coupling is effected using DCC/HOBt. Side-chain protecting groups were: Glu(O-t-Bu), Thr(t-Bu), Arg(Pbf), Gln(Trt), Trp(t-Boc) and Cys(Trt). For the first peptide precursor for pegylation, Dde is used for side chain protection of the Lys on the linker and Boc-Ile-OH is used for the last coupling. Dde is removed by using anhydrous hydrazine (2% in NMP, 3×2 min), followed by coupling with bromoacetic anhydride preformed by the action of DCC.

For peptide 18, the cysteine side chain in the linker is protected by a trityl group. The final deprotection and cleavage of all peptidyl-resins is effected at RT for 4 hr, using trifluoroacetic acid (TFA) containing 2.5% H$_2$O, 5% phenol, 2.5% triisopropylsilane and 2.5% thioanisole. After removal of TFA, the cleaved peptide is precipitated with cold anhydrous ether. Disulfide formation of the cyclic peptide is performed directly on the crude material by using 15% DMSO in H$_2$O (pH 7.5). All crude peptides are purified by preparative reverse phase HPLC and the structures are confirmed by ESI-MS and amino acid analysis.

Peptides are also prepared by phage library generation. The details on library generation methods and phage panning methods were described previously (see PCT/US02/32657 and US/2003/0176352). Phage panning methods are also performed using biotinylated MPL in the range of 10-0.01 μg per 100 μL of Streptavidin Dynabeads (Dynal, Lake Success, N.Y.). After phage are bound to the beads, they are washed 20-50 times before they are eluted. Phage ELISA for TPO-like activity and sequencing analysis are performed as described previously (PCT/US02/32657 and US/2003/0176352).

Alternatively, all peptides described in the application could also be prepared by using the t-Boc chemistry. In this case, the starting resins would be the classic Merrifield or Pam resin, and side chain protecting groups would be: Glu(OBzl), Thr(Bzl), Arg(Tos), Trp(CHO), Cys(p-MeBzl). Hydrogen fluoride (HF) would be used for the final cleavage of the peptidyl resins.

All peptides and tandem dimeric peptides described in herein that have linkers composed of natural amino acids can also be prepared by recombinant DNA technology.

PEGylation

A novel, convergent strategy for the pegylation of synthetic peptides was developed which consists of combining, through forming a conjugate linkage in solution, a peptide and a PEG moiety, each bearing a special functionality that is mutually reactive toward the other. The precursor peptides can be easily prepared with the conventional solid phase synthesis as described above. As described below, these peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The pegylated peptides can be easily purified by preparative HPLC and characterized by analytical HPLC, amino acid analysis and laser desorption mass spectrometry.

Bioactivity Assay

The TPO in vitro bioassay is a mitogenic assay utilizing an IL-3 dependent clone of murine 32D cells that have been transfected with human mp1 receptor. This assay is described in greater detail in WO 95/26746. Cells are maintained in MEM medium containing 10% Fetal Clone II and 1 ng/ml mIL-3. Prior to sample addition, cells are prepared by rinsing twice with growth medium lacking mIL-3. An extended twelve point TPO standard curve is prepared, ranging from 3333 to 39 pg/ml. Four dilutions, estimated to fall within the linear portion of the standard curve, (1000 to 125 pg/ml), are prepared for each sample and run in triplicate. A volume of 100 Φ1 of each dilution of sample or standard is added to appropriate wells of a 96 well microtiter plate containing 10,000 cells/well. After forty-four hours at 37EC and 10% CO$_2$, MTS (a tetrazolium compound which is bioreduced by cells to a formazan) is added to each well. Approximately six hours later, the optical density is read on a plate reader at 490 nm. A dose response curve (log TPO concentration vs. O.D.-Background) is generated and linear regression analysis of points which fall in the linear portion of the standard curve is performed. Concentrations of unknown test samples are determined using the resulting linear equation and a correction for the dilution factor. The TPO in vivo bioassay tests for platelet production in mice after administration of the compounds of the invention.

Abbreviations

HPLC: high performance liquid chromatography; ESI-MS: Electron spray ionization mass spectrometry; MALDI-MS: Matrix-assisted laser desorption ionization mass spectrometry; PEG: Poly(ethylene glycol). All amino acids are represented in the standard three-letter or single-letter codes. t-Boc: tert-Butoxycarbonyl; tBu: tert-Butyl; Bzl: Benzyl; DCC: Dicylcohexylcarbodiimide; HOBt: 1-Hydroxybenzotriazole; NMP: N-methyl-2-pyrrolidinone; Pbf: 2,2,4,6,7-pendamethyldihydro-benzofuran-5-sulfonyl; Trt: trityl; Dde: 1-(4,4-dimethyl-2,6-dioxo-cyclohexylidene)ethyl.

Results

TMP Monomers, Multimers and Fc-TMP Fusion Proteins

A series of TPO-mimetic peptides and TPO-mimetic fusion proteins were synthesized. TPO-mimetic peptides are readily synthesized by conventional solid phase peptide synthesis methods (Merrifiled, R. B., Journal of the American Chemical Society 85:2149 (1963)) with either Fmoc or t-Boc chemistry, by phage peptide library synthesis, or any other method known in the art. In such libraries, random peptide sequences are displayed by fusion with coat proteins of filamentous phage. Typically, the displayed peptides are affinity-eluted against an antibody-immobilized extracellular domain of a receptor. The retained phages may be enriched by successive rounds of affinity purification and repropagation. The best binding peptides may be sequenced to identify key residues within one or more structurally related families of peptides.

The synthetic peptides are tested directly for biological activity (platelet number: 10$^9$ cells/L) in vivo in mice (see FIGS. 2 and 3) or for relative activity in vitro (see Table 2 and Table 7). As the test results showed (see FIGS. 2 and 3), some TPO-mimetic peptides and TPO-mimetic fusion proteins are more effective than others in stimulating platelet production in mice.

Tables 1-10 and 12 set out some of the TPO-mimetic peptides of the invention. Bolded amino acids indicate Y$^1$—Y$^7$ amino acids. The string of N-terminal amino acids at the N-terminus of the bolded amino acids are part of the U$^1$ subgroup. The string of C-terminal amino acids at the C-terminus of the bolded amino acids are part of the U$^2$ subgroup.

TABLE 1

TPO-Mimetic Peptides

| TPO-Mimetic | AMINO ACID SEQUENCE | SEQ ID NO: |
|---|---|---|
| 8 | QGCSSGGPTQREWLQCRRMQHS | 8 |
| 9 | QGCSSGGPTLREWQQCRRMQHS | 9 |
| 10 | QGCSWGGPTLKIWLQCVRAKHS | 10 |
| 11 | QGCSWGCPTLKNWLQCVRAKHS | 11 |
| 12 | QGCSWGGPTLKLWLQCVRAKHS | 12 |
| 13 | QGCSWGGPTLKHWLQCVRAKHS | 13 |
| 14 | QGGCRSGPTNREWLACREVQHS | 14 |

TABLE 1-continued

TPO-Mimetic Peptides

| TPO-Mimetic | AMINO ACID SEQUENCE | SEQ ID NO: |
|---|---|---|
| 15 | QGTCEQGPTLRQWPLCRQGRHS | 15 |
| 16 | QGTCEQGPTLRLWLLCRQGRHS | 16 |
| 17 | QGTCEQGPTLRIWLLCRQGRHS | 17 |

Table 2 summarizes relative activities (% control activity) of some of the TPO-mimetic fusion proteins of the invention in terms of relative potencies based on in vitro assays as described above. An Fc molecule is fused at either the N-terminus or the C-terminus of the peptide. Some TPO-mimetics comprise an Fc molecule connected at the N-terminus of a dimer of the peptide (see, e.g., Fc-2-(SEQ ID NO: 9)). "Fc-2-peptide" and "Fc-2X-peptide" are used interchangeably to indicate that an Fc molecule is fused at the N-terminus of two copies of a peptide connected in tandem. As with all of the TPO-mimetic compounds, the peptide may be attached at the C-terminus of the Fc molecule with a linker/spacer or inserted into an Fc-Loop, optionally with the use of symmetric or asymmetric linkers/spacers.

TABLE 2

TPO-Mimetic Fusion Proteins

| TPO-Mimetic | % CONTROL ACTIVITY | % ERROR |
|---|---|---|
| Fc-(SEQ ID NO: 9) | 88.5 | 24.9 |
| Fc-2-(SEQ ID NO: 9) | 80.5 | 14.9 |
| Fc-(SEQ ID NO: 11) | 78.6 | 19.1 |
| Fc-2-(SEQ ID NO: 8) | 74.8 | 11.4 |
| Fc-(SEQ ID NO: 12) | 67.4 | 16.0 |
| Fc-(SEQ ID NO: 13) | 60.9 | 7.7 |
| (SEQ ID NO: 10)-Fc | 45.7 | 11.2 |
| Fc-(SEQ ID NO: 10) | 40.5 | 9.8 |
| Fc-2-(SEQ ID NO: 12) | 37.7 | 8.7 |
| Fc-(SEQ ID NO: 15) | 26.2 | 6.1 |
| Fc-(SEQ ID NO: 8) | 25.8 | 6.1 |
| (SEQ ID NO: 15)-Fc | 24.6 | 6.1 |
| Fc-(SEQ ID NO: 13) | 23.2 | 2.5 |
| Fc-2-(SEQ ID NO: 14) | 22.0 | 8.5 |

Table 3 sets out some further TPO-mimetic peptides ($Y^1$—$Y^7$) of the invention. $Y^4$ is designated $Y^4$ in the amino acid sequence because it may comprise any amino acid and the like as set out infra. These peptides were tested and were found to have c-mp1 receptor binding activity.

TABLE 3

TPO-Mimetic Peptides ($Y^1$-$Y^7$)

| TPO-Mimetic | AMINO ACID SEQUENCE | SEQ ID NO: |
|---|---|---|
| 28 | ETLY$^4$QWL | 28 |
| 29 | HTLY$^4$QWL | 29 |
| 30 | KTLY$^4$QWL | 30 |
| 31 | GTGY$^4$QWL | 31 |
| 32 | PTLY$^4$IWL | 32 |
| 33 | PTLY$^4$LWL | 33 |

TABLE 3-continued

TPO-Mimetic Peptides ($Y^1$-$Y^7$)

| TPO-Mimetic | AMINO ACID SEQUENCE | SEQ ID NO: |
|---|---|---|
| 34 | PTLY$^4$EWF | 34 |
| 35 | PTLY$^4$HWL | 35 |
| 36 | PILY$^4$EWL | 36 |
| 37 | KTLY$^4$EWL | 37 |
| 38 | PTLY$^4$LWL | 38 |
| 39 | PMLY$^4$EWL | 39 |
| 40 | PTLY$^4$NWL | 40 |
| 41 | PPLY$^4$EWL | 41 |
| 42 | PTQY$^4$EWQ | 42 |
| 43 | PTLY$^4$EWS | 43 |
| 44 | PTYY$^4$EWL | 44 |
| 45 | PTAY$^4$QWL | 45 |
| 46 | PCLY$^4$QWL | 46 |
| 47 | PTLY$^4$FWL | 47 |
| 48 | PTGY$^4$QWL | 48 |
| 49 | PTLY$^4$HWL | 49 |
| 50 | PILY$^4$IWL | 50 |
| 51 | PTLY$^4$LWL | 51 |
| 52 | PMLY$^4$QWL | 52 |
| 53 | PTLY$^4$NWL | 53 |
| 54 | PTPY$^4$QWL | 54 |
| 55 | PTLY$^4$QWQ | 55 |
| 56 | PTLY$^4$QWS | 56 |
| 57 | PTTY$^4$QWT | 57 |
| 58 | PTLY$^4$WWL | 58 |
| 59 | PTYY$^4$QWL | 59 |
| 60 | PTLY$^4$EWF | 60 |
| 61 | GTLY$^4$EWL | 61 |
| 62 | PTLY$^4$HWL | 62 |
| 63 | PILY$^4$EWL | 63 |
| 64 | PTLY$^4$LWL | 64 |
| 65 | PTQY$^4$EWL | 65 |
| 66 | PTLY$^4$EWS | 66 |
| 67 | PTLY$^4$FWF | 67 |
| 68 | GTLY$^4$QWL | 68 |
| 69 | PTLY$^4$IWL | 69 |
| 70 | PTLY$^4$LWL | 70 |
| 71 | PTLY$^4$NWL | 71 |

TABLE 3-continued

TPO-Mimetic Peptides (Y¹-Y⁷)

| TPO-Mimetic | AMINO ACID SEQUENCE | SEQ ID NO: |
|---|---|---|
| 72 | PTLY⁴QWP | 72 |
| 73 | PTLY⁴WWL | 73 |
| 74 | PTYY⁴QWL | 74 |

Table 4 sets out additional TPO-mimetic peptides contemplated and found to have c-mp1 receptor binding activity.

TABLE 4

TPO-Mimetic Peptides

| AMINO ACID SEQUENCE | SEQ ID NO: |
|---|---|
| KDTEVTAPRLWMVASVDE | 75 |
| REMEGPTMRQWLAYRAVL | 76 |
| CQNAGPTLRCWLAGRAYM | 77 |
| CEREGPTLRCWLATREGS | 78 |
| WRIEGPTLRHWLAARAWD | 79 |
| ANMEGPTLRHWLAMRARV | 80 |
| LDMEGPTLRHWLAARANG | 81 |
| WRMEGPTLRHWLAARAWG | 82 |
| WAMEGPTLRHWLAARAVL | 83 |
| KSMEGPSLRQWLAARAQL | 84 |
| TKIEGPTLRHWLAARAEL | 85 |
| PRIEGPTLRLWLVTRALS | 86 |
| IYMEGPTLRHWLANRAAK | 87 |
| WPIEGATLRQWLKIRAGY | 88 |
| RNMEGPTLRNWLAARAQH | 89 |
| NGIEGPTLRLWLSERAKK | 90 |
| MWMEGPTLRHWLEARARY | 91 |
| YGIDGPTLRHWLAARARY | 92 |
| RIIDGQTLRHWLAAGADP | 93 |
| NGRDGPTVRHRLAGRAQK | 94 |
| THIEGPTLRIWLASRAKA | 95 |
| KGMEGPTLRHWLAARAHL | 96 |
| QRIEGPTLRHWLAARASH | 97 |
| KDTEVTAPRLWMVASVDE | 98 |

Table 5 sets out still other TPO-mimetic peptides contemplated and found to have c-mp1 receptor binding activity.

TABLE 5

TPO-Mimetic Peptides

| AMINO ACID SEQUENCE | SEQ ID NO: |
|---|---|
| ENMEGPTLRHWLAARAHE | 99 |
| SWMEGPTLRHWLMNRATY | 100 |
| SMMEGPTLRHWLAARAKD | 101 |
| QGIEGPTLRLWLAARTHP | 102 |
| YMMEGPTLRHWLATRAGR | 103 |
| GNMEGPTLRHWLAANERD | 104 |
| NRMEGPTLRHWLAERAGS | 105 |
| NMMEGPTLRHWLAARVAA | 106 |
| SPIEGPTLRQQLCARAVK | 107 |
| VQMEGTTLRQWLAERALD | 108 |
| KRKDGHRPRQWLAPLACK | 109 |
| EMMEGPTLRHWLAARAEK | 110 |
| NMIEGPTLRHWLAERASQ | 111 |
| KLMEGPTLRHWLAYRAGL | 112 |
| YMMEGPTLRHWLAARALV | 113 |
| GNMEGPTLRHWLAARALL | 114 |
| WMMEGPTLRHWLAARARY | 115 |
| TDRGGYTLRQWLAARAVL | 116 |
| SAIEGPTLRHWLAWRAML | 117 |
| RAIEGPTLRHCLAAGAGL | 118 |
| VKRKGPTLRHWLAAWAFP | 119 |
| TCMEGPTLRHWLAARAEG | 120 |
| WFMEGPTLRHWLAARAYR | 121 |
| ADIEGPTLRHWLAARALV | 122 |
| WVMEGPTLRHWLAARASL | 123 |
| PPGDGPTLRHWLAARARM | 124 |
| DFMEGPTLRQRVDARAHY | 125 |
| RWIEGPTQRQWLAARAYF | 126 |
| IRMEGPTLRHWLASRAEI | 127 |
| YYLEGPTLRHWLAARAYL | 128 |
| GVIEGPTLRHWLAARAAQ | 129 |
| GAMEGPTLRCWLAASDEK | 130 |
| SVIDGPTLRQRLAARARY | 131 |
| GGIERPTLRHCLAARPTS | 132 |
| TKMEGPTLRHWLAWRAAY | 133 |
| LKMEGPTLRNWLAWRAFQ | 134 |
| GLVEGPTLRFWLAARAAE | 135 |
| GLTDGPNLRHCLAARAPI | 136 |

TABLE 5-continued

TPO-Mimetic Peptides

| AMINO ACID SEQUENCE | SEQ ID NO: |
|---|---|
| DRNKGPTLRHWLAARAHA | 137 |
| ASMVGPKLRHGLAAVAKK | 138 |
| DAIEGPTLRLWLEARRKQ | 139 |
| NIIKRATDREWLDARTAL | 140 |
| GDNEGPSPRVCLAARAVL | 141 |
| EFMEGPTLRHWLASRARV | 142 |
| WGMEGPTLRHWLAARGKR | 143 |
| RWMEGPTLRHWLAERAML | 144 |
| LMVEGPTLRHWLAARWRM | 145 |
| NYIEGPTLRHWLAARAKL | 146 |
| TWMEGPTLRLWLMARALY | 147 |
| QYMEGPTLRHWLAARAAL | 148 |
| AWMEGPTLRHWLAARAAY | 149 |
| KQFEGPPMRRSLAGVNTP | 150 |
| ALMEGPTLRQRLAARAAQ | 151 |
| ARMKGTTLRQWVAARAFV | 152 |
| DKIEIPTVQLRRAAYACQ | 153 |
| YRMEGPTLRHWLAARAGV | 154 |
| ALMEGPTLRHWLAARALM | 155 |
| IWAGGPTLRHWLAARAAL | 156 |
| GWVDGPTLRHWLAARARM | 157 |
| ARMEGPTLRHWLAARAKM | 158 |
| ESMEGASQRHCMAARAGG | 159 |
| MPVDGPVLRTWHAAQAIE | 160 |
| LEHNRPLTNPIPKPRTPIRP | 161 |
| TTMEDPTLRHWLATGAPT | 162 |
| HPIEGPTLRLWLAARARA | 163 |
| FPMEGTTLRHWLAARVQM | 164 |
| RGMNGPTLRHWLEESAKD | 165 |
| DQMEGSMVHQWLARHVWG | 166 |
| RNMEGPTLRHWLAARATY | 167 |
| DGMEGPTLRLWMAARAGE | 168 |
| ASMYGPTVSQRLAARTRG | 169 |
| PMMEGPTLRHWLAARALR | 170 |
| WPMEGPTLRHWLAARAAR | 171 |
| VQMEGPTLRHWLAGRAPN | 172 |
| HGIEGPTHRQWLAARADI | 173 |
| GMMEGPTLRHWLAARAML | 174 |
| HDMEGPTLRHWLALRATG | 175 |
| DNMERTRRRHSLAAHFML | 176 |
| RNMEGPTLRHWLAARADR | 177 |
| WKFEGPTLRQWLTARAFG | 178 |
| RGMEGPTLRQRLVERAQM | 179 |
| DVMEGTTLRQWLACRALM | 180 |
| RKMERATLRQWLTARANM | 181 |
| GTKEGPTLRQWPAARANE | 182 |
| CAIEGPTLRHWLAARAAT | 183 |
| LTMEGPTLRHWLRARAYA | 184 |
| MTMEGPTLRQWFAARADT | 185 |
| SPMEGPTLRHSAAGRPWG | 186 |
| VHMEDPTLRHGNAARAAE | 187 |
| YPMEGPTLRHWLAARARH | 188 |
| GKTQGPKQLKWQVGSSLP | 189 |
| GEMEGPTLLHWRAARAMQ | 190 |
| INMEGPTLRLWLAARAAA | 191 |
| FRIEGPTLRNWLAARAAK | 192 |
| GRMEGPTLRHWLAARAHP | 193 |
| VLLQGHTVRNCMVARVDA | 194 |
| DWIEGPTLRHWLAARALY | 195 |
| SWTEGPTLRHWLAARARN | 196 |
| RELEGPTLRLWLVERARM | 197 |
| VSMEGPTLRNWLAARARM | 198 |
| TTMEGPTLRHWLATRAVD | 199 |
| AKLEGPTLRLWLAERAGR | 200 |
| ARMEGPTLRHWLAARARY | 201 |
| NIMDGPALRHWLPARAIQ | 202 |
| NMIGGPTLGHRLADPAIQ | 203 |
| VWMEGATLRQWLAARALI | 204 |
| RVMEGPTLLQRLAARARS | 205 |
| QPMDEPARRQWLSARAGL | 206 |
| AWTEGPTLRHWLAARGRS | 207 |
| ATMEGPTLRHWLAARAAL | 208 |
| GRMEGPTLRHWLAARALF | 209 |
| ENMQGRTLRHWLAARDYF | 210 |
| KGVEGPTLRLWLAARALM | 211 |
| VEMEGPTLRHWLAARASV | 212 |

TABLE 5-continued

TPO-Mimetic Peptides

| AMINO ACID SEQUENCE | SEQ ID NO: |
|---|---|
| AFIEGPTLKNWLAARAIM | 213 |
| TVMEGPTLRHWLAARSRS | 214 |
| AHMEGPTLRHWLATRAKM | 215 |
| KDIEGPTLRHWLAARANY | 216 |
| RIHDGRKLRQWLTVRDTM | 217 |
| KPIEGPTLKLWLAERMAA | 218 |
| AKDVGTRLRQWLAAGARA | 219 |
| QSQEGPTLRLWLAERAKW | 220 |
| MYTEGATLRQWLAARARI | 221 |
| PKMEGPTRRTRLADRSTS | 222 |
| NVMEGPTLRHWLAYRARM | 223 |
| TWMEGPTLRHWLAARALG | 224 |
| LTMEGPTLRHWLAARATR | 225 |
| YTMEGPTLRHWLAARALH | 226 |
| NEMEGATLRQWLAARAKW | 227 |
| FSKEGATLRQWLAARALD | 228 |
| SNGVCRTLRQWLAARAEE | 229 |
| KGMEGPTLRNWLAERAML | 230 |
| QDMVGPTLRHWLAARARL | 231 |
| YSHEGPTLRHWLAARALL | 232 |
| GVIEGPTLRHWLAARMKV | 233 |
| MHMEGPTLRHWLATRALI | 234 |
| CRSEGPTLRCWLAARAGY | 235 |
| MCIEGPTLRQWQVCRVGL | 236 |
| CRVEGPSQRQCLAARACW | 237 |
| CTMEGPTLRHWLAARACI | 238 |
| CQVDGPTVRHCRAARAGL | 239 |
| CDMAGATLRQWLACRSGT | 240 |
| ICTEGCTLRLWLAERSRV | 241 |
| CGMEGPALRQWLACRAVD | 242 |

Table 6 sets out still other TPO-mimetic peptides having c-mpl receptor binding activity. These peptides are contemplated for use alone or as TPO-mimetic fusion proteins, wherein the TPO-mimetic peptide is fused to either an N-terminus of an Fc region or within an Fc-Loop, a modified Fc molecule. Fc-Loops are described herein and in U.S. Patent Application Publication No. US2006/0140934 incorporated herein by reference in its entirety.

TABLE 6

TPO-Mimetic Peptides

| AMINO ACID SEQUENCE | SEQ ID NO: |
|---|---|
| QGCSSGGPTLREWQQCRRMQHS | 9 |
| QGCSSGGPTLREWQQCVRMQHS | 243 |
| QGCSSGGPTLREWQQCRRAQHS | 244 |
| QGCSSGGPTLREWQQCVRAQHS | 245 |
| IEGQSWEFENDRVPAHSLERVLLLRRVPTEPSGPSICAQIEGPTFKQWQECINGHS | 246 |
| IEGPTFKQWQKCRNMHS | 247 |

TABLE 6-continued

TPO-Mimetic Peptides

| AMINO ACID SEQUENCE | SEQ ID NO: |
|---|---|
| IEGPTFKQWQKLRRVHS | 248 |
| IEGEPVSDGKRRPRVHSLERVDAVHAKVGPSICAQIEGPTFKQWQKCKRAHS | 249 |
| IEGRWPPPQFPVTQQHSLERVGRPPPSVELPRPTFVCAQIEGPTFKQWQRCLREHS | 250 |
| IEGPTFKQWQRWRLLHS | 251 |
| IEGPTFKQWQAWRKKHS | 252 |
| IEGPTFKQWQRWRKMHS | 253 |
| IEGRWPPPQFPVTEHHSLERVGRRPPNAQMPQSIFICGQNEGPTFQYCQRCLREHS | 254 |
| IEGWWQFYFHAKEDHS | 255 |
| PSICAQIEGPTFKQWQTCMRAHS | 256 |
| IEGYVGGPYEQTNSLERVPPTLAWKYGPRTPSICAQIEGPTFKQWQQCLSDHS | 257 |
| IEGPTFKQWQGRSKRHS | 258 |
| IEGWPWQLYVHPEGEHS | 259 |
| IEGWWWQLYFHAKDDHS | 260 |
| IEGPTFKQWQKLRRSHS | 261 |
| IEGWWQFYFHPKEDHS | 262 |
| IEGPTFKQWQKSRTKHS | 263 |
| IEGWTWQFYVHPKGDHS | 264 |
| IEGPTFKQWQAARMHHS | 265 |
| IEGPTFKQWQACLHSHS | 266 |
| IEGWSWQFYAHPQGDHS | 267 |
| IEGPSFTPWFHERRSHS | 268 |
| IEGPTFKQWQWLRRHHS | 269 |
| IEGWWQFYVHAKGDHS | 270 |
| IEGPTFKQWQVWRNRHS | 271 |
| IEGQSWLRRLHWKEEHS | 272 |
| IEGWPWQFYALSRESGTSPSSAARTSSYLRSCAQIEGPTFKQWQICKDQHS | 273 |
| IEGPTFKQWQKWRKTHS | 274 |
| IEGPTFKQWQYWRAKHS | 275 |
| IEGPTFKQWQVRQKTHS | 276 |
| IEGWSWQFYFHAKGDHS | 277 |
| IEGRTWQLYFHAKEEHS | 278 |
| IEGWSWQFYAHPQGDHS | 279 |
| IEGWPRQLYAHAKEDHS | 280 |
| IEGWWWQFYAHPQGDHS | 281 |
| IEGWSWQFYAHPQGDHS | 282 |
| IEGWSWQFYAHPQGDHS | 283 |
| IEGHGSQKPTAARALESTSSLTTRTRTTSICAQQDMVGPTIRQWLAARACI | 284 |

TABLE 6-continued

TPO-Mimetic Peptides

| AMINO ACID SEQUENCE | SEQ ID NO: |
|---|---|
| IEGPTFEQWQHWRRGHS | 285 |
| IEGWIWRQWLAARA | 286 |
| IEGWIWRPWLAARA | 287 |
| IEGYWWYASWAARA | 288 |
| IEGWPWQFYAHPQGDHS | 289 |
| IEGWVWCQWLAARA | 290 |
| IEGPTLHEWLRWLRQHS | 291 |
| IEGWVWRPWLAARA | 292 |
| IEGWVWCPWLAARA | 293 |
| IEGEALVFWWRVRGGHS | 294 |
| IEGWVWCPWLAARA | 295 |
| IEGWVWWPWLAARA | 296 |
| IEGWTWQFYALPRGDHS | 297 |
| IEGWPWQFYALSRESGTSPSSAARTSSYLRSCAQIEGPTFKQWQICKDQHS | 298 |
| IEGPTLRQRLAARA | 299 |
| IEGWSWQFYAHPKGDHS | 300 |
| IEGWVWRQWLAARA | 301 |
| IEGRHYQKWPARRLGHS | 302 |
| LEGFVGTVDWRQGRPHS | 303 |
| IEGQEPTRLRLqMDRHS | 304 |
| IAQVRMLGRFTLLVLSRARAASTQLSFQHSICAQIEGGAQTQWDAARA | 305 |
| IEGEIWAGPGAARA | 306 |
| IEGEALVFWWAARA | 307 |
| IEGSYRERQQAARA | 308 |
| IEGWVWRPWLAARA | 309 |
| IEGWNPWRGAASRV | 310 |
| IEGWTRRQWLAARA | 311 |
| IEGWVWRPWLAARA | 312 |
| IEGPTFKQWQAMRRHS | 313 |
| IEGMVKLGVIRLLVL | 314 |
| IEGPTFKQWQAWRRWHS | 315 |
| IEVWQSHWYQAARALESTSSRLLPMRPPPSICAQIEGPTLPQRMAARA | 316 |
| IEGWTWQFYAHPQGDHS | 317 |
| IEGPTFKQWQALRKRHS | 318 |
| IEGPTFKQWQKLRLGHS | 319 |
| IEGPTFKQWQLMGFPHS | 320 |
| IEGWIWRQWLMQTLWHS | 321 |

TABLE 6-continued

TPO-Mimetic Peptides

| AMINO ACID SEQUENCE | SEQ ID NO: |
|---|---|
| IEGPTFKQWQAMRKNHS | 322 |
| IEGPTFKQWQKWRLSHS | 323 |
| IEGWQEGRQSAARA | 324 |
| IEGPTFKQWQRWLKYHS | 325 |
| IEGNYWFWQQVGQENTLSREWIQTLGQKYWYRPPSICAQIEGWSRHQHYSAMSGHS | 326 |
| IEGPTFKQWQLWRLQHS | 327 |
| IEGPTFKQWQMLRRHHS | 328 |
| IEGPTFKQWQRLRKNHS | 329 |
| IEGLLSQLWQAARA | 330 |
| IEGPSLPEWLHVWRHHS | 331 |
| IEGPTLHEWLAERRKHS | 332 |
| IEGPTLHEWLALLRSHS | 333 |
| IEGPTLHEWLAQRREHS | 334 |
| IEGPTLHEWLLYRRAHS | 335 |
| IEGPTLHEWLRQRRQHS | 336 |

Fc-Loops

As set out above, all of the peptides discussed herein are contemplated for use alone or as TPO-mimetic fusion proteins, wherein the TPO-mimetic peptide is fused to either an N-terminus of an Fc region or within an Fc-Loop, a modified Fc molecule.

Fc-Loops comprising a TPO-mimetic peptide are prepared in a process in which at least one biologically active peptide is incorporated as an internal sequence into an Fc domain. Such an internal sequence may be added by insertion (i.e., between amino acids in the previously existing Fc domain) or by replacement of amino acids in the previously existing Fc domain (i.e., removing amino acids in the previously existing Fc domain and adding peptide amino acids). In the latter case, the number of peptide amino acids added need not correspond to the number of amino acids removed from the previously existing Fc domain. For example, in one aspect, a molecule in which 10 amino acids are removed and 15 amino acids are added is provided. Pharmacologically active compounds provided are prepared by a process comprising: a) selecting at least one peptide that modulates the activity of a protein of interest; and b) preparing a pharmacologic agent comprising an amino acid sequence of the selected peptide as an internal sequence of an Fc domain. This process may be employed to modify an Fc domain that is already linked through an N- or C-terminus or sidechain to a peptide, e.g., as described in U.S. Pat. App. Nos. 2003/0195156, 2003/0176352, 2003/0229023, and 2003/0236193, and international publication numbers WO 00/24770 and WO 04/026329. The process described in U.S. Patent Application Publication No. US2006/0140934 may also be employed to modify an Fc domain that is part of an antibody. In this way, different molecules can be produced that have additional functionalities, such as a binding domain to a different epitope or an additional binding domain to the precursor molecule's existing epitope. Molecules comprising an internal peptide sequence are also referred to as "Fc internal peptibodies" or "Fc internal peptide molecules."

The Fc internal peptide molecules may include more than one peptide sequence in tandem in a particular internal region, and they may include further peptides in other internal regions. While the putative loop regions are preferred, insertions in any other non-terminal domains of the Fc are also considered part of this invention. Variants and derivatives of the above compounds (described below) are also encompassed by this invention.

The compounds of this invention may be prepared by standard synthetic methods, recombinant DNA techniques, or any other methods of preparing peptides and fusion proteins.

A use contemplated for Fc internal peptide molecules is as a therapeutic or a prophylactic agent. A selected peptide may have activity comparable to—or even greater than—the natural ligand mimicked by the peptide. In addition, certain natural ligand-based therapeutic agents might induce antibodies against the patient's own endogenous ligand. In contrast, the unique sequence of the vehicle-linked peptide avoids this pitfall by having little or typically no sequence identity with the natural ligand. Furthermore, the Fc internal peptibodies may have advantages in refolding and purification over N- or C-terminally linked Fc molecules. Further still, Fc internal peptibodies may be more stable in both thermodynamically, due to the stabilization of chimeric domains, and chemically, due to increased resistance to proteolytic degradation from amino- and carboxy-peptidases. Fc internal peptibodies may also exhibit improved pharmacokinetic properties.

In one embodiment, the invention includes Fc-Loop-QGC-SSGGPTLREWQQCRRMQHS (SEQ ID NO: 9) wherein the peptide sequence of SEQ ID NO: 9 is inserted in the Fc molecule (SEQ ID NO: 3) in the loop region between amino acids 139 (Leu) and 140 (Thr) using a linker. In one aspect, the linker comprises four glycine residues at the N-terminus of the amino acid sequence of SEQ ID NO: 9. In another aspect, the linker comprises two glycine residues at the N-terminus and two glycine residues at the C-terminus of SEQ ID NO: 9.

In another embodiment, the invention includes Fc-Loop-QGCSSGGPTLREWQQCVRMQHS (SEQ ID NO: 243) wherein the peptide sequence of SEQ ID NO: 9 is inserted in the Fc molecule (SEQ ID NO: 3) in the loop region between amino acids 139 (L) and 140 (Thr) using a linker. In one aspect, the linker comprises four glycine residues at the N-terminus of the amino acid sequence of SEQ ID NO: 243. In another aspect, the linker comprises two glycine residues at the N-terminus and two glycine residues at the C-terminus of SEQ ID NO: 243.

Other linkers, as discussed in U.S. Patent Application Publication No. US2006/0140934, are also contemplated for use in modifying Fc-Loop molecules in this embodiment.

Table 7 sets out still other TPO-mimetic peptides having c-mp1 receptor binding activity. Like all of the peptides discussed herein, these peptides are contemplated for use alone or as TPO-mimetic fusion proteins, wherein the TPO-mimetic peptide is fused to either an N-terminus of an Fc region or within an Fc-Loop, a modified Fc molecule. Fc-Loops are described in U.S. Patent Application Publication No. US2006/0140934, incorporated herein by reference in its entirety.

The compounds of the invention are screened in dose response assays in hematologically normal mice (BDF1). Platelet numbers are measured every other day until platelets returned to baseline, usually less than three weeks.

The compounds of the invention are also screened using a phage-ELISA. Phage-ELISA methods are described in US 2003/0176352. Phage-ELISA TPO activity of the some of the peptides set out in Table 6 are shown below in Table 7. All ELISA activity values have error values less than 10%. TPO-mimetic peptides with various levels of activity are useful as therapeutics.

TABLE 7

Phage-ELISA Activity of Some TPO-Mimetic Peptides

| AMINO ACID SEQUENCE | SEQ ID NO: | Relative activity |
|---|---|---|
| IEGPTLRQWLAARA (positive control) | 337 | 150 |
| Sequence unknown (negative control) | | <2.0 |
| IEGQSWEFENDRVPAHSLERVLLLRRVPTEPSGPSICAQIEGPTFKQWQECINGHS | 246 | 173.43 |
| IEGPTFKQWQKCRNMHS | 247 | 164.21 |
| IEGPTFKQWQKLRRVHS | 248 | 154.55 |
| IEGEPVSDGKRRPRVHSLERVDAVHAKVGPSICAQIEGPTFKQWQKCKRAHS | 249 | 150.03 |
| IEGRWPPPQFPVTQQHSLERVGRPPPSVELPRPTFVCAQIEGPTFKQWQRCLREHS | 250 | 149.48 |
| IEGPTFKQWQRWRLLHS | 251 | 149.28 |
| IEGPTFKQWQAWRKKHS | 252 | 145.97 |
| IEGPTFKQWQRWRKMHS | 253 | 143.61 |
| IEGRWPPPQFPVTEHHSLERVGRRPPNAQMPQSIFICGQNEGPTFQYCQRCLREHS | 254 | 137.49 |
| IEGWWWQFYPHAKEDHS | 255 | 135.88 |
| PSICAQIEGPTFKQWQTCMRAHS | 256 | 133.12 |
| IEGYVGGPYEQTNSLERVPPTLAWKYGPRTPSICAQIEGPTFKQWQQCLSDHS | 257 | 131.28 |
| IEGPTFKQWQGRSKRHS | 258 | 130.94 |
| IEGWPWQLYVHPEGEHS | 259 | 129.31 |
| IEGWWWQLYFHAKDDHS | 260 | 126.15 |
| IEGPTFKQWQKLRRSHS | 261 | 124.92 |
| IEGWWWQFYFHPKEDHS | 262 | 124.27 |
| IEGPTFKQWQKSRTKHS | 263 | 123.60 |
| IEGWTWQFYVHPKGDHS | 264 | 122.24 |
| IEGPTFKQWQAARMHHS | 265 | 121.50 |

TABLE 7-continued

Phage-ELISA Activity of Some TPO-Mimetic Peptides

| AMINO ACID SEQUENCE | SEQ ID NO: | Relative activity |
|---|---|---|
| IEGPTFKQWQACLHSHS | 266 | 114.00 |
| IEGWSWQFYAHPQGDHS | 267 | 112.55 |
| IEGPSFTPWFHERRSHS | 268 | 109.80 |
| IEGPTFKQWQWLRRHHS | 269 | 109.46 |
| IEGWWWQFYVHAKGDHS | 270 | 108.67 |
| IEGPTFKQWQVWRNRHS | 271 | 108.23 |
| IEGQSWLRRLHWKEEHS | 272 | 108.03 |
| IEGWPWQFYALSRESGTSPSSAARTSSYLRSCAQIEGPTFKQWQICKDQHS | 273 | 105.68 |
| IEGPTFKQWQKWRKTHS | 274 | 105.28 |
| IEGPTFKQWQYWRAKHS | 275 | 105.24 |
| IEGPTFKQWQVRQKTHS | 276 | 105.18 |
| IEGWSWQFYFHAKGDHS | 277 | 103.56 |
| IEGRTWQLYFHAKEEHS | 278 | 101.72 |
| IEGWSWQFYAHPQGDHS | 279 | 98.46 |
| IEGWPRQLYAHAKEDHS | 280 | 95.57 |
| IEGWWWQFYAHPQGDHS | 281 | 94.99 |
| IEGWSWQFYAHPQGDHS | 282 | 93.70 |
| IEGWSWQFYAHPQGDHS | 283 | 93.70 |
| IEGHGSQKPTAARALESTSSLTTRTRTTSICAQQDMVGPTIRQWLAARACI | 284 | 92.11 |
| IEGPTFEQWQHWRRGHS | 285 | 91.49 |
| IEGWIWRQWLAARA | 286 | 91.41 |
| IEGWIWRPWLAARA | 287 | 83.33 |
| IEGYWWYASWAARA | 288 | 80.41 |
| IEGWPWQFYAHPQGDHS | 289 | 80.26 |
| IEGWVWCQWLAARA | 290 | 79.14 |
| IEGPTLHEWLRWLRQHS | 291 | 78.29 |
| IEGWVWRPWLAARA | 292 | 76.04 |
| IEGWVWCPWLAARA | 293 | 74.05 |
| IEGEALVFWWRVRGCHS | 294 | 73.91 |
| IEGWVWCPWLAARA | 295 | 73.05 |
| IEGWVWWPWLAARA | 296 | 63.46 |
| IEGWTWQFYALPRGDHS | 297 | 63.25 |
| IEGWPWQFYALSRESGTSPSSAARTSSYLRSCAQIEGPTFKQWQICKDQHS | 298 | 62.08 |
| IEGPTLRQRLAARA | 299 | 57.27 |
| IEGWSWQFYAHPKGDHS | 300 | 52.59 |
| IEGWVWRQWLAARA | 301 | 52.14 |

TABLE 7-continued

Phage-ELISA Activity of Some TPO-Mimetic Peptides

| AMINO ACID SEQUENCE | SEQ ID NO: | Relative activity |
|---|---|---|
| IEGRHYQKWPARRLGHS | 302 | 51.98 |
| IEGFVGTVDWRQGRPHS | 303 | 49.81 |
| IEGQEPTRLRLQMDRHS | 304 | 48.29 |
| IAQVRMLGRFTLLVLSRARAASTQLSFQHSICAQIEGGAQTQWDAARA | 305 | 47.37 |
| IEGEIWAGPGAARA | 306 | 46.50 |
| IEGEALVFWWAARA | 307 | 40.33 |
| IEGSYRERQQAARA | 308 | 35.23 |
| IEGWVWRPWLAARA | 309 | 33.96 |
| IEGWNPWRGAASRV | 310 | 33.90 |
| IEGWTRRQWLAARA | 311 | 33.29 |
| IEGWVWRPWLAARA | 312 | 28.88 |
| IEGPTFKQWQAMRRHS | 313 | 28.41 |
| IEGMVKLGVIRLLVL | 314 | 28.30 |
| IEGPTFKQWQAWRRWHS | 315 | 28.15 |
| IEVWQSHWYQAARALESTSSRLLPMRPPPSICAQIEGPTLPQRMAARA | 316 | 24.91 |
| IEGWTWQFYAHPQGDHS | 317 | 24.20 |
| IEGPTFKQWQALRKRHS | 318 | 21.63 |
| IEGPTFKQWQKLRLGHS | 319 | 17.86 |
| IEGPTFKQWQLMGFPHS | 320 | 17.79 |
| IEGWIWRQWLMQTLWHS | 321 | 16.43 |
| IEGPTFKQWQAMRKNHS | 322 | 16.35 |
| IEGPTFKQWQKWRLSHS | 323 | 14.65 |
| IEGWQEGRQSAARA | 324 | 13.75 |
| IEGPTFKQWQRWLKYHS | 325 | 13.51 |
| IEGNYWFWQQVGQENTLSREWIQTLGQKYWYRPPSICAQIEGWSRHQHYSAMSGHS | 326 | 13.21 |
| IEGPTFKQWQLWRLQHS | 327 | 12.61 |
| IEGPTFKQWQMLRRHHS | 328 | 12.49 |
| IEGPTFKQWQRLRKNHS | 329 | 12.14 |
| IEGLLSQLWQAARA | 330 | 7.11 |
| IEGPSLPEWLHVWRHHS | 331 | 117.03 |
| IEGPTLHEWLAERRKHS | 332 | 88.36 |
| IEGPTLHEWLALLRSHS | 333 | 80.68 |
| IEGPTLHEWLAQRREHS | 334 | 75.86 |
| IEGPTLHEWLLYRRAHS | 335 | 73.66 |
| IEGPTLHEWLRQRRQHS | 336 | 64.53 |

Table 8 sets out still other TPO-mimetic peptides having c-mp1 receptor binding activity, which were used in the invention.

TABLE 8

TPO-Mimetic Peptides

| AMINO ACID SEQUENCE | SEQ ID NO: |
|---|---|
| YSHCAQGAVPQGPTLKQWLLWRRCAHSLETVES | 338 |
| YSHCAQGYCDEGPTLKQWLVCLGLQHSLETVES | 339 |
| YSHCAQGCSSGGPTLREWLQCRRMQHSLETVES | 340 |
| YSHCAQGCSWGGPTLKQWLQCVRAKHSLETVES | 341 |
| YSHCAQGGCRSGPTLREWLACREVQHSLETVES | 342 |
| YSHCAQGTCEQGPTLRQWLLCRQGRHSLETVES | 343 |

Fc-Loop Insertion Sites

As set out above, all of the peptides discussed herein are contemplated for use alone or as TPO-mimetic fusion proteins, wherein the TPO-mimetic peptide is fused to either an N-terminus of an Fc region or within an Fc-Loop, a modified Fc molecule. Fc-Loops are described in U.S. Patent Application Publication No. US2006/0140934 incorporated herein by reference in its entirety. Preferred internal sites for peptide addition into an Fc-Loop are shown in boldface below:

```
                                          (SEQ ID NO: 3)
  1 MDKTHTCPPC PAPELLGGPS VFLFPPKPKD TLMISRTPEV
    TCVVVDVSHE

51 DPEVKFNWYV DGVEVHNAKT KPREEQYNST YRVVSVLTVL
    HQDWLNGKEY

101 KCKVSNKALP APIEKTISKA KGQPREPQVY TLPPSRDELT
    KNQVSLTCLV

151 KGFYPSDIAV EWESNGQPEN NYKTTPPVLD SDGSFFLYSK
    LTVDKSRWQQ

201 GNVFSCSVMH EALHNHYTQK SLSLSPGK.
```

Particularly preferred sites are the insertion sites (H49/E50), (Y77/N78), (K107/A108), (L139/T140), (E169/N170), (S181/D182), and (G201/N202) of SEQ ID NO: 3. Most preferable are the insertion site (L139/T140) of SEQ ID NO: 3 and two additional loops in the CH2 domain (H49/E50) and (Y77/N78).

In one embodiment, a TPO-mimetic peptide is inserted into the human IgG1 Fc-Loop domain between Leu139 and Thr140 of SEQ ID NO: 3 and includes 2 Gly residues as linkers flanking either side of the inserted peptide.

Other exemplary amino acid sequences of human Fc regions from IgA, IgM and IgG subtypes (SEQ ID NOS: 344 to 351), as set out in Table 9 below, may also be used in the invention in addition to the Fc region set out in SEQ ID NO: 3. A consensus sequence is set out in (SEQ ID NO: 352).

TABLE 9

Amino Acid Sequences of Additional Human Fc Regions

| AMINO ACID SEQUENCE | SEQ ID NO: |
|---|---|
| Ala Gly Lys Ser Val Thr Cys His Val Lys His Tyr Thr Asn Pro Ser Gln Asp Val Thr Val Pro Cys Pro Val Pro Ser Thr Pro Pro Thr Pro Ser Pro Ser Thr Pro Pro Thr Pro Ser Pro Ser Cys Cys His Pro Arg Leu Ser Leu His Arg Pro Ala Leu Glu Asp Leu Leu Leu Gly Ser Glu Ala Asn Leu Thr Cys Thr Leu Thr Gly Leu Arg Asp Ala Ser Gly Val Thr Phe Thr Trp Thr Pro Ser Ser Gly Lys Ser Ala Val Gln Gly Pro Pro Glu Arg Asp Leu Cys Gly Cys Tyr Ser Val Ser Ser Val Leu Pro Gly Cys Ala Glu Pro Trp Asn His Gly Lys Thr Phe Thr Cys Thr Ala Ala Tyr Pro Glu Ser Lys Thr Pro Leu Thr Ala Thr Leu Ser Lys Ser Gly Asn Thr Phe Arg Pro Glu Val His Leu Leu Pro Pro Pro Ser Glu Glu Leu Ala Leu Asn Glu Leu Val Thr Leu Thr Cys Leu Ala Arg Gly Phe Ser Pro Lys Asp Val Leu Val Arg Trp Leu Gln Gly Ser Gln Glu Leu Pro Arg Glu Lys Tyr Leu Thr Trp Ala Ser Arg Gln Glu Pro Ser Gln Gly Thr Thr Thr Phe Ala Val Thr Ser Ile Leu Arg Val Ala Ala Glu Asp Trp Lys Lys Gly Asp Thr Phe Ser Cys Met Val Gly His Glu Ala Leu Pro Leu Ala Phe Thr Gln Lys Thr Ile Asp Arg Leu Ala Gly Lys Pro Thr His Val Asn Val Ser Val Val Met Ala Glu Val Asp Gly Thr Cys Tyr | 344 |
| Asp Gly Lys Ser Val Thr Cys His Val Lys His Tyr Thr Asn Pro Ser Gln Asp Val Thr Val Pro Cys Pro Val Pro Pro Pro Pro Pro Cys Cys His Pro Arg Leu Ser Leu His Arg Pro Ala Leu Glu Asp Leu Leu Leu Gly Ser Glu Ala Asn Leu Thr Cys Thr Leu Thr Gly Leu Arg Asp Ala Ser Gly Ala Thr Phe Thr Thr Thr Pro Ser Ser Gly Lys Ser Ala Val Gln Gly Pro Pro Glu Arg Asp Leu Cys Gly Cys Tyr Ser Val Ser Ser Val Leu Pro Gly Cys Ala Gln Pro Thr Asn His Gly Glu Thr Phe Thr Cys Thr Ala Ala His Pro Glu Leu Lys Thr Pro Leu Thr Ala Asn Ile Thr Lys Ser Gly Asn Thr Phe Arg Pro Glu Val His Leu Leu Pro Pro Pro Ser Glu Glu Leu Ala Leu Asn Glu Leu Val Thr Leu Thr Cys Leu Ala Arg Gly Phe Ser Pro Lys Asp Val Leu Val Arg Trp Leu Gln Gly Ser Gln Glu Leu Pro Arg Glu Lys Tyr Leu Thr Thr Ala Ser Arg Gln Glu Pro Ser Gln Gly Thr Thr Thr Phe Ala Val Thr Ser Ile Leu Arg Val Ala Ala Glu Asp Thr Lys Lys Gly Asp Thr Phe Ser Cys Met Val Gly His Glu Ala Leu Pro Leu Ala Phe Thr Gln Lys Thr Ile Asp Arg Leu Ala Gly Lys Pro Thr His Val Asn Val Ser Val Val Met Ala Glu Val Asp Gly Thr Cys Tyr | 345 |
| Glu Gly Lys Gln Val Gly Ser Gly Val Thr Thr Asp Gln Val Gln Ala Glu Ala Lys Glu Ser Gly Pro Thr Thr Tyr Lys Val Thr Ser Thr Leu Thr Ile Lys Glu Asp His Arg Gly Leu Thr Phe Gln Gln Asn Ala Ser Ser Met Cys Val Pro Asp Gln Asp Thr Ala Ile Arg Val Phe Ala Ile Pro Pro Ser Phe Ala Ser Ile Phe Leu Thr Lys Ser Thr Lys Leu Thr Cys Leu Val Thr Asp Leu Thr Thr Tyr Asp Ser Val Thr Ile Ser Thr Asn Ser Gly Glu Ala Phe Thr Cys Thr Val Thr His Thr Asp Leu Pro Ser Pro Leu Lys Gln Thr Ile Ser Arg Pro Lys Gly Val Ala Leu His Arg Pro Asp Val Tyr Leu Leu Pro Pro Ala Arg Glu Gln Leu Asn Leu Arg Glu Ser Ala Thr Ile Thr Cys Leu Val Thr Gly Phe Ser Pro Ala Asp Val Phe Val Gln Trp Met Gln Arg Gly Gln Pro Leu Ser Pro Glu Lys Tyr Val Thr Ser Ala Pro Met Pro Glu Pro Gln Ala Pro Gly Arg Tyr Phe Ala His Ser Ile Leu Thr Val Ser Glu Glu Glu Trp Asn Thr Gly Glu Thr Tyr Thr Cys Val Ala His Glu Ala Leu Pro Asn Arg Val Thr Glu Arg Thr Val Asp Lys Ser Thr Gly Lys Pro Thr Leu Tyr Asn Val Ser Leu Val Met Ser Asp Thr Ala Gly Thr Cys Tyr | 346 |
| Glu Pro Lys Ser Cys Asp Lys Thr His Thr Cys Pro Pro Cys Pro Ala Pro Glu Leu Leu Gly Gly Pro Ser Val Phe Leu Phe Pro Pro Lys Pro Lys Asp Thr Leu | 347 |

TABLE 9-continued

Amino Acid Sequences of Additional Human Fc Regions

| AMINO ACID SEQUENCE | SEQ ID NO: |
|---|---|
| Met Ile Ser Arg Thr Pro Glu Val Thr Cys Val Val | |
| Val Asp Val Ser His Glu Asp Pro Glu Val Lys Phe | |
| Asn Trp Tyr Val Asp Gly Val Glu Val His Asn Ala | |
| Lys Thr Lys Pro Arg Glu Glu Gln Tyr Asn Ser Thr | |
| Tyr Arg Val Val Ser Val Leu Thr Val Leu His Gln | |
| Asp Trp Leu Asn Gly Lys Glu Tyr Lys Cys Lys Val | |
| Ser Asn Lys Ala Leu Pro Ala Pro Ile Glu Lys Thr | |
| Ile Ser Lys Ala Lys Gly Gln Pro Arg Glu Pro Gln | |
| Val Tyr Thr Leu Pro Pro Ser Arg Asp Glu Leu Thr | |
| Lys Asn Gln Val Ser Leu Thr Cys Leu Val Lys Gly | |
| Phe Tyr Pro Ser Asp Ile Ala Val Glu Trp Glu Ser | |
| Asn Gly Gln Pro Glu Asn Asn Tyr Lys Thr Thr Pro | |
| Pro Val Leu Asp Ser Asp Gly Ser Phe Phe Leu Tyr | |
| Ser Lys Leu Thr Val Asp Lys Ser Arg Trp Gln Gln | |
| Gly Asn Val Phe Ser Cys Ser Val Met His Glu Ala | |
| Leu His Asn His Tyr Thr Gln Lys Ser Leu Ser Leu | |
| Ser Pro Gly Lys | |
| | |
| Glu Pro Lys Ser Cys Asp Lys Thr His Thr Cys Pro | 348 |
| Pro Cys Pro Ala Pro Glu Leu Leu Gly Gly Pro Ser | |
| Val Phe Leu Phe Pro Pro Lys Pro Lys Asp Thr Leu | |
| Met Ile Ser Arg Thr Pro Glu Val Thr Cys Val Val | |
| Val Asp Val Ser His Glu Asp Pro Glu Val Lys Phe | |
| Asn Trp Tyr Val Asp Gly Val Glu Val His Asn Ala | |
| Lys Thr Lys Pro Arg Glu Glu Gln Tyr Asn Ser Thr | |
| Tyr Arg Val Val Ser Val Leu Thr Val Leu His Gln | |
| Asp Trp Leu Asn Gly Lys Glu Tyr Lys Cys Lys Val | |
| Ser Asn Lys Ala Leu Pro Ala Pro Ile Glu Lys Thr | |
| Ile Ser Lys Ala Lys Gly Gln Pro Arg Glu Pro Gln | |
| Val Tyr Thr Leu Pro Pro Ser Arg Glu Glu Met Thr | |
| Lys Asn Gln Val Ser Leu Thr Cys Leu Val Lys Gly | |
| Phe Tyr Pro Ser Asp Ile Ala Val Glu Trp Glu Ser | |
| Asn Gly Gln Pro Glu Asn Asn Tyr Lys Thr Thr Pro | |
| Pro Val Leu Asp Ser Asp Gly Ser Phe Phe Leu Tyr | |
| Ser Lys Leu Thr Val Asp Lys Ser Arg Trp Gln Gln | |
| Gly Asn Val Phe Ser Cys Ser Val Met His Glu Ala | |
| Leu His Asn His Tyr Thr Gln Lys Ser Leu Ser Leu | |
| Ser Pro Gly Lys | |
| | |
| Glu Leu Lys Thr Pro Leu Gly Asp Thr Thr His Thr | 349 |
| Cys Pro Arg Cys Pro Glu Pro Lys Ser Cys Asp Thr | |
| Pro Pro Pro Cys Pro Arg Cys Pro Glu Pro Lys Ser | |
| Cys Asp Thr Pro Pro Pro Cys Pro Arg Cys Pro Glu | |
| Pro Lys Ser Cys Asp Thr Pro Pro Pro Cys Pro Arg | |
| Cys Pro Ala Pro Glu Leu Leu Gly Gly Pro Ser Val | |
| Phe Leu Phe Pro Pro Lys Pro Lys Asp Thr Leu Met | |
| Ile Ser Arg Thr Pro Glu Val Thr Cys Val Val Val | |
| Asp Val Ser His Glu Asp Pro Glu Val Gln Phe Lys | |
| Trp Tyr Val Asp Gly Val Glu Val His Asn Ala Lys | |
| Thr Lys Pro Arg Glu Glu Gln Phe Asn Ser Thr Phe | |
| Arg Val Val Ser Val Leu Thr Val Leu His Gln Asp | |
| Trp Leu Asn Gly Lys Glu Tyr Lys Cys Lys Val Ser | |
| Asn Lys Ala Leu Pro Ala Pro Ile Glu Lys Thr Ile | |
| Ser Lys Thr Lys Gly Gln Pro Arg Glu Pro Gln Val | |
| Tyr Thr Leu Pro Pro Ser Arg Glu Glu Met Thr Lys | |
| Asn Gln Val Ser Leu Thr Cys Leu Val Lys Gly Phe | |
| Tyr Pro Ser Asp Ile Ala Val Glu Trp Glu Ser Ser | |
| Gly Gln Pro Glu Asn Asn Tyr Asn Thr Thr Pro Pro | |
| Met Leu Asp Ser Asp Gly Ser Phe Phe Leu Tyr Ser | |
| Lys Leu Thr Val Asp Lys Ser Arg Trp Gln Gln Gly | |
| Asn Ile Phe Ser Cys Ser Val Met His Glu Ala Leu | |
| His Asn Arg Phe Thr Gln Lys Ser Leu Ser Leu Ser | |
| Pro Gly Lys | |
| | |
| Glu Arg Lys Cys Cys Val Glu Cys Pro Pro Cys Pro | 350 |
| Ala Pro Pro Val Ala Gly Pro Ser Val Phe Leu Phe | |
| Pro Pro Lys Pro Lys Asp Thr Leu Met Ile Ser Arg | |
| Thr Pro Glu Val Thr Cys Val Val Val Asp Val Ser | |
| His Glu Asp Pro Glu Val Gln Phe Asn Trp Tyr Val | |
| Asp Gly Val Glu Val His Asn Ala Lys Thr Lys Pro | |
| Arg Glu Glu Gln Phe Asn Ser Thr Phe Arg Val Val | |
| Ser Val Leu Thr Val Val His Gln Asp Trp Leu Asn | |
| Gly Lys Glu Tyr Lys Cys Lys Val Ser Asn Lys Gly | |

| AMINO ACID SEQUENCE | SEQ ID NO: |
|---|---|
| Leu Pro Ala Pro Ile Glu Lys Thr Ile Ser Lys Thr | |
| Lys Gly Gln Pro Arg Glu Pro Gln Val Tyr Thr Leu | |
| Pro Pro Ser Arg Glu Glu Met Thr Lys Asn Gln Val | |
| Ser Leu Thr Cys Leu Val Lys Gly Phe Tyr Pro Ser | |
| Asp Ile Ala Val Glu Trp Glu Ser Asn Gly Gln Pro | |
| Glu Asn Asn Tyr Lys Thr Thr Pro Pro Met Leu Asp | |
| Ser Asp Gly Ser Phe Phe Leu Tyr Ser Lys Leu Thr | |
| Val Asp Lys Ser Arg Trp Gln Gln Gly Asn Val Phe | |
| Ser Cys Ser Val Met His Glu Ala Leu His Asn His | |
| Tyr Thr Gln Lys Ser Leu Ser Leu Ser Pro Gly Lys | |
| | |
| Glu Ser Lys Tyr Gly Pro Pro Cys Pro Ser Cys Pro | 351 |
| Ala Pro Glu Phe Leu Gly Gly Pro Ser Val Phe Leu | |
| Phe Pro Pro Lys Pro Lys Asp Thr Leu Met Ile Ser | |
| Arg Thr Pro Glu Val Thr Cys Val Val Val Asp Val | |
| Ser Gln Glu Asp Pro Glu Val Gln Phe Asn Trp Tyr | |
| Val Asp Gly Val Glu Val His Asn Ala Lys Thr Lys | |
| Pro Arg Glu Glu Gln Phe Asn Ser Thr Tyr Arg Val | |
| Val Ser Val Leu Thr Val Leu His Gln Asp Trp Leu | |
| Asn Gly Lys Glu Tyr Lys Cys Lys Val Ser Asn Lys | |
| Gly Leu Pro Ser Ser Ile Glu Lys Thr Ile Ser Lys | |
| Ala Lys Gly Gln Pro Arg Glu Pro Gln Val Tyr Thr | |
| Leu Pro Pro Ser Gln Glu Glu Met Thr Lys Asn Gln | |
| Val Ser Leu Thr Cys Leu Val Lys Gly Phe Tyr Pro | |
| Ser Asp Ile Ala Val Glu Trp Glu Ser Asn Gly Gln | |
| Pro Glu Asn Asn Tyr Lys Thr Thr Pro Pro Val Leu | |
| Asp Ser Asp Gly Ser Phe Phe Leu Tyr Ser Arg Leu | |
| Thr Val Asp Lys Ser Arg Trp Gln Glu Gly Asn Val | |
| Phe Ser Cys Ser Val Met His Glu Ala Leu His Asn | |
| His Tyr Thr Gln Lys Ser Leu Ser Leu Ser Leu Gly | |
| Lys | |
| | |
| Glu Xaa Lys Ser Xaa Asp Xaa Thr Val Pro Cys Pro | 352 |
| Xaa Cys Pro Ala Pro Glu Leu Leu Gly Gly Xaa Xaa | |
| Xaa Xaa Xaa Xaa Xaa Xaa Xaa Xaa Xaa Pro Ser | |
| Val Phe Leu Phe Pro Pro Lys Pro Lys Asp Thr Leu | |
| Met Ile Ser Arg Thr Pro Glu Val Thr Cys Val Val | |
| Val Asp Val Ser His Glu Asp Pro Glu Val Xaa Phe | |
| Asn Trp Tyr Val Asp Gly Val Glu Val His Asn Ala | |
| Lys Thr Lys Pro Arg Glu Glu Gln Phe Asn Ser Thr | |
| Tyr Arg Val Val Ser Val Leu Thr Val Leu His Gln | |
| Asp Trp Leu Asn Gly Lys Glu Tyr Lys Cys Lys Val | |
| Ser Asn Lys Ala Leu Pro Ala Pro Ile Glu Lys Thr | |
| Ile Ser Lys Ala Lys Xaa Gly Gln Pro Arg Glu Pro | |
| Gln Val Tyr Thr Leu Pro Pro Xaa Ser Arg Glu Glu | |
| Met Thr Lys Asn Gln Val Ser Leu Thr Cys Leu Val | |
| Lys Gly Phe Tyr Pro Ser Asp Ile Ala Leu Glu Trp | |
| Glu Ser Asn Gly Gln Xaa Xaa Pro Glu Asn Asn Tyr | |
| Lys Thr Thr Pro Pro Met Leu Asp Ser Asp Gly Xaa | |
| Xaa Xaa Ser Phe Phe Leu Tyr Ser Lys Leu Thr Val | |
| Asp Lys Ser Arg Trp Gln Gln Gly Asn Val Phe Ser | |
| Cys Ser Val Met His Glu Ala Leu His Asn His Tyr | |
| Thr Gln Lys Ser Leu Ser Leu Ser Pro Gly Lys Xaa | |

An Fc-Loop TPO-mimetic clone is transformed into *E. coli* by conventional methods known to those in the art. The isolated inclusion body fraction (1g) is solubilized in 6 M guanidine-HCl, 50 mM Tris, 8 mM DTT, pH 9 (10 ml) at room temperature with mixing, for 1 hour. The denatured and reduced peptibody is refolded from the solubilized inclusion body fraction by a 1:25 (v/v) dilution into 2 M urea, 50 mM Tris, 4 mM cysteine, 1 mM cystamine, pH 8.5. The solubilized peptibody is added drop wise to the refold buffer at 4° C. with stirring. The refold reactions are allowed to stir for 48 hours, and then aliquots are evaluated by SDS-PAGE and reversed-phase HPLC.

Purification is achieved using a 2-column process. First a recombinant Protein-A column is equilibrated in 2 M urea, 50 mM Tris, pH 8.5 and loaded with the filtered peptibody refold reaction. The column is then washed with 2 column volumes of equilibration buffer, followed by 2 column volumes of PBS. The peptibody fraction is eluted with 50 mM NaOAc, pH3 and quickly neutralized by a 1:4 dilution into 10 mM NaOAc, 50 mM NaCl, pH 5. The diluted Protein-A eluate is again filtered and loaded to an SP Sepharose HP cation exchange column (Pharmacia) equilibrated in 10 mM NaOAc, 50 mM NaCl, pH 5. The peptibody fractions are then eluted with a linear 50-500 mM NaCl gradient, pooled and concentrated to about 2 mg/ml. The final pools of Fc-Loop TPO-mimetics are evaluated by SDS-PAGE and RP-HPLC. The final preparation of Fc-Loop TPO-mimetics are tested in an in vivo mouse bioassay.

Table 10 sets out the amino acid sequences of some TPO-mimetic peptides inserted into an Fc-Loop of SEQ ID NO: 3.

TABLE 10

TPO-Mimetic Peptides in an Fc-Loop

| AMINO ACID SEQUENCE | SEQ ID NO: |
|---|---|
| Fc-Loop H49/E50 | |
| MDKTHTCPPCPAPELLGGPSVFLFPPKPKDTLMISRTPEVTCV VVDVSHGGQGCSSGGPTLREWQQCRRMQHSGGEDPEVK FNWYVDGVEVHNAKTKPREEQYNSTYRVVSVLTVLHQDWL NGKEYKCKVSNKALPAPIEKTISKAKGQPREPQVYTLPPSRD ELTKNQVSLTCLVKGFYPSDIAVEWESNGQPENNYKTTPPVL DSDGSFFLYSKLTVDKSRWQQGNVFSCSVMHEALHNHYTQ KSLSLSPGK | 353 |
| MDKTHTCPPCPAPELLGGPSVFLFPPKPKDTLMISRTPEVTCV VVDVSHGGQGCSSGGPTLREWQQCRRMQHSGGEDPEVK FNWYVDGVEVHNAKTKPREEQYNSTYRVVSVLTVLHQDWL NGKEYKCKVSNKALPAPIEKTISKAKGQPREPQVYTLPPSRD ELTKNQVSLTCLVKGFYPSDIAVEWESNGQPENNYKTTPPVL DSDGSFFLYSKLTVDKSRWQQGNVFSCSVMHEALHNHYTQ KSLSLSPGK | 354 |
| MDKTHTCPPCPAPELLGGPSVFLFPPKPKDTLMISRTPEVTCV VVDVSHGGQGCSSGGPTLREWQQCRRMQHSGGEDPEVK FNWYVDGVEVHNAKTKYREEQYNSTYRVVSVLTVLHQDWL NGKEYKCKVSNKALPAPIEKTISKAKGQPREPQVYTLPPSRD ELTKNQVSLTCLVKGFYPSDIAVEWESNGQPENNYKTTPPVL DSDGSFFLYSKLTVDKSRWQQGNVFSCSVMHEALHNHYTQ KSLSLSPGK | 355 |
| MDKTHTCPPCPAPELLGGPSVFLFPPKPKDTLMISRTPEVTCV VVDVSHGGQGCSSGGPTLREWQQCVRAQHSGGEDPEVK FNWYVDGVEVHNAKTKPREEQYNSTYRVVSVLTVLHQDWL NGKEYKCKVSNKALPAPIEKTISKAKGQPREPQVYTLPPSRD ELTKNQVSLTCLVKGFYPSDIAVEWESNGQPENNYKTTPPVL DSDGSFFLYSKLTVDKSRWQQGNVFSCSVMHEALHNHYTQ KSLSLSPGK | 356 |
| MDKTHTCPPCPAPELLGGPSVFLFPPKPKDTLMISRTPEVTCV VVDVSHGGLDMEGPTLRHWLAARANGGEDPEVKFNWY VDGVEVHNAKTKPREEQYNSTYRVVSVLTVLHQDWLNGKE YKCKVSNKALPAPIEKTISKAKGQPREPQVYTLPPSRDELTK NQVSLTCLVKGFYPSDIAVEWESNGQPENNYKTTPPVLDSD GSFFLYSKLTVDKSRWQQGNVFSCSVMHEALHNHYTQKSLS LSPGK | 357 |
| MDKTHTCPPCPAPELLGGPSVFLFPPKPKDTLMISRTPEVTCV VVDVSHGGYMMEGPTLRHWLATRAGRGGEDPEVKFNW YVDGVEVHNAKTKPREEQYNSTYRVVSVLTVLHQDWLNGK EYKCKVSNKALPAPIEKTISKAKGQPREPQVYTLPPSRDELTK NQVSLTCLVKGFYPSDIAVEWESNGQPENNYKTTPPVLDSD GSFFLYSKLTVDKSRWQQGNVFSCSVMHEALHNHYTQKSLS LSPGK | 358 |
| MDKTHTCPPCPAPELLGGPSVFLFPPKPKDTLMISRTPEVTCV VVDVSHGGTHIEGPTLRIWLASRAKAGGEDPEVKFNWYV DGVEVHNAKTKPREEQYNSTYRVVSVLTVLHQDWLNGKEY KCKVSNKALPAPIEKTISKAKGQPREPQVYTLPPSRDELTKN | 359 |

TABLE 10-continued

TPO-Mimetic Peptides in an Fc-Loop

| AMINO ACID SEQUENCE | SEQ ID NO: |
|---|---|
| QVSLTCLVKGFYPSDIAVEWESNGQPENNYKTTPPVLDSDGS FFLYSKLTVDKSRWQQGNVFSCSVMHEALHNHYTQKSLSLS PGK | |
| MDKTHTCPPCPAPELLGGPSVFLFPPKPKDTLMISRTPEVTCV VVDVSHGGSAIEGPTLRHWLAWRAMLGGEDPEVKFNWY VDGVEVHNAKTKPREEQYNSTYRVVSVLTVLHQDWLNGKE YKCKVSNKALPAPIEKTISKAKGQPREPQVYTLPPSRDELTK NQVSLTCLVKGFYPSDIAVEWESNGQPENNYKTTPPVLDSD GSFFLYSKLTVDKSRWQQGNVFSCSVMHEALHNHYTQKSLS LSPGK | 360 |
| MDKTHTCPPCPAPELLGGPSVFLFPPKPKDTLMISRTPEVTCV VVDVSHGGWMMEGPTLRHWLAARARYGGEDPEVKFNW YVDGVEVHNAKTKPREEQYNSTYRVVSVLTVLHQDWLNGK EYKCKVSNKALPAPIEKTISKAKGQPREPQVYTLPPSRDELTK NQVSLTCLVKGFYPSDIAVEWESNGQPENNYKTTPPVLDSD GSFFLYSKLTVDKSRWQQGNVFSCSVMHEALHNHYTQKSLS LSPGK | 361 |
| MDKTHTCPPCPAPELLGGPSVFLFPPKPKDTLMISRTPEVTCV VVDVSHGGAWMEGPTLRHWLAARAAYGGEDPEVKFNW YVDGVEVHNAKTKPREEQYNSTYRVVSVLTVLHQDWLNGK EYKCKVSNKALPAPIEKTISKAKGQPREPQVYTLPPSRDELTK NQVSLTCLVKGFYPSDIAVEWESNGQPENNYKTTPPVLDSD GSFFLYSKLTVDKSRWQQGNVFSCSVMHEALHNHYTQKSLS LSPGK | 362 |
| Fc-Loop Y77/N78 | |
| MDKTHTCPPCPAPELLGGPSVFLFPPKPKDTLMISRTPEVTCV VVDVSHEDPEVKFNWYVDGVEVHNAKTKPREEQYGGQGC SSGGPTLREWQQCRRMQHSGGNSTYRVVSVLTVLHQDW LNGKEYKCKVSNKALPAPIEKTISKAKGQPREPQVYTLPPSR DELTKNQVSLTCLVKGFYPSDIAVEWESNGQPENNYKTTPPV LDSDGSFFLYSKLTVDKSRWQQGNVFSCSVMHEALHNHYT QKSLSLSPGK | 363 |
| MDKTHTCPPCPAPELLGGPSVFLFPPKPKDTLMISRTPEVTCV VVDVSHEDPEVKFNWYVDGVEVHNAKTKPREEQYGGQGC SSGGPTLREWQQCVRMQHSGGNSTYRVVSVLTVLHQDW LNGKEYKCKVSNKALPAPIEKTISKAKGQPREPQVYTLPPSR DELTKNQVSLTCLVKGFYPSDIAVEWESNGQPENNYKTTPPV LDSDGSFFLYSKLTVDKSRWQQGNVFSCSVMHEALHNHYT QKSLSLSPGK | 364 |
| MDKTHTCPPCPAPELLGGPSVFLFPPKPKDTLMISRTPEVTCV VVDVSHEDPEVKFNWYVDGVEVHNAKTKPREEQYGGQGC SSGGPTLREWQQCRRAQHSGGNSTYRVVSVLTVLHQDWL NGKEYKCKVSNKALPAPIEKTISKAKGQPREPQVYTLPPSRD ELTKNQVSLTCLVKGFYPSDIAVEWESNGQPENNYKTTPPVL DSDGSFFLYSKLTVDKSRWQQGNVFSCSVMHEALHNHYTQ KSLSLSPGK | 365 |
| MDKTHTCPPCPAPELLGGPSVFLFPPKPKDTLMISRTPEVTCV VVDVSHEDPEVKFNWYVDGVEVHNAKTKPREEQYGGQGC SSGGPTLREWQQCVRAQHSGGNSTYRVVSVLTVLHQDWL NGKEYKCKVSNKALPAPIEKTISKAKGQPREPQVYTLPPSRD ELTKNQVSLTCLVKGFYPSDIAVEWESNGQPENNYKTTPPVL DSDGSFFLYSKLTVDKSRWQQGNVFSCSVMHEALHNHYTQ KSLSLSPGK | 366 |
| MDKTHTCPPCPAPELLGGPSVFLFPPKPKDTLMISRTPEVTCV VVDVSHEDPEVKFNWYVDGVEVHNAKTKPREEQYGGLDM EGPTLRHWLAARANGGNSTYRVVSVLTVLHQDWLNGKE YKCKVSNKALPAPIEKTISKAKGQPREPQVYTLPPSRDELTK NQVSLTCLVKGFYPSDIAVEWESNGQPENNYKTTPPVLDSD GSFFLYSKLTVDKSRWQQGNVFSCSVMHEALHNHYTQKSLS LSPGK | 367 |
| MDKTHTCPPCPAPELLGGPSVFLFPPKPKDTLMISRTPEVTCV VVDVSHEDPEVKFNWYVDGVEVHNAKTKPREEQYGGYMM EGPTLRHWLATRAGRGGNSTYRVVSVLTVLHQDWLNGKE YKCKVSNKALPAPIEKTISKAKGQPREPQVYTLPPSRDELTK | 368 |

TABLE 10-continued

TPO-Mimetic Peptides in an Fc-Loop

| AMINO ACID SEQUENCE | SEQ ID NO: |
|---|---|
| NQVSLTCLVKGFYPSDIAVEWESNGQPENNYKTTPPVLDSDGSFFLYSKLTVDKSRWQQGNVFSCSVMHEALHNHYTQKSLSLSPGK | |
| MDKTHTCPPCPAPELLGGPSVFLFPPKPKDTLMISRTPEVTCVVVDVSHEDPEVKFNWYVDGVEVHNAKTKPREEQYGGTHIEGPTLRIWLASRAKAGGNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 369 |
| MDKTHTCPPCPAPELLGGPSVFLFPPKPKDTLMISRTPEVTCVVVDVSHEDPBVKFNWYVDGVEVHNAKTKPREEQYGGSAIEGPTLRHWLAWRAMLGGNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 370 |
| MDKTHTCPPCPAPELLGGPSVFLFPPKPKDTLMISRTPEVTCVVVDVSHEDPEVKFNWYVDGVEVHNAKTKPREEQYGGWMMEGPTLRHWLAARARYGGNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 371 |
| MDKTHTCPPCPAPELLGGPSVFLFPPKPKDTLMISRTPEVTCVVVDVSHEDPEVKFNWYVDGVEVHNAKTKPREEQYGGAWMEGPTLRHWLAARAAYGGNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 372 |

Fc-Loop K107/A108

| | |
|---|---|
| MDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKGGQGCSSGGPTLREWQQCRRMQHSGGALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 373 |
| MDKTHTCPPCPAPELLGGPSVFLFPPKPKDTLMISRTPEVTCVVVDVSHEDPEVKFNWYVDGYEVHNAKTKPREEQYNSTYRVVSVLTVLHQDWLNGKEYKCKVSNKGGQGCSSGGPTLREWQQCVRMQHSGGALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 374 |
| MDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKGGQGCSSGGPTLREWQQCRRAQHSGGALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 375 |
| MDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKGGQGCSSGGPTLREWQQCVRAQHSGGALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 376 |
| MDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKGGLDMEGPTLRHWLAARANGGGALPAPIEKTISKAKGQPREPQVYTLPPSRDELTK | 377 |

TABLE 10-continued

TPO-Mimetic Peptides in an Fc-Loop

| AMINO ACID SEQUENCE | SEQ ID NO: |
|---|---|
| NQVSLTCLVKGFYPSDIAVEWESNGQPENNYKTTPPVLDSDGSFFLYSKLTVDKSRWQQGNVFSCSVMHEALHNHYTQKSLSLSPGK | |
| MDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKGGYMMEGPTLRHWLATRAGRGGALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 378 |
| MDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKGGTHIEGPTLRIWLASRAKAGGALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 379 |
| MDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKGGSAIEGPTLRHWLAWRAMLGGALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 380 |
| MDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKGGWMMEGPTLRHWLAARARYGGALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 381 |
| MDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKGGAWMEGPTLRHWLAARAAYGGALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 382 |

Fc-Loop L139/T140

| | |
|---|---|
| MDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELGGQGCSSGGPTLREWQQCRRMQHSGGTKNQVSLTCLVKGFYPSDIAVEWESNGQPENNYKTTPPVLDSDGSFFLYSKLTVDKSRWQQGNVFSCSVMHEALHNHYTQKSLSLSPGK | 383 |
| MDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELGGQGCSSGGPTLREWQQCVRMQHSGGTKNQVSLTCLVKGFYPSDIAVEWESNGQPENNYKTTPPVLDSDGSFFLYSKLTVDKSRWQQGNVFSCSVMHEALHNHYTQKSLSLSPGK | 384 |
| MDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELGGQGCSSGGPTLREWQQCRRAQHSGGTKNQVSLTCLVKGFY PSDIAVEWESNGQPENNYKTTPPVLDSDGSFFLYSKLTVDKSRWQQGNVFSCSVMHEALHNHYTQKSLSLSPGK | 385 |

TABLE 10-continued

TPO-Mimetic Peptides in an Fc-Loop

| AMINO ACID SEQUENCE | SEQ ID NO: |
|---|---|
| MDKTHTCPPCPAPELLGGPSVFLFPPKPKDTLMISRTPEVTCV VVDVSHEDPEVKFNWYVDGVEVHNAKTKPREEQYNSTYRV VSVLTVL HQDWLNGKEYKCKVSNKALPAPIEKTISKAKGQPREPQVYT LPPSRDELGGQGCSSGGPTLREWQQCVRAQHSGGTKNQV SLTCLVKGFY PSDIAVEWESNGQPENNYKTTPPVLDSDGSFFLYSKLTVDKS RWQQGNVFSCSVMHEALHNHYTQKSLSLSPGK | 386 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVL HQDWLNGKEYKCKVSNKALPAPIEKTISKAKGQPREPQVYT LPPSRDELGGLDMEGPTLRHWLAARANGGGTKNQVSLTC LVKGFY PSDIAVEWESNGQPENNYKTTPPVLDSDGSFFLYSKLTVDKS RWQQGNVFSCSVMHEALHNHYTQKSLSLSPGK | 387 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVL HQDWLNGKEYKCKVSNKALPAPIEKTISKAKGQPREPQVYT LPPSRDELGGYMMEGPTLRHWLATRAGRGGTKNQVSLTC LVKGFY PSDIAVEWESNGQPENNYKTTPPVLDSDGSFFLYSKLTVDKS RWQQGNVFSCSVMHEALHNHYTQKSLSLSPGK | 388 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVL HQDWLNGKEYKCKVSNKALPAPIEKTISKAKGQPREPQVYT LPPSRDELGGTHIEGPTLRIWLASRAKAGGTKNQVSLTCLV KGFY PSDIAVEWESNGQPENNYKTTPPVLDSDGSFFLYSKLTVDKS RWQQGNVFSCSVMHEALHNHYTQKSLSLSPGK | 389 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVL HQDWLNGKEYKCKVSNKALPAPIEKTISKAKGQPREPQVYT LPPSRDELGGSAIEGPTLRHWLAWRAMLGGTKNQVSLTCL VKGFY PSDIAVEWESNGQPENNYKTTPPVLDSDGSFFLYSKLTVDKS RWQQGNVFSCSVMHEALHNHYTQKSLSLSPGK | 390 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVL HQDWLNGKEYKCKVSNKALPAPIEKTISKAKGQPREPQVYT LPPSRDELGGWMMEGPTLRHWLAARARYGGTKNQVSLT CLVKGFY PSDIAVEWESNGQPENNYKTTPPVLDSDGSFFLYSKLTVDKS RWQQGNVFSCSVMHEALHNHYTQKSLSLSPGK | 391 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVL HQDWLNGKEYKCKVSNKALPAPIEKTISKAKGQPREPQVYT LPPSRDELGGAWMEGPTLRHWLAARAAYGGTKNQVSLTC LVKGFY PSDIAVEWESNGQPENNYKTTPPVLDSDGSFFLYSKLTVDKS RWQQGNVFSCSVMHEALHNHYTQKSLSLSPGK | 392 |

Fc-Loop E169/N170

| AMINO ACID SEQUENCE | SEQ ID NO: |
|---|---|
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPEGGQGCSSGGPTLREWQQCRRMQHSGGNNYKTTPPV LDSDGSFFLYSKLTVDKSRWQQGNVFSCSVMHEALHNHYT QKSLSLSPGK | 393 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPEGGQGCSSGGPTLREWQQCVRMQHSGGNNYKTTPPV LDSDGSFFLYSKLTVDKSRWQQGNVFSCSVMHEALHNHYT QKSLSLSPGK | 394 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPEGGQGCSSGGPTLREWQQCRAQHSGGNNYKTTPPVL DSDGSFFLYSKLTVDKSRWQQGNVFSCSVMHEALHNHYTQ KSLSLSPGK | 395 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPEGGQGCSSGGPTLREWQQCVRAQHSGGNNYKTTPPVL DSDGSFFLYSKLTVDKSRWQQGNVFSCSVMHEALHNHYTQ KSLSLSPGK | 396 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPEGGLDMEGPTLRHWLAARANGGGNNYKTTPPVLDSDG SFFLYSKLTVDKSRWQQGNVFSCSVMHEALHNHYTQKSLSL SPGK | 397 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPEGGYMMEGPTLRHWLATRAGRGGNNYKTTPPVLDSD GSFFLYSKLTVDKSRWQQGNVFSCSVMHEALHNHYTQKSLS LSPGK | 398 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPEGGTHIEGPTLRIWLASRAKAGGNNYKTTPPVLDSDGS FFLYSKLTVDKSRWQQGNVFSCSVMHEALHNHYTQKSLSLS PGK | 399 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPEGGAIEGPTLRHWLAWRAMLGGNNYKTTPPVLDSDG SFFLYSKLTVDKSRWQQGNVFSCSVMHEALHNHYTQKSLSL SPGK | 400 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPEGGWMMEGPTLRHWLAARARYGGNNYKTTPPVLDSD GSFFLYSKLTVDKSRWQQGNVFSCSVMHEALHNHYTQKSLS LSPGK | 401 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP | 402 |

TABLE 10-continued

TPO-Mimetic Peptides in an Fc-Loop

| AMINO ACID SEQUENCE | SEQ ID NO: |
|---|---|
| REPQVYTLPPSRDELTKNQVSLTCLVKGFYPSDIAVEWESNG QPEGGAWMEGPTLRHWLAARAAYGGNNYKTTPPVLDSD GSFFLYSKLTVDKSRWQQGNVFSCSVMHEALHNHYTQKSLS LSPGK | |

Fc-Loop S181/D182

| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPENNYKTTPPVLDSGGQGCSSGGPTLREWQQCRRMQHS GGDGSFFLYSKLTVDKSRWQQGNVFSCSVMHEALHNHYTQ KSLSLSPGK | 403 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPENNYKTTPPVLDSGGQGCSSGGPTLREWQQCVRMQHS GGDGSFFLYSKLTVDKSRWQQGNVFSCSVMHEALHNHYTQ KSLSLSPGK | 404 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPENNYKTTPPVLDSGGQGCSSGGPTLREWQQCRRAQHS GGDGSFFLYSKLTVDKSRWQQGNVFSCSVMHEALHNHYTQ KSLSLSPGK | 405 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPENNYKTTPPVLDSGGQGCSSGGPTLREWQQCVRAQHS GGDGSFFLYSKLTVDKSRWQQGNVFSCSVMHEALHNHYTQ KSLSLSPGK | 406 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPENNYKTTPPVLDSGGLDMEGPTLRHWLAARANGGDG SFFLYSKLTVDKSRWQQGNVFSCSVMHEALHNHYTQKSLSL SPGK | 407 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPENNYKTTPPVLDSGGYMMEGPTLRHWLATRAGRGGD GSFFLYSKLTVDKSRWQQGNVFSCSVMHEALHNHYTQKSLS LSPGK | 408 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPENNYKTTPPVLDSGGTHIEGPTLRIWLASPAKAGGDGS FFLYSKLTVDKSRWQQGNVFSCSVMHEALHNHYTQKSLSLS PGK | 409 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPENNYKTTPPVLDSGGSAIEGPTLRHWLAWRAMLGGDG SFFLYSKLTVDKSRWQQGNVFSCSVMHEALHNHYTQKSLSL SPGK | 410 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPENNYKTTPPVLDSGGWMMEGPTLRHWLAARARYGGD GSFFLYSKLTVDKSRWQQGNVFSCSVMHEALHNHYTQKSLS LSPGK | 411 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPENNYKTTPPVLDSGGAWMEGPTLRHWLAARAAYGGD GSFFLYSKLTVDKSRWQQGNVFSCSVMHEALHNHYTQKSLS LSPGK | 412 |

Fc-Loop G201/N202

| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPENNYKTTPPVLDSDGSFFLYSKLTVDKSRWQQGGGQGCS SGGPTLREWQQCRRMQHSGGNVFSCSVMHEALHNHYTQ KSLSLSPGK | 413 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPENNYKTTPPVLDSDGSFFLYSKLTVDKSRWQQGGGQGCS SGGPTLREWQQCVRMQHSGGNVFSCSVMHEALHNHYTQ KSLSLSPGK | 414 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPENNYKTTPPVLDSDGSFFLYSKLTVDKSRWQQGGGQGCS SGGPTLREWQQCRRAQHSGGNVFSCSVMHEALHNHYTQK SLSLSPGK | 415 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPENNYKTTPPVLDSDGSFFLYSKLTVDKSRWQQGGGQGCS SGGPTLREWQQCVRAQHSGGNVFSCSVMHEALHNHYTQK SLSLSPGK | 416 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPENNYKTTPPVLDSDGSFFLYSKLTVDKSRWQQGGGLDM EGPTLRHWLAARANGGGNVFSCSVMHEALHNHYTQKSLS LSPGK | 417 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPENNYKTTPPVLDSDGSFFLYSKLTVDKSRWQQGGGYMM EGPTLRHWLATRAGRGGNVFSCSVMHEALHNHYTQKSLS LSPGK | 418 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPENNYKTTPPVLDSDGSFFLYSKLTVDKSRWQQGGGTHIE GPTLRIWLASRAKAGGNVFSCSVMHEALHNHYTQKSLSLS PGK | 419 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP | 420 |

TABLE 10-continued

TPO-Mimetic Peptides in an Fc-Loop

| AMINO ACID SEQUENCE | SEQ ID NO: |
|---|---|
| REPQVYTLPPSRDELTKNQVSLTCLVKGFYPSDIAVEWESNG QPENNYKTTPPVLDSDGSFFLYSKLTVDKSRWQQGGSAIE GPTLRHWLAWRAMLGGNVFSCSVMHEALHNHYTQKSLSL SPGK | |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPENNYKTTPPVLDSDGSFFLYSKLTVDKSRWQQGGGWM MEGPTLRHWLAARARYGGNVFSCSVMHEALHNHYTQKSL SLSPGK | 421 |
| MDKTHTCPPCPAPELLGGPSVFLFPPKPKDTLMISRTPEVTCV VVDVSHEDPEVKFNWYVDGVEVHNAKTKPREEQYNSTYRV VSVLTVLHQDWLNGKEYKCKVSNKALPAPIEKTISKAKGQP REPQVYTLPPSRDELTKNQVSLTCLVKGFYPSDIAVEWESNG QPENNYKTTPPVLDSDGSFFLYSKLTVDKSRWQQGGGAWM EGPTLRHWLAARAAYGGNVFSCSVMHEALHNHYTQKSLS LSPGK | 422 |

There is a high degree of homology in the secondary and tertiary structural conformations within the Fc domains of different IgG subtypes and between species. The x-ray crystal structure coordinates for these structures can be found in the RCSB Protein Data Bank (www.rcsb.org/pdb/).

In the human IgG1 Fc sequence (SEQ ID NO: 3) used for peptibody fusions, predicted Fc-Loop regions are found in SEQ ID NOS: 428, 429, 431, 432, 434, 435, 437, 439, 441, and 443. Any, or all of these sites may be suitable for full or partial replacement by or insertion of peptide sequences and are considered part of this invention. Specifically preferred internal sites are SEQ ID NOS: 430, 433, 436, 438, 440, 442, and 444. One preferred site is SEQ ID NO: 438, between $Leu_{139}$ and $Thr_{140}$ in the DELTK (SEQ ID NO: 437) loop. Potential loop sites in other Ig subtypes are understood in the art.

Exemplary amino acid sequences of human Fc regions from IgA, IgM and IgG subtypes are SEQ ID NOS: 344 to 351). A consensus sequence is provided in SEQ ID NO: 352.

Preferred internal sites for peptide addition that correspond to those of the Fc sequence in SEQ ID NO: 3 are set out as follows:

SEQ ID NO: 428 within SEQ ID NOS: 347 to 352;
SEQ ID NO: 429 within SEQ ID NOS: 347 to 350 and 352;
SEQ ID NO: 445 within SEQ ID NO: 351;
SEQ ID NO: 431 within SEQ ID NO: 347 to 352;
SEQ ID NO: 432 within SEQ ID NOS: 347 and 348;
SEQ ID NO: 446 within SEQ ID NOS: 349 to 352;
SEQ ID NO: 434 within SEQ ID NOS: 347 to 349, 351, and 352;
SEQ ID NO: 447 within SEQ ID NO: 350;
SEQ ID NO: 435 within SEQ ID NOS: 347, 348, and 352;
SEQ ID NO: 448 within SEQ ID NO: 349;
SEQ ID NO: 449 within SEQ ID NO: 350;
SEQ ID NO: 450 within SEQ ID NO: 351;
SEQ ID NO: 437 within SEQ ID NO: 347;
SEQ ID NO: 451 within SEQ ID NOS: 348 to 352;
SEQ ID NO: 439 within SEQ ID NOS: 347, 348, 350, 351, and 352;
SEQ ID NO: 452 within SEQ ID NO: 349;
SEQ ID NO: 441 within SEQ ID NOS: 347, 348, and 351;
SEQ ID NO: 453 within SEQ ID NOS: 349, 350 and 352;
SEQ ID NO: 443 within SEQ ID NOS: 347, 348, 350, and 352;
SEQ ID NO: 426 within SEQ ID NO: 349; and
SEQ ID NO: 427 within SEQ ID NO: 351.

Sequence alignments suggest two more potential insertion sites at $Q_{167}/P_{168}$ and/or $G_{183}/S_{184}$ (using the numbering of SEQ ID NO: 3). These positions correspond to gaps in the IgG sequences where there are two and three residue insertions found in the aligned IgA and IgM sequences. Some preferred insertion sites are set out as follows:

$H_{53}/E_{54}$ in SEQ ID NOS: 347 and 348;
$H_{100}/E_{101}$ in SEQ ID NO: 349;
$H_{49}/E_{50}$ in SEQ ID NO: 350;
$Q_{50}/E_{51}$ in SEQ ID NO: 351;
$H_{112}/E_{113}$ in SEQ ID NO: 352;
$Y_{81}/N_{82}$ in SEQ ID NOS: 347 and 348;
$F_{128}/N_{129}$ in SEQ ID NO: 349;
$F_{77}/N_{78}$ in SEQ ID NO: 350;
$F_{78}/N_{79}$ in SEQ ID NO: 351;
$F_{140}/N_{141}$ in SEQ ID NO: 352;
$N_{110}/K_{111}$ in SEQ ID NOS: 347 and 348;
$N_{157}/K_{158}$ in SEQ ID NO: 349;
$N_{106}/K_{107}$ in SEQ ID NO: 350;
$N_{107}/K_{108}$ in SEQ ID NO: 351;
$N_{169}/K_{170}$ in SEQ ID NO: 352;
$L_{143}/T_{144}$ in SEQ ID NOS: 347 and 348;
$M_{190}/T_{191}$ in SEQ ID NO: 349;
$M_{139}/T_{140}$ in SEQ ID NO: 350;
$M_{140}/T_{141}$ in SEQ ID NO: 351;
$M_{204}/T_{205}$ in SEQ ID NO: 352;
$Q_{171}P_{172}$ in SEQ ID NOS: 347 and 348;
$Q_{218}/P_{219}$ in SEQ ID NO: 349;
$Q_{167}/P_{168}$ in SEQ ID NO: 350;
$Q_{168}/P_{169}$ in SEQ ID NO: 351;
$Q_{232}/P_{233}$ in SEQ ID NO: 352;
$E_{173}N_{174}$ in SEQ ID NOS: 347 and 348;
$E_{220}/N_{221}$ in SEQ ID NO: 349;
$E_{169}/N_{170}$ in SEQ ID NO: 350;
$E_{170}/N_{171}$ in SEQ ID NO: 351;
$E_{234}/N_{235}$ in SEQ ID NO: 352;
$S_{186}/D_{187}$ in SEQ ID NOS: 347 and 348;
$S_{232}/D_{233}$ in SEQ ID NO: 349;
$S_{181}/D_{182}$ in SEQ ID NO: 350;
$S_{182}/D_{183}$ in SEQ ID NO: 351;
$S_{246}/D_{247}$ in SEQ ID NO: 352;
$G_{188}/S_{189}$ in SEQ ID NOS: 347 and 348;
$G_{234}/S_{235}$ in SEQ ID NO: 349;
$G_{183}/S_{184}$ in SEQ ID NO: 350;
$G_{184}/S_{185}$ in SEQ ID NO: 351;
$G_{248}/S_{249}$ in SEQ ID NO: 352;
$G_{205}/N_{206}$ in SEQ ID NOS: 347 and 348;
$G_{252}/N_{253}$ in SEQ ID NO: 349;
$G_{201}/N_{202}$ in SEQ ID NO: 350;
$G_{202}/N_{203}$ in SEQ ID NO: 351; and
$G_{268}/N_{269}$ in SEQ ID NO: 352.

An alignment of human IgG1 Fc domain (SEQ ID NO: 423) used for the peptibody platform with rat IgG2A from crystal structure of FcRn/Fc complex (SEQ ID NO: 424) provided a consensus sequence (SEQ ID NO: 425).

Table 11 sets out amino acid sequences of some of the Fc sequences for use in the present invention and some of the internal sites for peptide addition/insertion.

TABLE 11

Amino Acid Sequences of IgG sequences and Insertion Sites

| AMINO ACID SEQUENCE | SEQ ID NO: |
|---|---|
| Glu Gly Gly Gly Gly Gly Asp Lys Thr His Thr Cys Pro Pro Cys Pro Ala Pro Glu Leu Leu Gly Gly Pro Ser Val Phe Leu Phe Pro Pro Lys Pro Lys Asp Thr Leu Met Ile Ser Arg Thr Pro Glu Val Thr Cys Val Val Val Asp Val Ser His Glu Asp Pro Glu Val Lys Phe Asn Trp Tyr Val Asp Gly Val Glu Val His Asn Ala Lys Thr Lys Pro Arg Glu Glu Gln Tyr Asn Ser Thr Tyr Arg Val Val Ser Val Leu Thr Val Leu His Gln Asp Trp Leu Asn Gly Lys Glu Tyr Lys Cys Lys Val Ser Asn Lys Ala Leu Pro Ala Pro Ile Glu Lys Thr Ile Ser Lys Ala Lys Gly Gln Pro Arg Glu Pro Gln Val Tyr Thr Leu Pro Pro Ser Arg Asp Glu Leu Thr Lys Asn Gln Val Ser Ser Arg Trp Gln Gln Gly Asn Val Phe Ser Cys Ser Val Met His Glu Ala Leu His Asn His Tyr Thr Gln Lys Ser Leu Ser Leu Ser Pro Gly Lys | 423 |
| Ser Val Phe Ile Phe Pro Pro Lys Thr Lys Asp Val Leu Thr Ile Thr Leu Thr Pro Lys Val Thr Cys Val Val Val Asp Ile Ser Gln Asn Asp Pro Glu Val Arg Phe Ser Trp Phe Ile Asp Asp Val Glu Val His Thr Ala Gln Thr His Ala Pro Glu Lys Gln Ser Asn Ser Thr Leu Arg Ser Val Ser Glu Leu Pro Ile Val His Arg Asp Trp Leu Asn Gly Lys Thr Phe Lys Cys Lys Val Asn Ser Gly Ala Phe Pro Ala Pro Ile Glu Lys Ser Ile Ser Lys Pro Glu Gly Thr Pro Arg Gly Pro Gln Val Tyr Thr Met Ala Pro Pro Lys Glu Glu Met Thr Gln Ser Gln Val Ser Ile Thr Cys Met Val Lys Gly Phe Tyr Pro Pro Asp Ile Tyr Thr Glu Trp Lys Met Asn Gly Gln Pro Gln Glu Asn Tyr Lys Asn Thr Pro Pro Thr Met Asp Thr Asp Gly Ser Tyr Phe Leu Tyr Ser Lys Leu Asn Val Lys Lys Glu Thr Trp Gln Gln Gly Asn Thr Phe Thr Cys Ser Val Leu His Glu Gly Leu His Asn His His Thr Glu Lys Ser Leu Ser His | 424 |
| Ser Val Phe Ile Phe Pro Pro Lys Xaa Lys Asp Xaa Leu Xaa Ile Ser Xaa Thr Pro Xaa Val Thr Cys Val Val Val Asp Ile Ser Xaa Xaa Asp Pro Glu Val Lys Phe Xaa Trp Phe Ile Asp Xaa Val Glu Val His Xaa Ala Xaa Thr Xaa Xaa Xaa Glu Xaa Gln Xaa Asn Ser Thr Xaa Arg Xaa Val Ser Xaa Leu Ile Leu His Xaa Asp Trp Leu Asn Gly Lys Xaa Phe Lys Cys Lys Val Xaa Xaa Xaa Ala Xaa Pro Ala Pro Ile Glu Lys Ser Ile Ser Lys Xaa Xaa Gly Xaa Pro Arg Xaa Pro Gln Val Tyr Thr Leu Xaa Pro Xaa Lys Asp Glu Leu Thr Xaa Xaa Gln Val Ser Ile Thr Cys Leu Val Lys Gly Phe Tyr Pro Xaa Asp Ile Xaa Xaa Glu Trp Xaa Xaa Asn Gly Gln Pro Xaa Xaa Asn Tyr Lys Xaa Thr Pro Pro Xaa Leu Asp Ser Asp Ser Phe Phe Leu Tyr Ser Lys Leu Xaa Val Xaa Lys Xaa Xaa Trp Gln Gln Gly Asn Xaa Phe Ser Cys Ser Val Leu His Glu Ala Leu His Asn His His Thr Xaa Lys Ser Leu Ser Xaa | 425 |
| Lys Ser Arg Trp Gln Gln Gly Asn Ile | 426 |
| Lys Ser Arg Trp Gln Glu Gly Asn Val | 427 |
| Pro Pro | 428 |
| Asp Val Ser His Glu Asp Pro Glu | 429 |
| Ser His Glu | 430 |
| Val His Asn Ala | 431 |
| Glu Glu Gln Tyr Asn Ser Thr | 432 |
| Tyr Asn Ser | 433 |
| Val Leu His Gln Asp Trp Leu Asn Gly Lys Glu | 434 |
| Asn Lys Ala Leu Pro Ala Pro Ile Glu Lys Thr Ile Ser Lys Ala Lys | 435 |
| Asn Lys Ala | 436 |
| Asp Glu Leu Thr Lys | 437 |
| Leu Thr Lys | 438 |
| Asn Gly Gln Pro Glu Asn Asn | 439 |
| Glu Asn Asn | 440 |
| Thr Thr Pro Pro Val Leu Asp Ser Asp Gly Ser | 441 |
| Val Leu Asp Ser Asp | 442 |
| Lys Ser Arg Trp Gln Gln Gly Asn Val | 443 |
| Gln Gly Asn | 444 |
| Asp Val Ser Gln Glu Asp Pro Glu | 445 |
| Glu Glu Gln Phe Asn Ser Thr | 446 |
| Val Val His Gln Asp Trp Leu Asn Gly Lys Glu | 447 |
| Asn Lys Ala Leu Pro Ala Pro Ile Glu Lys Thr Ile Ser Lys Thr Lys Gly Gln Pro Arg Glu Pro | 448 |
| Asn Lys Gly Leu Pro Ala Pro Ile Glu Lys Thr Ile Ser Lys Thr Lys Gly Gln Pro Arg Glu Pro | 449 |
| Asn Lys Gly Leu Pro Ser Ser Ile Glu Lys Ala Lys Gly Gln Pro Arg Glu Pro | 450 |
| Glu Glu Met Thr Lys | 451 |
| Ser Gly Gln Pro Glu Asn Asn | 452 |
| Thr Thr Pro Pro Met Leu Asp Ser Asp Gly Ser | 453 |

Table 12 sets out still other TPO-mimetic peptides having c-mp1 receptor binding activity. These peptides are contemplated for use alone or as TPO-mimetic fusion proteins, wherein the TPO-mimetic peptide is fused to either an N-terminus of an Fc region or within an Fc-Loop, a modified Fc molecule. Fc-Loops are described herein and in U.S. Patent Application Publication No. US2006/0140934 incorporated herein by reference in its entirety.

TABLE 12

TPO-Mimetic Peptides

| AMINO ACID SEQUENCE | SEQ ID NO: |
|---|---|
| cssggptlrewqqcsraq | 454 |
| cssggptlrewqqcqraq | 455 |
| cssggptlrewqqcgraq | 456 |

Table 13 reports the effective concentration (Pb EC50 in ng/ml) at which some of the TPO-mimetic fusion proteins of the invention demonstrate peptibody activity based on an in vitro activity assay using murine 32D cells expressing human MPL in a reporter assay format as described herein above.

This TPO in vitro bioassay is a mitogenic assay utilizing an IL-3 dependent clone of murine 32D cells that have been transfected with human mp1 receptor. This assay is described in greater detail in WO 95/26746. An Fc molecule is fused at either the N-terminus or the C-terminus of the peptide. Some TPO-mimetics in this table were inserted into an Fc-Loop (see, e.g., Fc-Loop-(SEQ ID NO: X)), comprise an Fc molecule connected at the N-terminus of two different peptide sequences connected in tandem (see, e.g., Fc-(SEQ ID NO: 91)-(SEQ ID NO: 81), or comprise an Fc molecule connected at the N-terminus of two tandem copies of the same peptide (see, e.g., Fc-2X-(SEQ ID NO: 81)).

The constructs were also subjected to an in vivo activity study by injecting mice with 3, 5, 50, 100, or 200 µg/kg of the noted construct and then observing the change in platelet number over a 17-day period. An in vivo activity of "++++" indicates high activity, while an in vivo activity of "+" denotes low activity. Using this in vivo assay system, all eight TPO-mimetic compounds shown in Table 14 appeared to be indistinguishable.

Fc-(SEQ ID NO: 9) (M19A) indicates that the M at amino acid position 19 in SEQ ID NO: 9 is replaced with an A. Fc-(SEQ ID NO: 9) (R17V) indicates that the R at amino acid position 17 is replaced with a V. Accordingly, Fc-(SEQ ID

TABLE 13

Activity of Some TPO-Mimetic Peptides

| TPO-Mimetic | Peptide Sequences Used in the TPO-Mimetic | | Pb EC50 (ng/ml) |
|---|---|---|---|
| Fc-Loop-(SEQ ID NO: 454) | cssggptlrewqqcsraq | (SEQ ID NO: 454) | 0.28 |
| Fc-Loop-(SEQ ID NO: 455) | cssggptlrewqqcqraq | (SEQ ID NO: 455) | 0.27 |
| Fc-Loop-(SEQ ID NO: 456) | cssggptlrewqqcgraq | (SEQ ID NO: 456) | 2.31 |
| SEQ ID NO: 9 | cssggptlrewqqcrrmq | (SEQ ID NO: 9) | 0.44 |
| SEQ ID NO: 11 | cswggptlknwlqcvrak | (SEQ ID NO: 11) | 4.01 |
| Fc-(SEQ ID NO: 91)-(SEQ ID NO: 81) | MWMEGPTLRHWLEARARY LDMEGPTLRHWLAARANG | (SEQ ID NO: 91)- (SEQ ID NO: 81) | 0.65 |
| SEQ ID NO: 103 | YMMEGPTLRHWLATRAGR | (SEQ ID NO: 103) | 0.79 |
| Fc-(SEQ ID NO: 95) | THIEGPTLRIWLASRAKA | (SEQ ID NO: 95) | 1.04 |
| SEQ ID NO: 117 | SAIEGPTLRHWLAWRAML | (SEQ ID NO: 117) | 1.09 |
| SEQ ID NO: 115 | WMMEGPTLRHWLAARARY | (SEQ ID NO: 115) | 1.43 |
| SEQ ID NO: 115 | WMMEGPTLRHWLAARARY | (SEQ ID NO: 115) | 1.81 |
| SEQ ID NO: 149 | AWMEGPTLRHWLAARAAY | (SEQ ID NO: 149) | 1.84 |
| SEQ ID NO: 171 | WPMEGPTLRHWLAARAAR | (SEQ ID NO: 171) | 1.56 |
| SEQ ID NO: 241 | ICTEGCTLRLWLAERSRV | (SEQ ID NO: 241) | 1.83 |
| SEQ ID NO: 139 | DAIEGPTLRLWLEARRKQ | (SEQ ID NO: 139) | 1.89 |
| SEQ ID NO: 128 | YYLEGPTLRHWLAARAYL | (SEQ ID NO: 128) | 1.82 |
| Fc-2x-(SEQ ID NO: 81) | LDMEGPTLRHWLAARANG | (SEQ ID NO: 81) | 2.56 |
| SEQ ID NO: 123 | WVMEGPTLRHWLAARASL | (SEQ ID NO: 123) | 2.08 |
| SEQ ID NO: 225 | LTMEGPTLRHWLAARATR | (SEQ ID NO: 225) | 3.10 |
| SEQ ID NO: 163 | HPIEGPTLRLWLAARARA | (SEQ ID NO: 163) | 2.80 |

Table 14 reports the in vitro and in vivo activity of some TPO-mimetic compounds of the invention. The constructs set out in Table 14 were assessed for in vitro activity using murine 32D cells expressing human MPL in a reporter assay format as described herein above. This TPO in vitro bioassay is a mitogenic assay utilizing an IL-3 dependent clone of murine 32D cells that have been transfected with human mpl receptor. This assay is described in greater detail in WO 95/26746. The activity of the constructs was determined to be comparable when considering reasonable assay variance.

NO: 9) (R17V/M19A) denotes that there are two substitutions in SEQ ID NO: 9; the R at position 17 is replaced with a V and the M at position 19 is replaced with an A. Fc-Loop (Asym) (SEQ ID NO: 9) in Table 14 denotes that SEQ ID NO: 9 is inserted into the loop region of the Fc at position L139/T140 using four glycine spacers at the N-terminus and two glycine spacers at the C-terminus. Fc-Loop (Sym) (SEQ ID NO: 9) in Table 14 denotes that SEQ ID NO: 9 is inserted into the loop region of the Fc at position L139/T140 using two glycine spacers at both the N- and C-termini.

TABLE 14

TPO-Mimetic Fusion Protein Activity In Vitro and In Vivo

| Construct | In vitro EC$_{50}$ (pM) | In vitro EC$_{50}$ (95% CI) | In vivo |
|---|---|---|---|
| Fc-(SEQ ID NO: 9) | 14.6 | 8.9-24.0 | ++++ |
| Fc-(SEQ ID NO: 9) (M19A) | 10.4 | 8.0-13.6 | ++++ |
| Fc-(SEQ ID NO: 9) (R17V) | 25.1 | 14.0-45.2 | ++++ |
| Fc-(SEQ ID NO: 9) (R17V/M19A) | 5.5 | 3.6-8.4 | ++++ |
| Fc-Loop(Asym) (SEQ ID NO: 9) | 12.7 | 9.1-17.7 | ++++ |
| Fc-Loop(Sym) (SEQ ID NO: 9) | 13.7 | 10.1-18.5 | ++++ |
| Fc-Loop(Asym-R17V) | 5.7 | 4.2-7.7 | ++++ |
| Fc-Loop(Sym-R17V) | 9.9 | 6.9-14.0 | ++++ |

Table 15 further reports the in vitro activity of some TPO-mimetic compounds of the invention. Fc-Loop (Asym) (SEQ ID NO: 9) in Table 15 denotes that SEQ ID NO: 9 was inserted into the loop region of the Fc at position L139/T140 using four glycine spacers at the N-terminus. Fc-Loop (Asym) (SEQ ID NO: 243) in Table 15 denotes that SEQ ID NO: 243 was inserted into the loop region of the Fc at position L139/T140 using four glycine spacers at the N-terminus and two glycine spacers at the C-terminus. The appended "-C" at the end of the construct name in Table 15 denotes that the purified cyclic form (the cysteines in SEQ ID NO: 9 form an intrachain disulfide bond). The appended "XL" at the end of the construct name in Table 15 denotes that the purified cross-linked form (the cysteines in SEQ ID NO: 9 form an interchain disulfide bond). The appended "-Mixed" at the end of the construct name in Table 15 denotes that there is a mixture of the cyclic and cross-linked forms. Fc-Loop (Sym) (SEQ ID NO: 9 or 243 or 244) in Table 15 denotes that SEQ ID NO: 9, 243, or 244 was inserted into the loop region of the Fc at position L139/T140 using two glycine spacers at the N-terminus and two glycine spacers at the C-terminus.

TPO-dependent proliferation of 32Dc123/Mp1 cells and differentiation of primary human CD34+ progenitors were used to measure the in vitro potency of TPO-mimetic compounds. In the latter assay, the percentage of cells expressing the CD61 surface marker was chosen as the key parameter to measure megakaryocytic differentiation. For both assays, measurements were expressed as POC relative to the peak value (cell proliferation or differentiation) measured for a well-characterized positive control, Fc-2X-(SEQ ID NO: 337). At least three determinations for each molecule were performed in the 32Dc123/Mp1 proliferation assay, and at least three determinations on two separate donors were performed for each molecule in the CD34+ differentiation assay.

CD34+ Liquid Culture Assay

StemPro-34 Serum-Free Media supplemented with 100 ng/mL recombinant human Stem Cell Factor (rhSCF, Amgen, Inc.) was used as the growth medium. CD34+ cells were obtained from normal, G-CSF mobilized donors, provided by All Cells, Inc. All experiments were performed in 96-well plates using 5-20×10$^3$ CD34+ cells/well.

Two solutions of each TPO-mimetic compound (or peptibody) were prepared at a concentration of 2 µg/mL and 0.6 µg/mL, respectively. From each of these solutions, 1:10 serial dilutions were made into a 96-well tissue culture plate containing a volume of 180 µl/well (20 µl of sample into 200 µl final) of growth medium to obtain a concentration curve of 200, 60, 20, 6, 2, 0.6, and 0.2 ng/mL. Next, 100 µl from each well was transferred into another 96-well plate and 100 µl (5-20,000 CD34+ cells) of cells resuspended in SP34 media (supplemented with 100 ng/mL SCF) were added. The final concentration of the test molecules was 100, 30, 10, 3, 1.0, 0.3 and 0.1 ng/mL.

The tissue culture plate was cultured in 5% $CO_2$ in 100% humidified air at 37° C. for 7 days. Next, the cells were stained in the 96-well plate (per BD Biosciences protocol) with 2 µl (0.1 µg)/well FITC-CD15 or 0.5 µl (0.1 µg)/well APC-CD61 along with the appropriate isotype controls. Just before analysis, 1 µl (0.05 µg) of propidium iodide was added to each well, to stain dead cells. Live cells were identified by appropriate FSC/SSC gating and propidium iodide exclusion. Data were acquired on a FACSCalibur flow cytometer (Beckton Dickinson).

32Dc123/Mp1 Cell Proliferation Assay

2Dc123/Mp1 cells were cultured at 37° C. in 5% $CO_2$, in MEM containing 10% FBS, PGS (100 units/mL penicillin G sodium, 100 µg/mL streptomycin sulfate, 292 µg/mL L-glutamine), and 5 ng/mL murine IL-3. Cell viability greater than 80% was confirmed by the Beckman Coulter Vi-Cell XR instrument (Beckman Coulter Inc., Fullerton, Calif.).

For each experiment, 32Dc123/Mp1 cells were washed twice in growth medium, and the cells pellet was resuspended in 1×10$^6$ cells per mL. Cells were plated in 96-well Costar round bottom plates at a cell density of 60,000 cells per well (60 µL per well).

Test molecules were serially diluted 1:3 in growth medium, to obtain a dose range from 40 ng/mL to 0.01 ng/mL. Sixty microliters of the diluted peptibody were added to the cell plate containing 60 µL of 60,000 cells per well. The treated cells were incubated for 24 hours in 5% $CO_2$ humidifier incubator. Cellular ATP was then measured as surrogate marker for cell proliferation with the Promega CellTiter-Glo reagent (Cat # G7572), according to the manufacturer's specifications. Luminescence signal was measured with Molecular Devices LMax$^{384}$ instrument (Molecular Devices Inc., Sunnyvale, Calif.).

Data Analysis

Percentages of cells expressing CD61 were calculated with the FCS Express v3.0 software, gating for live cells based on forward scatter/side scatter and propidium iodide exclusion. Dose responses were plotted with Spotfire DecisionSite v8.2.1.

Statistical Analysis

Data were plotted as mean ±SD. For relevant candidates, EC$_{50}$s were calculated with the GraphPad Prism v4.01 software package using the following sigmoidal dose-response equation:

$$Y = min + (max - min)/(1 + 10^{\wedge}((LogEC50 - X)))$$

where X is the logarithm of concentration, and Y the response.

TABLE 15

TPO-Mimetic Fusion Protein Activity

| Construct Sequence | EC$_{50}$ on 32Dcl23/Mp1 (pM) | EC$_{50}$ on CD34+ (pM) |
|---|---|---|
| Fc-Loop (Asym) (SEQ ID NO: 9) | 13 | 0.1 |
| Fc-Loop (Sym) (SEQ ID NO: 9) | 15 | 2 |
| Fc-Loop (Asym) (SEQ ID NO: 243) | 6 | 5 |
| Fc-(SEQ ID NO: 9) (M19A) | 10 | 6 |

TABLE 15-continued

TPO-Mimetic Fusion Protein Activity

| Construct Sequence | EC$_{50}$ on 32Dcl23/ Mpl (pM) | EC$_{50}$ on CD34+ (pM) |
|---|---|---|
| Fc-(SEQ ID NO: 9) (R17V/M19A)-C | 5 | 6 |
| Fc-(SEQ ID NO: 9) (R17V/M19A)-XL | 9 | 5 |
| Fc-(SEQ ID NO: 9) (R17V)-XL | 15 | 5 |
| Fc-(SEQ ID NO: 9) (R17V)-Mixed | 11 | 0.01 |
| Fc-(SEQ ID NO: 9) (R17V) | 25 | 3 |
| Fc-(SEQ ID NO: 9) | 15 | 5 |
| Fc-Loop (Sym) (SEQ ID NO: 243) | 10 | 5 |
| Fc-Loop (Sym) (SEQ ID NO: 244) | 12 | 0.6 |
| Fc-2X-(SEQ ID NO: 337) (positive control) | 15 | 4.5 |

Figure 4:
FIG. 4 shows exemplary platelet values of mice given positive control or a TPO-mimetic compound of the invention (at dosages from 3-200 μg/kg) six days post-injection.

Some of the TPO-mimetics set out above also have been tested directly for biological activity in vivo in mice (see FIG. 4). Platelet values in FIG. 4 were expressed as the area under the curve (AUC), or the integral of the curve. GraphPad Prism 4.1 statistical software (GraphPad Software, Inc., San Diego, Calif.) was used to calculate platelet values. This program uses the trapezoidal rule with the following equation: ResultY(i)=ResultY(i−1)+0.5 [Y(i−1)+Y(i)] [X(i)−X(i−1)]. The positive control (Fc-2X-(SEQ ID NO: 337)) was the same positive control for experiments shown in Table 15. Some TPO-mimetic peptides and TPO-mimetic fusion proteins are more effective than others in stimulating platelet production in mice.

The invention now being fully described, it will be apparent to one of ordinary skill in the art that many changes and modifications can be made thereto, without departing from the spirit and scope of the invention as set forth herein.

SEQUENCE LISTING

<160> NUMBER OF SEQ ID NOS: 456

<210> SEQ ID NO 1
<211> LENGTH: 684
<212> TYPE: DNA
<213> ORGANISM: Homo sapiens

<400> SEQUENCE: 1

```
atggacaaaa ctcacacatg tccaccttgt ccagctccgg aactcctggg gggaccgtca      60
gtcttcctct tccccccaaa acccaaggac accctcatga tctcccggac ccctgaggtc     120
acatgcgtgg tggtggacgt gagccacgaa gaccctgagg tcaagttcaa ctggtacgtg     180
gacggcgtgg aggtgcataa tgccaagaca aagccgcggg aggagcagta caacagcacg     240
taccgtgtgg tcagcgtcct caccgtcctg caccaggact ggctgaatgg caaggagtac     300
aagtgcaagg tctccaacaa agcccctcca gcccccatcg agaaaaccat ctccaaagcc     360
aaagggcagc cccgagaacc acaggtgtac accctgcccc catcccggga tgagctgacc     420
aagaaccagg tcagcctgac ctgcctggtc aaaggcttct atcccagcga catcgccgtg     480
gagtgggaga gcaatgggca gccggagaac aactacaaga ccacgcctcc cgtgctggac     540
tccgacggct ccttcttcct ctacagcaag ctcaccgtgg acaagagcag gtggcagcag     600
gggaacgtct tctcatgctc cgtgatgcat gaggctctgc acaaccacta cacgcagaag     660
agcctctccc tgtctccggg taaa                                            684
```

<210> SEQ ID NO 2
<211> LENGTH: 684
<212> TYPE: DNA
<213> ORGANISM: Homo sapiens

<400> SEQUENCE: 2

```
tacctgtttt gagtgtgtac aggtggaaca ggtcgaggcc ttgaggaccc ccctggcagt      60
cagaaggaga aggggggttt tgggttcctg tgggagtact agagggcctg ggactccag     120 tgtacgcacc accacctgca ctcggtgctt ctgggactcc agttcaagtt gaccatgcac     180
ctgccgcacc tccacgtatt acggttctgt ttcggcgccc tcctcgtcat gttgtcgtgc     240
atggcacacc agtcgcagga gtggcaggac gtggtcctga ccgacttacc gttcctcatg     300
ttcacgttcc agaggttgtt tcgggagggt cgggggtagc tcttttggta gaggtttcgg     360
tttcccgtcg gggctcttgg tgtccacatg tgggacgggg gtagggccct actcgactgg     420
```

```
ttcttggtcc agtcggactg gacggaccag tttccgaaga tagggtcgct gtagcggcac    480
ctcaccctct cgttacccgt cggcctcttg ttgatgttct ggtgcggagg gcacgacctg    540
aggctgccga ggaagaagga gatgtcgttc gagtggcacc tgttctcgtc caccgtcgtc    600
cccttgcaga agagtacgag gcactacgta ctccgagacg tgttggtgat gtgcgtcttc    660
tcggagaggg acagaggccc attt                                           684
```

```
<210> SEQ ID NO 3
<211> LENGTH: 228
<212> TYPE: PRT
<213> ORGANISM: Artificial sequence
<220> FEATURE:
<223> OTHER INFORMATION: Synthetic peptide

<400> SEQUENCE: 3

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225
```

```
<210> SEQ ID NO 4
<211> LENGTH: 8
<212> TYPE: PRT
<213> ORGANISM: Artificial sequence
<220> FEATURE:
<223> OTHER INFORMATION: Synthetic peptide

<400> SEQUENCE: 4

Gly Gly Gly Lys Gly Gly Gly Gly
1               5
```

```
<210> SEQ ID NO 5
<211> LENGTH: 8
<212> TYPE: PRT
<213> ORGANISM: Artificial sequence
<220> FEATURE:
<223> OTHER INFORMATION: Synthetic peptide

<400> SEQUENCE: 5

Gly Gly Gly Asn Gly Ser Gly Gly
1               5

<210> SEQ ID NO 6
<211> LENGTH: 8
<212> TYPE: PRT
<213> ORGANISM: Artificial sequence
<220> FEATURE:
<223> OTHER INFORMATION: Synthetic peptide

<400> SEQUENCE: 6

Gly Gly Gly Cys Gly Gly Gly Gly
1               5

<210> SEQ ID NO 7
<211> LENGTH: 4
<212> TYPE: PRT
<213> ORGANISM: Artificial sequence
<220> FEATURE:
<223> OTHER INFORMATION: Synthetic peptide

<400> SEQUENCE: 7

Gly Pro Asn Gly
1

<210> SEQ ID NO 8
<211> LENGTH: 22
<212> TYPE: PRT
<213> ORGANISM: Artificial sequence
<220> FEATURE:
<223> OTHER INFORMATION: Synthetic peptide

<400> SEQUENCE: 8

Gln Gly Cys Ser Ser Gly Gly Pro Thr Gln Arg Glu Trp Leu Gln Cys
1               5                   10                  15

Arg Arg Met Gln His Ser
            20

<210> SEQ ID NO 9
<211> LENGTH: 22
<212> TYPE: PRT
<213> ORGANISM: Artificial sequence
<220> FEATURE:
<223> OTHER INFORMATION: Synthetic peptide

<400> SEQUENCE: 9

Gln Gly Cys Ser Ser Gly Gly Pro Thr Leu Arg Glu Trp Gln Gln Cys
1               5                   10                  15

Arg Arg Met Gln His Ser
            20

<210> SEQ ID NO 10
<211> LENGTH: 22
<212> TYPE: PRT
<213> ORGANISM: Artificial sequence
<220> FEATURE:
<223> OTHER INFORMATION: Synthetic peptide

<400> SEQUENCE: 10
```

Gln Gly Cys Ser Trp Gly Gly Pro Thr Leu Lys Ile Trp Leu Gln Cys
1               5                   10                  15

Val Arg Ala Lys His Ser
            20

<210> SEQ ID NO 11
<211> LENGTH: 22
<212> TYPE: PRT
<213> ORGANISM: Artificial sequence
<220> FEATURE:
<223> OTHER INFORMATION: Synthetic peptide

<400> SEQUENCE: 11

Gln Gly Cys Ser Trp Gly Gly Pro Thr Leu Lys Asn Trp Leu Gln Cys
1               5                   10                  15

Val Arg Ala Lys His Ser
            20

<210> SEQ ID NO 12
<211> LENGTH: 22
<212> TYPE: PRT
<213> ORGANISM: Artificial sequence
<220> FEATURE:
<223> OTHER INFORMATION: Synthetic peptide

<400> SEQUENCE: 12

Gln Gly Cys Ser Trp Gly Gly Pro Thr Leu Lys Leu Trp Leu Gln Cys
1               5                   10                  15

Val Arg Ala Lys His Ser
            20

<210> SEQ ID NO 13
<211> LENGTH: 22
<212> TYPE: PRT
<213> ORGANISM: Artificial sequence
<220> FEATURE:
<223> OTHER INFORMATION: Synthetic peptide

<400> SEQUENCE: 13

Gln Gly Cys Ser Trp Gly Gly Pro Thr Leu Lys His Trp Leu Gln Cys
1               5                   10                  15

Val Arg Ala Lys His Ser
            20

<210> SEQ ID NO 14
<211> LENGTH: 22
<212> TYPE: PRT
<213> ORGANISM: Artificial sequence
<220> FEATURE:
<223> OTHER INFORMATION: Synthetic peptide

<400> SEQUENCE: 14

Gln Gly Gly Cys Arg Ser Gly Pro Thr Asn Arg Glu Trp Leu Ala Cys
1               5                   10                  15

Arg Glu Val Gln His Ser
            20

<210> SEQ ID NO 15
<211> LENGTH: 22
<212> TYPE: PRT
<213> ORGANISM: Artificial sequence
<220> FEATURE:
<223> OTHER INFORMATION: Synthetic peptide

<400> SEQUENCE: 15

Gln Gly Thr Cys Glu Gln Gly Pro Thr Leu Arg Gln Trp Pro Leu Cys
1               5                   10                  15

Arg Gln Gly Arg His Ser
            20

<210> SEQ ID NO 16
<211> LENGTH: 22
<212> TYPE: PRT
<213> ORGANISM: Artificial sequence
<220> FEATURE:
<223> OTHER INFORMATION: Synthetic peptide

<400> SEQUENCE: 16

Gln Gly Thr Cys Glu Gln Gly Pro Thr Leu Arg Leu Trp Leu Leu Cys
1               5                   10                  15

Arg Gln Gly Arg His Ser
            20

<210> SEQ ID NO 17
<211> LENGTH: 22
<212> TYPE: PRT
<213> ORGANISM: Artificial sequence
<220> FEATURE:
<223> OTHER INFORMATION: Synthetic peptide

<400> SEQUENCE: 17

Gln Gly Thr Cys Glu Gln Gly Pro Thr Leu Arg Ile Trp Leu Leu Cys
1               5                   10                  15

Arg Gln Gly Arg His Ser
            20

<210> SEQ ID NO 18
<211> LENGTH: 22
<212> TYPE: PRT
<213> ORGANISM: Artificial sequence
<220> FEATURE:
<223> OTHER INFORMATION: Synthetic peptide

<400> SEQUENCE: 18

Gln Gly Cys Ser Ser Gly Gly Pro Thr Gln Arg Glu Trp Leu Gln Cys
1               5                   10                  15

Arg Arg Met Gln His Ser
            20

<210> SEQ ID NO 19
<211> LENGTH: 22
<212> TYPE: PRT
<213> ORGANISM: Artificial sequence
<220> FEATURE:
<223> OTHER INFORMATION: Synthetic peptide

<400> SEQUENCE: 19

Gln Gly Cys Ser Ser Gly Gly Pro Thr Leu Arg Glu Trp Gln Gln Cys
1               5                   10                  15

Arg Arg Met Gln His Ser
            20

<210> SEQ ID NO 20
<211> LENGTH: 22
<212> TYPE: PRT
<213> ORGANISM: Artificial sequence
<220> FEATURE:
<223> OTHER INFORMATION: Synthetic peptide

<400> SEQUENCE: 20

Gln Gly Cys Ser Trp Gly Gly Pro Thr Leu Lys Ile Trp Leu Gln Cys
1               5                   10                  15

Val Arg Ala Lys His Ser
            20

<210> SEQ ID NO 21
<211> LENGTH: 22
<212> TYPE: PRT
<213> ORGANISM: Artificial sequence
<220> FEATURE:
<223> OTHER INFORMATION: Synthetic peptide

<400> SEQUENCE: 21

Gln Gly Cys Ser Trp Gly Gly Pro Thr Leu Lys Asn Trp Leu Gln Cys
1               5                   10                  15

Val Arg Ala Lys His Ser
            20

<210> SEQ ID NO 22
<211> LENGTH: 22
<212> TYPE: PRT
<213> ORGANISM: Artificial sequence
<220> FEATURE:
<223> OTHER INFORMATION: Synthetic peptide

<400> SEQUENCE: 22

Gln Gly Cys Ser Trp Gly Gly Pro Thr Leu Lys Leu Trp Leu Gln Cys
1               5                   10                  15

Val Arg Ala Lys His Ser
            20

<210> SEQ ID NO 23
<211> LENGTH: 22
<212> TYPE: PRT
<213> ORGANISM: Artificial sequence
<220> FEATURE:
<223> OTHER INFORMATION: Synthetic peptide

<400> SEQUENCE: 23

Gln Gly Cys Ser Trp Gly Gly Pro Thr Leu Lys Ile Trp Leu Gln Cys
1               5                   10                  15

Val Arg Ala Lys His Ser
            20

<210> SEQ ID NO 24
<211> LENGTH: 22
<212> TYPE: PRT
<213> ORGANISM: Artificial sequence
<220> FEATURE:
<223> OTHER INFORMATION: Synthetic peptide

<400> SEQUENCE: 24

Gln Gly Gly Cys Arg Ser Gly Pro Thr Asn Arg Glu Trp Leu Ala Cys
1               5                   10                  15

Arg Glu Val Gln His Ser
            20

<210> SEQ ID NO 25
<211> LENGTH: 22
<212> TYPE: PRT
<213> ORGANISM: Artificial sequence
<220> FEATURE:
<223> OTHER INFORMATION: Synthetic peptide

<400> SEQUENCE: 25

```
Gln Gly Cys Ser Trp Gly Gly Pro Thr Leu Lys Leu Trp Leu Gln Cys
1               5                   10                  15

Val Arg Ala Lys His Ser
            20

<210> SEQ ID NO 26
<211> LENGTH: 22
<212> TYPE: PRT
<213> ORGANISM: Artificial sequence
<220> FEATURE:
<223> OTHER INFORMATION: Synthetic peptide

<400> SEQUENCE: 26

Gln Gly Thr Cys Glu Gln Gly Pro Thr Leu Arg Gln Trp Pro Leu Cys
1               5                   10                  15

Arg Gln Gly Arg His Ser
            20

<210> SEQ ID NO 27
<211> LENGTH: 22
<212> TYPE: PRT
<213> ORGANISM: Artificial sequence
<220> FEATURE:
<223> OTHER INFORMATION: Synthetic peptide

<400> SEQUENCE: 27

Gln Gly Thr Cys Glu Gln Gly Pro Thr Leu Arg Gln Trp Pro Leu Cys
1               5                   10                  15

Arg Gln Gly Arg His Ser
            20

<210> SEQ ID NO 28
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 28

Glu Thr Leu Xaa Gln Trp Leu
1               5

<210> SEQ ID NO 29
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 29

His Thr Leu Xaa Gln Trp Leu
1               5

<210> SEQ ID NO 30
<211> LENGTH: 7
<212> TYPE: PRT
<213> ORGANISM: Artificial sequence
<220> FEATURE:
<223> OTHER INFORMATION: Synthetic peptide
<220> FEATURE:
```

```
<221> NAME/KEY: misc_feature
<222> LOCATION: (4)..(4)
<223> OTHER INFORMATION: Xaa can be any naturally occurring amino acid

<400> SEQUENCE: 30

Lys Thr Leu Xaa Gln Trp Leu
1               5

<210> SEQ ID NO 31
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 31

Gly Thr Gly Xaa Gln Trp Leu
1               5

<210> SEQ ID NO 32
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 32

Pro Thr Leu Xaa Ile Trp Leu
1               5

<210> SEQ ID NO 33
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 33

Pro Thr Leu Xaa Leu Trp Leu
1               5

<210> SEQ ID NO 34
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 34

Pro Thr Leu Xaa Glu Trp Phe
1               5

<210> SEQ ID NO 35
<211> LENGTH: 7
```

```
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 35

Pro Thr Leu Xaa His Trp Leu
1               5

<210> SEQ ID NO 36
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 36

Pro Ile Leu Xaa Glu Trp Leu
1               5

<210> SEQ ID NO 37
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 37

Lys Thr Leu Xaa Glu Trp Leu
1               5

<210> SEQ ID NO 38
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 38

Pro Thr Leu Xaa Leu Trp Leu
1               5

<210> SEQ ID NO 39
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 39

Pro Met Leu Xaa Glu Trp Leu
```

-continued

```
<210> SEQ ID NO 40
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 40

Pro Thr Leu Xaa Asn Trp Leu
1               5

<210> SEQ ID NO 41
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 41

Pro Pro Leu Xaa Glu Trp Leu
1               5

<210> SEQ ID NO 42
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 42

Pro Thr Gln Xaa Glu Trp Gln
1               5

<210> SEQ ID NO 43
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 43

Pro Thr Leu Xaa Glu Trp Ser
1               5

<210> SEQ ID NO 44
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
```

```
<223> OTHER INFORMATION: Xaa can be any naturally occurring amino acid

<400> SEQUENCE: 44

Pro Thr Tyr Xaa Glu Trp Leu
1               5

<210> SEQ ID NO 45
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 45

Pro Thr Ala Xaa Gln Trp Leu
1               5

<210> SEQ ID NO 46
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 46

Pro Cys Leu Xaa Gln Trp Leu
1               5

<210> SEQ ID NO 47
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 47

Pro Thr Leu Xaa Phe Trp Leu
1               5

<210> SEQ ID NO 48
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 48

Pro Thr Gly Xaa Gln Trp Leu
1               5

<210> SEQ ID NO 49
<211> LENGTH: 7
<212> TYPE: PRT
<213> ORGANISM: Artificial sequence
```

```
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 49

Pro Thr Leu Xaa His Trp Leu
1               5

<210> SEQ ID NO 50
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 50

Pro Ile Leu Xaa Ile Trp Leu
1               5

<210> SEQ ID NO 51
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 51

Pro Thr Leu Xaa Leu Trp Leu
1               5

<210> SEQ ID NO 52
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 52

Pro Met Leu Xaa Gln Trp Leu
1               5

<210> SEQ ID NO 53
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 53

Pro Thr Leu Xaa Asn Trp Leu
1               5
```

```
<210> SEQ ID NO 54
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 54

Pro Thr Pro Xaa Gln Trp Leu
1               5

<210> SEQ ID NO 55
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 55

Pro Thr Leu Xaa Gln Trp Gln
1               5

<210> SEQ ID NO 56
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 56

Pro Thr Leu Xaa Gln Trp Ser
1               5

<210> SEQ ID NO 57
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 57

Pro Thr Thr Xaa Gln Trp Thr
1               5

<210> SEQ ID NO 58
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid
```

```
<400> SEQUENCE: 58

Pro Thr Leu Xaa Trp Trp Leu
1               5

<210> SEQ ID NO 59
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 59

Pro Thr Tyr Xaa Gln Trp Leu
1               5

<210> SEQ ID NO 60
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 60

Pro Thr Leu Xaa Glu Trp Phe
1               5

<210> SEQ ID NO 61
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 61

Gly Thr Leu Xaa Glu Trp Leu
1               5

<210> SEQ ID NO 62
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 62

Pro Thr Leu Xaa His Trp Leu
1               5

<210> SEQ ID NO 63
<211> LENGTH: 7
<212> TYPE: PRT
<213> ORGANISM: Artificial sequence
<220> FEATURE:
<223> OTHER INFORMATION: Synthetic peptide
```

```
<220> FEATURE:
<221> NAME/KEY: misc_feature
<222> LOCATION: (4)..(4)
<223> OTHER INFORMATION: Xaa can be any naturally occurring amino acid

<400> SEQUENCE: 63

Pro Ile Leu Xaa Glu Trp Leu
1               5

<210> SEQ ID NO 64
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 64

Pro Thr Leu Xaa Leu Trp Leu
1               5

<210> SEQ ID NO 65
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 65

Pro Thr Gln Xaa Glu Trp Leu
1               5

<210> SEQ ID NO 66
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 66

Pro Thr Leu Xaa Glu Trp Ser
1               5

<210> SEQ ID NO 67
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 67

Pro Thr Leu Xaa Phe Trp Phe
1               5

<210> SEQ ID NO 68
```

```
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 68

Gly Thr Leu Xaa Gln Trp Leu
1               5

<210> SEQ ID NO 69
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 69

Pro Thr Leu Xaa Ile Trp Leu
1               5

<210> SEQ ID NO 70
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 70

Pro Thr Leu Xaa Leu Trp Leu
1               5

<210> SEQ ID NO 71
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 71

Pro Thr Leu Xaa Asn Trp Leu
1               5

<210> SEQ ID NO 72
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 72
```

```
Pro Thr Leu Xaa Gln Trp Pro
1               5
```

<210> SEQ ID NO 73
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 73

```
Pro Thr Leu Xaa Trp Trp Leu
1               5
```

<210> SEQ ID NO 74
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 74

```
Pro Thr Tyr Xaa Gln Trp Leu
1               5
```

<210> SEQ ID NO 75
<211> LENGTH: 18
<212> TYPE: PRT
<213> ORGANISM: Artificial sequence
<220> FEATURE:
<223> OTHER INFORMATION: Synthetic peptide

<400> SEQUENCE: 75

```
Lys Asp Thr Glu Val Thr Ala Pro Arg Leu Trp Met Val Ala Ser Val
1               5                   10                  15

Asp Glu
```

<210> SEQ ID NO 76
<211> LENGTH: 18
<212> TYPE: PRT
<213> ORGANISM: Artificial sequence
<220> FEATURE:
<223> OTHER INFORMATION: Synthetic peptide

<400> SEQUENCE: 76

```
Arg Glu Met Glu Gly Pro Thr Met Arg Gln Trp Leu Ala Tyr Arg Ala
1               5                   10                  15

Val Leu
```

<210> SEQ ID NO 77
<211> LENGTH: 18
<212> TYPE: PRT
<213> ORGANISM: Artificial sequence
<220> FEATURE:
<223> OTHER INFORMATION: Synthetic peptide

<400> SEQUENCE: 77

```
Cys Gln Asn Ala Gly Pro Thr Leu Arg Cys Trp Leu Ala Gly Arg Ala
1               5                   10                  15
```

Tyr Met

<210> SEQ ID NO 78
<211> LENGTH: 18
<212> TYPE: PRT
<213> ORGANISM: Artificial sequence
<220> FEATURE:
<223> OTHER INFORMATION: Synthetic peptide

<400> SEQUENCE: 78

Cys Glu Arg Glu Gly Pro Thr Leu Arg Cys Trp Leu Ala Thr Arg Glu
1               5                   10                  15

Gly Ser

<210> SEQ ID NO 79
<211> LENGTH: 18
<212> TYPE: PRT
<213> ORGANISM: Artificial sequence
<220> FEATURE:
<223> OTHER INFORMATION: Synthetic peptide

<400> SEQUENCE: 79

Trp Arg Ile Glu Gly Pro Thr Leu Arg His Trp Leu Ala Ala Arg Ala
1               5                   10                  15

Trp Asp

<210> SEQ ID NO 80
<211> LENGTH: 18
<212> TYPE: PRT
<213> ORGANISM: Artificial sequence
<220> FEATURE:
<223> OTHER INFORMATION: Synthetic peptide

<400> SEQUENCE: 80

Ala Asn Met Glu Gly Pro Thr Leu Arg His Trp Leu Ala Met Arg Ala
1               5                   10                  15

Arg Val

<210> SEQ ID NO 81
<211> LENGTH: 18
<212> TYPE: PRT
<213> ORGANISM: Artificial sequence
<220> FEATURE:
<223> OTHER INFORMATION: Synthetic peptide

<400> SEQUENCE: 81

Leu Asp Met Glu Gly Pro Thr Leu Arg His Trp Leu Ala Ala Arg Ala
1               5                   10                  15

Asn Gly

<210> SEQ ID NO 82
<211> LENGTH: 18
<212> TYPE: PRT
<213> ORGANISM: Artificial sequence
<220> FEATURE:
<223> OTHER INFORMATION: Synthetic peptide

<400> SEQUENCE: 82

Trp Arg Met Glu Gly Pro Thr Leu Arg His Trp Leu Ala Ala Arg Ala
1               5                   10                  15

Trp Gly

<210> SEQ ID NO 83
<211> LENGTH: 18

```
<212> TYPE: PRT
<213> ORGANISM: Artificial sequence
<220> FEATURE:
<223> OTHER INFORMATION: Synthetic peptide

<400> SEQUENCE: 83

Trp Ala Met Glu Gly Pro Thr Leu Arg His Trp Leu Ala Ala Arg Ala
1               5                   10                  15

Val Leu

<210> SEQ ID NO 84
<211> LENGTH: 18
<212> TYPE: PRT
<213> ORGANISM: Artificial sequence
<220> FEATURE:
<223> OTHER INFORMATION: Synthetic peptide

<400> SEQUENCE: 84

Lys Ser Met Glu Gly Pro Ser Leu Arg Gln Trp Leu Ala Ala Arg Ala
1               5                   10                  15

Gln Leu

<210> SEQ ID NO 85
<211> LENGTH: 18
<212> TYPE: PRT
<213> ORGANISM: Artificial sequence
<220> FEATURE:
<223> OTHER INFORMATION: Synthetic peptide

<400> SEQUENCE: 85

Thr Lys Ile Glu Gly Pro Thr Leu Arg His Trp Leu Ala Ala Arg Ala
1               5                   10                  15

Glu Leu

<210> SEQ ID NO 86
<211> LENGTH: 18
<212> TYPE: PRT
<213> ORGANISM: Artificial sequence
<220> FEATURE:
<223> OTHER INFORMATION: Synthetic peptide

<400> SEQUENCE: 86

Pro Arg Ile Glu Gly Pro Thr Leu Arg Leu Trp Leu Val Thr Arg Ala
1               5                   10                  15

Leu Ser

<210> SEQ ID NO 87
<211> LENGTH: 18
<212> TYPE: PRT
<213> ORGANISM: Artificial sequence
<220> FEATURE:
<223> OTHER INFORMATION: Synthetic peptide

<400> SEQUENCE: 87

Ile Tyr Met Glu Gly Pro Thr Leu Arg His Trp Leu Ala Asn Arg Ala
1               5                   10                  15

Ala Lys

<210> SEQ ID NO 88
<211> LENGTH: 18
<212> TYPE: PRT
<213> ORGANISM: Artificial sequence
<220> FEATURE:
<223> OTHER INFORMATION: Synthetic peptide
```

```
<400> SEQUENCE: 88

Trp Pro Ile Glu Gly Ala Thr Leu Arg Gln Trp Leu Lys Ile Arg Ala
1               5                   10                  15

Gly Tyr

<210> SEQ ID NO 89
<211> LENGTH: 18
<212> TYPE: PRT
<213> ORGANISM: Artificial sequence
<220> FEATURE:
<223> OTHER INFORMATION: Synthetic peptide

<400> SEQUENCE: 89

Arg Asn Met Glu Gly Pro Thr Leu Arg Asn Trp Leu Ala Ala Arg Ala
1               5                   10                  15

Gln His

<210> SEQ ID NO 90
<211> LENGTH: 18
<212> TYPE: PRT
<213> ORGANISM: Artificial sequence
<220> FEATURE:
<223> OTHER INFORMATION: Synthetic peptide

<400> SEQUENCE: 90

Asn Gly Ile Glu Gly Pro Thr Leu Arg Leu Trp Leu Ser Glu Arg Ala
1               5                   10                  15

Lys Lys

<210> SEQ ID NO 91
<211> LENGTH: 18
<212> TYPE: PRT
<213> ORGANISM: Artificial sequence
<220> FEATURE:
<223> OTHER INFORMATION: Synthetic peptide

<400> SEQUENCE: 91

Met Trp Met Glu Gly Pro Thr Leu Arg His Trp Leu Glu Ala Arg Ala
1               5                   10                  15

Arg Tyr

<210> SEQ ID NO 92
<211> LENGTH: 18
<212> TYPE: PRT
<213> ORGANISM: Artificial sequence
<220> FEATURE:
<223> OTHER INFORMATION: Synthetic peptide

<400> SEQUENCE: 92

Tyr Gly Ile Asp Gly Pro Thr Leu Arg His Trp Leu Ala Ala Arg Ala
1               5                   10                  15

Arg Tyr

<210> SEQ ID NO 93
<211> LENGTH: 18
<212> TYPE: PRT
<213> ORGANISM: Artificial sequence
<220> FEATURE:
<223> OTHER INFORMATION: Synthetic peptide

<400> SEQUENCE: 93

Arg Ile Ile Asp Gly Gln Thr Leu Arg His Trp Leu Ala Ala Gly Ala
1               5                   10                  15
```

Asp Pro

<210> SEQ ID NO 94
<211> LENGTH: 18
<212> TYPE: PRT
<213> ORGANISM: Artificial sequence
<220> FEATURE:
<223> OTHER INFORMATION: Synthetic peptide

<400> SEQUENCE: 94

Asn Gly Arg Asp Gly Pro Thr Val Arg His Arg Leu Ala Gly Arg Ala
1               5                   10                  15

Gln Lys

<210> SEQ ID NO 95
<211> LENGTH: 18
<212> TYPE: PRT
<213> ORGANISM: Artificial sequence
<220> FEATURE:
<223> OTHER INFORMATION: Synthetic peptide

<400> SEQUENCE: 95

Thr His Ile Glu Gly Pro Thr Leu Arg Ile Trp Leu Ala Ser Arg Ala
1               5                   10                  15

Lys Ala

<210> SEQ ID NO 96
<211> LENGTH: 18
<212> TYPE: PRT
<213> ORGANISM: Artificial sequence
<220> FEATURE:
<223> OTHER INFORMATION: Synthetic peptide

<400> SEQUENCE: 96

Lys Gly Met Glu Gly Pro Thr Leu Arg His Trp Leu Ala Ala Arg Ala
1               5                   10                  15

His Leu

<210> SEQ ID NO 97
<211> LENGTH: 18
<212> TYPE: PRT
<213> ORGANISM: Artificial sequence
<220> FEATURE:
<223> OTHER INFORMATION: Synthetic peptide

<400> SEQUENCE: 97

Gln Arg Ile Glu Gly Pro Thr Leu Arg His Trp Leu Ala Ala Arg Ala
1               5                   10                  15

Ser His

<210> SEQ ID NO 98
<211> LENGTH: 18
<212> TYPE: PRT
<213> ORGANISM: Artificial sequence
<220> FEATURE:
<223> OTHER INFORMATION: Synthetic peptide

<400> SEQUENCE: 98

Lys Asp Thr Glu Val Thr Ala Pro Arg Leu Trp Met Val Ala Ser Val
1               5                   10                  15

Asp Glu

<210> SEQ ID NO 99
<211> LENGTH: 18

```
<212> TYPE: PRT
<213> ORGANISM: Artificial sequence
<220> FEATURE:
<223> OTHER INFORMATION: Synthetic peptide

<400> SEQUENCE: 99

Glu Asn Met Glu Gly Pro Thr Leu Arg His Trp Leu Ala Ala Arg Ala
1               5                   10                  15

His Glu

<210> SEQ ID NO 100
<211> LENGTH: 18
<212> TYPE: PRT
<213> ORGANISM: Artificial sequence
<220> FEATURE:
<223> OTHER INFORMATION: Synthetic peptide

<400> SEQUENCE: 100

Ser Trp Met Glu Gly Pro Thr Leu Arg His Trp Leu Met Asn Arg Ala
1               5                   10                  15

Thr Tyr

<210> SEQ ID NO 101
<211> LENGTH: 18
<212> TYPE: PRT
<213> ORGANISM: Artificial sequence
<220> FEATURE:
<223> OTHER INFORMATION: Synthetic peptide

<400> SEQUENCE: 101

Ser Met Met Glu Gly Pro Thr Leu Arg His Trp Leu Ala Ala Arg Ala
1               5                   10                  15

Lys Asp

<210> SEQ ID NO 102
<211> LENGTH: 18
<212> TYPE: PRT
<213> ORGANISM: Artificial sequence
<220> FEATURE:
<223> OTHER INFORMATION: Synthetic peptide

<400> SEQUENCE: 102

Gln Gly Ile Glu Gly Pro Thr Leu Arg Leu Trp Leu Ala Ala Arg Thr
1               5                   10                  15

His Pro

<210> SEQ ID NO 103
<211> LENGTH: 18
<212> TYPE: PRT
<213> ORGANISM: Artificial sequence
<220> FEATURE:
<223> OTHER INFORMATION: Synthetic peptide

<400> SEQUENCE: 103

Tyr Met Met Glu Gly Pro Thr Leu Arg His Trp Leu Ala Thr Arg Ala
1               5                   10                  15

Gly Arg

<210> SEQ ID NO 104
<211> LENGTH: 18
<212> TYPE: PRT
<213> ORGANISM: Artificial sequence
<220> FEATURE:
<223> OTHER INFORMATION: Synthetic peptide
```

```
<400> SEQUENCE: 104

Gly Asn Met Glu Gly Pro Thr Leu Arg His Trp Leu Ala Ala Asn Glu
1               5                   10                  15

Arg Asp

<210> SEQ ID NO 105
<211> LENGTH: 18
<212> TYPE: PRT
<213> ORGANISM: Artificial sequence
<220> FEATURE:
<223> OTHER INFORMATION: Synthetic peptide

<400> SEQUENCE: 105

Asn Arg Met Glu Gly Pro Thr Leu Arg His Trp Leu Ala Glu Arg Ala
1               5                   10                  15

Gly Ser

<210> SEQ ID NO 106
<211> LENGTH: 18
<212> TYPE: PRT
<213> ORGANISM: Artificial sequence
<220> FEATURE:
<223> OTHER INFORMATION: Synthetic peptide

<400> SEQUENCE: 106

Asn Met Met Glu Gly Pro Thr Leu Arg His Trp Leu Ala Ala Arg Val
1               5                   10                  15

Ala Ala

<210> SEQ ID NO 107
<211> LENGTH: 18
<212> TYPE: PRT
<213> ORGANISM: Artificial sequence
<220> FEATURE:
<223> OTHER INFORMATION: Synthetic peptide

<400> SEQUENCE: 107

Ser Pro Ile Glu Gly Pro Thr Leu Arg Gln Gln Leu Cys Ala Arg Ala
1               5                   10                  15

Val Lys

<210> SEQ ID NO 108
<211> LENGTH: 18
<212> TYPE: PRT
<213> ORGANISM: Artificial sequence
<220> FEATURE:
<223> OTHER INFORMATION: Synthetic peptide

<400> SEQUENCE: 108

Val Gln Met Glu Gly Thr Thr Leu Arg Gln Trp Leu Ala Glu Arg Ala
1               5                   10                  15

Leu Asp

<210> SEQ ID NO 109
<211> LENGTH: 18
<212> TYPE: PRT
<213> ORGANISM: Artificial sequence
<220> FEATURE:
<223> OTHER INFORMATION: Synthetic peptide

<400> SEQUENCE: 109

Lys Arg Lys Asp Gly His Arg Pro Arg Gln Trp Leu Ala Pro Leu Ala
1               5                   10                  15
```

Cys Lys

<210> SEQ ID NO 110
<211> LENGTH: 18
<212> TYPE: PRT
<213> ORGANISM: Artificial sequence
<220> FEATURE:
<223> OTHER INFORMATION: Synthetic peptide

<400> SEQUENCE: 110

Glu Met Met Glu Gly Pro Thr Leu Arg His Trp Leu Ala Ala Arg Ala
1               5                   10                  15

Glu Lys

<210> SEQ ID NO 111
<211> LENGTH: 18
<212> TYPE: PRT
<213> ORGANISM: Artificial sequence
<220> FEATURE:
<223> OTHER INFORMATION: Synthetic peptide

<400> SEQUENCE: 111

Asn Met Ile Glu Gly Pro Thr Leu Arg His Trp Leu Ala Glu Arg Ala
1               5                   10                  15

Ser Gln

<210> SEQ ID NO 112
<211> LENGTH: 18
<212> TYPE: PRT
<213> ORGANISM: Artificial sequence
<220> FEATURE:
<223> OTHER INFORMATION: Synthetic peptide

<400> SEQUENCE: 112

Lys Leu Met Glu Gly Pro Thr Leu Arg His Trp Leu Ala Tyr Arg Ala
1               5                   10                  15

Gly Leu

<210> SEQ ID NO 113
<211> LENGTH: 18
<212> TYPE: PRT
<213> ORGANISM: Artificial sequence
<220> FEATURE:
<223> OTHER INFORMATION: Synthetic peptide

<400> SEQUENCE: 113

Tyr Met Met Glu Gly Pro Thr Leu Arg His Trp Leu Ala Ala Arg Ala
1               5                   10                  15

Leu Val

<210> SEQ ID NO 114
<211> LENGTH: 18
<212> TYPE: PRT
<213> ORGANISM: Artificial sequence
<220> FEATURE:
<223> OTHER INFORMATION: Synthetic peptide

<400> SEQUENCE: 114

Gly Asn Met Glu Gly Pro Thr Leu Arg His Trp Leu Ala Ala Arg Ala
1               5                   10                  15

Leu Leu

<210> SEQ ID NO 115
<211> LENGTH: 18

```
<212> TYPE: PRT
<213> ORGANISM: Artificial sequence
<220> FEATURE:
<223> OTHER INFORMATION: Synthetic peptide

<400> SEQUENCE: 115

Trp Met Met Glu Gly Pro Thr Leu Arg His Trp Leu Ala Ala Arg Ala
1               5                   10                  15
Arg Tyr

<210> SEQ ID NO 116
<211> LENGTH: 18
<212> TYPE: PRT
<213> ORGANISM: Artificial sequence
<220> FEATURE:
<223> OTHER INFORMATION: Synthetic peptide

<400> SEQUENCE: 116

Thr Asp Arg Gly Gly Tyr Thr Leu Arg Gln Trp Leu Ala Ala Arg Ala
1               5                   10                  15
Val Leu

<210> SEQ ID NO 117
<211> LENGTH: 18
<212> TYPE: PRT
<213> ORGANISM: Artificial sequence
<220> FEATURE:
<223> OTHER INFORMATION: Synthetic peptide

<400> SEQUENCE: 117

Ser Ala Ile Glu Gly Pro Thr Leu Arg His Trp Leu Ala Trp Arg Ala
1               5                   10                  15
Met Leu

<210> SEQ ID NO 118
<211> LENGTH: 18
<212> TYPE: PRT
<213> ORGANISM: Artificial sequence
<220> FEATURE:
<223> OTHER INFORMATION: Synthetic peptide

<400> SEQUENCE: 118

Arg Ala Ile Glu Gly Pro Thr Leu Arg His Cys Leu Ala Ala Gly Ala
1               5                   10                  15
Gly Leu

<210> SEQ ID NO 119
<211> LENGTH: 18
<212> TYPE: PRT
<213> ORGANISM: Artificial sequence
<220> FEATURE:
<223> OTHER INFORMATION: Synthetic peptide

<400> SEQUENCE: 119

Val Lys Arg Lys Gly Pro Thr Leu Arg His Trp Leu Ala Ala Trp Ala
1               5                   10                  15
Phe Pro

<210> SEQ ID NO 120
<211> LENGTH: 18
<212> TYPE: PRT
<213> ORGANISM: Artificial sequence
<220> FEATURE:
<223> OTHER INFORMATION: Synthetic peptide
```

-continued

<400> SEQUENCE: 120

Thr Cys Met Glu Gly Pro Thr Leu Arg His Trp Leu Ala Ala Arg Ala
1               5                   10                  15

Glu Gly

<210> SEQ ID NO 121
<211> LENGTH: 18
<212> TYPE: PRT
<213> ORGANISM: Artificial sequence
<220> FEATURE:
<223> OTHER INFORMATION: Synthetic peptide

<400> SEQUENCE: 121

Trp Phe Met Glu Gly Pro Thr Leu Arg His Trp Leu Ala Ala Arg Ala
1               5                   10                  15

Tyr Arg

<210> SEQ ID NO 122
<211> LENGTH: 18
<212> TYPE: PRT
<213> ORGANISM: Artificial sequence
<220> FEATURE:
<223> OTHER INFORMATION: Synthetic peptide

<400> SEQUENCE: 122

Ala Asp Ile Glu Gly Pro Thr Leu Arg His Trp Leu Ala Ala Arg Ala
1               5                   10                  15

Leu Val

<210> SEQ ID NO 123
<211> LENGTH: 18
<212> TYPE: PRT
<213> ORGANISM: Artificial sequence
<220> FEATURE:
<223> OTHER INFORMATION: Synthetic peptide

<400> SEQUENCE: 123

Trp Val Met Glu Gly Pro Thr Leu Arg His Trp Leu Ala Ala Arg Ala
1               5                   10                  15

Ser Leu

<210> SEQ ID NO 124
<211> LENGTH: 18
<212> TYPE: PRT
<213> ORGANISM: Artificial sequence
<220> FEATURE:
<223> OTHER INFORMATION: Synthetic peptide

<400> SEQUENCE: 124

Pro Pro Gly Asp Gly Pro Thr Leu Arg His Trp Leu Ala Ala Arg Ala
1               5                   10                  15

Arg Met

<210> SEQ ID NO 125
<211> LENGTH: 18
<212> TYPE: PRT
<213> ORGANISM: Artificial sequence
<220> FEATURE:
<223> OTHER INFORMATION: Synthetic peptide

<400> SEQUENCE: 125

Asp Phe Met Glu Gly Pro Thr Leu Arg Gln Arg Val Asp Ala Arg Ala
1               5                   10                  15

His Tyr

<210> SEQ ID NO 126
<211> LENGTH: 18
<212> TYPE: PRT
<213> ORGANISM: Artificial sequence
<220> FEATURE:
<223> OTHER INFORMATION: Synthetic peptide

<400> SEQUENCE: 126

Arg Trp Ile Glu Gly Pro Thr Gln Arg Gln Trp Leu Ala Ala Arg Ala
1               5                   10                  15

Tyr Phe

<210> SEQ ID NO 127
<211> LENGTH: 18
<212> TYPE: PRT
<213> ORGANISM: Artificial sequence
<220> FEATURE:
<223> OTHER INFORMATION: Synthetic peptide

<400> SEQUENCE: 127

Ile Arg Met Glu Gly Pro Thr Leu Arg His Trp Leu Ala Ser Arg Ala
1               5                   10                  15

Glu Ile

<210> SEQ ID NO 128
<211> LENGTH: 18
<212> TYPE: PRT
<213> ORGANISM: Artificial sequence
<220> FEATURE:
<223> OTHER INFORMATION: Synthetic peptide

<400> SEQUENCE: 128

Tyr Tyr Leu Glu Gly Pro Thr Leu Arg His Trp Leu Ala Ala Arg Ala
1               5                   10                  15

Tyr Leu

<210> SEQ ID NO 129
<211> LENGTH: 18
<212> TYPE: PRT
<213> ORGANISM: Artificial sequence
<220> FEATURE:
<223> OTHER INFORMATION: Synthetic peptide

<400> SEQUENCE: 129

Gly Val Ile Glu Gly Pro Thr Leu Arg His Trp Leu Ala Ala Arg Ala
1               5                   10                  15

Ala Gln

<210> SEQ ID NO 130
<211> LENGTH: 18
<212> TYPE: PRT
<213> ORGANISM: Artificial sequence
<220> FEATURE:
<223> OTHER INFORMATION: Synthetic peptide

<400> SEQUENCE: 130

Gly Ala Met Glu Gly Pro Thr Leu Arg Cys Trp Leu Ala Ala Ser Asp
1               5                   10                  15

Glu Lys

<210> SEQ ID NO 131
<211> LENGTH: 18

```
<212> TYPE: PRT
<213> ORGANISM: Artificial sequence
<220> FEATURE:
<223> OTHER INFORMATION: Synthetic peptide

<400> SEQUENCE: 131

Ser Val Ile Asp Gly Pro Thr Leu Arg Gln Arg Leu Ala Ala Arg Ala
1               5                   10                  15

Arg Tyr

<210> SEQ ID NO 132
<211> LENGTH: 18
<212> TYPE: PRT
<213> ORGANISM: Artificial sequence
<220> FEATURE:
<223> OTHER INFORMATION: Synthetic peptide

<400> SEQUENCE: 132

Gly Gly Ile Glu Arg Pro Thr Leu Arg His Cys Leu Ala Ala Arg Pro
1               5                   10                  15

Thr Ser

<210> SEQ ID NO 133
<211> LENGTH: 18
<212> TYPE: PRT
<213> ORGANISM: Artificial sequence
<220> FEATURE:
<223> OTHER INFORMATION: Synthetic peptide

<400> SEQUENCE: 133

Thr Lys Met Glu Gly Pro Thr Leu Arg His Trp Leu Ala Trp Arg Ala
1               5                   10                  15

Ala Tyr

<210> SEQ ID NO 134
<211> LENGTH: 18
<212> TYPE: PRT
<213> ORGANISM: Artificial sequence
<220> FEATURE:
<223> OTHER INFORMATION: Synthetic peptide

<400> SEQUENCE: 134

Leu Lys Met Glu Gly Pro Thr Leu Arg Asn Trp Leu Ala Trp Arg Ala
1               5                   10                  15

Phe Gln

<210> SEQ ID NO 135
<211> LENGTH: 18
<212> TYPE: PRT
<213> ORGANISM: Artificial sequence
<220> FEATURE:
<223> OTHER INFORMATION: Synthetic peptide

<400> SEQUENCE: 135

Gly Leu Val Glu Gly Pro Thr Leu Arg Phe Trp Leu Ala Ala Arg Ala
1               5                   10                  15

Ala Glu

<210> SEQ ID NO 136
<211> LENGTH: 18
<212> TYPE: PRT
<213> ORGANISM: Artificial sequence
<220> FEATURE:
<223> OTHER INFORMATION: Synthetic peptide
```

-continued

```
<400> SEQUENCE: 136

Gly Leu Thr Asp Gly Pro Asn Leu Arg His Cys Leu Ala Ala Arg Ala
1               5                   10                  15

Pro Ile

<210> SEQ ID NO 137
<211> LENGTH: 18
<212> TYPE: PRT
<213> ORGANISM: Artificial sequence
<220> FEATURE:
<223> OTHER INFORMATION: Synthetic peptide

<400> SEQUENCE: 137

Asp Arg Asn Lys Gly Pro Thr Leu Arg His Trp Leu Ala Ala Arg Ala
1               5                   10                  15

His Ala

<210> SEQ ID NO 138
<211> LENGTH: 18
<212> TYPE: PRT
<213> ORGANISM: Artificial sequence
<220> FEATURE:
<223> OTHER INFORMATION: Synthetic peptide

<400> SEQUENCE: 138

Ala Ser Met Val Gly Pro Lys Leu Arg His Gly Leu Ala Ala Val Ala
1               5                   10                  15

Lys Lys

<210> SEQ ID NO 139
<211> LENGTH: 18
<212> TYPE: PRT
<213> ORGANISM: Artificial sequence
<220> FEATURE:
<223> OTHER INFORMATION: Synthetic peptide

<400> SEQUENCE: 139

Asp Ala Ile Glu Gly Pro Thr Leu Arg Leu Trp Leu Glu Ala Arg Arg
1               5                   10                  15

Lys Gln

<210> SEQ ID NO 140
<211> LENGTH: 18
<212> TYPE: PRT
<213> ORGANISM: Artificial sequence
<220> FEATURE:
<223> OTHER INFORMATION: Synthetic peptide

<400> SEQUENCE: 140

Asn Ile Ile Lys Arg Ala Thr Asp Arg Glu Trp Leu Asp Ala Arg Thr
1               5                   10                  15

Ala Leu

<210> SEQ ID NO 141
<211> LENGTH: 18
<212> TYPE: PRT
<213> ORGANISM: Artificial sequence
<220> FEATURE:
<223> OTHER INFORMATION: Synthetic peptide

<400> SEQUENCE: 141

Gly Asp Asn Glu Gly Pro Ser Pro Arg Val Cys Leu Ala Ala Arg Ala
1               5                   10                  15
```

Val Leu

<210> SEQ ID NO 142
<211> LENGTH: 18
<212> TYPE: PRT
<213> ORGANISM: Artificial sequence
<220> FEATURE:
<223> OTHER INFORMATION: Synthetic peptide

<400> SEQUENCE: 142

Glu Phe Met Glu Gly Pro Thr Leu Arg His Trp Leu Ala Ser Arg Ala
1               5                   10                  15

Arg Val

<210> SEQ ID NO 143
<211> LENGTH: 18
<212> TYPE: PRT
<213> ORGANISM: Artificial sequence
<220> FEATURE:
<223> OTHER INFORMATION: Synthetic peptide

<400> SEQUENCE: 143

Trp Gly Met Glu Gly Pro Thr Leu Arg His Trp Leu Ala Ala Arg Gly
1               5                   10                  15

Lys Arg

<210> SEQ ID NO 144
<211> LENGTH: 18
<212> TYPE: PRT
<213> ORGANISM: Artificial sequence
<220> FEATURE:
<223> OTHER INFORMATION: Synthetic peptide

<400> SEQUENCE: 144

Arg Trp Met Glu Gly Pro Thr Leu Arg His Trp Leu Ala Glu Arg Ala
1               5                   10                  15

Met Leu

<210> SEQ ID NO 145
<211> LENGTH: 18
<212> TYPE: PRT
<213> ORGANISM: Artificial sequence
<220> FEATURE:
<223> OTHER INFORMATION: Synthetic peptide

<400> SEQUENCE: 145

Leu Met Val Glu Gly Pro Thr Leu Arg His Trp Leu Ala Ala Arg Trp
1               5                   10                  15

Arg Met

<210> SEQ ID NO 146
<211> LENGTH: 18
<212> TYPE: PRT
<213> ORGANISM: Artificial sequence
<220> FEATURE:
<223> OTHER INFORMATION: Synthetic peptide

<400> SEQUENCE: 146

Asn Tyr Ile Glu Gly Pro Thr Leu Arg His Trp Leu Ala Ala Arg Ala
1               5                   10                  15

Lys Leu

<210> SEQ ID NO 147
<211> LENGTH: 18

<212> TYPE: PRT
<213> ORGANISM: Artificial sequence
<220> FEATURE:
<223> OTHER INFORMATION: Synthetic peptide

<400> SEQUENCE: 147

Thr Trp Met Glu Gly Pro Thr Leu Arg Leu Trp Leu Met Ala Arg Ala
1               5                   10                  15
Leu Tyr

<210> SEQ ID NO 148
<211> LENGTH: 18
<212> TYPE: PRT
<213> ORGANISM: Artificial sequence
<220> FEATURE:
<223> OTHER INFORMATION: Synthetic peptide

<400> SEQUENCE: 148

Gln Tyr Met Glu Gly Pro Thr Leu Arg His Trp Leu Ala Ala Arg Ala
1               5                   10                  15
Ala Leu

<210> SEQ ID NO 149
<211> LENGTH: 18
<212> TYPE: PRT
<213> ORGANISM: Artificial sequence
<220> FEATURE:
<223> OTHER INFORMATION: Synthetic peptide

<400> SEQUENCE: 149

Ala Trp Met Glu Gly Pro Thr Leu Arg His Trp Leu Ala Ala Arg Ala
1               5                   10                  15
Ala Tyr

<210> SEQ ID NO 150
<211> LENGTH: 18
<212> TYPE: PRT
<213> ORGANISM: Artificial sequence
<220> FEATURE:
<223> OTHER INFORMATION: Synthetic peptide

<400> SEQUENCE: 150

Lys Gln Phe Glu Gly Pro Pro Met Arg Arg Ser Leu Ala Gly Val Asn
1               5                   10                  15
Thr Pro

<210> SEQ ID NO 151
<211> LENGTH: 18
<212> TYPE: PRT
<213> ORGANISM: Artificial sequence
<220> FEATURE:
<223> OTHER INFORMATION: Synthetic peptide

<400> SEQUENCE: 151

Ala Leu Met Glu Gly Pro Thr Leu Arg Gln Arg Leu Ala Ala Arg Ala
1               5                   10                  15
Ala Gln

<210> SEQ ID NO 152
<211> LENGTH: 18
<212> TYPE: PRT
<213> ORGANISM: Artificial sequence
<220> FEATURE:
<223> OTHER INFORMATION: Synthetic peptide -continued

```
<400> SEQUENCE: 152

Ala Arg Met Lys Gly Thr Thr Leu Arg Gln Trp Val Ala Ala Arg Ala
1               5                   10                  15

Phe Val

<210> SEQ ID NO 153
<211> LENGTH: 18
<212> TYPE: PRT
<213> ORGANISM: Artificial sequence
<220> FEATURE:
<223> OTHER INFORMATION: Synthetic peptide

<400> SEQUENCE: 153

Asp Lys Ile Glu Ile Pro Thr Val Gln Leu Arg Arg Ala Ala Tyr Ala
1               5                   10                  15

Cys Gln

<210> SEQ ID NO 154
<211> LENGTH: 18
<212> TYPE: PRT
<213> ORGANISM: Artificial sequence
<220> FEATURE:
<223> OTHER INFORMATION: Synthetic peptide

<400> SEQUENCE: 154

Tyr Arg Met Glu Gly Pro Thr Leu Arg His Trp Leu Ala Ala Arg Ala
1               5                   10                  15

Gly Val

<210> SEQ ID NO 155
<211> LENGTH: 18
<212> TYPE: PRT
<213> ORGANISM: Artificial sequence
<220> FEATURE:
<223> OTHER INFORMATION: Synthetic peptide

<400> SEQUENCE: 155

Ala Leu Met Glu Gly Pro Thr Leu Arg His Trp Leu Ala Ala Arg Ala
1               5                   10                  15

Leu Met

<210> SEQ ID NO 156
<211> LENGTH: 18
<212> TYPE: PRT
<213> ORGANISM: Artificial sequence
<220> FEATURE:
<223> OTHER INFORMATION: Synthetic peptide

<400> SEQUENCE: 156

Ile Trp Ala Gly Gly Pro Thr Leu Arg His Trp Leu Ala Ala Arg Ala
1               5                   10                  15

Ala Leu

<210> SEQ ID NO 157
<211> LENGTH: 18
<212> TYPE: PRT
<213> ORGANISM: Artificial sequence
<220> FEATURE:
<223> OTHER INFORMATION: Synthetic peptide

<400> SEQUENCE: 157

Gly Trp Val Asp Gly Pro Thr Leu Arg His Trp Leu Ala Ala Arg Ala
1               5                   10                  15
```

Arg Met

<210> SEQ ID NO 158
<211> LENGTH: 18
<212> TYPE: PRT
<213> ORGANISM: Artificial sequence
<220> FEATURE:
<223> OTHER INFORMATION: Synthetic peptide

<400> SEQUENCE: 158

Ala Arg Met Glu Gly Pro Thr Leu Arg His Trp Leu Ala Ala Arg Ala
1               5                   10                  15

Lys Met

<210> SEQ ID NO 159
<211> LENGTH: 18
<212> TYPE: PRT
<213> ORGANISM: Artificial sequence
<220> FEATURE:
<223> OTHER INFORMATION: Synthetic peptide

<400> SEQUENCE: 159

Glu Ser Met Glu Gly Ala Ser Gln Arg His Cys Met Ala Ala Arg Ala
1               5                   10                  15

Gly Gly

<210> SEQ ID NO 160
<211> LENGTH: 18
<212> TYPE: PRT
<213> ORGANISM: Artificial sequence
<220> FEATURE:
<223> OTHER INFORMATION: Synthetic peptide

<400> SEQUENCE: 160

Met Pro Val Asp Gly Pro Val Leu Arg Thr Trp His Ala Ala Gln Ala
1               5                   10                  15

Ile Glu

<210> SEQ ID NO 161
<211> LENGTH: 20
<212> TYPE: PRT
<213> ORGANISM: Artificial sequence
<220> FEATURE:
<223> OTHER INFORMATION: Synthetic peptide

<400> SEQUENCE: 161

Leu Glu His Asn Arg Pro Leu Thr Asn Pro Ile Pro Lys Pro Arg Thr
1               5                   10                  15

Pro Ile Arg Pro
            20

<210> SEQ ID NO 162
<211> LENGTH: 18
<212> TYPE: PRT
<213> ORGANISM: Artificial sequence
<220> FEATURE:
<223> OTHER INFORMATION: Synthetic peptide

<400> SEQUENCE: 162

Thr Thr Met Glu Asp Pro Thr Leu Arg His Trp Leu Ala Thr Gly Ala
1               5                   10                  15

Pro Thr

<210> SEQ ID NO 163

```
<211> LENGTH: 18
<212> TYPE: PRT
<213> ORGANISM: Artificial sequence
<220> FEATURE:
<223> OTHER INFORMATION: Synthetic peptide

<400> SEQUENCE: 163

His Pro Ile Glu Gly Pro Thr Leu Arg Leu Trp Leu Ala Ala Arg Ala
1               5                   10                  15
Arg Ala

<210> SEQ ID NO 164
<211> LENGTH: 18
<212> TYPE: PRT
<213> ORGANISM: Artificial sequence
<220> FEATURE:
<223> OTHER INFORMATION: Synthetic peptide

<400> SEQUENCE: 164

Phe Pro Met Glu Gly Thr Thr Leu Arg His Trp Leu Ala Ala Arg Val
1               5                   10                  15
Gln Met

<210> SEQ ID NO 165
<211> LENGTH: 18
<212> TYPE: PRT
<213> ORGANISM: Artificial sequence
<220> FEATURE:
<223> OTHER INFORMATION: Synthetic peptide

<400> SEQUENCE: 165

Arg Gly Met Asn Gly Pro Thr Leu Arg His Trp Leu Glu Glu Ser Ala
1               5                   10                  15
Lys Asp

<210> SEQ ID NO 166
<211> LENGTH: 18
<212> TYPE: PRT
<213> ORGANISM: Artificial sequence
<220> FEATURE:
<223> OTHER INFORMATION: Synthetic peptide

<400> SEQUENCE: 166

Asp Gln Met Glu Gly Ser Met Val His Gln Trp Leu Ala Arg His Val
1               5                   10                  15
Trp Gly

<210> SEQ ID NO 167
<211> LENGTH: 18
<212> TYPE: PRT
<213> ORGANISM: Artificial sequence
<220> FEATURE:
<223> OTHER INFORMATION: Synthetic peptide

<400> SEQUENCE: 167

Arg Asn Met Glu Gly Pro Thr Leu Arg His Trp Leu Ala Ala Arg Ala
1               5                   10                  15
Thr Tyr

<210> SEQ ID NO 168
<211> LENGTH: 18
<212> TYPE: PRT
<213> ORGANISM: Artificial sequence
<220> FEATURE:
<223> OTHER INFORMATION: Synthetic peptide
```

```
<400> SEQUENCE: 168

Asp Gly Met Glu Gly Pro Thr Leu Arg Leu Trp Met Ala Ala Arg Ala
1               5                   10                  15
Gly Glu

<210> SEQ ID NO 169
<211> LENGTH: 18
<212> TYPE: PRT
<213> ORGANISM: Artificial sequence
<220> FEATURE:
<223> OTHER INFORMATION: Synthetic peptide

<400> SEQUENCE: 169

Ala Ser Met Tyr Gly Pro Thr Val Ser Gln Arg Leu Ala Ala Arg Thr
1               5                   10                  15
Arg Gly

<210> SEQ ID NO 170
<211> LENGTH: 18
<212> TYPE: PRT
<213> ORGANISM: Artificial sequence
<220> FEATURE:
<223> OTHER INFORMATION: Synthetic peptide

<400> SEQUENCE: 170

Pro Met Met Glu Gly Pro Thr Leu Arg His Trp Leu Ala Ala Arg Ala
1               5                   10                  15
Leu Arg

<210> SEQ ID NO 171
<211> LENGTH: 18
<212> TYPE: PRT
<213> ORGANISM: Artificial sequence
<220> FEATURE:
<223> OTHER INFORMATION: Synthetic peptide

<400> SEQUENCE: 171

Trp Pro Met Glu Gly Pro Thr Leu Arg His Trp Leu Ala Ala Arg Ala
1               5                   10                  15
Ala Arg

<210> SEQ ID NO 172
<211> LENGTH: 18
<212> TYPE: PRT
<213> ORGANISM: Artificial sequence
<220> FEATURE:
<223> OTHER INFORMATION: Synthetic peptide

<400> SEQUENCE: 172

Val Gln Met Glu Gly Pro Thr Leu Arg His Trp Leu Ala Gly Arg Ala
1               5                   10                  15
Pro Asn

<210> SEQ ID NO 173
<211> LENGTH: 18
<212> TYPE: PRT
<213> ORGANISM: Artificial sequence
<220> FEATURE:
<223> OTHER INFORMATION: Synthetic peptide

<400> SEQUENCE: 173

His Gly Ile Glu Gly Pro Thr His Arg Gln Trp Leu Ala Ala Arg Ala
1               5                   10                  15
```

Asp Ile

<210> SEQ ID NO 174
<211> LENGTH: 18
<212> TYPE: PRT
<213> ORGANISM: Artificial sequence
<220> FEATURE:
<223> OTHER INFORMATION: Synthetic peptide

<400> SEQUENCE: 174

Gly Met Met Glu Gly Pro Thr Leu Arg His Trp Leu Ala Ala Arg Ala
1               5                   10                  15
Met Leu

<210> SEQ ID NO 175
<211> LENGTH: 18
<212> TYPE: PRT
<213> ORGANISM: Artificial sequence
<220> FEATURE:
<223> OTHER INFORMATION: Synthetic peptide

<400> SEQUENCE: 175

His Asp Met Glu Gly Pro Thr Leu Arg His Trp Leu Ala Leu Arg Ala
1               5                   10                  15
Thr Gly

<210> SEQ ID NO 176
<211> LENGTH: 18
<212> TYPE: PRT
<213> ORGANISM: Artificial sequence
<220> FEATURE:
<223> OTHER INFORMATION: Synthetic peptide

<400> SEQUENCE: 176

Asp Asn Met Glu Arg Thr Arg Arg Arg His Ser Leu Ala Ala His Phe
1               5                   10                  15
Met Leu

<210> SEQ ID NO 177
<211> LENGTH: 18
<212> TYPE: PRT
<213> ORGANISM: Artificial sequence
<220> FEATURE:
<223> OTHER INFORMATION: Synthetic peptide

<400> SEQUENCE: 177

Arg Asn Met Glu Gly Pro Thr Leu Arg His Trp Leu Ala Ala Arg Ala
1               5                   10                  15
Asp Arg

<210> SEQ ID NO 178
<211> LENGTH: 18
<212> TYPE: PRT
<213> ORGANISM: Artificial sequence
<220> FEATURE:
<223> OTHER INFORMATION: Synthetic peptide

<400> SEQUENCE: 178

Trp Lys Phe Glu Gly Phe Thr Leu Arg Gln Trp Leu Thr Ala Arg Ala
1               5                   10                  15
Phe Gly

<210> SEQ ID NO 179

```
<211> LENGTH: 18
<212> TYPE: PRT
<213> ORGANISM: Artificial sequence
<220> FEATURE:
<223> OTHER INFORMATION: Synthetic peptide

<400> SEQUENCE: 179

Arg Gly Met Glu Gly Pro Thr Leu Arg Gln Arg Leu Val Glu Arg Ala
1               5                   10                  15

Gln Met

<210> SEQ ID NO 180
<211> LENGTH: 18
<212> TYPE: PRT
<213> ORGANISM: Artificial sequence
<220> FEATURE:
<223> OTHER INFORMATION: Synthetic peptide

<400> SEQUENCE: 180

Asp Val Met Glu Gly Thr Thr Leu Arg Gln Trp Leu Ala Cys Arg Ala
1               5                   10                  15

Leu Met

<210> SEQ ID NO 181
<211> LENGTH: 18
<212> TYPE: PRT
<213> ORGANISM: Artificial sequence
<220> FEATURE:
<223> OTHER INFORMATION: Synthetic peptide

<400> SEQUENCE: 181

Arg Lys Met Glu Arg Ala Thr Leu Arg Gln Trp Leu Thr Ala Arg Ala
1               5                   10                  15

Asn Met

<210> SEQ ID NO 182
<211> LENGTH: 18
<212> TYPE: PRT
<213> ORGANISM: Artificial sequence
<220> FEATURE:
<223> OTHER INFORMATION: Synthetic peptide

<400> SEQUENCE: 182

Gly Thr Lys Glu Gly Pro Thr Leu Arg Gln Trp Pro Ala Ala Arg Ala
1               5                   10                  15

Asn Glu

<210> SEQ ID NO 183
<211> LENGTH: 18
<212> TYPE: PRT
<213> ORGANISM: Artificial sequence
<220> FEATURE:
<223> OTHER INFORMATION: Synthetic peptide

<400> SEQUENCE: 183

Cys Ala Ile Glu Gly Pro Thr Leu Arg His Trp Leu Ala Ala Arg Ala
1               5                   10                  15

Ala Thr

<210> SEQ ID NO 184
<211> LENGTH: 18
<212> TYPE: PRT
<213> ORGANISM: Artificial sequence
<220> FEATURE:
<223> OTHER INFORMATION: Synthetic peptide
```

<400> SEQUENCE: 184

Leu Thr Met Glu Gly Pro Thr Leu Arg His Trp Leu Arg Ala Arg Ala
1               5                   10                  15

Tyr Ala

<210> SEQ ID NO 185
<211> LENGTH: 18
<212> TYPE: PRT
<213> ORGANISM: Artificial sequence
<220> FEATURE:
<223> OTHER INFORMATION: Synthetic peptide

<400> SEQUENCE: 185

Met Thr Met Glu Gly Pro Thr Leu Arg Gln Trp Phe Ala Ala Arg Ala
1               5                   10                  15

Asp Thr

<210> SEQ ID NO 186
<211> LENGTH: 18
<212> TYPE: PRT
<213> ORGANISM: Artificial sequence
<220> FEATURE:
<223> OTHER INFORMATION: Synthetic peptide

<400> SEQUENCE: 186

Ser Pro Met Glu Gly Pro Thr Leu Arg His Ser Ala Ala Gly Arg Pro
1               5                   10                  15

Trp Gly

<210> SEQ ID NO 187
<211> LENGTH: 18
<212> TYPE: PRT
<213> ORGANISM: Artificial sequence
<220> FEATURE:
<223> OTHER INFORMATION: Synthetic peptide

<400> SEQUENCE: 187

Val His Met Glu Asp Pro Thr Leu Arg His Gly Asn Ala Ala Arg Ala
1               5                   10                  15

Ala Glu

<210> SEQ ID NO 188
<211> LENGTH: 18
<212> TYPE: PRT
<213> ORGANISM: Artificial sequence
<220> FEATURE:
<223> OTHER INFORMATION: Synthetic peptide

<400> SEQUENCE: 188

Tyr Pro Met Glu Gly Pro Thr Leu Arg His Trp Leu Ala Ala Arg Ala
1               5                   10                  15

Arg His

<210> SEQ ID NO 189
<211> LENGTH: 18
<212> TYPE: PRT
<213> ORGANISM: Artificial sequence
<220> FEATURE:
<223> OTHER INFORMATION: Synthetic peptide

<400> SEQUENCE: 189

Gly Lys Thr Gln Gly Pro Lys Gln Leu Lys Trp Gln Val Gly Ser Ser
1               5                   10                  15

Leu Pro

<210> SEQ ID NO 190
<211> LENGTH: 18
<212> TYPE: PRT
<213> ORGANISM: Artificial sequence
<220> FEATURE:
<223> OTHER INFORMATION: Synthetic peptide

<400> SEQUENCE: 190

Gly Glu Met Glu Gly Pro Thr Leu Leu His Trp Arg Ala Ala Arg Ala
1               5                   10                  15

Met Gln

<210> SEQ ID NO 191
<211> LENGTH: 18
<212> TYPE: PRT
<213> ORGANISM: Artificial sequence
<220> FEATURE:
<223> OTHER INFORMATION: Synthetic peptide

<400> SEQUENCE: 191

Ile Asn Met Glu Gly Pro Thr Leu Arg Leu Trp Leu Ala Ala Arg Ala
1               5                   10                  15

Ala Ala

<210> SEQ ID NO 192
<211> LENGTH: 18
<212> TYPE: PRT
<213> ORGANISM: Artificial sequence
<220> FEATURE:
<223> OTHER INFORMATION: Synthetic peptide

<400> SEQUENCE: 192

Phe Arg Ile Glu Gly Pro Thr Leu Arg Asn Trp Leu Ala Ala Arg Ala
1               5                   10                  15

Ala Lys

<210> SEQ ID NO 193
<211> LENGTH: 18
<212> TYPE: PRT
<213> ORGANISM: Artificial sequence
<220> FEATURE:
<223> OTHER INFORMATION: Synthetic peptide

<400> SEQUENCE: 193

Gly Arg Met Glu Gly Pro Thr Leu Arg His Trp Leu Ala Ala Arg Ala
1               5                   10                  15

His Pro

<210> SEQ ID NO 194
<211> LENGTH: 18
<212> TYPE: PRT
<213> ORGANISM: Artificial sequence
<220> FEATURE:
<223> OTHER INFORMATION: Synthetic peptide

<400> SEQUENCE: 194

Val Leu Ile Gln Gly His Thr Val Arg Asn Cys Met Val Ala Arg Val
1               5                   10                  15

Asp Ala

<210> SEQ ID NO 195

```
<211> LENGTH: 18
<212> TYPE: PRT
<213> ORGANISM: Artificial sequence
<220> FEATURE:
<223> OTHER INFORMATION: Synthetic peptide

<400> SEQUENCE: 195

Asp Trp Ile Glu Gly Pro Thr Leu Arg His Trp Leu Ala Ala Arg Ala
1               5                   10                  15

Leu Tyr

<210> SEQ ID NO 196
<211> LENGTH: 18
<212> TYPE: PRT
<213> ORGANISM: Artificial sequence
<220> FEATURE:
<223> OTHER INFORMATION: Synthetic peptide

<400> SEQUENCE: 196

Ser Trp Thr Glu Gly Pro Thr Leu Arg His Trp Leu Ala Ala Arg Ala
1               5                   10                  15

Arg Asn

<210> SEQ ID NO 197
<211> LENGTH: 18
<212> TYPE: PRT
<213> ORGANISM: Artificial sequence
<220> FEATURE:
<223> OTHER INFORMATION: Synthetic peptide

<400> SEQUENCE: 197

Arg Glu Leu Glu Gly Pro Thr Leu Arg Leu Trp Leu Val Glu Arg Ala
1               5                   10                  15

Arg Met

<210> SEQ ID NO 198
<211> LENGTH: 18
<212> TYPE: PRT
<213> ORGANISM: Artificial sequence
<220> FEATURE:
<223> OTHER INFORMATION: Synthetic peptide

<400> SEQUENCE: 198

Val Ser Met Glu Gly Pro Thr Leu Arg Asn Trp Leu Ala Ala Arg Ala
1               5                   10                  15

Arg Met

<210> SEQ ID NO 199
<211> LENGTH: 18
<212> TYPE: PRT
<213> ORGANISM: Artificial sequence
<220> FEATURE:
<223> OTHER INFORMATION: Synthetic peptide

<400> SEQUENCE: 199

Thr Thr Met Glu Gly Pro Thr Leu Arg His Trp Leu Ala Thr Arg Ala
1               5                   10                  15

Val Asp

<210> SEQ ID NO 200
<211> LENGTH: 18
<212> TYPE: PRT
<213> ORGANISM: Artificial sequence
<220> FEATURE:
<223> OTHER INFORMATION: Synthetic peptide
```

<400> SEQUENCE: 200

Ala Lys Leu Glu Gly Pro Thr Leu Arg Leu Trp Leu Ala Glu Arg Ala
1               5                   10                  15

Gly Arg

<210> SEQ ID NO 201
<211> LENGTH: 18
<212> TYPE: PRT
<213> ORGANISM: Artificial sequence
<220> FEATURE:
<223> OTHER INFORMATION: Synthetic peptide

<400> SEQUENCE: 201

Ala Arg Met Glu Gly Pro Thr Leu Arg His Trp Leu Ala Ala Arg Ala
1               5                   10                  15

Arg Tyr

<210> SEQ ID NO 202
<211> LENGTH: 18
<212> TYPE: PRT
<213> ORGANISM: Artificial sequence
<220> FEATURE:
<223> OTHER INFORMATION: Synthetic peptide

<400> SEQUENCE: 202

Asn Ile Met Asp Gly Pro Ala Leu Arg His Trp Leu Pro Ala Arg Ala
1               5                   10                  15

Ile Gln

<210> SEQ ID NO 203
<211> LENGTH: 18
<212> TYPE: PRT
<213> ORGANISM: Artificial sequence
<220> FEATURE:
<223> OTHER INFORMATION: Synthetic peptide

<400> SEQUENCE: 203

Asn Met Ile Gly Gly Pro Thr Leu Gly His Arg Leu Ala Asp Pro Ala
1               5                   10                  15

Ile Gln

<210> SEQ ID NO 204
<211> LENGTH: 18
<212> TYPE: PRT
<213> ORGANISM: Artificial sequence
<220> FEATURE:
<223> OTHER INFORMATION: Synthetic peptide

<400> SEQUENCE: 204

Val Trp Met Glu Gly Ala Thr Leu Arg Gln Trp Leu Ala Ala Arg Ala
1               5                   10                  15

Leu Ile

<210> SEQ ID NO 205
<211> LENGTH: 18
<212> TYPE: PRT
<213> ORGANISM: Artificial sequence
<220> FEATURE:
<223> OTHER INFORMATION: Synthetic peptide

<400> SEQUENCE: 205

Arg Val Met Glu Gly Pro Thr Leu Leu Gln Arg Leu Ala Ala Arg Ala
1               5                   10                  15

Arg Ser

<210> SEQ ID NO 206
<211> LENGTH: 18
<212> TYPE: PRT
<213> ORGANISM: Artificial sequence
<220> FEATURE:
<223> OTHER INFORMATION: Synthetic peptide

<400> SEQUENCE: 206

Gln Pro Met Asp Glu Pro Ala Arg Arg Gln Trp Leu Ser Ala Arg Ala
1               5                   10                  15

Gly Leu

<210> SEQ ID NO 207
<211> LENGTH: 18
<212> TYPE: PRT
<213> ORGANISM: Artificial sequence
<220> FEATURE:
<223> OTHER INFORMATION: Synthetic peptide

<400> SEQUENCE: 207

Ala Trp Thr Glu Gly Pro Thr Leu Arg His Trp Leu Ala Ala Arg Gly
1               5                   10                  15

Arg Ser

<210> SEQ ID NO 208
<211> LENGTH: 18
<212> TYPE: PRT
<213> ORGANISM: Artificial sequence
<220> FEATURE:
<223> OTHER INFORMATION: Synthetic peptide

<400> SEQUENCE: 208

Ala Thr Met Glu Gly Pro Thr Leu Arg His Trp Leu Ala Ala Arg Ala
1               5                   10                  15

Ala Leu

<210> SEQ ID NO 209
<211> LENGTH: 18
<212> TYPE: PRT
<213> ORGANISM: Artificial sequence
<220> FEATURE:
<223> OTHER INFORMATION: Synthetic peptide

<400> SEQUENCE: 209

Gly Arg Met Glu Gly Pro Thr Leu Arg His Trp Leu Ala Ala Arg Ala
1               5                   10                  15

Leu Phe

<210> SEQ ID NO 210
<211> LENGTH: 18
<212> TYPE: PRT
<213> ORGANISM: Artificial sequence
<220> FEATURE:
<223> OTHER INFORMATION: Synthetic peptide

<400> SEQUENCE: 210

Glu Asn Met Gln Gly Arg Thr Leu Arg His Trp Leu Ala Ala Arg Asp
1               5                   10                  15

Tyr Phe

<210> SEQ ID NO 211

```
<211> LENGTH: 18
<212> TYPE: PRT
<213> ORGANISM: Artificial sequence
<220> FEATURE:
<223> OTHER INFORMATION: Synthetic peptide

<400> SEQUENCE: 211

Lys Gly Val Glu Gly Pro Thr Leu Arg Leu Trp Leu Ala Ala Arg Ala
1               5                   10                  15

Leu Met

<210> SEQ ID NO 212
<211> LENGTH: 18
<212> TYPE: PRT
<213> ORGANISM: Artificial sequence
<220> FEATURE:
<223> OTHER INFORMATION: Synthetic peptide

<400> SEQUENCE: 212

Val Glu Met Glu Gly Pro Thr Leu Arg His Trp Leu Ala Ala Arg Ala
1               5                   10                  15

Ser Val

<210> SEQ ID NO 213
<211> LENGTH: 18
<212> TYPE: PRT
<213> ORGANISM: Artificial sequence
<220> FEATURE:
<223> OTHER INFORMATION: Synthetic peptide

<400> SEQUENCE: 213

Ala Phe Ile Glu Gly Pro Thr Leu Lys Asn Trp Leu Ala Ala Arg Ala
1               5                   10                  15

Ile Met

<210> SEQ ID NO 214
<211> LENGTH: 18
<212> TYPE: PRT
<213> ORGANISM: Artificial sequence
<220> FEATURE:
<223> OTHER INFORMATION: Synthetic peptide

<400> SEQUENCE: 214

Thr Val Met Glu Gly Pro Thr Leu Arg His Trp Leu Ala Ala Arg Ser
1               5                   10                  15

Arg Ser

<210> SEQ ID NO 215
<211> LENGTH: 18
<212> TYPE: PRT
<213> ORGANISM: Artificial sequence
<220> FEATURE:
<223> OTHER INFORMATION: Synthetic peptide

<400> SEQUENCE: 215

Ala His Met Glu Gly Pro Thr Leu Arg His Trp Leu Ala Thr Arg Ala
1               5                   10                  15

Lys Met

<210> SEQ ID NO 216
<211> LENGTH: 18
<212> TYPE: PRT
<213> ORGANISM: Artificial sequence
<220> FEATURE:
<223> OTHER INFORMATION: Synthetic peptide
```

```
<400> SEQUENCE: 216

Lys Asp Ile Glu Gly Pro Thr Leu Arg His Trp Leu Ala Ala Arg Ala
1               5                   10                  15

Asn Tyr

<210> SEQ ID NO 217
<211> LENGTH: 18
<212> TYPE: PRT
<213> ORGANISM: Artificial sequence
<220> FEATURE:
<223> OTHER INFORMATION: Synthetic peptide

<400> SEQUENCE: 217

Arg Ile His Asp Gly Arg Lys Leu Arg Gln Trp Leu Thr Val Arg Asp
1               5                   10                  15

Thr Met

<210> SEQ ID NO 218
<211> LENGTH: 18
<212> TYPE: PRT
<213> ORGANISM: Artificial sequence
<220> FEATURE:
<223> OTHER INFORMATION: Synthetic peptide

<400> SEQUENCE: 218

Lys Pro Ile Glu Gly Pro Thr Leu Lys Leu Trp Leu Ala Glu Arg Met
1               5                   10                  15

Ala Ala

<210> SEQ ID NO 219
<211> LENGTH: 18
<212> TYPE: PRT
<213> ORGANISM: Artificial sequence
<220> FEATURE:
<223> OTHER INFORMATION: Synthetic peptide

<400> SEQUENCE: 219

Ala Lys Asp Val Gly Thr Arg Leu Arg Gln Trp Leu Ala Ala Gly Ala
1               5                   10                  15

Arg Ala

<210> SEQ ID NO 220
<211> LENGTH: 18
<212> TYPE: PRT
<213> ORGANISM: Artificial sequence
<220> FEATURE:
<223> OTHER INFORMATION: Synthetic peptide

<400> SEQUENCE: 220

Gln Ser Gln Glu Gly Pro Thr Leu Arg Leu Trp Leu Ala Glu Arg Ala
1               5                   10                  15

Lys Trp

<210> SEQ ID NO 221
<211> LENGTH: 18
<212> TYPE: PRT
<213> ORGANISM: Artificial sequence
<220> FEATURE:
<223> OTHER INFORMATION: Synthetic peptide

<400> SEQUENCE: 221

Met Tyr Thr Glu Gly Ala Thr Leu Arg Gln Trp Leu Ala Ala Arg Ala
1               5                   10                  15
```

Arg Ile

<210> SEQ ID NO 222
<211> LENGTH: 18
<212> TYPE: PRT
<213> ORGANISM: Artificial sequence
<220> FEATURE:
<223> OTHER INFORMATION: Synthetic peptide

<400> SEQUENCE: 222

Pro Lys Met Glu Gly Pro Thr Arg Arg Thr Arg Leu Ala Asp Arg Ser
1               5                   10                  15

Thr Ser

<210> SEQ ID NO 223
<211> LENGTH: 18
<212> TYPE: PRT
<213> ORGANISM: Artificial sequence
<220> FEATURE:
<223> OTHER INFORMATION: Synthetic peptide

<400> SEQUENCE: 223

Asn Val Met Glu Gly Pro Thr Leu Arg His Trp Leu Ala Tyr Arg Ala
1               5                   10                  15

Arg Met

<210> SEQ ID NO 224
<211> LENGTH: 18
<212> TYPE: PRT
<213> ORGANISM: Artificial sequence
<220> FEATURE:
<223> OTHER INFORMATION: Sythetic peptide

<400> SEQUENCE: 224

Thr Trp Met Glu Gly Pro Thr Leu Arg His Trp Leu Ala Ala Arg Ala
1               5                   10                  15

Leu Gly

<210> SEQ ID NO 225
<211> LENGTH: 18
<212> TYPE: PRT
<213> ORGANISM: Artificial sequence
<220> FEATURE:
<223> OTHER INFORMATION: Synthetic peptide

<400> SEQUENCE: 225

Leu Thr Met Glu Gly Pro Thr Leu Arg His Trp Leu Ala Ala Arg Ala
1               5                   10                  15

Thr Arg

<210> SEQ ID NO 226
<211> LENGTH: 18
<212> TYPE: PRT
<213> ORGANISM: Artificial sequence
<220> FEATURE:
<223> OTHER INFORMATION: Synthetic peptide

<400> SEQUENCE: 226

Tyr Thr Met Glu Gly Pro Thr Leu Arg His Trp Leu Ala Ala Arg Ala
1               5                   10                  15

Leu His

<210> SEQ ID NO 227

```
<211> LENGTH: 18
<212> TYPE: PRT
<213> ORGANISM: Artificial sequence
<220> FEATURE:
<223> OTHER INFORMATION: Synethetic peptide

<400> SEQUENCE: 227

Asn Glu Met Glu Gly Ala Thr Leu Arg Gln Trp Leu Ala Ala Arg Ala
1               5                   10                  15

Lys Trp

<210> SEQ ID NO 228
<211> LENGTH: 18
<212> TYPE: PRT
<213> ORGANISM: Artificial sequence
<220> FEATURE:
<223> OTHER INFORMATION: Synthetic peptide

<400> SEQUENCE: 228

Phe Ser Lys Glu Gly Ala Thr Leu Arg Gln Trp Leu Ala Ala Arg Ala
1               5                   10                  15

Leu Asp

<210> SEQ ID NO 229
<211> LENGTH: 18
<212> TYPE: PRT
<213> ORGANISM: Artificial sequence
<220> FEATURE:
<223> OTHER INFORMATION: Synthetic peptide

<400> SEQUENCE: 229

Ser Asn Gly Val Cys Arg Thr Leu Arg Gln Trp Leu Ala Ala Arg Ala
1               5                   10                  15

Glu Glu

<210> SEQ ID NO 230
<211> LENGTH: 18
<212> TYPE: PRT
<213> ORGANISM: Artificial sequence
<220> FEATURE:
<223> OTHER INFORMATION: Synthetic peptide

<400> SEQUENCE: 230

Lys Gly Met Glu Gly Pro Thr Leu Arg Asn Trp Leu Ala Glu Arg Ala
1               5                   10                  15

Met Leu

<210> SEQ ID NO 231
<211> LENGTH: 18
<212> TYPE: PRT
<213> ORGANISM: Artificial sequence
<220> FEATURE:
<223> OTHER INFORMATION: Synthetic peptide

<400> SEQUENCE: 231

Gln Asp Met Val Gly Pro Thr Leu Arg His Trp Leu Ala Ala Arg Ala
1               5                   10                  15

Arg Leu

<210> SEQ ID NO 232
<211> LENGTH: 18
<212> TYPE: PRT
<213> ORGANISM: Artificial sequence
<220> FEATURE:
<223> OTHER INFORMATION: Synthetic peptide
```

<400> SEQUENCE: 232

Tyr Ser His Glu Gly Pro Thr Leu Arg His Trp Leu Ala Ala Arg Ala
1               5                   10                  15

Leu Leu

<210> SEQ ID NO 233
<211> LENGTH: 18
<212> TYPE: PRT
<213> ORGANISM: Artificial sequence
<220> FEATURE:
<223> OTHER INFORMATION: Synthetic peptide

<400> SEQUENCE: 233

Gly Val Ile Glu Gly Pro Thr Leu Arg His Trp Leu Ala Ala Arg Met
1               5                   10                  15

Lys Val

<210> SEQ ID NO 234
<211> LENGTH: 18
<212> TYPE: PRT
<213> ORGANISM: Artificial sequence
<220> FEATURE:
<223> OTHER INFORMATION: Synthetic peptide

<400> SEQUENCE: 234

Met His Met Glu Gly Pro Thr Leu Arg His Trp Leu Ala Thr Arg Ala
1               5                   10                  15

Leu Ile

<210> SEQ ID NO 235
<211> LENGTH: 18
<212> TYPE: PRT
<213> ORGANISM: Artificial sequence
<220> FEATURE:
<223> OTHER INFORMATION: Synthetic peptide

<400> SEQUENCE: 235

Cys Arg Ser Glu Gly Pro Thr Leu Arg Cys Trp Leu Ala Ala Arg Ala
1               5                   10                  15

Gly Tyr

<210> SEQ ID NO 236
<211> LENGTH: 18
<212> TYPE: PRT
<213> ORGANISM: Artificial sequence
<220> FEATURE:
<223> OTHER INFORMATION: Synthetic peptide

<400> SEQUENCE: 236

Met Cys Ile Glu Gly Pro Thr Leu Arg Gln Trp Gln Val Cys Arg Val
1               5                   10                  15

Gly Leu

<210> SEQ ID NO 237
<211> LENGTH: 18
<212> TYPE: PRT
<213> ORGANISM: Artificial sequence
<220> FEATURE:
<223> OTHER INFORMATION: Synthetic peptide

<400> SEQUENCE: 237

Cys Arg Val Glu Gly Pro Ser Gln Arg Gln Cys Leu Ala Ala Arg Ala
1               5                   10                  15

Cys Trp

<210> SEQ ID NO 238
<211> LENGTH: 18
<212> TYPE: PRT
<213> ORGANISM: Artificial sequence
<220> FEATURE:
<223> OTHER INFORMATION: Synthetic peptide

<400> SEQUENCE: 238

Cys Thr Met Glu Gly Pro Thr Leu Arg His Trp Leu Ala Ala Arg Ala
1               5                   10                  15

Cys Ile

<210> SEQ ID NO 239
<211> LENGTH: 18
<212> TYPE: PRT
<213> ORGANISM: Artificial sequence
<220> FEATURE:
<223> OTHER INFORMATION: Synthetic peptide

<400> SEQUENCE: 239

Cys Gln Val Asp Gly Pro Thr Val Arg His Cys Arg Ala Ala Arg Ala
1               5                   10                  15

Gly Leu

<210> SEQ ID NO 240
<211> LENGTH: 18
<212> TYPE: PRT
<213> ORGANISM: Artificial sequence
<220> FEATURE:
<223> OTHER INFORMATION: Synthetic peptide

<400> SEQUENCE: 240

Cys Asp Met Ala Gly Ala Thr Leu Arg Gln Trp Leu Ala Cys Arg Ser
1               5                   10                  15

Gly Thr

<210> SEQ ID NO 241
<211> LENGTH: 18
<212> TYPE: PRT
<213> ORGANISM: Artificial sequence
<220> FEATURE:
<223> OTHER INFORMATION: Synthetic peptide

<400> SEQUENCE: 241

Ile Cys Thr Glu Gly Cys Thr Leu Arg Leu Trp Leu Ala Glu Arg Ser
1               5                   10                  15

Arg Val

<210> SEQ ID NO 242
<211> LENGTH: 18
<212> TYPE: PRT
<213> ORGANISM: Artificial sequence
<220> FEATURE:
<223> OTHER INFORMATION: Synthetic peptide

<400> SEQUENCE: 242

Cys Gly Met Glu Gly Pro Ala Leu Arg Gln Trp Leu Ala Cys Arg Ala
1               5                   10                  15

Val Asp

<210> SEQ ID NO 243

```
<211> LENGTH: 22
<212> TYPE: PRT
<213> ORGANISM: Artificial sequence
<220> FEATURE:
<223> OTHER INFORMATION: Synthetic peptide

<400> SEQUENCE: 243

Gln Gly Cys Ser Ser Gly Gly Pro Thr Leu Arg Glu Trp Gln Gln Cys
1               5                   10                  15

Val Arg Met Gln His Ser
            20

<210> SEQ ID NO 244
<211> LENGTH: 22
<212> TYPE: PRT
<213> ORGANISM: Artificial sequence
<220> FEATURE:
<223> OTHER INFORMATION: Synthetic peptide

<400> SEQUENCE: 244

Gln Gly Cys Ser Ser Gly Gly Pro Thr Leu Arg Glu Trp Gln Gln Cys
1               5                   10                  15

Arg Arg Ala Gln His Ser
            20

<210> SEQ ID NO 245
<211> LENGTH: 22
<212> TYPE: PRT
<213> ORGANISM: Artificial sequence
<220> FEATURE:
<223> OTHER INFORMATION: Synthetic peptide

<400> SEQUENCE: 245

Gln Gly Cys Ser Ser Gly Gly Pro Thr Leu Arg Glu Trp Gln Gln Cys
1               5                   10                  15

Val Arg Ala Gln His Ser
            20

<210> SEQ ID NO 246
<211> LENGTH: 56
<212> TYPE: PRT
<213> ORGANISM: Artificial sequence
<220> FEATURE:
<223> OTHER INFORMATION: Synthetic peptide

<400> SEQUENCE: 246

Ile Glu Gly Gln Ser Trp Glu Phe Glu Asn Asp Arg Val Pro Ala His
1               5                   10                  15

Ser Leu Glu Arg Val Leu Leu Leu Arg Arg Val Pro Thr Glu Pro Ser
            20                  25                  30

Gly Pro Ser Ile Cys Ala Gln Ile Glu Gly Pro Thr Phe Lys Gln Trp
        35                  40                  45

Gln Glu Cys Ile Asn Gly His Ser
    50                  55

<210> SEQ ID NO 247
<211> LENGTH: 17
<212> TYPE: PRT
<213> ORGANISM: Artificial sequence
<220> FEATURE:
<223> OTHER INFORMATION: Synthetic peptide

<400> SEQUENCE: 247

Ile Glu Gly Pro Thr Phe Lys Gln Trp Gln Lys Cys Arg Asn Met His
1               5                   10                  15
```

Ser

<210> SEQ ID NO 248
<211> LENGTH: 17
<212> TYPE: PRT
<213> ORGANISM: Artificial sequence
<220> FEATURE:
<223> OTHER INFORMATION: Synthetic peptide

<400> SEQUENCE: 248

Ile Glu Gly Pro Thr Phe Lys Gln Trp Gln Lys Leu Arg Arg Val His
1               5                   10                  15

Ser

<210> SEQ ID NO 249
<211> LENGTH: 52
<212> TYPE: PRT
<213> ORGANISM: Artificial sequence
<220> FEATURE:
<223> OTHER INFORMATION: Synthetic peptide

<400> SEQUENCE: 249

Ile Glu Gly Glu Pro Val Ser Asp Gly Lys Arg Arg Pro Arg Val His
1               5                   10                  15

Ser Leu Glu Arg Val Asp Ala Val His Ala Lys Val Gly Pro Ser Ile
            20                  25                  30

Cys Ala Gln Ile Glu Gly Pro Thr Phe Lys Gln Trp Gln Lys Cys Lys
        35                  40                  45

Arg Ala His Ser
    50

<210> SEQ ID NO 250
<211> LENGTH: 56
<212> TYPE: PRT
<213> ORGANISM: Artificial sequence
<220> FEATURE:
<223> OTHER INFORMATION: Synthetic peptide

<400> SEQUENCE: 250

Ile Glu Gly Arg Trp Pro Pro Gln Phe Pro Val Thr Gln Gln His
1               5                   10                  15

Ser Leu Glu Arg Val Gly Arg Pro Pro Ser Val Glu Leu Pro Arg
            20                  25                  30

Pro Thr Phe Val Cys Ala Gln Ile Glu Gly Pro Thr Phe Lys Gln Trp
        35                  40                  45

Gln Arg Cys Leu Arg Glu His Ser
    50                  55

<210> SEQ ID NO 251
<211> LENGTH: 17
<212> TYPE: PRT
<213> ORGANISM: Artificial sequence
<220> FEATURE:
<223> OTHER INFORMATION: Synthetic peptide

<400> SEQUENCE: 251

Ile Glu Gly Pro Thr Phe Lys Gln Trp Gln Arg Trp Arg Leu Leu His
1               5                   10                  15

Ser

<210> SEQ ID NO 252
<211> LENGTH: 17

```
<212> TYPE: PRT
<213> ORGANISM: Artificial sequence
<220> FEATURE:
<223> OTHER INFORMATION: Synthetic peptide

<400> SEQUENCE: 252

Ile Glu Gly Pro Thr Phe Lys Gln Trp Gln Ala Trp Arg Lys Lys His
1               5                   10                  15

Ser

<210> SEQ ID NO 253
<211> LENGTH: 17
<212> TYPE: PRT
<213> ORGANISM: Artificial sequence
<220> FEATURE:
<223> OTHER INFORMATION: Synthetic peptide

<400> SEQUENCE: 253

Ile Glu Gly Pro Thr Phe Lys Gln Trp Gln Arg Trp Arg Lys Met His
1               5                   10                  15

Ser

<210> SEQ ID NO 254
<211> LENGTH: 56
<212> TYPE: PRT
<213> ORGANISM: Artificial sequence
<220> FEATURE:
<223> OTHER INFORMATION: Synthetic peptide

<400> SEQUENCE: 254

Ile Glu Gly Arg Trp Pro Pro Gln Phe Pro Val Thr Glu His His
1               5                   10                  15

Ser Leu Glu Arg Val Gly Arg Arg Pro Pro Asn Ala Gln Met Pro Gln
            20                  25                  30

Ser Ile Phe Ile Cys Gly Gln Asn Gly Gly Pro Thr Phe Gln Tyr Cys
        35                  40                  45

Gln Arg Cys Leu Arg Glu His Ser
    50                  55

<210> SEQ ID NO 255
<211> LENGTH: 17
<212> TYPE: PRT
<213> ORGANISM: Artificial sequence
<220> FEATURE:
<223> OTHER INFORMATION: Synthetic peptide

<400> SEQUENCE: 255

Ile Glu Gly Trp Trp Trp Gln Phe Tyr Phe His Ala Lys Glu Asp His
1               5                   10                  15

Ser

<210> SEQ ID NO 256
<211> LENGTH: 23
<212> TYPE: PRT
<213> ORGANISM: Artificial sequence
<220> FEATURE:
<223> OTHER INFORMATION: Synthetic peptide

<400> SEQUENCE: 256

Pro Ser Ile Cys Ala Gln Ile Glu Gly Pro Thr Phe Lys Gln Trp Gln
1               5                   10                  15

Thr Cys Met Arg Ala His Ser
            20
```

```
<210> SEQ ID NO 257
<211> LENGTH: 53
<212> TYPE: PRT
<213> ORGANISM: Artificial sequence
<220> FEATURE:
<223> OTHER INFORMATION: Synthetic peptide

<400> SEQUENCE: 257

Ile Glu Gly Tyr Val Gly Gly Pro Tyr Glu Gln Thr Asn Ser Leu Glu
1               5                   10                  15

Arg Val Pro Pro Thr Leu Ala Trp Lys Tyr Gly Pro Arg Thr Pro Ser
                20                  25                  30

Ile Cys Ala Gln Ile Glu Gly Pro Thr Phe Lys Gln Trp Gln Gln Cys
            35                  40                  45

Leu Ser Asp His Ser
        50

<210> SEQ ID NO 258
<211> LENGTH: 17
<212> TYPE: PRT
<213> ORGANISM: Artificial sequence
<220> FEATURE:
<223> OTHER INFORMATION: Synthetic peptide

<400> SEQUENCE: 258

Ile Glu Gly Pro Thr Phe Lys Gln Trp Gln Gly Arg Ser Lys Arg His
1               5                   10                  15

Ser

<210> SEQ ID NO 259
<211> LENGTH: 17
<212> TYPE: PRT
<213> ORGANISM: Artificial sequence
<220> FEATURE:
<223> OTHER INFORMATION: Synthetic peptide

<400> SEQUENCE: 259

Ile Glu Gly Trp Pro Trp Gln Leu Tyr Val His Pro Glu Gly Glu His
1               5                   10                  15

Ser

<210> SEQ ID NO 260
<211> LENGTH: 17
<212> TYPE: PRT
<213> ORGANISM: Artificial sequence
<220> FEATURE:
<223> OTHER INFORMATION: Synthetic peptide

<400> SEQUENCE: 260

Ile Glu Gly Trp Trp Trp Gln Leu Tyr Phe His Ala Lys Asp Asp His
1               5                   10                  15

Ser

<210> SEQ ID NO 261
<211> LENGTH: 17
<212> TYPE: PRT
<213> ORGANISM: Artificial sequence
<220> FEATURE:
<223> OTHER INFORMATION: Synthetic peptide

<400> SEQUENCE: 261

Ile Glu Gly Pro Thr Phe Lys Gln Trp Gln Lys Leu Arg Arg Ser His
1               5                   10                  15
```

-continued

Ser

<210> SEQ ID NO 262
<211> LENGTH: 17
<212> TYPE: PRT
<213> ORGANISM: Artificial sequence
<220> FEATURE:
<223> OTHER INFORMATION: Synthetic peptide

<400> SEQUENCE: 262

Ile Glu Gly Trp Trp Trp Gln Phe Tyr Phe His Pro Lys Glu Asp His
1               5                   10                  15

Ser

<210> SEQ ID NO 263
<211> LENGTH: 17
<212> TYPE: PRT
<213> ORGANISM: Artificial sequence
<220> FEATURE:
<223> OTHER INFORMATION: Synthetic peptide

<400> SEQUENCE: 263

Ile Glu Gly Pro Thr Phe Lys Gln Trp Gln Lys Ser Arg Thr Lys His
1               5                   10                  15

Ser

<210> SEQ ID NO 264
<211> LENGTH: 17
<212> TYPE: PRT
<213> ORGANISM: Artificial sequence
<220> FEATURE:
<223> OTHER INFORMATION: Synthetic peptide

<400> SEQUENCE: 264

Ile Glu Gly Trp Thr Trp Gln Phe Tyr Val His Pro Lys Gly Asp His
1               5                   10                  15

Ser

<210> SEQ ID NO 265
<211> LENGTH: 17
<212> TYPE: PRT
<213> ORGANISM: Artificial sequence
<220> FEATURE:
<223> OTHER INFORMATION: Synthetic peptide

<400> SEQUENCE: 265

Ile Glu Gly Pro Thr Phe Lys Gln Trp Gln Ala Ala Arg Met His His
1               5                   10                  15

Ser

<210> SEQ ID NO 266
<211> LENGTH: 17
<212> TYPE: PRT
<213> ORGANISM: Artificial sequence
<220> FEATURE:
<223> OTHER INFORMATION: Synthetic peptide

<400> SEQUENCE: 266

Ile Glu Gly Pro Thr Phe Lys Gln Trp Gln Ala Cys Leu His Ser His
1               5                   10                  15

Ser

<210> SEQ ID NO 267
<211> LENGTH: 17

```
<212> TYPE: PRT
<213> ORGANISM: Artificial sequence
<220> FEATURE:
<223> OTHER INFORMATION: Synthetic peptide

<400> SEQUENCE: 267

Ile Glu Gly Trp Ser Trp Gln Phe Tyr Ala His Pro Gln Gly Asp His
1               5                   10                  15

Ser

<210> SEQ ID NO 268
<211> LENGTH: 17
<212> TYPE: PRT
<213> ORGANISM: Artificial sequence
<220> FEATURE:
<223> OTHER INFORMATION: Synthetic peptide

<400> SEQUENCE: 268

Ile Glu Gly Pro Ser Phe Thr Pro Trp Phe His Glu Arg Arg Ser His
1               5                   10                  15

Ser

<210> SEQ ID NO 269
<211> LENGTH: 17
<212> TYPE: PRT
<213> ORGANISM: Artificial sequence
<220> FEATURE:
<223> OTHER INFORMATION: Synthetic peptide

<400> SEQUENCE: 269

Ile Glu Gly Pro Thr Phe Lys Gln Trp Gln Trp Leu Arg Arg His His
1               5                   10                  15

Ser

<210> SEQ ID NO 270
<211> LENGTH: 17
<212> TYPE: PRT
<213> ORGANISM: Artificial sequence
<220> FEATURE:
<223> OTHER INFORMATION: Synthetic peptide

<400> SEQUENCE: 270

Ile Glu Gly Trp Trp Trp Gln Phe Tyr Val His Ala Lys Gly Asp His
1               5                   10                  15

Ser

<210> SEQ ID NO 271
<211> LENGTH: 17
<212> TYPE: PRT
<213> ORGANISM: Artificial sequence
<220> FEATURE:
<223> OTHER INFORMATION: Synthetic peptide

<400> SEQUENCE: 271

Ile Glu Gly Pro Thr Phe Lys Gln Trp Gln Val Trp Arg Asn Arg His
1               5                   10                  15

Ser

<210> SEQ ID NO 272
<211> LENGTH: 17
<212> TYPE: PRT
<213> ORGANISM: Artificial sequence
<220> FEATURE:
<223> OTHER INFORMATION: Synthetic peptide
```

```
<400> SEQUENCE: 272

Ile Glu Gly Gln Ser Trp Leu Arg Arg Leu His Trp Lys Glu His
1               5                   10                  15

Ser

<210> SEQ ID NO 273
<211> LENGTH: 51
<212> TYPE: PRT
<213> ORGANISM: Artificial sequence
<220> FEATURE:
<223> OTHER INFORMATION: Synthetic peptide

<400> SEQUENCE: 273

Ile Glu Gly Trp Pro Trp Gln Phe Tyr Ala Leu Ser Arg Glu Ser Gly
1               5                   10                  15

Thr Ser Pro Ser Ser Ala Ala Arg Thr Ser Ser Tyr Leu Arg Ser Cys
            20                  25                  30

Ala Gln Ile Glu Gly Pro Thr Phe Lys Gln Trp Gln Ile Cys Lys Asp
        35                  40                  45

Gln His Ser
    50

<210> SEQ ID NO 274
<211> LENGTH: 17
<212> TYPE: PRT
<213> ORGANISM: Artificial sequence
<220> FEATURE:
<223> OTHER INFORMATION: Synthetic peptide

<400> SEQUENCE: 274

Ile Glu Gly Pro Thr Phe Lys Gln Trp Gln Lys Trp Arg Lys Thr His
1               5                   10                  15

Ser

<210> SEQ ID NO 275
<211> LENGTH: 17
<212> TYPE: PRT
<213> ORGANISM: Artificial sequence
<220> FEATURE:
<223> OTHER INFORMATION: Synthetic peptide

<400> SEQUENCE: 275

Ile Glu Gly Pro Thr Phe Lys Gln Trp Gln Tyr Trp Arg Ala Lys His
1               5                   10                  15

Ser

<210> SEQ ID NO 276
<211> LENGTH: 17
<212> TYPE: PRT
<213> ORGANISM: Artificial sequence
<220> FEATURE:
<223> OTHER INFORMATION: Synthetic peptide

<400> SEQUENCE: 276

Ile Glu Gly Pro Thr Phe Lys Gln Trp Gln Val Arg Gln Lys Thr His
1               5                   10                  15

Ser

<210> SEQ ID NO 277
<211> LENGTH: 17
<212> TYPE: PRT
<213> ORGANISM: Artificial sequence
<220> FEATURE:
```

<223> OTHER INFORMATION: Synthetic peptide

<400> SEQUENCE: 277

Ile Glu Gly Trp Ser Trp Gln Phe Tyr Phe His Ala Lys Gly Asp His
1               5                   10                  15

Ser

<210> SEQ ID NO 278
<211> LENGTH: 17
<212> TYPE: PRT
<213> ORGANISM: Artificial sequence
<220> FEATURE:
<223> OTHER INFORMATION: Synthetic peptide

<400> SEQUENCE: 278

Ile Glu Gly Arg Thr Trp Gln Leu Tyr Phe His Ala Lys Glu Glu His
1               5                   10                  15

Ser

<210> SEQ ID NO 279
<211> LENGTH: 17
<212> TYPE: PRT
<213> ORGANISM: Artificial sequence
<220> FEATURE:
<223> OTHER INFORMATION: Synthetic peptide

<400> SEQUENCE: 279

Ile Glu Gly Trp Ser Trp Gln Phe Tyr Ala His Pro Gln Gly Asp His
1               5                   10                  15

Ser

<210> SEQ ID NO 280
<211> LENGTH: 17
<212> TYPE: PRT
<213> ORGANISM: Artificial sequence
<220> FEATURE:
<223> OTHER INFORMATION: Synthetic peptide

<400> SEQUENCE: 280

Ile Glu Gly Trp Pro Arg Gln Leu Tyr Ala His Ala Lys Glu Asp His
1               5                   10                  15

Ser

<210> SEQ ID NO 281
<211> LENGTH: 17
<212> TYPE: PRT
<213> ORGANISM: Artificial sequence
<220> FEATURE:
<223> OTHER INFORMATION: Synthetic peptide

<400> SEQUENCE: 281

Ile Glu Gly Trp Trp Trp Gln Phe Tyr Ala His Pro Gln Gly Asp His
1               5                   10                  15

Ser

<210> SEQ ID NO 282
<211> LENGTH: 17
<212> TYPE: PRT
<213> ORGANISM: Artificial sequence
<220> FEATURE:
<223> OTHER INFORMATION: Synthetic peptide

<400> SEQUENCE: 282

Ile Glu Gly Trp Ser Trp Gln Phe Tyr Ala His Pro Gln Gly Asp His

```
1               5                   10                  15
Ser

<210> SEQ ID NO 283
<211> LENGTH: 17
<212> TYPE: PRT
<213> ORGANISM: Artificial sequence
<220> FEATURE:
<223> OTHER INFORMATION: Synthetic peptide

<400> SEQUENCE: 283

Ile Glu Gly Trp Ser Trp Gln Phe Tyr Ala His Pro Gln Gly Asp His
1               5                   10                  15
Ser

<210> SEQ ID NO 284
<211> LENGTH: 51
<212> TYPE: PRT
<213> ORGANISM: Artificial sequence
<220> FEATURE:
<223> OTHER INFORMATION: Synthetic peptide

<400> SEQUENCE: 284

Ile Glu Gly His Gly Ser Gln Lys Pro Thr Ala Ala Arg Ala Leu Glu
1               5                   10                  15

Ser Thr Ser Ser Leu Thr Thr Arg Thr Arg Thr Ser Ile Cys Ala
            20                  25                  30

Gln Gln Asp Met Val Gly Pro Thr Ile Arg Gln Trp Leu Ala Ala Arg
        35                  40                  45

Ala Cys Ile
    50

<210> SEQ ID NO 285
<211> LENGTH: 17
<212> TYPE: PRT
<213> ORGANISM: Artificial sequence
<220> FEATURE:
<223> OTHER INFORMATION: Synthetic peptide

<400> SEQUENCE: 285

Ile Glu Gly Pro Thr Phe Glu Gln Trp Gln His Trp Arg Arg Gly His
1               5                   10                  15
Ser

<210> SEQ ID NO 286
<211> LENGTH: 14
<212> TYPE: PRT
<213> ORGANISM: Artificial sequence
<220> FEATURE:
<223> OTHER INFORMATION: Synthetic peptide

<400> SEQUENCE: 286

Ile Glu Gly Trp Ile Trp Arg Gln Trp Leu Ala Ala Arg Ala
1               5                   10

<210> SEQ ID NO 287
<211> LENGTH: 14
<212> TYPE: PRT
<213> ORGANISM: Artificial sequence
<220> FEATURE:
<223> OTHER INFORMATION: Synthetic peptide

<400> SEQUENCE: 287

Ile Glu Gly Trp Ile Trp Arg Pro Trp Leu Ala Ala Arg Ala
```

```
<210> SEQ ID NO 288
<211> LENGTH: 14
<212> TYPE: PRT
<213> ORGANISM: Artificial sequence
<220> FEATURE:
<223> OTHER INFORMATION: Synthetic peptide

<400> SEQUENCE: 288

Ile Glu Gly Tyr Trp Trp Tyr Ala Ser Trp Ala Ala Arg Ala
1               5                   10

<210> SEQ ID NO 289
<211> LENGTH: 17
<212> TYPE: PRT
<213> ORGANISM: Artificial sequence
<220> FEATURE:
<223> OTHER INFORMATION: Synthetic peptide

<400> SEQUENCE: 289

Ile Glu Gly Trp Pro Trp Gln Phe Tyr Ala His Pro Gln Gly Asp His
1               5                   10                  15

Ser

<210> SEQ ID NO 290
<211> LENGTH: 14
<212> TYPE: PRT
<213> ORGANISM: Artificial sequence
<220> FEATURE:
<223> OTHER INFORMATION: Synthetic peptide

<400> SEQUENCE: 290

Ile Glu Gly Trp Val Trp Cys Gln Trp Leu Ala Ala Arg Ala
1               5                   10

<210> SEQ ID NO 291
<211> LENGTH: 17
<212> TYPE: PRT
<213> ORGANISM: Artificial sequence
<220> FEATURE:
<223> OTHER INFORMATION: Synthetic peptide

<400> SEQUENCE: 291

Ile Glu Gly Pro Thr Leu His Glu Trp Leu Arg Trp Leu Arg Gln His
1               5                   10                  15

Ser

<210> SEQ ID NO 292
<211> LENGTH: 14
<212> TYPE: PRT
<213> ORGANISM: Artificial sequence
<220> FEATURE:
<223> OTHER INFORMATION: Synthetic peptide

<400> SEQUENCE: 292

Ile Glu Gly Trp Val Trp Arg Pro Trp Leu Ala Ala Arg Ala
1               5                   10

<210> SEQ ID NO 293
<211> LENGTH: 14
<212> TYPE: PRT
<213> ORGANISM: Artificial sequence
<220> FEATURE:
<223> OTHER INFORMATION: Synthetic peptide

<400> SEQUENCE: 293
```

Ile Glu Gly Trp Val Trp Cys Pro Trp Leu Ala Ala Arg Ala
1               5                   10

<210> SEQ ID NO 294
<211> LENGTH: 17
<212> TYPE: PRT
<213> ORGANISM: Artificial sequence
<220> FEATURE:
<223> OTHER INFORMATION: Synthetic peptide

<400> SEQUENCE: 294

Ile Glu Gly Glu Ala Leu Val Phe Trp Trp Arg Val Arg Gly Gly His
1               5                   10                  15

Ser

<210> SEQ ID NO 295
<211> LENGTH: 14
<212> TYPE: PRT
<213> ORGANISM: Artificial sequence
<220> FEATURE:
<223> OTHER INFORMATION: Synthetic peptide

<400> SEQUENCE: 295

Ile Glu Gly Trp Val Trp Cys Pro Trp Leu Ala Ala Arg Ala
1               5                   10

<210> SEQ ID NO 296
<211> LENGTH: 14
<212> TYPE: PRT
<213> ORGANISM: Artificial sequence
<220> FEATURE:
<223> OTHER INFORMATION: Synthetic peptide

<400> SEQUENCE: 296

Ile Glu Gly Trp Val Trp Trp Pro Trp Leu Ala Ala Arg Ala
1               5                   10

<210> SEQ ID NO 297
<211> LENGTH: 17
<212> TYPE: PRT
<213> ORGANISM: Artificial sequence
<220> FEATURE:
<223> OTHER INFORMATION: Synthetic peptide

<400> SEQUENCE: 297

Ile Glu Gly Trp Thr Trp Gln Phe Tyr Ala Leu Pro Arg Gly Asp His
1               5                   10                  15

Ser

<210> SEQ ID NO 298
<211> LENGTH: 51
<212> TYPE: PRT
<213> ORGANISM: Artificial sequence
<220> FEATURE:
<223> OTHER INFORMATION: Synthetic peptide

<400> SEQUENCE: 298

Ile Glu Gly Trp Pro Trp Gln Phe Tyr Ala Leu Ser Arg Glu Ser Gly
1               5                   10                  15

Thr Ser Pro Ser Ser Ala Ala Arg Thr Ser Ser Tyr Leu Arg Ser Cys
                20                  25                  30

Ala Gln Ile Glu Gly Pro Thr Phe Lys Gln Trp Gln Ile Cys Lys Asp
            35                  40                  45

Gln His Ser

<210> SEQ ID NO 299
<211> LENGTH: 14
<212> TYPE: PRT
<213> ORGANISM: Artificial sequence
<220> FEATURE:
<223> OTHER INFORMATION: Synthetic peptide

<400> SEQUENCE: 299

Ile Glu Gly Pro Thr Leu Arg Gln Arg Leu Ala Ala Arg Ala
1               5                   10

<210> SEQ ID NO 300
<211> LENGTH: 17
<212> TYPE: PRT
<213> ORGANISM: Artificial sequence
<220> FEATURE:
<223> OTHER INFORMATION: Synthetic peptide

<400> SEQUENCE: 300

Ile Glu Gly Trp Ser Trp Gln Phe Tyr Ala His Pro Lys Gly Asp His
1               5                   10                  15

Ser

<210> SEQ ID NO 301
<211> LENGTH: 14
<212> TYPE: PRT
<213> ORGANISM: Artificial sequence
<220> FEATURE:
<223> OTHER INFORMATION: Synthetic peptide

<400> SEQUENCE: 301

Ile Glu Gly Trp Val Trp Arg Gln Trp Leu Ala Ala Arg Ala
1               5                   10

<210> SEQ ID NO 302
<211> LENGTH: 17
<212> TYPE: PRT
<213> ORGANISM: Artificial sequence
<220> FEATURE:
<223> OTHER INFORMATION: Synthetic peptide

<400> SEQUENCE: 302

Ile Glu Gly Arg His Tyr Gln Lys Trp Pro Ala Arg Arg Leu Gly His
1               5                   10                  15

Ser

<210> SEQ ID NO 303
<211> LENGTH: 17
<212> TYPE: PRT
<213> ORGANISM: Artificial sequence
<220> FEATURE:
<223> OTHER INFORMATION: Synthetic peptide

<400> SEQUENCE: 303

Ile Glu Gly Phe Val Gly Thr Val Asp Trp Arg Gln Gly Arg Pro His
1               5                   10                  15

Ser

<210> SEQ ID NO 304
<211> LENGTH: 17
<212> TYPE: PRT
<213> ORGANISM: Artificial sequence
<220> FEATURE:
<223> OTHER INFORMATION: Synthetic peptide

```
<400> SEQUENCE: 304

Ile Glu Gly Gln Glu Pro Thr Arg Leu Arg Leu Gln Met Asp Arg His
1               5                   10                  15

Ser

<210> SEQ ID NO 305
<211> LENGTH: 48
<212> TYPE: PRT
<213> ORGANISM: Artificial sequence
<220> FEATURE:
<223> OTHER INFORMATION: Synthetic peptide

<400> SEQUENCE: 305

Ile Ala Gln Val Arg Met Leu Gly Arg Phe Thr Leu Leu Val Leu Ser
1               5                   10                  15

Arg Ala Arg Ala Ala Ser Thr Gln Leu Ser Phe Gln His Ser Ile Cys
            20                  25                  30

Ala Gln Ile Glu Gly Gly Ala Gln Thr Gln Trp Asp Ala Ala Arg Ala
        35                  40                  45

<210> SEQ ID NO 306
<211> LENGTH: 14
<212> TYPE: PRT
<213> ORGANISM: Artificial sequence
<220> FEATURE:
<223> OTHER INFORMATION: Synthetic peptide

<400> SEQUENCE: 306

Ile Glu Gly Glu Ile Trp Ala Gly Pro Gly Ala Ala Arg Ala
1               5                   10

<210> SEQ ID NO 307
<211> LENGTH: 14
<212> TYPE: PRT
<213> ORGANISM: Artificial sequence
<220> FEATURE:
<223> OTHER INFORMATION: Synthetic peptide

<400> SEQUENCE: 307

Ile Glu Gly Glu Ala Leu Val Phe Trp Trp Ala Ala Arg Ala
1               5                   10

<210> SEQ ID NO 308
<211> LENGTH: 14
<212> TYPE: PRT
<213> ORGANISM: Artificial sequence
<220> FEATURE:
<223> OTHER INFORMATION: Synthetic peptide

<400> SEQUENCE: 308

Ile Glu Gly Ser Tyr Arg Glu Arg Gln Gln Ala Ala Arg Ala
1               5                   10

<210> SEQ ID NO 309
<211> LENGTH: 14
<212> TYPE: PRT
<213> ORGANISM: Artificial sequence
<220> FEATURE:
<223> OTHER INFORMATION: Synthetic peptide

<400> SEQUENCE: 309

Ile Glu Gly Trp Val Trp Arg Pro Trp Leu Ala Ala Arg Ala
1               5                   10
```

```
<210> SEQ ID NO 310
<211> LENGTH: 14
<212> TYPE: PRT
<213> ORGANISM: Artificial sequence
<220> FEATURE:
<223> OTHER INFORMATION: Synthetic peptide

<400> SEQUENCE: 310

Ile Glu Gly Trp Asn Pro Trp Arg Gly Ala Ala Ser Arg Val
1               5                   10

<210> SEQ ID NO 311
<211> LENGTH: 14
<212> TYPE: PRT
<213> ORGANISM: Artificial sequence
<220> FEATURE:
<223> OTHER INFORMATION: Synthetic peptide

<400> SEQUENCE: 311

Ile Glu Gly Trp Thr Arg Arg Gln Trp Leu Ala Ala Arg Ala
1               5                   10

<210> SEQ ID NO 312
<211> LENGTH: 14
<212> TYPE: PRT
<213> ORGANISM: Artificial sequence
<220> FEATURE:
<223> OTHER INFORMATION: Synthetic peptide

<400> SEQUENCE: 312

Ile Glu Gly Trp Val Trp Arg Pro Trp Leu Ala Ala Arg Ala
1               5                   10

<210> SEQ ID NO 313
<211> LENGTH: 16
<212> TYPE: PRT
<213> ORGANISM: Artificial sequence
<220> FEATURE:
<223> OTHER INFORMATION: Synthetic peptide

<400> SEQUENCE: 313

Ile Glu Gly Pro Thr Phe Lys Gln Trp Gln Ala Met Arg Arg His Ser
1               5                   10                  15

<210> SEQ ID NO 314
<211> LENGTH: 15
<212> TYPE: PRT
<213> ORGANISM: Artificial sequence
<220> FEATURE:
<223> OTHER INFORMATION: Synthetic peptide

<400> SEQUENCE: 314

Ile Glu Gly Met Val Lys Leu Gly Val Ile Arg Leu Leu Val Leu
1               5                   10                  15

<210> SEQ ID NO 315
<211> LENGTH: 17
<212> TYPE: PRT
<213> ORGANISM: Artificial sequence
<220> FEATURE:
<223> OTHER INFORMATION: Synthetic peptide

<400> SEQUENCE: 315

Ile Glu Gly Pro Thr Phe Lys Gln Trp Gln Ala Trp Arg Arg Trp His
1               5                   10                  15
Ser
```

```
<210> SEQ ID NO 316
<211> LENGTH: 48
<212> TYPE: PRT
<213> ORGANISM: Artificial sequence
<220> FEATURE:
<223> OTHER INFORMATION: Synthetic peptide

<400> SEQUENCE: 316

Ile Glu Val Trp Gln Ser His Trp Tyr Gln Ala Ala Arg Ala Leu Glu
1               5                   10                  15

Ser Thr Ser Ser Arg Leu Leu Pro Met Arg Pro Pro Ser Ile Cys
                20                  25                  30

Ala Gln Ile Glu Gly Pro Thr Leu Pro Gln Arg Met Ala Ala Arg Ala
        35                  40                  45

<210> SEQ ID NO 317
<211> LENGTH: 17
<212> TYPE: PRT
<213> ORGANISM: Artificial sequence
<220> FEATURE:
<223> OTHER INFORMATION: Synthetic peptide

<400> SEQUENCE: 317

Ile Glu Gly Trp Thr Trp Gln Phe Tyr Ala His Pro Gln Gly Asp His
1               5                   10                  15

Ser

<210> SEQ ID NO 318
<211> LENGTH: 17
<212> TYPE: PRT
<213> ORGANISM: Artificial sequence
<220> FEATURE:
<223> OTHER INFORMATION: Synthetic peptide

<400> SEQUENCE: 318

Ile Glu Gly Pro Thr Phe Lys Gln Trp Gln Ala Leu Arg Lys Arg His
1               5                   10                  15

Ser

<210> SEQ ID NO 319
<211> LENGTH: 17
<212> TYPE: PRT
<213> ORGANISM: Artificial sequence
<220> FEATURE:
<223> OTHER INFORMATION: Synthetic peptide

<400> SEQUENCE: 319

Ile Glu Gly Pro Thr Phe Lys Gln Trp Gln Lys Leu Arg Leu Gly His
1               5                   10                  15

Ser

<210> SEQ ID NO 320
<211> LENGTH: 17
<212> TYPE: PRT
<213> ORGANISM: Artificial sequence
<220> FEATURE:
<223> OTHER INFORMATION: Synthetic peptide

<400> SEQUENCE: 320

Ile Glu Gly Pro Thr Phe Lys Gln Trp Gln Leu Met Gly Phe Pro His
1               5                   10                  15

Ser

<210> SEQ ID NO 321
```

```
<211> LENGTH: 17
<212> TYPE: PRT
<213> ORGANISM: Artificial sequence
<220> FEATURE:
<223> OTHER INFORMATION: Synthetic peptide

<400> SEQUENCE: 321

Ile Glu Gly Trp Ile Trp Arg Gln Trp Leu Met Gln Thr Leu Trp His
1               5                   10                  15

Ser

<210> SEQ ID NO 322
<211> LENGTH: 17
<212> TYPE: PRT
<213> ORGANISM: Artificial sequence
<220> FEATURE:
<223> OTHER INFORMATION: Synthetic peptide

<400> SEQUENCE: 322

Ile Glu Gly Pro Thr Phe Lys Gln Trp Gln Ala Met Arg Lys Asn His
1               5                   10                  15

Ser

<210> SEQ ID NO 323
<211> LENGTH: 17
<212> TYPE: PRT
<213> ORGANISM: Artificial sequence
<220> FEATURE:
<223> OTHER INFORMATION: Synthetic peptide

<400> SEQUENCE: 323

Ile Glu Gly Pro Thr Phe Lys Gln Trp Gln Lys Trp Arg Leu Ser His
1               5                   10                  15

Ser

<210> SEQ ID NO 324
<211> LENGTH: 14
<212> TYPE: PRT
<213> ORGANISM: Artificial sequence
<220> FEATURE:
<223> OTHER INFORMATION: Synthetic peptide

<400> SEQUENCE: 324

Ile Glu Gly Trp Gln Glu Gly Arg Gln Ser Ala Ala Arg Ala
1               5                   10

<210> SEQ ID NO 325
<211> LENGTH: 17
<212> TYPE: PRT
<213> ORGANISM: Artificial sequence
<220> FEATURE:
<223> OTHER INFORMATION: Synthetic peptide

<400> SEQUENCE: 325

Ile Glu Gly Pro Thr Phe Lys Gln Trp Gln Arg Trp Leu Lys Tyr His
1               5                   10                  15

Ser

<210> SEQ ID NO 326
<211> LENGTH: 56
<212> TYPE: PRT
<213> ORGANISM: Artificial sequence
<220> FEATURE:
<223> OTHER INFORMATION: Synthetic peptide

<400> SEQUENCE: 326
```

```
Ile Glu Gly Asn Tyr Trp Phe Trp Gln Gln Val Gly Gln Glu Asn Thr
1               5                   10                  15

Leu Ser Arg Glu Trp Ile Gln Thr Leu Gly Gln Lys Tyr Trp Tyr Arg
            20                  25                  30

Pro Pro Ser Ile Cys Ala Gln Ile Glu Gly Trp Ser His Gln His
        35                  40                  45

Tyr Ser Ala Met Ser Gly His Ser
    50                  55
```

<210> SEQ ID NO 327
<211> LENGTH: 17
<212> TYPE: PRT
<213> ORGANISM: Artificial sequence
<220> FEATURE:
<223> OTHER INFORMATION: Synthetic peptide

<400> SEQUENCE: 327

```
Ile Glu Gly Pro Thr Phe Lys Gln Trp Gln Leu Trp Arg Leu Gln His
1               5                   10                  15

Ser
```

<210> SEQ ID NO 328
<211> LENGTH: 17
<212> TYPE: PRT
<213> ORGANISM: Artificial sequence
<220> FEATURE:
<223> OTHER INFORMATION: Synthetic peptide

<400> SEQUENCE: 328

```
Ile Glu Gly Pro Thr Phe Lys Gln Trp Gln Met Leu Arg Arg His His
1               5                   10                  15

Ser
```

<210> SEQ ID NO 329
<211> LENGTH: 17
<212> TYPE: PRT
<213> ORGANISM: Artificial sequence
<220> FEATURE:
<223> OTHER INFORMATION: Synthetic peptide

<400> SEQUENCE: 329

```
Ile Glu Gly Pro Thr Phe Lys Gln Trp Gln Arg Leu Arg Lys Asn His
1               5                   10                  15

Ser
```

<210> SEQ ID NO 330
<211> LENGTH: 14
<212> TYPE: PRT
<213> ORGANISM: Artificial sequence
<220> FEATURE:
<223> OTHER INFORMATION: Synthetic peptide

<400> SEQUENCE: 330

```
Ile Glu Gly Leu Leu Ser Gln Leu Trp Gln Ala Ala Arg Ala
1               5                   10
```

<210> SEQ ID NO 331
<211> LENGTH: 17
<212> TYPE: PRT
<213> ORGANISM: Artificial sequence
<220> FEATURE:
<223> OTHER INFORMATION: Synthetic peptide

<400> SEQUENCE: 331

Ile Glu Gly Pro Ser Leu Pro Glu Trp Leu His Val Trp Arg His His
1               5                   10                  15

Ser

<210> SEQ ID NO 332
<211> LENGTH: 17
<212> TYPE: PRT
<213> ORGANISM: Artificial sequence
<220> FEATURE:
<223> OTHER INFORMATION: Synthetic peptide

<400> SEQUENCE: 332

Ile Glu Gly Pro Thr Leu His Glu Trp Leu Ala Glu Arg Arg Lys His
1               5                   10                  15

Ser

<210> SEQ ID NO 333
<211> LENGTH: 17
<212> TYPE: PRT
<213> ORGANISM: Artificial sequence
<220> FEATURE:
<223> OTHER INFORMATION: Synthetic peptide

<400> SEQUENCE: 333

Ile Glu Gly Pro Thr Leu His Glu Trp Leu Ala Leu Leu Arg Ser His
1               5                   10                  15

Ser

<210> SEQ ID NO 334
<211> LENGTH: 17
<212> TYPE: PRT
<213> ORGANISM: Artificial sequence
<220> FEATURE:
<223> OTHER INFORMATION: Synthetic peptide

<400> SEQUENCE: 334

Ile Glu Gly Pro Thr Leu His Glu Trp Leu Ala Gln Arg Arg Glu His
1               5                   10                  15

Ser

<210> SEQ ID NO 335
<211> LENGTH: 17
<212> TYPE: PRT
<213> ORGANISM: Artificial sequence
<220> FEATURE:
<223> OTHER INFORMATION: Synthetic peptide

<400> SEQUENCE: 335

Ile Glu Gly Pro Thr Leu His Glu Trp Leu Leu Tyr Arg Arg Ala His
1               5                   10                  15

Ser

<210> SEQ ID NO 336
<211> LENGTH: 17
<212> TYPE: PRT
<213> ORGANISM: Artificial sequence
<220> FEATURE:
<223> OTHER INFORMATION: Synthetic peptide

<400> SEQUENCE: 336

Ile Glu Gly Pro Thr Leu His Glu Trp Leu Arg Gln Arg Arg Gln His
1               5                   10                  15

Ser

<210> SEQ ID NO 337
<211> LENGTH: 14
<212> TYPE: PRT
<213> ORGANISM: Artificial sequence
<220> FEATURE:
<223> OTHER INFORMATION: Synthetic peptide

<400> SEQUENCE: 337

Ile Glu Gly Pro Thr Leu Arg Gln Trp Leu Ala Ala Arg Ala
1               5                   10

<210> SEQ ID NO 338
<211> LENGTH: 33
<212> TYPE: PRT
<213> ORGANISM: Artificial sequence
<220> FEATURE:
<223> OTHER INFORMATION: Synthetic peptide

<400> SEQUENCE: 338

Tyr Ser His Cys Ala Gln Gly Ala Val Pro Gln Gly Pro Thr Leu Lys
1               5                   10                  15

Gln Trp Leu Leu Trp Arg Arg Cys Ala His Ser Leu Glu Thr Val Glu
            20                  25                  30

Ser

<210> SEQ ID NO 339
<211> LENGTH: 33
<212> TYPE: PRT
<213> ORGANISM: Artificial sequence
<220> FEATURE:
<223> OTHER INFORMATION: Synthetic peptide

<400> SEQUENCE: 339

Tyr Ser His Cys Ala Gln Gly Tyr Cys Asp Glu Gly Pro Thr Leu Lys
1               5                   10                  15

Gln Trp Leu Val Cys Leu Gly Leu Gln His Ser Leu Glu Thr Val Glu
            20                  25                  30

Ser

<210> SEQ ID NO 340
<211> LENGTH: 33
<212> TYPE: PRT
<213> ORGANISM: Artificial sequence
<220> FEATURE:
<223> OTHER INFORMATION: Synthetic peptide

<400> SEQUENCE: 340

Tyr Ser His Cys Ala Gln Gly Cys Ser Ser Gly Gly Pro Thr Leu Arg
1               5                   10                  15

Glu Trp Leu Gln Cys Arg Arg Met Gln His Ser Leu Glu Thr Val Glu
            20                  25                  30

Ser

<210> SEQ ID NO 341
<211> LENGTH: 33
<212> TYPE: PRT
<213> ORGANISM: Artificial sequence
<220> FEATURE:
<223> OTHER INFORMATION: Synthetic peptide

<400> SEQUENCE: 341

Tyr Ser His Cys Ala Gln Gly Cys Ser Trp Gly Gly Pro Thr Leu Lys
1               5                   10                  15

```
Gln Trp Leu Gln Cys Val Arg Ala Lys His Ser Leu Glu Thr Val Glu
            20                  25                  30

Ser

<210> SEQ ID NO 342
<211> LENGTH: 33
<212> TYPE: PRT
<213> ORGANISM: Artificial sequence
<220> FEATURE:
<223> OTHER INFORMATION: Synthetic peptide

<400> SEQUENCE: 342

Tyr Ser His Cys Ala Gln Gly Gly Cys Arg Ser Gly Pro Thr Leu Arg
1               5                   10                  15

Glu Trp Leu Ala Cys Arg Glu Val Gln His Ser Leu Thr Val Glu
            20                  25                  30

Ser

<210> SEQ ID NO 343
<211> LENGTH: 33
<212> TYPE: PRT
<213> ORGANISM: Artificial sequence
<220> FEATURE:
<223> OTHER INFORMATION: Synthetic peptide

<400> SEQUENCE: 343

Tyr Ser His Cys Ala Gln Gly Thr Cys Glu Gln Gly Pro Thr Leu Arg
1               5                   10                  15

Gln Trp Leu Leu Cys Arg Gln Gly Arg His Ser Leu Glu Thr Val Glu
            20                  25                  30

Ser

<210> SEQ ID NO 344
<211> LENGTH: 275
<212> TYPE: PRT
<213> ORGANISM: Artificial sequence
<220> FEATURE:
<223> OTHER INFORMATION: Synthetic peptide

<400> SEQUENCE: 344

Ala Gly Lys Ser Val Thr Cys His Val Lys Tyr Thr Asn Pro Ser
1               5                   10                  15

Gln Asp Val Thr Val Pro Cys Pro Val Pro Ser Thr Pro Pro Thr Pro
            20                  25                  30

Ser Pro Ser Thr Pro Pro Thr Pro Ser Pro Ser Cys Cys His Pro Arg
        35                  40                  45

Leu Ser Leu His Arg Pro Ala Leu Glu Asp Leu Leu Gly Ser Glu
    50                  55                  60

Ala Asn Leu Thr Cys Thr Leu Thr Gly Leu Arg Asp Ala Ser Gly Val
65                  70                  75                  80

Thr Phe Thr Trp Thr Pro Ser Ser Gly Lys Ser Ala Val Gln Gly Pro
                85                  90                  95

Pro Glu Arg Asp Leu Cys Gly Cys Tyr Ser Val Ser Ser Val Leu Pro
            100                 105                 110

Gly Cys Ala Glu Pro Trp Asn His Gly Lys Thr Phe Thr Cys Thr Ala
        115                 120                 125

Ala Tyr Pro Glu Ser Lys Thr Pro Leu Thr Ala Thr Leu Ser Lys Ser
    130                 135                 140

Gly Asn Thr Phe Arg Pro Glu Val His Leu Leu Pro Pro Pro Ser Glu
```

```
                 145                 150                 155                 160
Glu Leu Ala Leu Asn Glu Leu Val Thr Leu Thr Cys Leu Ala Arg Gly
                165                 170                 175
Phe Ser Pro Lys Asp Val Leu Val Arg Trp Leu Gln Gly Ser Gln Glu
            180                 185                 190
Leu Pro Arg Glu Lys Tyr Leu Thr Trp Ala Ser Arg Gln Glu Pro Ser
        195                 200                 205
Gln Gly Thr Thr Thr Phe Ala Val Thr Ser Ile Leu Arg Val Ala Ala
    210                 215                 220
Glu Asp Trp Lys Lys Gly Asp Thr Phe Ser Cys Met Val Gly His Glu
225                 230                 235                 240
Ala Leu Pro Leu Ala Phe Thr Gln Lys Thr Ile Asp Arg Leu Ala Gly
                245                 250                 255
Lys Pro Thr His Val Asn Val Ser Val Val Met Ala Glu Val Asp Gly
                260                 265                 270
Thr Cys Tyr
        275

<210> SEQ ID NO 345
<211> LENGTH: 262
<212> TYPE: PRT
<213> ORGANISM: Artificial sequence
<220> FEATURE:
<223> OTHER INFORMATION: Synthetic peptide

<400> SEQUENCE: 345

Asp Gly Lys Ser Val Thr Cys His Val Lys His Tyr Thr Asn Pro Ser
1               5                   10                  15
Gln Asp Val Thr Val Pro Cys Pro Val Pro Pro Pro Pro Cys Cys
            20                  25                  30
His Pro Arg Leu Ser Leu His Arg Pro Ala Leu Glu Asp Leu Leu Leu
        35                  40                  45
Gly Ser Glu Ala Asn Leu Thr Cys Thr Leu Thr Gly Leu Arg Asp Ala
    50                  55                  60
Ser Gly Ala Thr Phe Thr Trp Thr Pro Ser Ser Gly Lys Ser Ala Val
65                  70                  75                  80
Gln Gly Pro Pro Glu Arg Asp Leu Cys Gly Cys Tyr Ser Val Ser Ser
                85                  90                  95
Val Leu Pro Gly Cys Ala Gln Pro Trp Asn His Gly Glu Thr Phe Thr
            100                 105                 110
Cys Thr Ala Ala His Pro Glu Leu Lys Thr Pro Leu Thr Ala Asn Ile
        115                 120                 125
Thr Lys Ser Gly Asn Thr Phe Arg Pro Glu Val His Leu Leu Pro Pro
    130                 135                 140
Pro Ser Glu Glu Leu Ala Leu Asn Glu Leu Val Thr Leu Thr Cys Leu
145                 150                 155                 160
Ala Arg Gly Phe Ser Pro Lys Asp Val Leu Val Arg Trp Leu Gln Gly
                165                 170                 175
Ser Gln Glu Leu Pro Arg Glu Lys Tyr Leu Thr Trp Ala Ser Arg Gln
            180                 185                 190
Glu Pro Ser Gln Gly Thr Thr Thr Phe Ala Val Thr Ser Ile Leu Arg
        195                 200                 205
Val Ala Ala Glu Asp Trp Lys Lys Gly Asp Thr Phe Ser Cys Met Val
    210                 215                 220
Gly His Glu Ala Leu Pro Leu Ala Phe Thr Gln Lys Thr Ile Asp Arg
225                 230                 235                 240
```

Leu Ala Gly Lys Pro Thr His Val Asn Val Ser Val Val Met Ala Glu
                245                 250                 255

Val Asp Gly Thr Cys Tyr
            260

<210> SEQ ID NO 346
<211> LENGTH: 253
<212> TYPE: PRT
<213> ORGANISM: Artificial sequence
<220> FEATURE:
<223> OTHER INFORMATION: Synthetic peptide

<400> SEQUENCE: 346

Glu Gly Lys Gln Val Gly Ser Gly Val Thr Thr Asp Gln Val Gln Ala
1               5                   10                  15

Glu Ala Lys Glu Ser Gly Pro Thr Thr Tyr Lys Val Thr Ser Thr Leu
                20                  25                  30

Thr Ile Lys Glu Asp His Arg Gly Leu Thr Phe Gln Gln Asn Ala Ser
                35                  40                  45

Ser Met Cys Val Pro Asp Gln Asp Thr Ala Ile Arg Val Phe Ala Ile
    50                  55                  60

Pro Pro Ser Phe Ala Ser Ile Phe Leu Thr Lys Ser Thr Lys Leu Thr
65                  70                  75                  80

Cys Leu Val Thr Asp Leu Thr Thr Tyr Asp Ser Val Thr Ile Ser Trp
                85                  90                  95

Asn Ser Gly Glu Arg Phe Thr Cys Thr Val Thr His Thr Asp Leu Pro
                100                 105                 110

Ser Pro Leu Lys Gln Thr Ile Ser Arg Pro Lys Gly Val Ala Leu His
                115                 120                 125

Arg Pro Asp Val Tyr Leu Leu Pro Pro Ala Arg Glu Gln Leu Asn Leu
            130                 135                 140

Arg Glu Ser Ala Thr Ile Thr Cys Leu Val Thr Gly Phe Ser Pro Ala
145                 150                 155                 160

Asp Val Phe Val Gln Trp Met Gln Arg Gly Gln Pro Leu Ser Pro Glu
                165                 170                 175

Lys Tyr Val Thr Ser Ala Pro Met Pro Glu Pro Gln Ala Pro Gly Arg
                180                 185                 190

Tyr Phe Ala His Ser Ile Leu Thr Val Ser Glu Glu Trp Asn Thr
            195                 200                 205

Gly Glu Thr Tyr Thr Cys Val Ala His Asp Ala Leu Pro Asn Arg Val
    210                 215                 220

Thr Glu Arg Thr Val Asp Lys Ser Thr Gly Lys Pro Thr Leu Tyr Asn
225                 230                 235                 240

Val Ser Leu Val Met Ser Asp Thr Ala Gly Thr Cys Tyr
                245                 250

<210> SEQ ID NO 347
<211> LENGTH: 232
<212> TYPE: PRT
<213> ORGANISM: Artificial sequence
<220> FEATURE:
<223> OTHER INFORMATION: Synthetic peptide

<400> SEQUENCE: 347

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
        210                 215                 220

Ser Leu Ser Leu Ser Pro Gly Lys
225                 230

<210> SEQ ID NO 348
<211> LENGTH: 232
<212> TYPE: PRT
<213> ORGANISM: Artificial sequence
<220> FEATURE:
<223> OTHER INFORMATION: Synthetic peptide

<400> SEQUENCE: 348

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
        130                 135                 140

Lys Asn Gln Val Ser Leu Thr Cys Leu Val Lys Gly Phe Tyr Pro Ser
145                 150                 155                 160

```
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 349
<211> LENGTH: 279
<212> TYPE: PRT
<213> ORGANISM: Artificial sequence
<220> FEATURE:
<223> OTHER INFORMATION: Synthetic peptide

<400> SEQUENCE: 349

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Phe
        115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
    210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
        275
```

```
<210> SEQ ID NO 350
<211> LENGTH: 228
<212> TYPE: PRT
<213> ORGANISM: Artificial sequence
<220> FEATURE:
<223> OTHER INFORMATION: Synthetic peptide

<400> SEQUENCE: 350

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 351
<211> LENGTH: 229
<212> TYPE: PRT
<213> ORGANISM: Artificial sequence
<220> FEATURE:
<223> OTHER INFORMATION: Synthetic peptide

<400> SEQUENCE: 351

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
```

```
                    85                  90                  95
Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 352
<211> LENGTH: 253
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (23)..(34)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (138)..(138)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (186)..(187)
<223> OTHER INFORMATION: Xaa can be any naturally occurring amino acid
<220> FEATURE:
<221> NAME/KEY: misc_feature
<222> LOCATION: (204)..(206)
<223> OTHER INFORMATION: Xaa can be any naturally occurring amino acid
<220> FEATURE:
<221> NAME/KEY: misc_feature
<222> LOCATION: (252)..(253)
<223> OTHER INFORMATION: Xaa can be any naturally occurring amino acid
```

<400> SEQUENCE: 352

```
Glu Xaa Lys Ser Xaa Asp Xaa Thr Val Pro Cys Pro Xaa Cys Pro Ala
1               5                   10                  15

Pro Glu Leu Leu Gly Gly Xaa Xaa Xaa Xaa Xaa Xaa Xaa Xaa Xaa Xaa
            20                  25                  30

Xaa Xaa Pro Ser Val Phe Leu Phe Pro Pro Lys Pro Lys Asp Thr Leu
        35                  40                  45

Met Ile Ser Arg Thr Pro Glu Val Thr Cys Val Val Val Asp Val Ser
    50                  55                  60

His Glu Asp Pro Glu Val Xaa Phe Asn Trp Tyr Val Asp Gly Val Glu
65                  70                  75                  80

Val His Asn Ala Lys Thr Lys Pro Arg Glu Glu Gln Phe Asn Ser Thr
                85                  90                  95

Tyr Arg Val Val Ser Val Leu Thr Val Leu His Gln Asp Trp Leu Asn
            100                 105                 110

Gly Lys Glu Tyr Lys Cys Lys Val Ser Asn Lys Ala Leu Pro Ala Pro
        115                 120                 125

Ile Glu Lys Thr Ile Ser Lys Ala Lys Xaa Gly Gln Pro Arg Glu Pro
130                 135                 140

Gln Val Tyr Thr Leu Pro Pro Xaa Ser Arg Glu Glu Met Thr Lys Asn
145                 150                 155                 160

Gln Val Ser Leu Thr Cys Leu Val Lys Gly Phe Tyr Pro Ser Asp Ile
            165                 170                 175

Ala Val Glu Trp Glu Ser Asn Gly Gln Xaa Xaa Pro Glu Asn Asn Tyr
        180                 185                 190

Lys Thr Thr Pro Pro Met Leu Asp Ser Asp Gly Xaa Xaa Xaa Ser Phe
            195                 200                 205

Phe Leu Tyr Ser Lys Leu Thr Val Asp Lys Ser Arg Trp Gln Gln Gly
        210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys Xaa Xaa
            245                 250
```

<210> SEQ ID NO 353
<211> LENGTH: 254
<212> TYPE: PRT
<213> ORGANISM: Artificial sequence
<220> FEATURE:
<223> OTHER INFORMATION: Synthetic peptide

<400> SEQUENCE: 353

```
Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Gly Gly Gln Gly Cys Ser Ser Gly Gly Pro Thr Leu Arg Glu Trp
    50                  55                  60

Gln Gln Cys Arg Arg Met Gln His Ser Gly Gly Glu Asp Pro Glu Val
65                  70                  75                  80

Lys Phe Asn Trp Tyr Val Asp Gly Val Glu Val His Asn Ala Lys Thr
                85                  90                  95

Lys Pro Arg Glu Glu Gln Tyr Asn Ser Thr Tyr Arg Val Val Ser Val
```

```
                          100                 105                 110
Leu Thr Val Leu His Gln Asp Trp Leu Asn Gly Lys Glu Tyr Lys Cys
            115                 120                 125

Lys Val Ser Asn Lys Ala Leu Pro Ala Pro Ile Glu Lys Thr Ile Ser
        130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
        195                 200                 205

Gly Ser Phe Phe Leu Tyr Ser Lys Leu Thr Val Asp Lys Ser Arg Trp
    210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 354
<211> LENGTH: 254
<212> TYPE: PRT
<213> ORGANISM: Artificial sequence
<220> FEATURE:
<223> OTHER INFORMATION: Synthetic peptide

<400> SEQUENCE: 354

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Gly Gly Gln Gly Cys Ser Ser Gly Gly Pro Thr Leu Arg Glu Trp
    50                  55                  60

Gln Gln Cys Val Arg Met Gln His Ser Gly Gly Glu Asp Pro Glu Val
65                  70                  75                  80

Lys Phe Asn Trp Tyr Val Asp Gly Val Glu Val His Asn Ala Lys Thr
                85                  90                  95

Lys Pro Arg Glu Glu Gln Tyr Asn Ser Thr Tyr Arg Val Val Ser Val
            100                 105                 110

Leu Thr Val Leu His Gln Asp Trp Leu Asn Gly Lys Glu Tyr Lys Cys
        115                 120                 125

Lys Val Ser Asn Lys Ala Leu Pro Ala Pro Ile Glu Lys Thr Ile Ser
    130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
        195                 200                 205

Gly Ser Phe Phe Leu Tyr Ser Lys Leu Thr Val Asp Lys Ser Arg Trp
    210                 215                 220
```

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 355
<211> LENGTH: 254
<212> TYPE: PRT
<213> ORGANISM: Artificial sequence
<220> FEATURE:
<223> OTHER INFORMATION: Synthetic peptide

<400> SEQUENCE: 355

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Gly Gly Gln Gly Cys Ser Ser Gly Gly Pro Thr Leu Arg Glu Trp
    50                  55                  60

Gln Gln Cys Arg Arg Ala Gln His Ser Gly Gly Glu Asp Pro Glu Val
65                  70                  75                  80

Lys Phe Asn Trp Tyr Val Asp Gly Val Glu Val His Asn Ala Lys Thr
                85                  90                  95

Lys Pro Arg Glu Glu Gln Tyr Asn Ser Thr Tyr Arg Val Val Ser Val
            100                 105                 110

Leu Thr Val Leu His Gln Asp Trp Leu Asn Gly Lys Glu Tyr Lys Cys
        115                 120                 125

Lys Val Ser Asn Lys Ala Leu Pro Ala Pro Ile Glu Lys Thr Ile Ser
    130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
        195                 200                 205

Gly Ser Phe Phe Leu Tyr Ser Lys Leu Thr Val Asp Lys Ser Arg Trp
    210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 356
<211> LENGTH: 254
<212> TYPE: PRT
<213> ORGANISM: Artificial sequence
<220> FEATURE:
<223> OTHER INFORMATION: Synthetic peptide

<400> SEQUENCE: 356

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Gly Gly Gln Gly Cys Ser Ser Gly Gly Pro Thr Leu Arg Glu Trp
 50                  55                  60

Gln Gln Cys Val Arg Ala Gln His Ser Gly Gly Glu Asp Pro Glu Val
 65                  70                  75                  80

Lys Phe Asn Trp Tyr Val Asp Gly Val Glu Val His Asn Ala Lys Thr
                    85                  90                  95

Lys Pro Arg Glu Glu Gln Tyr Asn Ser Thr Tyr Arg Val Val Ser Val
                100                 105                 110

Leu Thr Val Leu His Gln Asp Trp Leu Asn Gly Lys Glu Tyr Lys Cys
            115                 120                 125

Lys Val Ser Asn Lys Ala Leu Pro Ala Pro Ile Glu Lys Thr Ile Ser
130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
        195                 200                 205

Gly Ser Phe Phe Leu Tyr Ser Lys Leu Thr Val Asp Lys Ser Arg Trp
210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 357
<211> LENGTH: 250
<212> TYPE: PRT
<213> ORGANISM: Artificial sequence
<220> FEATURE:
<223> OTHER INFORMATION: Synthetic peptide

<400> SEQUENCE: 357

Met Asp Lys Thr His Thr Cys Pro Pro Cys Pro Ala Pro Glu Leu Leu
 1               5                  10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Gly Gly Leu Asp Met Glu Gly Pro Thr Leu Arg His Trp Leu Ala
 50                  55                  60

Ala Arg Ala Asn Gly Gly Gly Glu Asp Pro Glu Val Lys Phe Asn Trp
 65                  70                  75                  80

Tyr Val Asp Gly Val Glu Val His Asn Ala Lys Thr Lys Pro Arg Glu
                    85                  90                  95

Glu Gln Tyr Asn Ser Thr Tyr Arg Val Val Ser Val Leu Thr Val Leu
                100                 105                 110

His Gln Asp Trp Leu Asn Gly Lys Glu Tyr Lys Cys Lys Val Ser Asn
            115                 120                 125

Lys Ala Leu Pro Ala Pro Ile Glu Lys Thr Ile Ser Lys Ala Lys Gly
130                 135                 140

```
Gln Pro Arg Glu Pro Gln Val Tyr Thr Leu Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 358
<211> LENGTH: 250
<212> TYPE: PRT
<213> ORGANISM: Artificial sequence
<220> FEATURE:
<223> OTHER INFORMATION: Synthetic peptide

<400> SEQUENCE: 358

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Gly Gly Tyr Met Met Glu Gly Pro Thr Leu Arg Trp Leu Ala
    50                  55                  60

Thr Arg Ala Gly Arg Gly Gly Glu Asp Pro Glu Val Lys Phe Asn Trp
65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ser Asn
        115                 120                 125

Lys Ala Leu Pro Ala Pro Ile Glu Lys Thr Ile Ser Lys Ala Lys Gly
    130                 135                 140

Gln Pro Arg Glu Pro Gln Val Tyr Thr Leu Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250
```

```
<210> SEQ ID NO 359
<211> LENGTH: 250
<212> TYPE: PRT
<213> ORGANISM: Artificial sequence
<220> FEATURE:
<223> OTHER INFORMATION: Synthetic peptide

<400> SEQUENCE: 359

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Gly Gly Thr His Ile Glu Gly Pro Thr Leu Arg Ile Trp Leu Ala
    50                  55                  60

Ser Arg Ala Lys Ala Gly Gly Glu Asp Pro Glu Val Lys Phe Asn Trp
65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ser Asn
        115                 120                 125

Lys Ala Leu Pro Ala Pro Ile Glu Lys Thr Ile Ser Lys Ala Lys Gly
    130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 360
<211> LENGTH: 250
<212> TYPE: PRT
<213> ORGANISM: Artificial sequence
<220> FEATURE:
<223> OTHER INFORMATION: Synthetic peptide

<400> SEQUENCE: 360

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Gly Gly Ser Ala Ile Glu Gly Pro Thr Leu Arg His Trp Leu Ala
    50                  55                  60

Trp Arg Ala Met Leu Gly Gly Glu Asp Pro Glu Val Lys Phe Asn Trp
```

```
                65                  70                  75                  80
Tyr Val Asp Gly Val Glu Val His Asn Ala Lys Thr Lys Pro Arg Glu
                    85                  90                  95

Glu Gln Tyr Asn Ser Thr Tyr Arg Val Val Ser Val Leu Thr Val Leu
                100                 105                 110

His Gln Asp Trp Leu Asn Gly Lys Glu Tyr Lys Cys Lys Val Ser Asn
                115                 120                 125

Lys Ala Leu Pro Ala Pro Ile Glu Lys Thr Ile Ser Lys Ala Lys Gly
130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
                180                 185                 190

Asn Tyr Lys Thr Thr Pro Pro Val Leu Asp Ser Asp Gly Ser Phe Phe
                195                 200                 205

Leu Tyr Ser Lys Leu Thr Val Asp Lys Ser Arg Trp Gln Gln Gly Asn
210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 361
<211> LENGTH: 250
<212> TYPE: PRT
<213> ORGANISM: Artificial sequence
<220> FEATURE:
<223> OTHER INFORMATION: Synthetic peptide

<400> SEQUENCE: 361

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
                35                  40                  45

His Gly Gly Trp Met Met Glu Gly Pro Thr Leu Arg His Trp Leu Ala
50                  55                  60

Ala Arg Ala Arg Tyr Gly Gly Glu Asp Pro Glu Val Lys Phe Asn Trp
65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
                100                 105                 110

His Gln Asp Trp Leu Asn Gly Lys Glu Tyr Lys Cys Lys Val Ser Asn
                115                 120                 125

Lys Ala Leu Pro Ala Pro Ile Glu Lys Thr Ile Ser Lys Ala Lys Gly
130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
                180                 185                 190
```

```
Asn Tyr Lys Thr Thr Pro Pro Val Leu Asp Ser Asp Gly Ser Phe Phe
            195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
            245                 250

<210> SEQ ID NO 362
<211> LENGTH: 250
<212> TYPE: PRT
<213> ORGANISM: Artificial sequence
<220> FEATURE:
<223> OTHER INFORMATION: Synthetic peptide

<400> SEQUENCE: 362

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Gly Gly Ala Trp Met Glu Gly Pro Thr Leu Arg His Trp Leu Ala
50                  55                  60

Ala Arg Ala Ala Tyr Gly Gly Glu Asp Pro Glu Val Lys Phe Asn Trp
65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ser Asn
        115                 120                 125

Lys Ala Leu Pro Ala Pro Ile Glu Lys Thr Ile Ser Lys Ala Lys Gly
    130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
            245                 250

<210> SEQ ID NO 363
<211> LENGTH: 254
<212> TYPE: PRT
<213> ORGANISM: Artificial sequence
<220> FEATURE:
<223> OTHER INFORMATION: Synthetic peptide

<400> SEQUENCE: 363
```

```
Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Gly Gly Gln
65                  70                  75                  80

Gly Cys Ser Ser Gly Gly Pro Thr Leu Arg Glu Trp Gln Gln Cys Arg
                85                  90                  95

Arg Met Gln His Ser Gly Gly Asn Ser Thr Tyr Arg Val Val Ser Val
                100                 105                 110

Leu Thr Val Leu His Gln Asp Trp Leu Asn Gly Lys Glu Tyr Lys Cys
                115                 120                 125

Lys Val Ser Asn Lys Ala Leu Pro Ala Pro Ile Glu Lys Thr Ile Ser
            130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
                180                 185                 190

Gln Pro Glu Asn Asn Tyr Lys Thr Thr Pro Pro Val Leu Asp Ser Asp
            195                 200                 205

Gly Ser Phe Phe Leu Tyr Ser Lys Leu Thr Val Asp Lys Ser Arg Trp
    210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 364
<211> LENGTH: 254
<212> TYPE: PRT
<213> ORGANISM: Artificial sequence
<220> FEATURE:
<223> OTHER INFORMATION: Synthetic peptide

<400> SEQUENCE: 364

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Gly Gly Gln
65                  70                  75                  80

Gly Cys Ser Ser Gly Gly Pro Thr Leu Arg Glu Trp Gln Gln Cys Val
                85                  90                  95

Arg Met Gln His Ser Gly Gly Asn Ser Thr Tyr Arg Val Val Ser Val
                100                 105                 110
```

```
Leu Thr Val Leu His Gln Asp Trp Leu Asn Gly Lys Glu Tyr Lys Cys
            115                 120                 125

Lys Val Ser Asn Lys Ala Leu Pro Ala Pro Ile Glu Lys Thr Ile Ser
        130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
                180                 185                 190

Gln Pro Glu Asn Asn Tyr Lys Thr Thr Pro Pro Val Leu Asp Ser Asp
                195                 200                 205

Gly Ser Phe Phe Leu Tyr Ser Lys Leu Thr Val Asp Lys Ser Arg Trp
210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250
```

<210> SEQ ID NO 365
<211> LENGTH: 254
<212> TYPE: PRT
<213> ORGANISM: Artificial sequence
<220> FEATURE:
<223> OTHER INFORMATION: Synthetic peptide

<400> SEQUENCE: 365

```
Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Gly Gly Gln
65                  70                  75                  80

Gly Cys Ser Ser Gly Gly Pro Thr Leu Arg Glu Trp Gln Gln Cys Arg
                85                  90                  95

Arg Ala Gln His Ser Gly Gly Asn Ser Thr Tyr Arg Val Val Ser Val
            100                 105                 110

Leu Thr Val Leu His Gln Asp Trp Leu Asn Gly Lys Glu Tyr Lys Cys
        115                 120                 125

Lys Val Ser Asn Lys Ala Leu Pro Ala Pro Ile Glu Lys Thr Ile Ser
    130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
        195                 200                 205

Gly Ser Phe Phe Leu Tyr Ser Lys Leu Thr Val Asp Lys Ser Arg Trp
    210                 215                 220

Gln Gln Gly Asn Val Phe Ser Cys Ser Val Met His Glu Ala Leu His
```

```
                225                 230                 235                 240
Asn His Tyr Thr Gln Lys Ser Leu Ser Leu Ser Pro Gly Lys
                245                 250

<210> SEQ ID NO 366
<211> LENGTH: 254
<212> TYPE: PRT
<213> ORGANISM: Artificial sequence
<220> FEATURE:
<223> OTHER INFORMATION: Synthetic peptide

<400> SEQUENCE: 366

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Gly Gly Gln
65                  70                  75                  80

Gly Cys Ser Ser Gly Gly Pro Thr Leu Arg Glu Trp Gln Gln Cys Val
                85                  90                  95

Arg Ala Gln His Ser Gly Gly Asn Ser Thr Tyr Arg Val Val Ser Val
            100                 105                 110

Leu Thr Val Leu His Gln Asp Trp Leu Asn Gly Lys Glu Tyr Lys Cys
        115                 120                 125

Lys Val Ser Asn Lys Ala Leu Pro Ala Pro Ile Glu Lys Thr Ile Ser
    130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
        195                 200                 205

Gly Ser Phe Phe Leu Tyr Ser Lys Leu Thr Val Asp Lys Ser Arg Trp
    210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 367
<211> LENGTH: 250
<212> TYPE: PRT
<213> ORGANISM: Artificial sequence
<220> FEATURE:
<223> OTHER INFORMATION: Synthetic peptide

<400> SEQUENCE: 367

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
```

```
                35                  40                  45
His Glu Asp Pro Glu Val Lys Phe Asn Trp Tyr Val Asp Gly Val Glu
 50                  55                  60

Val His Asn Ala Lys Thr Lys Pro Arg Glu Glu Gln Tyr Gly Gly Leu
 65                  70                  75                  80

Asp Met Glu Gly Pro Thr Leu Arg His Trp Leu Ala Ala Arg Ala Asn
                 85                  90                  95

Gly Gly Gly Asn Ser Thr Tyr Arg Val Val Ser Val Leu Thr Val Leu
                100                 105                 110

His Gln Asp Trp Leu Asn Gly Lys Glu Tyr Lys Cys Lys Val Ser Asn
            115                 120                 125

Lys Ala Leu Pro Ala Pro Ile Glu Lys Thr Ile Ser Lys Ala Lys Gly
130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 368
<211> LENGTH: 250
<212> TYPE: PRT
<213> ORGANISM: Artificial sequence
<220> FEATURE:
<223> OTHER INFORMATION: Synthetic peptide

<400> SEQUENCE: 368

Met Asp Lys Thr His Thr Cys Pro Pro Cys Pro Ala Pro Glu Leu Leu
 1               5                  10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Asp Val Ser
             35                  40                  45

His Glu Asp Pro Glu Val Lys Phe Asn Trp Tyr Val Asp Gly Val Glu
 50                  55                  60

Val His Asn Ala Lys Thr Lys Pro Arg Glu Glu Gln Tyr Gly Gly Tyr
 65                  70                  75                  80

Met Met Glu Gly Pro Thr Leu Arg His Trp Leu Ala Thr Arg Ala Gly
                 85                  90                  95

Arg Gly Gly Asn Ser Thr Tyr Arg Val Val Ser Val Leu Thr Val Leu
                100                 105                 110

His Gln Asp Trp Leu Asn Gly Lys Glu Tyr Lys Cys Lys Val Ser Asn
            115                 120                 125

Lys Ala Leu Pro Ala Pro Ile Glu Lys Thr Ile Ser Lys Ala Lys Gly
130                 135                 140

Gln Pro Arg Glu Pro Gln Val Tyr Thr Leu Pro Pro Ser Arg Asp Glu
145                 150                 155                 160
```

```
Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 369
<211> LENGTH: 250
<212> TYPE: PRT
<213> ORGANISM: Artificial sequence
<220> FEATURE:
<223> OTHER INFORMATION: Synthetic peptide

<400> SEQUENCE: 369

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
50                  55                  60

Val His Asn Ala Lys Thr Lys Pro Arg Glu Glu Gln Tyr Gly Gly Thr
65                  70                  75                  80

His Ile Glu Gly Pro Thr Leu Arg Ile Trp Leu Ala Ser Arg Ala Lys
                85                  90                  95

Ala Gly Gly Asn Ser Thr Tyr Arg Val Val Ser Val Leu Thr Val Leu
            100                 105                 110

His Gln Asp Trp Leu Asn Gly Lys Glu Tyr Lys Cys Lys Val Ser Asn
        115                 120                 125

Lys Ala Leu Pro Ala Pro Ile Glu Lys Thr Ile Ser Lys Ala Lys Gly
130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 370
<211> LENGTH: 250
```

```
<212> TYPE: PRT
<213> ORGANISM: Artificial sequence
<220> FEATURE:
<223> OTHER INFORMATION: Synthetic peptide

<400> SEQUENCE: 370

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Gly Gly Ser
65                  70                  75                  80

Ala Ile Glu Gly Pro Thr Leu Arg His Trp Leu Ala Trp Arg Ala Met
                85                  90                  95

Leu Gly Gly Asn Ser Thr Tyr Arg Val Val Ser Val Leu Thr Val Leu
            100                 105                 110

His Gln Asp Trp Leu Asn Gly Lys Glu Tyr Lys Cys Lys Val Ser Asn
        115                 120                 125

Lys Ala Leu Pro Ala Pro Ile Glu Lys Thr Ile Ser Lys Ala Lys Gly
130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 371
<211> LENGTH: 250
<212> TYPE: PRT
<213> ORGANISM: Artificial sequence
<220> FEATURE:
<223> OTHER INFORMATION: Synthetic peptide

<400> SEQUENCE: 371

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Gly Gly Trp
65                  70                  75                  80
```

```
Met Met Glu Gly Pro Thr Leu Arg His Trp Leu Ala Ala Arg Ala Arg
                85                  90                  95

Tyr Gly Gly Asn Ser Thr Tyr Arg Val Val Ser Val Leu Thr Val Leu
                100                 105                 110

His Gln Asp Trp Leu Asn Gly Lys Glu Tyr Lys Cys Lys Val Ser Asn
                115                 120                 125

Lys Ala Leu Pro Ala Pro Ile Glu Lys Thr Ile Ser Lys Ala Lys Gly
                130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
                180                 185                 190

Asn Tyr Lys Thr Thr Pro Pro Val Leu Asp Ser Asp Gly Ser Phe Phe
                195                 200                 205

Leu Tyr Ser Lys Leu Thr Val Asp Lys Ser Arg Trp Gln Gln Gly Asn
                210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 372
<211> LENGTH: 250
<212> TYPE: PRT
<213> ORGANISM: Artificial sequence
<220> FEATURE:
<223> OTHER INFORMATION: Synthetic peptide

<400> SEQUENCE: 372

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
                35                  40                  45

His Glu Asp Pro Glu Val Lys Phe Asn Trp Tyr Val Asp Gly Val Glu
                50                  55                  60

Val His Asn Ala Lys Thr Lys Pro Arg Glu Glu Gln Tyr Gly Gly Ala
65                  70                  75                  80

Trp Met Glu Gly Pro Thr Leu Arg His Trp Leu Ala Ala Arg Ala Ala
                85                  90                  95

Tyr Gly Gly Asn Ser Thr Tyr Arg Val Val Ser Val Leu Thr Val Leu
                100                 105                 110

His Gln Asp Trp Leu Asn Gly Lys Glu Tyr Lys Cys Lys Val Ser Asn
                115                 120                 125

Lys Ala Leu Pro Ala Pro Ile Glu Lys Thr Ile Ser Lys Ala Lys Gly
                130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
                180                 185                 190

Asn Tyr Lys Thr Thr Pro Pro Val Leu Asp Ser Asp Gly Ser Phe Phe
```

```
                     195                 200                 205

Leu Tyr Ser Lys Leu Thr Val Asp Lys Ser Arg Trp Gln Gln Gly Asn
210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 373
<211> LENGTH: 254
<212> TYPE: PRT
<213> ORGANISM: Artificial sequence
<220> FEATURE:
<223> OTHER INFORMATION: Synthetic peptide

<400> SEQUENCE: 373

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
        50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Gln Gly Cys
                100                 105                 110

Ser Ser Gly Gly Pro Thr Leu Arg Glu Trp Gln Gln Cys Arg Arg Met
            115                 120                 125

Gln His Ser Gly Gly Ala Leu Pro Ala Pro Ile Glu Lys Thr Ile Ser
        130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
        195                 200                 205

Gly Ser Phe Phe Leu Tyr Ser Lys Leu Thr Val Asp Lys Ser Arg Trp
    210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 374
<211> LENGTH: 254
<212> TYPE: PRT
<213> ORGANISM: Artificial sequence
<220> FEATURE:
<223> OTHER INFORMATION: Synthetic peptide

<400> SEQUENCE: 374

Met Asp Lys Thr His Thr Cys Pro Pro Cys Pro Ala Pro Glu Leu Leu
```

```
                1               5                   10                  15
Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
                35                  40                  45

His Glu Asp Pro Glu Val Lys Phe Asn Trp Tyr Val Asp Gly Val Glu
            50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                    85                  90                  95

Gly Lys Glu Tyr Lys Cys Lys Val Ser Asn Lys Gly Gly Gln Gly Cys
                100                 105                 110

Ser Ser Gly Gly Pro Thr Leu Arg Glu Trp Gln Gln Cys Val Arg Met
                115                 120                 125

Gln His Ser Gly Gly Ala Leu Pro Ala Pro Ile Glu Lys Thr Ile Ser
            130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val Ser Leu Thr Cys Leu Val
                    165                 170                 175

Lys Gly Phe Tyr Pro Ser Asp Ile Ala Val Glu Trp Glu Ser Asn Gly
                180                 185                 190

Gln Pro Glu Asn Asn Tyr Lys Thr Thr Pro Pro Val Leu Asp Ser Asp
                195                 200                 205

Gly Ser Phe Phe Leu Tyr Ser Lys Leu Thr Val Asp Lys Ser Arg Trp
            210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                    245                 250

<210> SEQ ID NO 375
<211> LENGTH: 254
<212> TYPE: PRT
<213> ORGANISM: Artificial sequence
<220> FEATURE:
<223> OTHER INFORMATION: Synthetic peptide

<400> SEQUENCE: 375

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
                35                  40                  45

His Glu Asp Pro Glu Val Lys Phe Asn Trp Tyr Val Asp Gly Val Glu
            50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                    85                  90                  95

Gly Lys Glu Tyr Lys Cys Lys Val Ser Asn Lys Gly Gly Gln Gly Cys
                100                 105                 110

Ser Ser Gly Gly Pro Thr Leu Arg Glu Trp Gln Gln Cys Arg Arg Ala
                115                 120                 125
```

Gln His Ser Gly Gly Ala Leu Pro Ala Pro Ile Glu Lys Thr Ile Ser
         130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val Ser Leu Thr Cys Leu Val
                 165                 170                 175

Lys Gly Phe Tyr Pro Ser Asp Ile Ala Val Glu Trp Glu Ser Asn Gly
                 180                 185                 190

Gln Pro Glu Asn Asn Tyr Lys Thr Thr Pro Pro Val Leu Asp Ser Asp
                 195                 200                 205

Gly Ser Phe Phe Leu Tyr Ser Lys Leu Thr Val Asp Lys Ser Arg Trp
                 210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                 245                 250

<210> SEQ ID NO 376
<211> LENGTH: 254
<212> TYPE: PRT
<213> ORGANISM: Artificial sequence
<220> FEATURE:
<223> OTHER INFORMATION: Synthetic peptide

<400> SEQUENCE: 376

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
                 20                  25                  30

Met Ile Ser Arg Thr Pro Glu Val Thr Cys Val Val Val Asp Val Ser
             35                  40                  45

His Glu Asp Pro Glu Val Lys Phe Asn Trp Tyr Val Asp Gly Val Glu
         50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Gly Gln Gly Cys
                 100                 105                 110

Ser Ser Gly Gly Pro Thr Leu Arg Glu Trp Gln Gln Cys Val Arg Ala
                 115                 120                 125

Gln His Ser Gly Gly Ala Leu Pro Ala Pro Ile Glu Lys Thr Ile Ser
         130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val Ser Leu Thr Cys Leu Val
                 165                 170                 175

Lys Gly Phe Tyr Pro Ser Asp Ile Ala Val Glu Trp Glu Ser Asn Gly
                 180                 185                 190

Gln Pro Glu Asn Asn Tyr Lys Thr Thr Pro Pro Val Leu Asp Ser Asp
                 195                 200                 205

Gly Ser Phe Phe Leu Tyr Ser Lys Leu Thr Val Asp Lys Ser Arg Trp
                 210                 215                 220

Gln Gln Gly Asn Val Phe Ser Cys Ser Val Met His Glu Ala Leu His
225                 230                 235                 240

```
Asn His Tyr Thr Gln Lys Ser Leu Ser Leu Ser Pro Gly Lys
                245                 250
```

<210> SEQ ID NO 377
<211> LENGTH: 250
<212> TYPE: PRT
<213> ORGANISM: Artificial sequence
<220> FEATURE:
<223> OTHER INFORMATION: Synthetic peptide

<400> SEQUENCE: 377

```
Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Asp Met
            100                 105                 110

Glu Gly Pro Thr Leu Arg His Trp Leu Ala Ala Arg Ala Asn Gly Gly
        115                 120                 125

Gly Ala Leu Pro Ala Pro Ile Glu Lys Thr Ile Ser Lys Ala Lys Gly
    130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250
```

<210> SEQ ID NO 378
<211> LENGTH: 250
<212> TYPE: PRT
<213> ORGANISM: Artificial sequence
<220> FEATURE:
<223> OTHER INFORMATION: Synthetic peptide

<400> SEQUENCE: 378

```
Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45
```

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Gly Tyr Met Met
            100                 105                 110

Glu Gly Pro Thr Leu Arg His Trp Leu Ala Thr Arg Ala Gly Arg Gly
            115                 120                 125

Gly Ala Leu Pro Ala Pro Ile Glu Lys Thr Ile Ser Lys Ala Lys Gly
            130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
            195                 200                 205

Leu Tyr Ser Lys Leu Thr Val Asp Lys Ser Arg Trp Gln Gln Gly Asn
210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 379
<211> LENGTH: 250
<212> TYPE: PRT
<213> ORGANISM: Artificial sequence
<220> FEATURE:
<223> OTHER INFORMATION: Synthetic peptide

<400> SEQUENCE: 379

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Gly Thr His Ile
            100                 105                 110

Glu Gly Pro Thr Leu Arg Ile Trp Leu Ala Ser Arg Ala Lys Ala Gly
            115                 120                 125

Gly Ala Leu Pro Ala Pro Ile Glu Lys Thr Ile Ser Lys Ala Lys Gly
            130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr

-continued

```
                165                 170                 175
Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
            195                 200                 205

Leu Tyr Ser Lys Leu Thr Val Asp Lys Ser Arg Trp Gln Gln Gly Asn
            210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
            245                 250

<210> SEQ ID NO 380
<211> LENGTH: 250
<212> TYPE: PRT
<213> ORGANISM: Artificial sequence
<220> FEATURE:
<223> OTHER INFORMATION: Synthetic peptide

<400> SEQUENCE: 380

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Ser Ala Ile
            100                 105                 110

Glu Gly Pro Thr Leu Arg His Trp Leu Ala Trp Arg Ala Met Leu Gly
        115                 120                 125

Gly Ala Leu Pro Ala Pro Ile Glu Lys Thr Ile Ser Lys Ala Lys Gly
130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
            195                 200                 205

Leu Tyr Ser Lys Leu Thr Val Asp Lys Ser Arg Trp Gln Gln Gly Asn
            210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
            245                 250

<210> SEQ ID NO 381
<211> LENGTH: 250
<212> TYPE: PRT
<213> ORGANISM: Artificial sequence
```

```
<220> FEATURE:
<223> OTHER INFORMATION: Synthetic peptide

<400> SEQUENCE: 381

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Gly Trp Met Met
            100                 105                 110

Glu Gly Pro Thr Leu Arg His Trp Leu Ala Ala Arg Ala Arg Tyr Gly
        115                 120                 125

Gly Ala Leu Pro Ala Pro Ile Glu Lys Thr Ile Ser Lys Ala Lys Gly
    130                 135                 140

Gln Pro Arg Glu Pro Gln Val Tyr Thr Leu Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 382
<211> LENGTH: 250
<212> TYPE: PRT
<213> ORGANISM: Artificial sequence
<220> FEATURE:
<223> OTHER INFORMATION: Synthetic peptide

<400> SEQUENCE: 382

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95
```

Gly Lys Glu Tyr Lys Cys Lys Val Ser Asn Lys Gly Gly Ala Trp Met
                100                 105                 110

Glu Gly Pro Thr Leu Arg His Trp Leu Ala Ala Arg Ala Ala Tyr Gly
            115                 120                 125

Gly Ala Leu Pro Ala Pro Ile Glu Lys Thr Ile Ser Lys Ala Lys Gly
        130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 383
<211> LENGTH: 254
<212> TYPE: PRT
<213> ORGANISM: Artificial sequence
<220> FEATURE:
<223> OTHER INFORMATION: Synthetic peptide

<400> SEQUENCE: 383

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Gly Gln Gly Cys
    130                 135                 140

Ser Ser Gly Gly Pro Thr Leu Arg Glu Trp Gln Gln Cys Arg Arg Met
145                 150                 155                 160

Gln His Ser Gly Gly Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
        195                 200                 205

```
Gly Ser Phe Phe Leu Tyr Ser Lys Leu Thr Val Asp Lys Ser Arg Trp
            210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 384
<211> LENGTH: 254
<212> TYPE: PRT
<213> ORGANISM: Artificial sequence
<220> FEATURE:
<223> OTHER INFORMATION: Synthetic peptide

<400> SEQUENCE: 384

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Gly Gly Gln Gly Cys
    130                 135                 140

Ser Ser Gly Gly Pro Thr Leu Arg Glu Trp Gln Gln Cys Val Arg Met
145                 150                 155                 160

Gln His Ser Gly Gly Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
        195                 200                 205

Gly Ser Phe Phe Leu Tyr Ser Lys Leu Thr Val Asp Lys Ser Arg Trp
    210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 385
<211> LENGTH: 254
<212> TYPE: PRT
<213> ORGANISM: Artificial sequence
<220> FEATURE:
<223> OTHER INFORMATION: Synthetic peptide

<400> SEQUENCE: 385

Met Asp Lys Thr His Thr Cys Pro Pro Cys Pro Ala Pro Glu Leu Leu
1               5                   10                  15
```

```
Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Gly Gly Gln Gly Cys
            130                 135                 140

Ser Ser Gly Gly Pro Thr Leu Arg Glu Trp Gln Gln Cys Arg Arg Ala
145                 150                 155                 160

Gln His Ser Gly Gly Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
            195                 200                 205

Gly Ser Phe Phe Leu Tyr Ser Lys Leu Thr Val Asp Lys Ser Arg Trp
210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 386
<211> LENGTH: 254
<212> TYPE: PRT
<213> ORGANISM: Artificial sequence
<220> FEATURE:
<223> OTHER INFORMATION: Synthetic peptide

<400> SEQUENCE: 386

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Gly Gly Gln Gly Cys
```

-continued

```
            130                 135                 140
Ser Ser Gly Gly Pro Thr Leu Arg Glu Trp Gln Gln Cys Val Arg Ala
145                 150                 155                 160

Gln His Ser Gly Gly Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
        195                 200                 205

Gly Ser Phe Phe Leu Tyr Ser Lys Leu Thr Val Asp Lys Ser Arg Trp
    210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 387
<211> LENGTH: 250
<212> TYPE: PRT
<213> ORGANISM: Artificial sequence
<220> FEATURE:
<223> OTHER INFORMATION: Synthetic peptide

<400> SEQUENCE: 387

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Gly Gly Leu Asp Met
    130                 135                 140

Glu Gly Pro Thr Leu Arg His Trp Leu Ala Ala Arg Ala Asn Gly Gly
145                 150                 155                 160

Gly Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250
```

<210> SEQ ID NO 388
<211> LENGTH: 250
<212> TYPE: PRT
<213> ORGANISM: Artificial sequence
<220> FEATURE:
<223> OTHER INFORMATION: Synthetic peptide

<400> SEQUENCE: 388

```
Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Gly Gly Tyr Met Met
    130                 135                 140

Glu Gly Pro Thr Leu Arg His Trp Leu Ala Thr Arg Ala Gly Arg Gly
145                 150                 155                 160

Gly Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250
```

<210> SEQ ID NO 389
<211> LENGTH: 250
<212> TYPE: PRT
<213> ORGANISM: Artificial sequence
<220> FEATURE:
<223> OTHER INFORMATION: Synthetic peptide

<400> SEQUENCE: 389

```
Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60
```

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Gly Thr His Ile
    130                 135                 140

Glu Gly Pro Thr Leu Arg Ile Trp Leu Ala Ser Arg Ala Lys Ala Gly
145                 150                 155                 160

Gly Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 390
<211> LENGTH: 250
<212> TYPE: PRT
<213> ORGANISM: Artificial sequence
<220> FEATURE:
<223> OTHER INFORMATION: Synthetic peptide

<400> SEQUENCE: 390

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Gly Ser Ala Ile
    130                 135                 140

Glu Gly Pro Thr Leu Arg His Trp Leu Ala Trp Arg Ala Met Leu Gly
145                 150                 155                 160

Gly Thr Lys Asn Gln Val Ser Leu Thr Cys Leu Val Lys Gly Phe Tyr
                165                 170                 175

```
Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 391
<211> LENGTH: 250
<212> TYPE: PRT
<213> ORGANISM: Artificial sequence
<220> FEATURE:
<223> OTHER INFORMATION: Synthetic peptide

<400> SEQUENCE: 391

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Gly Gly Trp Met Met
    130                 135                 140

Glu Gly Pro Thr Leu Arg His Trp Leu Ala Ala Arg Ala Arg Tyr Gly
145                 150                 155                 160

Gly Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 392
<211> LENGTH: 250
<212> TYPE: PRT
<213> ORGANISM: Artificial sequence
<220> FEATURE:
<223> OTHER INFORMATION: Synthetic peptide
```

<400> SEQUENCE: 392

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Gly Gly Ala Trp Met
    130                 135                 140

Glu Gly Pro Thr Leu Arg His Trp Leu Ala Ala Arg Ala Ala Tyr Gly
145                 150                 155                 160

Gly Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 393
<211> LENGTH: 254
<212> TYPE: PRT
<213> ORGANISM: Artificial sequence
<220> FEATURE:
<223> OTHER INFORMATION: Synthetic peptide

<400> SEQUENCE: 393

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro

-continued

```
                100                 105                 110
Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Gly Gln Gly Cys Ser Ser
                165                 170                 175

Gly Gly Pro Thr Leu Arg Glu Trp Gln Gln Cys Arg Arg Met Gln His
            180                 185                 190

Ser Gly Gly Asn Asn Tyr Lys Thr Thr Pro Pro Val Leu Asp Ser Asp
                195                 200                 205

Gly Ser Phe Phe Leu Tyr Ser Lys Leu Thr Val Asp Lys Ser Arg Trp
            210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 394
<211> LENGTH: 254
<212> TYPE: PRT
<213> ORGANISM: Artificial sequence
<220> FEATURE:
<223> OTHER INFORMATION: Synthetic peptide

<400> SEQUENCE: 394

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Gly Gln Gly Cys Ser Ser
                165                 170                 175

Gly Gly Pro Thr Leu Arg Glu Trp Gln Gln Cys Val Arg Met Gln His
            180                 185                 190

Ser Gly Gly Asn Asn Tyr Lys Thr Thr Pro Pro Val Leu Asp Ser Asp
                195                 200                 205

Gly Ser Phe Phe Leu Tyr Ser Lys Leu Thr Val Asp Lys Ser Arg Trp
            210                 215                 220
```

```
Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250
```

<210> SEQ ID NO 395
<211> LENGTH: 254
<212> TYPE: PRT
<213> ORGANISM: Artificial sequence
<220> FEATURE:
<223> OTHER INFORMATION: Synthetic peptide

<400> SEQUENCE: 395

```
Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Gly Gly Gln Gly Cys Ser Ser
                165                 170                 175

Gly Gly Pro Thr Leu Arg Glu Trp Gln Gln Cys Arg Arg Ala Gln His
            180                 185                 190

Ser Gly Gly Asn Asn Tyr Lys Thr Thr Pro Pro Val Leu Asp Ser Asp
        195                 200                 205

Gly Ser Phe Phe Leu Tyr Ser Lys Leu Thr Val Asp Lys Ser Arg Trp
    210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250
```

<210> SEQ ID NO 396
<211> LENGTH: 254
<212> TYPE: PRT
<213> ORGANISM: Artificial sequence
<220> FEATURE:
<223> OTHER INFORMATION: Synthetic peptide

<400> SEQUENCE: 396

```
Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
                20                  25                  30
```

Met Ile Ser Arg Thr Pro Glu Val Thr Cys Val Val Asp Val Ser
            35                  40                  45

His Glu Asp Pro Glu Val Lys Phe Asn Trp Tyr Val Asp Gly Val Glu
 50                  55                  60

Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Gly Gly Gln Gly Cys Ser Ser
                165                 170                 175

Gly Gly Pro Thr Leu Arg Glu Trp Gln Gln Cys Val Arg Ala Gln His
            180                 185                 190

Ser Gly Gly Asn Asn Tyr Lys Thr Thr Pro Pro Val Leu Asp Ser Asp
        195                 200                 205

Gly Ser Phe Phe Leu Tyr Ser Lys Leu Thr Val Asp Lys Ser Arg Trp
    210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 397
<211> LENGTH: 250
<212> TYPE: PRT
<213> ORGANISM: Artificial sequence
<220> FEATURE:
<223> OTHER INFORMATION: Synthetic peptide

<400> SEQUENCE: 397

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Asp Val Ser
            35                  40                  45

His Glu Asp Pro Glu Val Lys Phe Asn Trp Tyr Val Asp Gly Val Glu
 50                  55                  60

Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
        130                 135                 140

```
Ser Leu Thr Cys Leu Val Lys Gly Phe Tyr Pro Ser Asp Ile Ala Val
145                 150                 155                 160

Glu Trp Glu Ser Asn Gly Gln Pro Glu Gly Leu Asp Met Glu Gly
                165                 170                 175

Pro Thr Leu Arg His Trp Leu Ala Ala Arg Ala Asn Gly Gly Gly Asn
            180                 185                 190

Asn Tyr Lys Thr Thr Pro Pro Val Leu Asp Ser Asp Gly Ser Phe Phe
            195                 200                 205

Leu Tyr Ser Lys Leu Thr Val Asp Lys Ser Arg Trp Gln Gln Gly Asn
            210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
            245                 250

<210> SEQ ID NO 398
<211> LENGTH: 250
<212> TYPE: PRT
<213> ORGANISM: Artificial sequence
<220> FEATURE:
<223> OTHER INFORMATION: Synthetic peptide

<400> SEQUENCE: 398

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
        50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Gly Gly Tyr Met Met Glu Gly
                165                 170                 175

Pro Thr Leu Arg His Trp Leu Ala Thr Arg Ala Gly Arg Gly Gly Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
            210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
            245                 250
```

<210> SEQ ID NO 399
<211> LENGTH: 250
<212> TYPE: PRT
<213> ORGANISM: Artificial sequence
<220> FEATURE:
<223> OTHER INFORMATION: Synthetic peptide

<400> SEQUENCE: 399

Met Asp Lys Thr His Thr Cys Pro Pro Cys Pro Ala Pro Glu Leu Leu
1               5                   10                  15
Gly Gly Pro Ser Val Phe Leu Phe Pro Pro Lys Pro Lys Asp Thr Leu
            20                  25                  30
Met Ile Ser Arg Thr Pro Glu Val Thr Cys Val Val Asp Val Ser
        35                  40                  45
His Glu Asp Pro Glu Val Lys Phe Asn Trp Tyr Val Asp Gly Val Glu
    50                  55                  60
Val His Asn Ala Lys Thr Lys Pro Arg Glu Glu Gln Tyr Asn Ser Thr
65                  70                  75                  80
Tyr Arg Val Val Ser Val Leu Thr Val Leu His Gln Asp Trp Leu Asn
                85                  90                  95
Gly Lys Glu Tyr Lys Cys Lys Val Ser Asn Lys Ala Leu Pro Ala Pro
            100                 105                 110
Ile Glu Lys Thr Ile Ser Lys Ala Lys Gly Gln Pro Arg Glu Pro Gln
        115                 120                 125
Val Tyr Thr Leu Pro Pro Ser Arg Asp Glu Leu Thr Lys Asn Gln Val
    130                 135                 140
Ser Leu Thr Cys Leu Val Lys Gly Phe Tyr Pro Ser Asp Ile Ala Val
145                 150                 155                 160
Glu Trp Glu Ser Asn Gly Gln Pro Glu Gly Gly Thr His Ile Glu Gly
                165                 170                 175
Pro Thr Leu Arg Ile Trp Leu Ala Ser Arg Ala Lys Ala Gly Gly Asn
            180                 185                 190
Asn Tyr Lys Thr Thr Pro Pro Val Leu Asp Ser Asp Gly Ser Phe Phe
        195                 200                 205
Leu Tyr Ser Lys Leu Thr Val Asp Lys Ser Arg Trp Gln Gln Gly Asn
    210                 215                 220
Val Phe Ser Cys Ser Val Met His Glu Ala Leu His Asn His Tyr Thr
225                 230                 235                 240
Gln Lys Ser Leu Ser Leu Ser Pro Gly Lys
                245                 250

<210> SEQ ID NO 400
<211> LENGTH: 250
<212> TYPE: PRT
<213> ORGANISM: Artificial sequence
<220> FEATURE:
<223> OTHER INFORMATION: Synthetic peptide

<400> SEQUENCE: 400

Met Asp Lys Thr His Thr Cys Pro Pro Cys Pro Ala Pro Glu Leu Leu
1               5                   10                  15
Gly Gly Pro Ser Val Phe Leu Phe Pro Pro Lys Pro Lys Asp Thr Leu
            20                  25                  30
Met Ile Ser Arg Thr Pro Glu Val Thr Cys Val Val Asp Val Ser
        35                  40                  45
His Glu Asp Pro Glu Val Lys Phe Asn Trp Tyr Val Asp Gly Val Glu
    50                  55                  60
Val His Asn Ala Lys Thr Lys Pro Arg Glu Glu Gln Tyr Asn Ser Thr

```
                65                  70                  75                  80
Tyr Arg Val Val Ser Val Leu Thr Val Leu His Gln Asp Trp Leu Asn
                    85                  90                  95
Gly Lys Glu Tyr Lys Cys Lys Val Ser Asn Lys Ala Leu Pro Ala Pro
                    100                 105                 110
Ile Glu Lys Thr Ile Ser Lys Ala Lys Gly Gln Pro Arg Glu Pro Gln
                    115                 120                 125
Val Tyr Thr Leu Pro Pro Ser Arg Asp Glu Leu Thr Lys Asn Gln Val
    130                 135                 140
Ser Leu Thr Cys Leu Val Lys Gly Phe Tyr Pro Ser Asp Ile Ala Val
145                 150                 155                 160
Glu Trp Glu Ser Asn Gly Gln Pro Glu Gly Gly Ser Ala Ile Glu Gly
                    165                 170                 175
Pro Thr Leu Arg His Trp Leu Ala Trp Arg Ala Met Leu Gly Gly Asn
                    180                 185                 190
Asn Tyr Lys Thr Thr Pro Pro Val Leu Asp Ser Asp Gly Ser Phe Phe
                    195                 200                 205
Leu Tyr Ser Lys Leu Thr Val Asp Lys Ser Arg Trp Gln Gln Gly Asn
    210                 215                 220
Val Phe Ser Cys Ser Val Met His Glu Ala Leu His Asn His Tyr Thr
225                 230                 235                 240
Gln Lys Ser Leu Ser Leu Ser Pro Gly Lys
                    245                 250

<210> SEQ ID NO 401
<211> LENGTH: 250
<212> TYPE: PRT
<213> ORGANISM: Artificial sequence
<220> FEATURE:
<223> OTHER INFORMATION: Synthetic peptide

<400> SEQUENCE: 401

Met Asp Lys Thr His Thr Cys Pro Pro Cys Pro Ala Pro Glu Leu Leu
1               5                   10                  15
Gly Gly Pro Ser Val Phe Leu Phe Pro Pro Lys Pro Lys Asp Thr Leu
                    20                  25                  30
Met Ile Ser Arg Thr Pro Glu Val Thr Cys Val Val Val Asp Val Ser
                    35                  40                  45
His Glu Asp Pro Glu Val Lys Phe Asn Trp Tyr Val Asp Gly Val Glu
    50                  55                  60
Val His Asn Ala Lys Thr Lys Pro Arg Glu Glu Gln Tyr Asn Ser Thr
65                  70                  75                  80
Tyr Arg Val Val Ser Val Leu Thr Val Leu His Gln Asp Trp Leu Asn
                    85                  90                  95
Gly Lys Glu Tyr Lys Cys Lys Val Ser Asn Lys Ala Leu Pro Ala Pro
                    100                 105                 110
Ile Glu Lys Thr Ile Ser Lys Ala Lys Gly Gln Pro Arg Glu Pro Gln
                    115                 120                 125
Val Tyr Thr Leu Pro Pro Ser Arg Asp Glu Leu Thr Lys Asn Gln Val
    130                 135                 140
Ser Leu Thr Cys Leu Val Lys Gly Phe Tyr Pro Ser Asp Ile Ala Val
145                 150                 155                 160
Glu Trp Glu Ser Asn Gly Gln Pro Glu Gly Gly Trp Met Met Glu Gly
                    165                 170                 175
Pro Thr Leu Arg His Trp Leu Ala Ala Arg Ala Arg Tyr Gly Gly Asn
                    180                 185                 190
```

Asn Tyr Lys Thr Thr Pro Pro Val Leu Asp Ser Asp Gly Ser Phe Phe
            195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
            245                 250

<210> SEQ ID NO 402
<211> LENGTH: 250
<212> TYPE: PRT
<213> ORGANISM: Artificial sequence
<220> FEATURE:
<223> OTHER INFORMATION: Synthetic peptide

<400> SEQUENCE: 402

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Gly Ala Trp Met Glu Gly
                165                 170                 175

Pro Thr Leu Arg His Trp Leu Ala Ala Arg Ala Ala Tyr Gly Gly Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
            245                 250

<210> SEQ ID NO 403
<211> LENGTH: 254
<212> TYPE: PRT
<213> ORGANISM: Artificial sequence
<220> FEATURE:
<223> OTHER INFORMATION: Synthetic peptide

<400> SEQUENCE: 403

```
Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
                100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Gly Gly Gln Cys Ser Ser Gly Pro Thr
            180                 185                 190

Leu Arg Glu Trp Gln Gln Cys Arg Arg Met Gln His Ser Gly Gly Asp
                195                 200                 205

Gly Ser Phe Phe Leu Tyr Ser Lys Leu Thr Val Asp Lys Ser Arg Trp
        210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250
```

<210> SEQ ID NO 404
<211> LENGTH: 254
<212> TYPE: PRT
<213> ORGANISM: Artificial sequence
<220> FEATURE:
<223> OTHER INFORMATION: Synthetic peptide

<400> SEQUENCE: 404

```
Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
                100                 105                 110
```

```
Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
            130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                    165                 170                 175

Pro Val Leu Asp Ser Gly Gly Gln Gly Cys Ser Ser Gly Gly Pro Thr
                180                 185                 190

Leu Arg Glu Trp Gln Gln Cys Val Arg Met Gln His Ser Gly Gly Asp
            195                 200                 205

Gly Ser Phe Phe Leu Tyr Ser Lys Leu Thr Val Asp Lys Ser Arg Trp
210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                    245                 250

<210> SEQ ID NO 405
<211> LENGTH: 254
<212> TYPE: PRT
<213> ORGANISM: Artificial sequence
<220> FEATURE:
<223> OTHER INFORMATION: Synthetic peptide

<400> SEQUENCE: 405

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
        50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
            130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                    165                 170                 175

Pro Val Leu Asp Ser Gly Gly Gln Gly Cys Ser Ser Gly Gly Pro Thr
                180                 185                 190

Leu Arg Glu Trp Gln Gln Cys Arg Arg Ala His Ser Gly Gly Asp
            195                 200                 205

Gly Ser Phe Phe Leu Tyr Ser Lys Leu Thr Val Asp Lys Ser Arg Trp
210                 215                 220

Gln Gln Gly Asn Val Phe Ser Cys Ser Val Met His Glu Ala Leu His
```

Asn His Tyr Thr Gln Lys Ser Leu Ser Leu Ser Pro Gly Lys
            245                 250

<210> SEQ ID NO 406
<211> LENGTH: 254
<212> TYPE: PRT
<213> ORGANISM: Artificial sequence
<220> FEATURE:
<223> OTHER INFORMATION: Synthetic peptide

<400> SEQUENCE: 406

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Gly Gly Gln Gly Cys Ser Ser Gly Gly Pro Thr
            180                 185                 190

Leu Arg Glu Trp Gln Gln Cys Val Arg Ala Gln His Ser Gly Gly Asp
        195                 200                 205

Gly Ser Phe Phe Leu Tyr Ser Lys Leu Thr Val Asp Lys Ser Arg Trp
    210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
            245                 250

<210> SEQ ID NO 407
<211> LENGTH: 250
<212> TYPE: PRT
<213> ORGANISM: Artificial sequence
<220> FEATURE:
<223> OTHER INFORMATION: Synthetic peptide

<400> SEQUENCE: 407

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser

-continued

```
                35                  40                  45
His Glu Asp Pro Glu Val Lys Phe Asn Trp Tyr Val Asp Gly Val Glu
 50                  55                  60

Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Ala Leu Pro Ala Pro
                100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Gly Gly Leu Asp Met Glu Gly Pro Thr Leu Arg
            180                 185                 190

His Trp Leu Ala Ala Arg Ala Asn Gly Gly Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 408
<211> LENGTH: 250
<212> TYPE: PRT
<213> ORGANISM: Artificial sequence
<220> FEATURE:
<223> OTHER INFORMATION: Synthetic peptide

<400> SEQUENCE: 408

Met Asp Lys Thr His Thr Cys Pro Pro Cys Pro Ala Pro Glu Leu Leu
 1               5                  10                  15

Gly Gly Pro Ser Val Phe Leu Phe Pro Pro Lys Pro Lys Asp Thr Leu
                 20                  25                  30

Met Ile Ser Arg Thr Pro Glu Val Thr Cys Val Val Val Asp Val Ser
             35                  40                  45

His Glu Asp Pro Glu Val Lys Phe Asn Trp Tyr Val Asp Gly Val Glu
 50                  55                  60

Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Ala Leu Pro Ala Pro
                100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
        130                 135                 140

Ser Leu Thr Cys Leu Val Lys Gly Phe Tyr Pro Ser Asp Ile Ala Val
145                 150                 155                 160
```

```
Glu Trp Glu Ser Asn Gly Gln Pro Glu Asn Asn Tyr Lys Thr Thr Pro
                165                 170                 175

Pro Val Leu Asp Ser Gly Gly Tyr Met Met Glu Gly Pro Thr Leu Arg
            180                 185                 190

His Trp Leu Ala Thr Arg Ala Gly Arg Gly Gly Asp Gly Ser Phe Phe
            195                 200                 205

Leu Tyr Ser Lys Leu Thr Val Asp Lys Ser Arg Trp Gln Gln Gly Asn
            210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 409
<211> LENGTH: 250
<212> TYPE: PRT
<213> ORGANISM: Artificial sequence
<220> FEATURE:
<223> OTHER INFORMATION: Synthetic peptide

<400> SEQUENCE: 409

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Gly Gly Thr His Ile Glu Gly Pro Thr Leu Arg
            180                 185                 190

Ile Trp Leu Ala Ser Arg Ala Lys Ala Gly Gly Asp Gly Ser Phe Phe
            195                 200                 205

Leu Tyr Ser Lys Leu Thr Val Asp Lys Ser Arg Trp Gln Gln Gly Asn
            210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 410
<211> LENGTH: 250
```

```
<212> TYPE: PRT
<213> ORGANISM: Artificial sequence
<220> FEATURE:
<223> OTHER INFORMATION: Synthetic peptide

<400> SEQUENCE: 410

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Gly Gly Ser Ala Ile Glu Gly Pro Thr Leu Arg
            180                 185                 190

His Trp Leu Ala Trp Arg Ala Met Leu Gly Gly Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 411
<211> LENGTH: 250
<212> TYPE: PRT
<213> ORGANISM: Artificial sequence
<220> FEATURE:
<223> OTHER INFORMATION: Synthetic peptide

<400> SEQUENCE: 411

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80
```

```
Tyr Arg Val Val Ser Val Leu Thr Val Leu His Gln Asp Trp Leu Asn
            85                  90                  95
Gly Lys Glu Tyr Lys Cys Lys Val Ser Asn Lys Ala Leu Pro Ala Pro
            100                 105                 110
Ile Glu Lys Thr Ile Ser Lys Ala Lys Gly Gln Pro Arg Glu Pro Gln
            115                 120                 125
Val Tyr Thr Leu Pro Pro Ser Arg Asp Glu Leu Thr Lys Asn Gln Val
            130                 135                 140
Ser Leu Thr Cys Leu Val Lys Gly Phe Tyr Pro Ser Asp Ile Ala Val
145                 150                 155                 160
Glu Trp Glu Ser Asn Gly Gln Pro Glu Asn Asn Tyr Lys Thr Thr Pro
            165                 170                 175
Pro Val Leu Asp Ser Gly Gly Trp Met Met Glu Gly Pro Thr Leu Arg
            180                 185                 190
His Trp Leu Ala Ala Arg Ala Arg Tyr Gly Gly Asp Gly Ser Phe Phe
            195                 200                 205
Leu Tyr Ser Lys Leu Thr Val Asp Lys Ser Arg Trp Gln Gln Gly Asn
            210                 215                 220
Val Phe Ser Cys Ser Val Met His Glu Ala Leu His Asn His Tyr Thr
225                 230                 235                 240
Gln Lys Ser Leu Ser Leu Ser Pro Gly Lys
            245                 250

<210> SEQ ID NO 412
<211> LENGTH: 250
<212> TYPE: PRT
<213> ORGANISM: Artificial sequence
<220> FEATURE:
<223> OTHER INFORMATION: Synthetic peptide

<400> SEQUENCE: 412

Met Asp Lys Thr His Thr Cys Pro Pro Cys Pro Ala Pro Glu Leu Leu
1               5                   10                  15
Gly Gly Pro Ser Val Phe Leu Phe Pro Pro Lys Pro Lys Asp Thr Leu
            20                  25                  30
Met Ile Ser Arg Thr Pro Glu Val Thr Cys Val Val Val Asp Val Ser
            35                  40                  45
His Glu Asp Pro Glu Val Lys Phe Asn Trp Tyr Val Asp Gly Val Glu
            50                  55                  60
Val His Asn Ala Lys Thr Lys Pro Arg Glu Glu Gln Tyr Asn Ser Thr
65                  70                  75                  80
Tyr Arg Val Val Ser Val Leu Thr Val Leu His Gln Asp Trp Leu Asn
            85                  90                  95
Gly Lys Glu Tyr Lys Cys Lys Val Ser Asn Lys Ala Leu Pro Ala Pro
            100                 105                 110
Ile Glu Lys Thr Ile Ser Lys Ala Lys Gly Gln Pro Arg Glu Pro Gln
            115                 120                 125
Val Tyr Thr Leu Pro Pro Ser Arg Asp Glu Leu Thr Lys Asn Gln Val
            130                 135                 140
Ser Leu Thr Cys Leu Val Lys Gly Phe Tyr Pro Ser Asp Ile Ala Val
145                 150                 155                 160
Glu Trp Glu Ser Asn Gly Gln Pro Glu Asn Asn Tyr Lys Thr Thr Pro
            165                 170                 175
Pro Val Leu Asp Ser Gly Gly Ala Trp Met Glu Gly Pro Thr Leu Arg
            180                 185                 190
His Trp Leu Ala Ala Arg Ala Ala Tyr Gly Gly Asp Gly Ser Phe Phe
```

195                 200                 205

Leu Tyr Ser Lys Leu Thr Val Asp Lys Ser Arg Trp Gln Gln Gly Asn
210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 413
<211> LENGTH: 254
<212> TYPE: PRT
<213> ORGANISM: Artificial sequence
<220> FEATURE:
<223> OTHER INFORMATION: Synthetic peptide

<400> SEQUENCE: 413

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
        50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Gly Gln Gly Cys Ser Ser
        195                 200                 205

Gly Gly Pro Thr Leu Arg Glu Trp Gln Gln Cys Arg Arg Met Gln His
    210                 215                 220

Ser Gly Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 414
<211> LENGTH: 254
<212> TYPE: PRT
<213> ORGANISM: Artificial sequence
<220> FEATURE:
<223> OTHER INFORMATION: Synthetic peptide

<400> SEQUENCE: 414

Met Asp Lys Thr His Thr Cys Pro Pro Cys Pro Ala Pro Glu Leu Leu

-continued

```
                1               5                  10                 15
Gly Gly Pro Ser Val Phe Leu Phe Pro Pro Lys Pro Lys Asp Thr Leu
                20                 25                 30

Met Ile Ser Arg Thr Pro Glu Val Thr Cys Val Val Val Asp Val Ser
            35                 40                 45

His Glu Asp Pro Glu Val Lys Phe Asn Trp Tyr Val Asp Gly Val Glu
        50                 55                 60

Val His Asn Ala Lys Thr Lys Pro Arg Glu Glu Gln Tyr Asn Ser Thr
65                  70                 75                     80

Tyr Arg Val Val Ser Val Leu Thr Val Leu His Gln Asp Trp Leu Asn
                85                 90                 95

Gly Lys Glu Tyr Lys Cys Lys Val Ser Asn Lys Ala Leu Pro Ala Pro
                100                105                110

Ile Glu Lys Thr Ile Ser Lys Ala Lys Gly Gln Pro Arg Glu Pro Gln
                115                120                125

Val Tyr Thr Leu Pro Pro Ser Arg Asp Glu Leu Thr Lys Asn Gln Val
                130                135                140

Ser Leu Thr Cys Leu Val Lys Gly Phe Tyr Pro Ser Asp Ile Ala Val
145                 150                155                160

Glu Trp Glu Ser Asn Gly Gln Pro Glu Asn Asn Tyr Lys Thr Thr Pro
                165                170                175

Pro Val Leu Asp Ser Asp Gly Ser Phe Phe Leu Tyr Ser Lys Leu Thr
                180                185                190

Val Asp Lys Ser Arg Trp Gln Gln Gly Gly Gly Gln Gly Cys Ser Ser
                195                200                205

Gly Gly Pro Thr Leu Arg Glu Trp Gln Gln Cys Val Arg Met Gln His
                210                215                220

Ser Gly Gly Asn Val Phe Ser Cys Ser Val Met His Glu Ala Leu His
225                 230                235                240

Asn His Tyr Thr Gln Lys Ser Leu Ser Leu Ser Pro Gly Lys
                245                250
```

<210> SEQ ID NO 415
<211> LENGTH: 254
<212> TYPE: PRT
<213> ORGANISM: Artificial sequence
<220> FEATURE:
<223> OTHER INFORMATION: Synthetic peptide

<400> SEQUENCE: 415

```
Met Asp Lys Thr His Thr Cys Pro Pro Cys Pro Ala Pro Glu Leu Leu
1               5                  10                 15

Gly Gly Pro Ser Val Phe Leu Phe Pro Pro Lys Pro Lys Asp Thr Leu
                20                 25                 30

Met Ile Ser Arg Thr Pro Glu Val Thr Cys Val Val Val Asp Val Ser
            35                 40                 45

His Glu Asp Pro Glu Val Lys Phe Asn Trp Tyr Val Asp Gly Val Glu
        50                 55                 60

Val His Asn Ala Lys Thr Lys Pro Arg Glu Glu Gln Tyr Asn Ser Thr
65                  70                 75                     80

Tyr Arg Val Val Ser Val Leu Thr Val Leu His Gln Asp Trp Leu Asn
                85                 90                 95

Gly Lys Glu Tyr Lys Cys Lys Val Ser Asn Lys Ala Leu Pro Ala Pro
                100                105                110

Ile Glu Lys Thr Ile Ser Lys Ala Lys Gly Gln Pro Arg Glu Pro Gln
                115                120                125
```

```
Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                    165                 170                 175

Pro Val Leu Asp Ser Asp Gly Ser Phe Phe Leu Tyr Ser Lys Leu Thr
                180                 185                 190

Val Asp Lys Ser Arg Trp Gln Gln Gly Gly Gln Gly Cys Ser Ser
                195                 200                 205

Gly Gly Pro Thr Leu Arg Glu Trp Gln Gln Cys Arg Arg Ala Gln His
    210                 215                 220

Ser Gly Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                    245                 250

<210> SEQ ID NO 416
<211> LENGTH: 254
<212> TYPE: PRT
<213> ORGANISM: Artificial sequence
<220> FEATURE:
<223> OTHER INFORMATION: Synthetic peptide

<400> SEQUENCE: 416

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
        50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
                100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                    165                 170                 175

Pro Val Leu Asp Ser Asp Gly Ser Phe Phe Leu Tyr Ser Lys Leu Thr
                180                 185                 190

Val Asp Lys Ser Arg Trp Gln Gln Gly Gly Gln Gly Cys Ser Ser
                195                 200                 205

Gly Gly Pro Thr Leu Arg Glu Trp Gln Gln Cys Val Arg Ala Gln His
    210                 215                 220

Ser Gly Gly Asn Val Phe Ser Cys Ser Val Met His Glu Ala Leu His
225                 230                 235                 240
```

```
Asn His Tyr Thr Gln Lys Ser Leu Ser Leu Ser Pro Gly Lys
                245                 250

<210> SEQ ID NO 417
<211> LENGTH: 250
<212> TYPE: PRT
<213> ORGANISM: Artificial sequence
<220> FEATURE:
<223> OTHER INFORMATION: Synthetic peptide

<400> SEQUENCE: 417

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Gly Leu Asp Met Glu Gly
        195                 200                 205

Pro Thr Leu Arg His Trp Leu Ala Ala Arg Ala Asn Gly Gly Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 418
<211> LENGTH: 250
<212> TYPE: PRT
<213> ORGANISM: Artificial sequence
<220> FEATURE:
<223> OTHER INFORMATION: Synthetic peptide

<400> SEQUENCE: 418

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45
```

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Ala Leu Pro Ala Pro
                100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Gly Tyr Met Met Glu Gly
        195                 200                 205

Pro Thr Leu Arg His Trp Leu Ala Thr Arg Ala Gly Arg Gly Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 419
<211> LENGTH: 250
<212> TYPE: PRT
<213> ORGANISM: Artificial sequence
<220> FEATURE:
<223> OTHER INFORMATION: Synthetic peptide

<400> SEQUENCE: 419

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Ala Leu Pro Ala Pro
                100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro

```
                        165                 170                 175
Pro Val Leu Asp Ser Asp Gly Ser Phe Phe Leu Tyr Ser Lys Leu Thr
            180                 185                 190

Val Asp Lys Ser Arg Trp Gln Gln Gly Gly Gly Thr His Ile Glu Gly
        195                 200                 205

Pro Thr Leu Arg Ile Trp Leu Ala Ser Arg Ala Lys Ala Gly Gly Asn
        210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 420
<211> LENGTH: 250
<212> TYPE: PRT
<213> ORGANISM: Artificial sequence
<220> FEATURE:
<223> OTHER INFORMATION: Synthetic peptide

<400> SEQUENCE: 420

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Gly Gly Ser Ala Ile Glu Gly
        195                 200                 205

Pro Thr Leu Arg His Trp Leu Ala Trp Arg Ala Met Leu Gly Gly Asn
        210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 421
<211> LENGTH: 250
<212> TYPE: PRT
<213> ORGANISM: Artificial sequence
```

```
<220> FEATURE:
<223> OTHER INFORMATION: Synthetic peptide

<400> SEQUENCE: 421

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Gly Trp Met Met Glu Gly
        195                 200                 205

Pro Thr Leu Arg His Trp Leu Ala Ala Arg Ala Arg Tyr Gly Gly Asn
        210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 422
<211> LENGTH: 250
<212> TYPE: PRT
<213> ORGANISM: Artificial sequence
<220> FEATURE:
<223> OTHER INFORMATION: Synthetic peptide

<400> SEQUENCE: 422

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95
```

```
Gly Lys Glu Tyr Lys Cys Lys Val Ser Asn Lys Ala Leu Pro Ala Pro
                100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Gly Ala Trp Met Glu Gly
        195                 200                 205

Pro Thr Leu Arg His Trp Leu Ala Ala Arg Ala Ala Tyr Gly Gly Asn
            210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 423
<211> LENGTH: 183
<212> TYPE: PRT
<213> ORGANISM: Artificial sequence
<220> FEATURE:
<223> OTHER INFORMATION: Synthetic peptide

<400> SEQUENCE: 423

Glu Gly Gly Gly Gly Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Ser Arg Trp Gln Gln Gly Asn Val Phe Ser
145                 150                 155                 160

Cys Ser Val Met His Glu Ala Leu His Asn His Tyr Thr Gln Lys Ser
                165                 170                 175

Leu Ser Leu Ser Pro Gly Lys
            180

<210> SEQ ID NO 424
<211> LENGTH: 205
```

<212> TYPE: PRT
<213> ORGANISM: Artificial sequence
<220> FEATURE:
<223> OTHER INFORMATION: Synthetic peptide

<400> SEQUENCE: 424

Ser Val Phe Ile Phe Pro Pro Lys Thr Lys Asp Val Leu Thr Ile Thr
1               5                   10                  15

Leu Thr Pro Lys Val Thr Cys Val Val Asp Ile Ser Gln Asn Asp
            20                  25                  30

Pro Glu Val Arg Phe Ser Trp Phe Ile Asp Asp Val Glu Val His Thr
                35                  40                  45

Ala Gln Thr His Ala Pro Glu Lys Gln Ser Asn Ser Thr Leu Arg Ser
        50                  55                  60

Val Ser Glu Leu Pro Ile Val His Arg Asp Trp Leu Asn Gly Lys Thr
65                  70                  75                  80

Phe Lys Cys Lys Val Asn Ser Gly Ala Phe Pro Ala Pro Ile Glu Lys
                85                  90                  95

Ser Ile Ser Lys Pro Glu Gly Thr Pro Arg Gly Pro Gln Val Tyr Thr
            100                 105                 110

Met Ala Pro Pro Lys Glu Glu Met Thr Gln Ser Gln Val Ser Ile Thr
            115                 120                 125

Cys Met Val Lys Gly Phe Tyr Pro Pro Asp Ile Tyr Thr Glu Trp Lys
130                 135                 140

Met Asn Gly Gln Pro Gln Glu Asn Tyr Lys Asn Thr Pro Pro Thr Met
145                 150                 155                 160

Asp Thr Asp Gly Ser Tyr Phe Leu Tyr Ser Lys Leu Asn Val Lys Lys
                165                 170                 175

Glu Thr Trp Gln Gln Gly Asn Thr Phe Thr Cys Ser Val Leu His Glu
            180                 185                 190

Gly Leu His Asn His His Thr Glu Lys Ser Leu Ser His
        195                 200                 205

<210> SEQ ID NO 425
<211> LENGTH: 204
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
<222> LOCATION: (38)..(38)

```
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (52)..(54)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (85)..(87)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (100)..(101)
<223> OTHER INFORMATION: Xaa can be any naturally occurring amino acid
<220> FEATURE:
<221> NAME/KEY: misc_feature
<222> LOCATION: (103)..(103)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
<221> NAME/KEY: misc_feature
<222> LOCATION: (121)..(122)
<223> OTHER INFORMATION: Xaa can be any naturally occurring amino acid
<220> FEATURE:
<221> NAME/KEY: misc_feature
<222> LOCATION: (136)..(136)
```

```
<223> OTHER INFORMATION: Xaa can be any naturally occurring amino acid
<220> FEATURE:
<221> NAME/KEY: misc_feature
<222> LOCATION: (139)..(140)
<223> OTHER INFORMATION: Xaa can be any naturally occurring amino acid
<220> FEATURE:
<221> NAME/KEY: misc_feature
<222> LOCATION: (143)..(144)
<223> OTHER INFORMATION: Xaa can be any naturally occurring amino acid
<220> FEATURE:
<221> NAME/KEY: misc_feature
<222> LOCATION: (149)..(150)
<223> OTHER INFORMATION: Xaa can be any naturally occurring amino acid
<220> FEATURE:
<221> NAME/KEY: misc_feature
<222> LOCATION: (154)..(154)
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (172)..(172)
<223> OTHER INFORMATION: Xaa can be any naturally occurring amino acid
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: misc_feature
<222> LOCATION: (176)..(177)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (199)..(199)
<223> OTHER INFORMATION: Xaa can be any naturally occurring amino acid
<220> FEATURE:
<221> NAME/KEY: misc_feature
<222> LOCATION: (204)..(204)
<223> OTHER INFORMATION: Xaa can be any naturally occurring amino acid

<400> SEQUENCE: 525

Ser Val Phe Ile Phe Pro Pro Lys Xaa Lys Asp Xaa Leu Xaa Ile Ser
1               5                   10                  15

Xaa Thr Pro Xaa Val Thr Cys Val Val Val Asp Ile Ser Xaa Xaa Asp
            20                  25                  30

Pro Glu Val Lys Phe Xaa Trp Phe Ile Asp Xaa Val Glu Val His Xaa
        35                  40                  45

Ala Xaa Thr Xaa Xaa Xaa Glu Xaa Gln Xaa Asn Ser Thr Xaa Arg Xaa
50                  55                  60

Val Ser Xaa Leu Ile Leu His Xaa Asp Trp Leu Asn Gly Lys Xaa Phe
65                  70                  75                  80

Lys Cys Lys Val Xaa Xaa Xaa Ala Xaa Pro Ala Pro Ile Glu Lys Ser
                85                  90                  95

Ile Ser Lys Xaa Xaa Gly Xaa Pro Arg Xaa Pro Gln Val Tyr Thr Leu
            100                 105                 110

Xaa Pro Xaa Lys Asp Glu Leu Thr Xaa Xaa Gln Val Ser Ile Thr Cys
        115                 120                 125

Leu Val Lys Gly Phe Tyr Pro Xaa Asp Ile Xaa Xaa Glu Trp Xaa Xaa
130                 135                 140

Asn Gly Gln Pro Xaa Xaa Asn Tyr Lys Xaa Thr Pro Pro Xaa Leu Asp
145                 150                 155                 160

Ser Asp Gly Ser Phe Phe Leu Tyr Ser Lys Leu Xaa Val Xaa Lys Xaa
                165                 170                 175
```

```
Xaa Trp Gln Gln Gly Asn Xaa Phe Ser Cys Ser Val Leu His Glu Ala
            180                 185                 190

Leu His Asn His His Thr Xaa Lys Ser Leu Ser Xaa
        195                 200

<210> SEQ ID NO 426
<211> LENGTH: 9
<212> TYPE: PRT
<213> ORGANISM: Artificial sequence
<220> FEATURE:
<223> OTHER INFORMATION: Synthetic peptide

<400> SEQUENCE: 426

Lys Ser Arg Trp Gln Gln Gly Asn Ile
1               5

<210> SEQ ID NO 427
<211> LENGTH: 9
<212> TYPE: PRT
<213> ORGANISM: Artificial sequence
<220> FEATURE:
<223> OTHER INFORMATION: Synthetic peptide

<400> SEQUENCE: 427

Lys Ser Arg Trp Gln Glu Gly Asn Val
1               5

<210> SEQ ID NO 428
<211> LENGTH: 2
<212> TYPE: PRT
<213> ORGANISM: Artificial sequence
<220> FEATURE:
<223> OTHER INFORMATION: Synthetic peptide

<400> SEQUENCE: 428

Pro Pro
1

<210> SEQ ID NO 429
<211> LENGTH: 8
<212> TYPE: PRT
<213> ORGANISM: Artificial sequence
<220> FEATURE:
<223> OTHER INFORMATION: Synthetic peptide

<400> SEQUENCE: 429

Asp Val Ser His Glu Asp Pro Glu
1               5

<210> SEQ ID NO 430
<211> LENGTH: 3
<212> TYPE: PRT
<213> ORGANISM: Artificial sequence
<220> FEATURE:
<223> OTHER INFORMATION: Synthetic peptide

<400> SEQUENCE: 430

Ser His Glu
1

<210> SEQ ID NO 431
<211> LENGTH: 4
<212> TYPE: PRT
<213> ORGANISM: Artificial sequence
<220> FEATURE:
<223> OTHER INFORMATION: Synthetic peptide
```

```
<400> SEQUENCE: 431

Val His Asn Ala
1

<210> SEQ ID NO 432
<211> LENGTH: 7
<212> TYPE: PRT
<213> ORGANISM: Artificial sequence
<220> FEATURE:
<223> OTHER INFORMATION: Synthetic peptide

<400> SEQUENCE: 432

Glu Glu Gln Tyr Asn Ser Thr
1               5

<210> SEQ ID NO 433
<211> LENGTH: 3
<212> TYPE: PRT
<213> ORGANISM: Artificial sequence
<220> FEATURE:
<223> OTHER INFORMATION: Synthetic peptide

<400> SEQUENCE: 433

Tyr Asn Ser
1

<210> SEQ ID NO 434
<211> LENGTH: 11
<212> TYPE: PRT
<213> ORGANISM: Artificial sequence
<220> FEATURE:
<223> OTHER INFORMATION: Synthetic peptide

<400> SEQUENCE: 434

Val Leu His Gln Asp Trp Leu Asn Gly Lys Glu
1               5                   10

<210> SEQ ID NO 435
<211> LENGTH: 16
<212> TYPE: PRT
<213> ORGANISM: Artificial sequence
<220> FEATURE:
<223> OTHER INFORMATION: Synthetic peptide

<400> SEQUENCE: 435

Asn Lys Ala Leu Pro Ala Pro Ile Glu Lys Thr Ile Ser Lys Ala Lys
1               5                   10                  15

<210> SEQ ID NO 436
<211> LENGTH: 3
<212> TYPE: PRT
<213> ORGANISM: Artificial sequence
<220> FEATURE:
<223> OTHER INFORMATION: Synthetic peptide

<400> SEQUENCE: 436

Asn Lys Ala
1

<210> SEQ ID NO 437
<211> LENGTH: 5
<212> TYPE: PRT
<213> ORGANISM: Artificial sequence
<220> FEATURE:
<223> OTHER INFORMATION: Synthetic peptide

<400> SEQUENCE: 437
```

```
Asp Glu Leu Thr Lys
1               5

<210> SEQ ID NO 438
<211> LENGTH: 3
<212> TYPE: PRT
<213> ORGANISM: Artificial sequence
<220> FEATURE:
<223> OTHER INFORMATION: Synthetic peptide

<400> SEQUENCE: 438

Leu Thr Lys
1

<210> SEQ ID NO 439
<211> LENGTH: 7
<212> TYPE: PRT
<213> ORGANISM: Artificial sequence
<220> FEATURE:
<223> OTHER INFORMATION: Synthetic peptide

<400> SEQUENCE: 439

Asn Gly Gln Pro Glu Asn Asn
1               5

<210> SEQ ID NO 440
<211> LENGTH: 3
<212> TYPE: PRT
<213> ORGANISM: Artificial sequence
<220> FEATURE:
<223> OTHER INFORMATION: Synthetic peptide

<400> SEQUENCE: 440

Glu Asn Asn
1

<210> SEQ ID NO 441
<211> LENGTH: 11
<212> TYPE: PRT
<213> ORGANISM: Artificial sequence
<220> FEATURE:
<223> OTHER INFORMATION: Synthetic peptide

<400> SEQUENCE: 441

Thr Thr Pro Pro Val Leu Asp Ser Asp Gly Ser
1               5                   10

<210> SEQ ID NO 442
<211> LENGTH: 5
<212> TYPE: PRT
<213> ORGANISM: Artificial sequence
<220> FEATURE:
<223> OTHER INFORMATION: Synthetic peptide

<400> SEQUENCE: 442

Val Leu Asp Ser Asp
1               5

<210> SEQ ID NO 443
<211> LENGTH: 9
<212> TYPE: PRT
<213> ORGANISM: Artificial sequence
<220> FEATURE:
<223> OTHER INFORMATION: Synthetic peptide

<400> SEQUENCE: 443

Lys Ser Arg Trp Gln Gln Gly Asn Val
1               5
```

```
<210> SEQ ID NO 444
<211> LENGTH: 3
<212> TYPE: PRT
<213> ORGANISM: Artificial sequence
<220> FEATURE:
<223> OTHER INFORMATION: Synthetic peptide

<400> SEQUENCE: 444

Gln Gly Asn
1

<210> SEQ ID NO 445
<211> LENGTH: 8
<212> TYPE: PRT
<213> ORGANISM: Artificial sequence
<220> FEATURE:
<223> OTHER INFORMATION: Synthetic peptide

<400> SEQUENCE: 445

Asp Val Ser Gln Glu Asp Pro Glu
1               5

<210> SEQ ID NO 446
<211> LENGTH: 7
<212> TYPE: PRT
<213> ORGANISM: Artificial sequence
<220> FEATURE:
<223> OTHER INFORMATION: Synthetic peptide

<400> SEQUENCE: 446

Glu Glu Gln Phe Asn Ser Thr
1               5

<210> SEQ ID NO 447
<211> LENGTH: 11
<212> TYPE: PRT
<213> ORGANISM: Artificial sequence
<220> FEATURE:
<223> OTHER INFORMATION: Synthetic peptide

<400> SEQUENCE: 447

Val Val His Gln Asp Trp Leu Asn Gly Lys Glu
1               5                   10

<210> SEQ ID NO 448
<211> LENGTH: 22
<212> TYPE: PRT
<213> ORGANISM: Artificial sequence
<220> FEATURE:
<223> OTHER INFORMATION: Synthetic peptide

<400> SEQUENCE: 448

Asn Lys Ala Leu Pro Ala Pro Ile Glu Lys Thr Ile Ser Lys Thr Lys
1               5                   10                  15

Gly Gln Pro Arg Glu Pro
            20

<210> SEQ ID NO 449
<211> LENGTH: 22
<212> TYPE: PRT
<213> ORGANISM: Artificial sequence
<220> FEATURE:
<223> OTHER INFORMATION: Synthetic peptide

<400> SEQUENCE: 449

Asn Lys Gly Leu Pro Ala Pro Ile Glu Lys Thr Ile Ser Lys Thr Lys
```

```
1               5                  10                 15

Gly Gln Pro Arg Glu Pro
            20

<210> SEQ ID NO 450
<211> LENGTH: 18
<212> TYPE: PRT
<213> ORGANISM: Artificial sequence
<220> FEATURE:
<223> OTHER INFORMATION: Synthetic peptide

<400> SEQUENCE: 450

Asn Lys Gly Leu Pro Ser Ser Ile Glu Lys Ala Lys Gly Gln Pro Arg
1               5                   10                  15

Glu Pro

<210> SEQ ID NO 451
<211> LENGTH: 5
<212> TYPE: PRT
<213> ORGANISM: Artificial sequence
<220> FEATURE:
<223> OTHER INFORMATION: Synthetic peptide

<400> SEQUENCE: 451

Glu Glu Met Thr Lys
1               5

<210> SEQ ID NO 452
<211> LENGTH: 7
<212> TYPE: PRT
<213> ORGANISM: Artificial sequence
<220> FEATURE:
<223> OTHER INFORMATION: Synthetic peptide

<400> SEQUENCE: 452

Ser Gly Gln Pro Glu Asn Asn
1               5

<210> SEQ ID NO 453
<211> LENGTH: 11
<212> TYPE: PRT
<213> ORGANISM: Artificial sequence
<220> FEATURE:
<223> OTHER INFORMATION: Synthetic peptide

<400> SEQUENCE: 453

Thr Thr Pro Pro Met Leu Asp Ser Asp Gly Ser
1               5                   10

<210> SEQ ID NO 454
<211> LENGTH: 18
<212> TYPE: PRT
<213> ORGANISM: Artificial sequence
<220> FEATURE:
<223> OTHER INFORMATION: Synthetic peptide

<400> SEQUENCE: 454

Cys Ser Ser Gly Gly Pro Thr Leu Arg Glu Trp Gln Gln Cys Ser Arg
1               5                   10                  15

Ala Gln

<210> SEQ ID NO 455
<211> LENGTH: 18
<212> TYPE: PRT
<213> ORGANISM: Artificial sequence
<220> FEATURE:
```

```
<223> OTHER INFORMATION: Synthetic peptide

<400> SEQUENCE: 455

Cys Ser Ser Gly Gly Pro Thr Leu Arg Glu Trp Gln Gln Cys Gln Arg
1               5                   10                  15

Ala Gln

<210> SEQ ID NO 456
<211> LENGTH: 18
<212> TYPE: PRT
<213> ORGANISM: Artificial sequence
<220> FEATURE:
<223> OTHER INFORMATION: Synthetic peptide

<400> SEQUENCE: 456

Cys Ser Ser Gly Gly Pro Thr Leu Arg Glu Trp Gln Gln Cys Gly Arg
1               5                   10                  15

Ala Gln
```

We claim:

1. A compound that binds to a thrombopoietin (TPO) receptor, wherein the compound comprises a structure which is selected from the group consisting of SEQ ID NOS: 353-422, or a physiologically acceptable salt thereof.

* * * * *